(12) United States Patent
Chowdhury et al.

(10) Patent No.: US 9,527,927 B2
(45) Date of Patent: Dec. 27, 2016

(54) MODIFIED POLYPEPTIDES FOR BISPECIFIC ANTIBODY SCAFFOLDS

(71) Applicant: MedImmune, LLC, Gaithersburg, MD (US)

(72) Inventors: Partha S. Chowdhury, Gaithersburg, MD (US); Vaheh Oganesyan, Gaithersburg, MD (US); Yariv Mazor, Gaithersburg, MD (US); Nazzareno Dimasi, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/366,582

(22) PCT Filed: Dec. 18, 2012

(86) PCT No.: PCT/US2012/070310
§ 371 (c)(1),
(2) Date: Jun. 18, 2014

(87) PCT Pub. No.: WO2013/096291
PCT Pub. Date: Jun. 27, 2013

(65) Prior Publication Data
US 2014/0348839 A1    Nov. 27, 2014

Related U.S. Application Data

(60) Provisional application No. 61/577,956, filed on Dec. 20, 2011.

(51) Int. Cl.
| | | |
|---|---|---|
| *C07K 16/46* | (2006.01) | |
| *C07K 16/24* | (2006.01) | |
| *C07K 16/28* | (2006.01) | |
| *C07K 16/30* | (2006.01) | |
| *C07K 16/32* | (2006.01) | |

(52) U.S. Cl.
CPC ........... *C07K 16/468* (2013.01); *C07K 16/248* (2013.01); *C07K 16/2863* (2013.01); *C07K 16/30* (2013.01); *C07K 16/32* (2013.01); *C07K 2317/31* (2013.01); *C07K 2317/526* (2013.01); *C07K 2317/732* (2013.01); *C07K 2317/92* (2013.01); *C07K 2317/94* (2013.01)

(58) Field of Classification Search
CPC .......................... C07K 16/468; C07K 2317/31
USPC .................. 424/133.1, 136.1; 530/387.3
See application file for complete search history.

(56) References Cited

U.S. PATENT DOCUMENTS

| | | |
|---|---|---|
| 2008/0269466 A1 | 10/2008 | Humphreys |
| 2010/0226925 A1 | 9/2010 | Dillon et al. |
| 2010/0256340 A1 | 10/2010 | Brinkmann |
| 2010/0331527 A1 | 12/2010 | Davis |
| 2012/0009621 A1 | 1/2012 | Yamasaki |

FOREIGN PATENT DOCUMENTS

| | | | |
|---|---|---|---|
| WO | WO2011090754 A1 | | 7/2011 |
| WO | WO2011/069104 A2 | | 9/2011 |
| WO | WO2011/117653 A1 | | 9/2011 |
| WO | WO2011/118739 A1 | | 9/2011 |
| WO | WO 2011117653 | * | 9/2011 |

OTHER PUBLICATIONS

Mazor et al. (MAbs 7(2):377-89 (2015); abstract only).*
Muller et al. FEBS 422:259-264 (1998).*
Leong et al., "A standardized conversion of IgG antibody to bispecific form with inversely altered affinities for Fc-receptors II and III", Molecular Immunology, Pergamon, GB, vol. 48, No. 5, (Nov. 23, 2010), pp. 760-768, XP02815, ISSN 0161-5890, DOI: 10.1016/J. Molimm.2010.11.019 [retrieved on Dec. 13, 2010] abstract, p. 763, c. I , par. 1 , fig. 1 [Y] 8-9.
Muller et al, "The first constant domain (CH1 and CL) of an antibody used as heterodimerization domain for bispecific miniantibodies", FEBS, vol. 422, pg. 259-264 (1998).
PCT/US2012/070310 International Search Report dated Jun. 5, 2013.
PCT/US2012/070310 International Preliminary Report on Patentability dated Jul. 31, 2013.
EP12860127.5 Supplementary European Search Report dated Oct. 12, 2015.

* cited by examiner

*Primary Examiner* — Lynn Bristol

(57) ABSTRACT

The technology relates in part to engineered antibodies. In particular, multispecific engineered antibodies. Such antibodies can be utilized for diagnostic and therapeutic applications in some aspects.

11 Claims, 52 Drawing Sheets

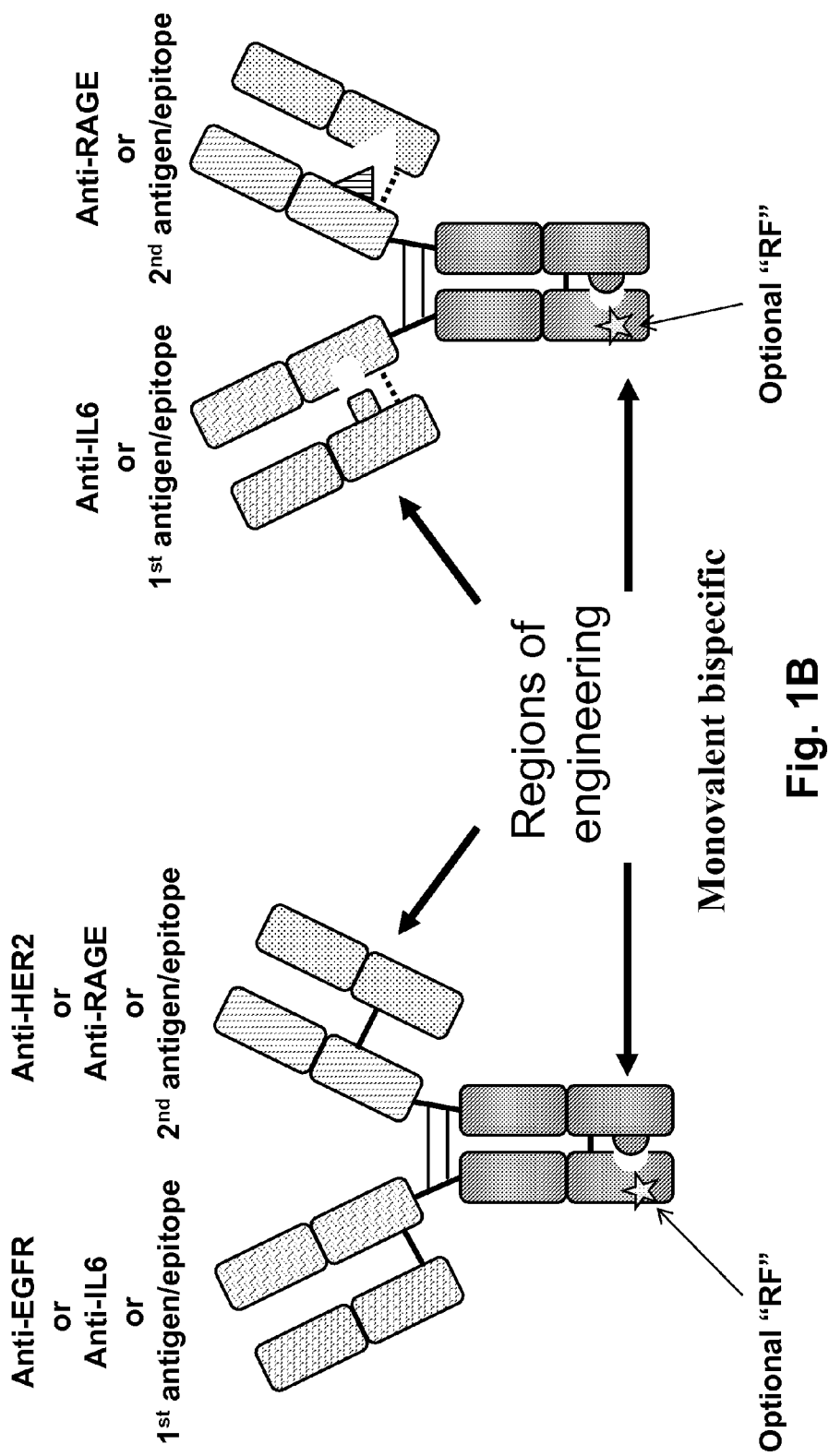

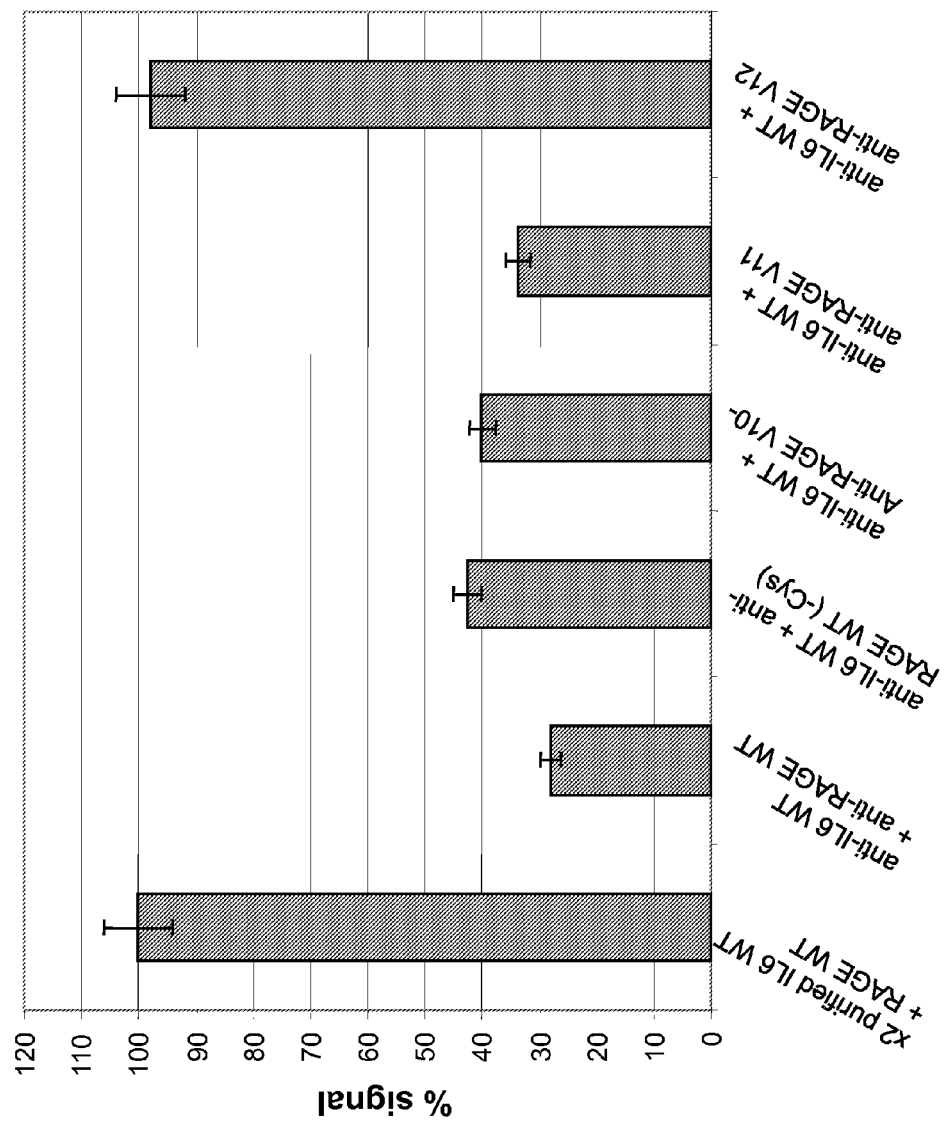

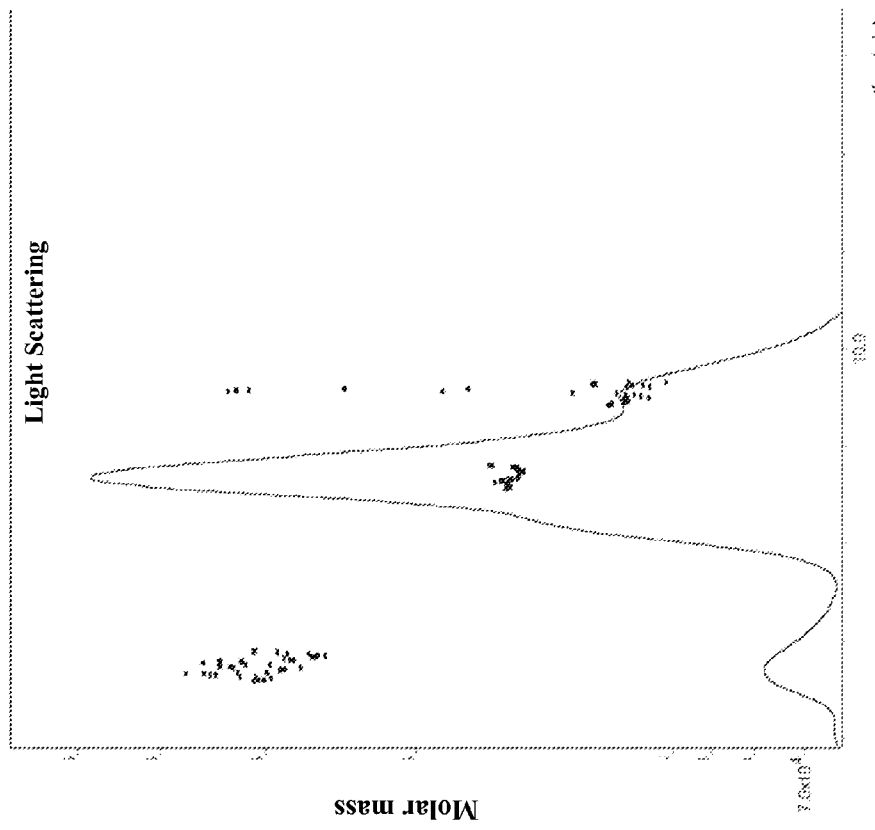
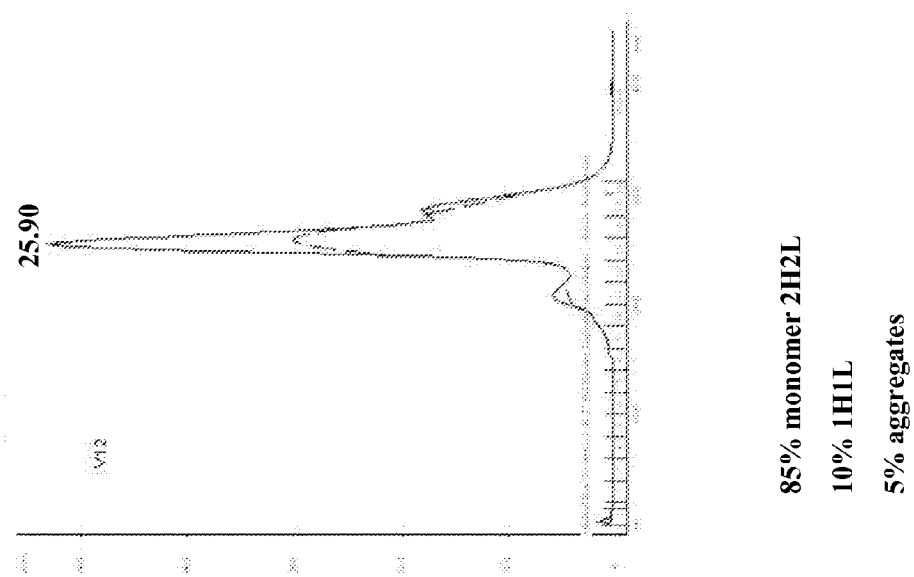
85% monomer 2H2L
10% 1H1L
5% aggregates
Fig. 6B

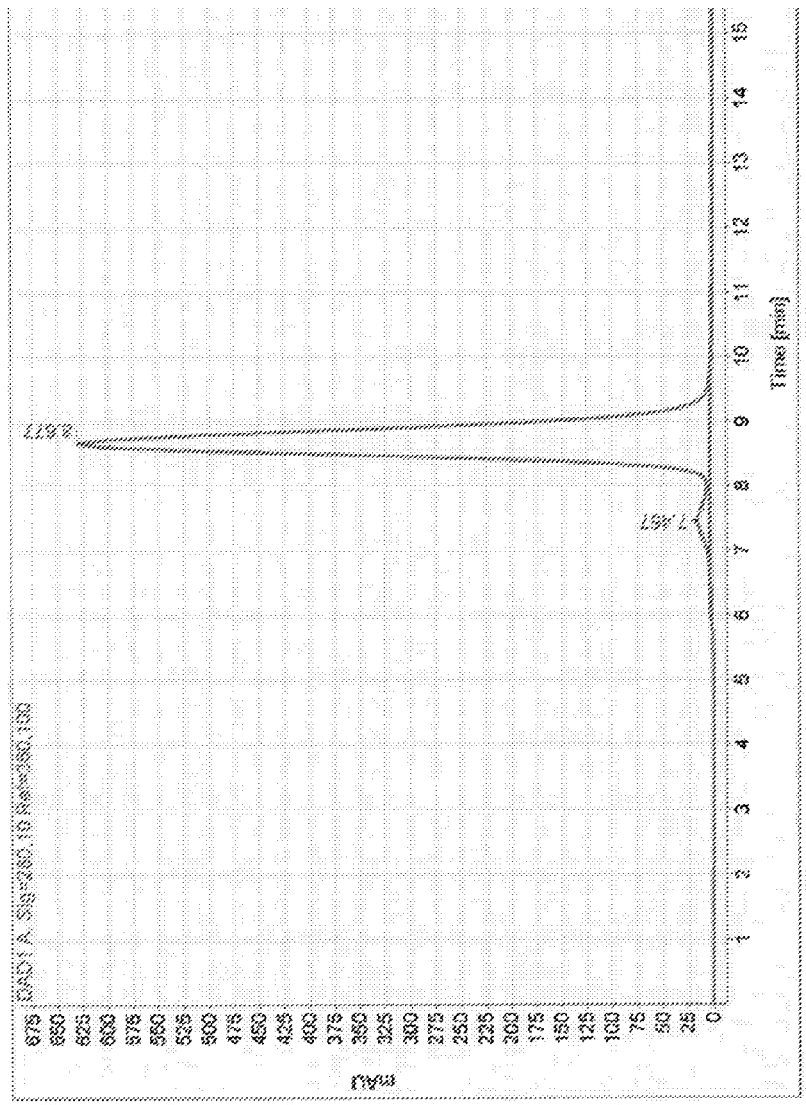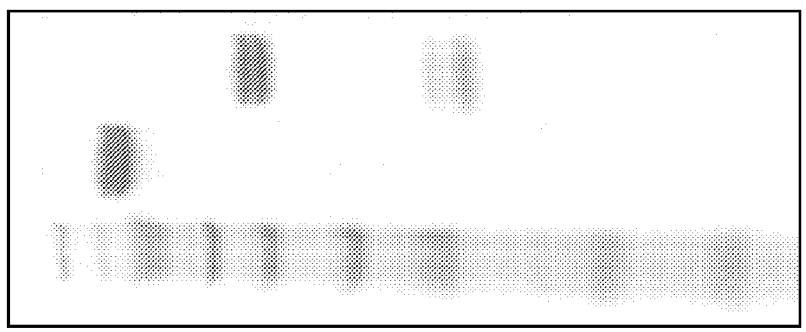
Fig. 7A

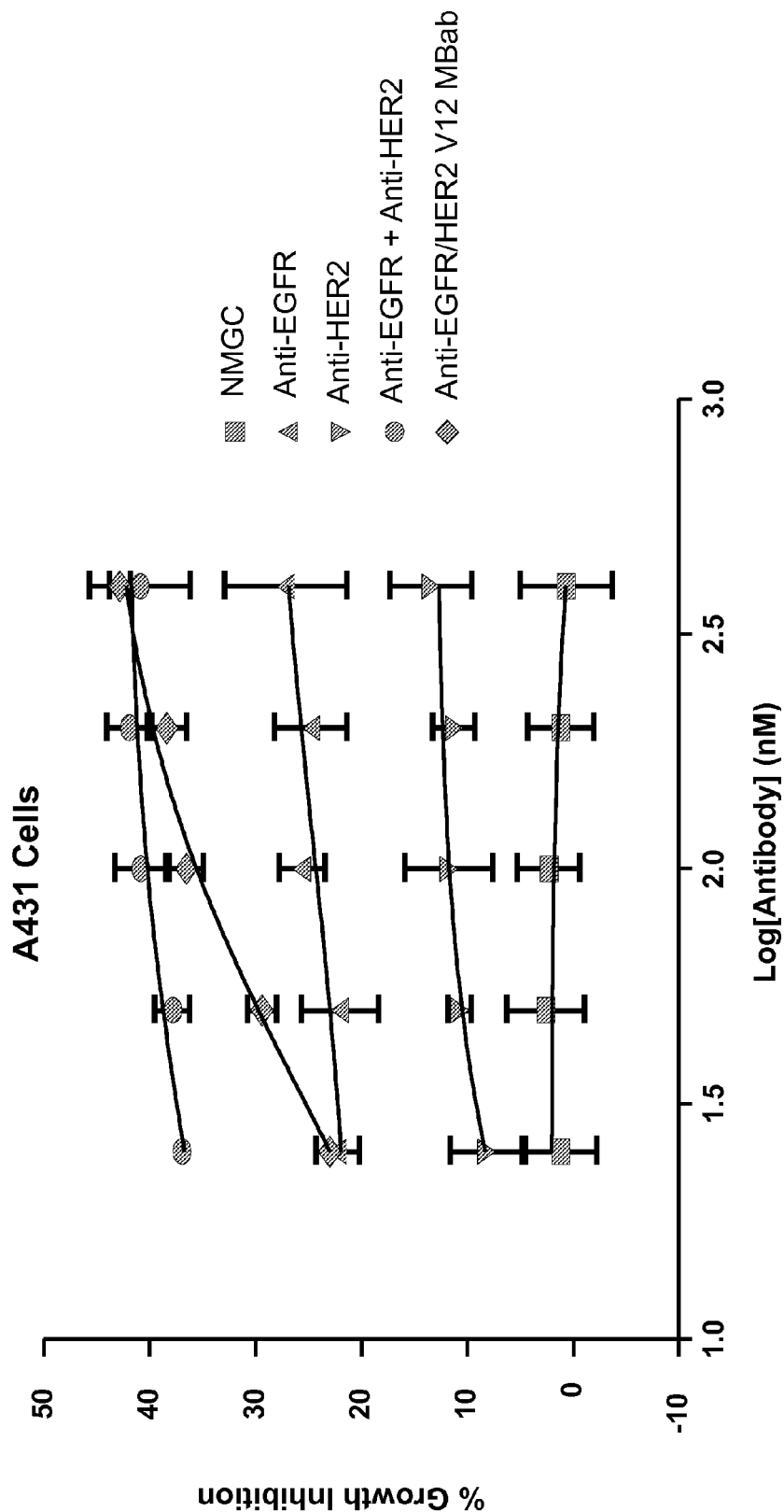

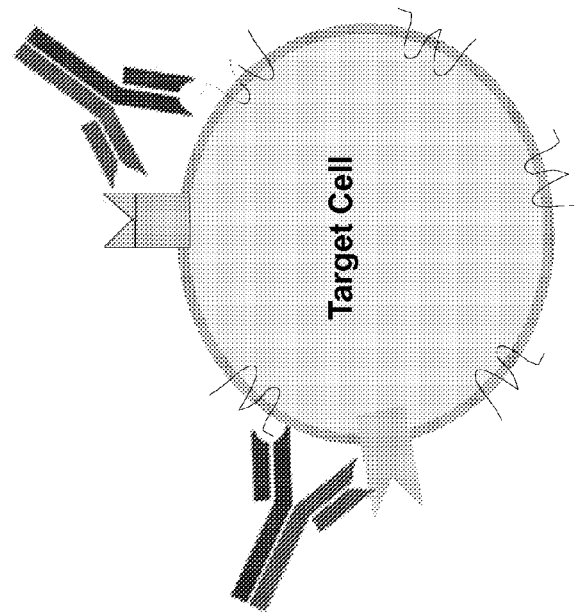
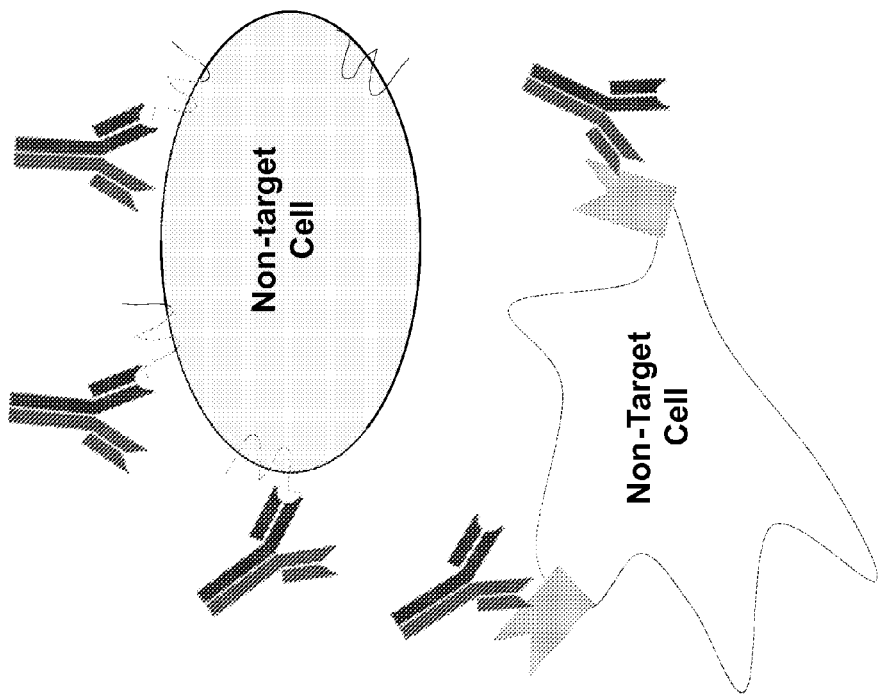
Fig. 19

| Region | FR1 | | | | | | | | | | | | | | | | | | | | | |
|---|---|---|---|---|---|---|---|---|---|---|---|---|---|---|---|---|---|---|---|---|---|---|
| Kabat | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| anti CD52 | D | I | Q | M | T | Q | S | P | S | S | L | S | A | S | V | G | D | R | V | T | I | T |
| anti-Her2 | D | I | Q | M | T | Q | S | P | S | S | L | S | A | S | V | G | D | R | V | T | I | T |
| anti-VEGF | D | I | Q | M | T | Q | S | P | S | S | L | S | A | S | V | G | D | R | V | T | I | T |
| anti-EGFR | D | I | L | L | T | Q | S | P | V | I | L | S | V | S | P | G | E | R | V | S | F | S |

| Region | CDR1 | | | | | | | | | | | | FW2 | | | | | | | | | |
|---|---|---|---|---|---|---|---|---|---|---|---|---|---|---|---|---|---|---|---|---|---|---|
| Kabat | 23 | 24 | 25 | 26 | 27 | 27‡ | 28 | 29 | 30 | 31 | 32 | 33 | 34 | 35 | 36 | 37 | 38 | 39 | 40 | 41 | 42 | 43 | 44 |
| anti CD52 | C | K | A | S | Q | | N | I | D | K | Y | L | N | W | Y | Q | Q | K | P | G | K | A | P |
| anti-Her2 | C | R | A | S | Q | | D | V | N | T | A | V | A | W | Y | Q | Q | K | P | G | K | A | P |
| anti-VEGF | C | S | A | S | Q | | D | I | S | N | Y | L | N | W | Y | Q | Q | K | P | G | K | A | P |
| anti-EGFR | C | R | A | S | Q | | S | I | G | T | N | I | H | W | Y | Q | Q | R | T | N | G | S | P |

| Region | | | | | CDR2 | | | | | | | | | | FW3 | | | | | | | |
|---|---|---|---|---|---|---|---|---|---|---|---|---|---|---|---|---|---|---|---|---|---|---|---|
| Kabat | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
| anti CD52 | K | L | L | I | Y | N | T | N | N | L | Q | T | G | V | P | S | R | F | S | G | S | G |
| anti-Her2 | K | L | L | I | Y | S | A | S | F | L | Y | S | G | V | P | S | R | F | S | G | S | G |
| anti-VEGF | K | V | L | I | Y | F | T | S | S | L | H | S | G | V | P | S | R | F | S | G | S | G |
| anti-EGFR | R | L | L | I | K | Y | A | S | E | S | I | S | G | I | P | S | R | F | S | G | S | G |

Fig. 21A

| Region | | | | | | | | | | | | | | | | | | | | | | | |
|---|---|---|---|---|---|---|---|---|---|---|---|---|---|---|---|---|---|---|---|---|---|---|---|
| Kabat | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| anti CD52 | S | G | T | D | F | T | F | T | I | S | S | L | Q | P | E | D | I | A | T | Y | Y | C |
| anti-Her2 | S | G | T | D | F | T | L | T | I | S | S | L | Q | P | E | D | F | A | T | Y | Y | C |
| anti-VEGF | S | G | T | D | F | T | L | T | I | S | S | L | Q | P | E | D | F | A | T | Y | Y | C |
| anti-EGFR | S | G | T | D | F | T | F | T | I | N | S | V | E | S | E | D | I | A | D | Y | Y | C |

| Region | CDR3 | | | | | | | | | | FW4 | | | | | | | | | |
|---|---|---|---|---|---|---|---|---|---|---|---|---|---|---|---|---|---|---|---|---|
| Kabat | 89 | 90 | 91 | 92 | 93 | 94 | 95‡ | 96 | 97 | | 98 | 99 | 100 | 101 | 102 | 103 | 104 | 105 | 106 | 107 |
| anti CD52 | L | Q | H | I | S | R | P | R | T | | F | G | Q | G | T | K | V | E | I | K |
| anti-Her2 | Q | Q | H | Y | T | T | P | P | T | | F | G | Q | G | T | K | V | E | I | K |
| anti-VEGF | Q | Q | Y | S | T | V | P | W | T | | F | G | Q | G | T | K | V | E | I | K |
| anti-EGFR | Q | Q | N | N | N | W | P | T | T | | F | G | A | G | T | K | L | E | L | K | anti-CD52 see for example US 7923538
anti-Her2 see or example US 6719971
anti-VEGF see for example US7117096
anti-EGFR see for example US 7060808

‡ May include additional CDR residues 27a, 27b, 27c, etc.
† May include additional CDR residues 95a, 95b, 95c, etc.

| EU | 108 | 109 | 110 | 111 | 112 | 113 | 114 | 115 | 116 | 117 | 118 | 119 | 120 | 121 | 122 | 123 | 124 | 125 | 126 | 127 | 128 | 129 |
|---|---|---|---|---|---|---|---|---|---|---|---|---|---|---|---|---|---|---|---|---|---|---|
| Ck | R | T | V | A | A | P | S | V | F | I | F | P | S | D | E | Q | L | K | S | G | T |
| CA | Q | P | K | A* | P | | V | T | L | F | P | S | S | E | E | L | Q | A | N | K |

| EU | 130 | 131 | 132 | 133 | 134 | 135 | 136 | 137 | 138 | 139 | 140 | 141 | 142 | 143 | 144 | 145 | 146 | 147 | 148 | 149 | 150 | 151 |
|---|---|---|---|---|---|---|---|---|---|---|---|---|---|---|---|---|---|---|---|---|---|---|
| Ck | A | S | V | C | L | N | F | Y | P | R | E | A | K | V | Q | W | K | V | D |
| CA | A | T | L | V | C | L | I | S | D | F | Y | P | G | A | V | T | V | A | W | K | A | D |

| EU | | 152 | 153 | 154 | 155 | 156 | 157 | 158 | 159 | 160 | 161 | 162 | 163 | 164 | 165 | 166 | 167 | 168 | 169 | 170 | 171 | 172 |
|---|---|---|---|---|---|---|---|---|---|---|---|---|---|---|---|---|---|---|---|---|---|---|
| Ck | | N | A* | L | Q | S | G | N | S | Q | E | S | V | T | E | Q | D | S | K | D | S | T |
| CA | | S* | S | P | V | K | A | G | - | V | E | T | T | T | P | S | K | Q | N | N | S | K |

| EU | 173 | 174 | 175 | 176 | 177 | 178 | 179 | 180 | 181 | 182 | 183 | 184 | 185 | 186 | 187 | 188 | 189 | 190 | 191 | 192 | 193 | 194 |
|---|---|---|---|---|---|---|---|---|---|---|---|---|---|---|---|---|---|---|---|---|---|---|
| Ck | Y | S | L | S | S | T | L | T | L | S | K | A | D | Y | E | K | H | K | V* | Y | A | C |
| CA | Y | A | S | S | Y | L | S | L | T | P | E | Q | W | K | S | H | R* | S | Y | S | C |

| EU | 195 | 196 | 197 | 198 | 199 | 200 | 201 | 202 | 203 | 204 | 205 | 206 | 207 | 208 | 209 | 210 | 211 | 212 | 213 | 214 |
|---|---|---|---|---|---|---|---|---|---|---|---|---|---|---|---|---|---|---|---|---|
| Ck | E | V | T | H | Q | G | L | S | S | P | V | T | K | S | F | N | R | G | E | C |
| CA | Q | V | T | H | E | G | | | S | T | V | E | K | T | V | A | P | T | E | C |

*site of known allelic variation

| Region | FW1 | | | | | | | | | | | | | | | | | | | | |
|---|---|---|---|---|---|---|---|---|---|---|---|---|---|---|---|---|---|---|---|---|---|
| Kabat | 1 | 2 | 3 | 4 | 5 | 6 | 7 | 8 | 9 | 10 | 11 | 12 | 13 | 14 | 15 | 16 | 17 | 18 | 19 | 20 | 21 |
| anti CD52 | Q | V | Q | L | Q | E | S | G | P | G | L | V | R | P | S | Q | T | L | S | L | T |
| anti-Her2 | E | V | Q | L | V | E | S | G | G | G | L | V | Q | P | G | G | S | L | R | L | S |
| anti-VEGF | E | V | Q | L | V | E | S | G | G | G | L | V | Q | P | G | G | S | L | R | L | S |
| anti-EGFR | Q | V | Q | L | K | Q | S | G | P | G | L | V | Q | P | S | Q | S | L | S | I | T |

| Region | | | | | | | | | | CDR1 | | | | | FW2 | | | | | | |
|---|---|---|---|---|---|---|---|---|---|---|---|---|---|---|---|---|---|---|---|---|---|
| Kabat | 22 | 23 | 24 | 25 | 26 | 27 | 28 | 29 | 30 | 31 | 32 | 33 | 34 | 35 ‡ | 36 | 37 | 38 | 39 | 40 | 41 | 42 |
| anti CD52 | C | T | V | S | G | F | T | F | T | D | F | Y | M | N | W | V | R | Q | P | P | G |
| anti-Her2 | C | A | A | S | G | F | N | I | K | D | T | Y | I | H | W | V | R | Q | A | P | G |
| anti-VEGF | C | A | A | S | G | Y | T | F | T | N | Y | G | M | N | W | V | R | Q | A | P | G |
| anti-EGFR | C | T | V | S | G | F | S | L | T | N | Y | G | V | H | W | V | R | Q | S | P | G |

| Region | | | | | | | | CDR2 | | | | | | | | | | | | |
|---|---|---|---|---|---|---|---|---|---|---|---|---|---|---|---|---|---|---|---|---|
| Kabat | 43 | 44 | 45 | 46 | 47 | 48 | 49 | 50 | 51 | 52 | 52a | 52b | 52c | 53 | 54 | 55 | 56 | 57 | 58 | 59 | 60 |
| anti CD52 | R | G | L | E | W | I | G | F | I | R | D | K | A | K | G | Y | T | T | E | Y | N |
| anti-Her2 | K | G | L | E | W | V | A | R | I | Y | P | T | - | T | N | G | Y | T | R | Y | A |
| anti-VEGF | K | G | L | E | W | V | G | W | I | N | T | Y | - | Y | G | E | P | T | Y | A |
| anti-EGFR | K | G | L | E | W | L | G | V | I | W | S | G | - | S | G | N | T | D | Y | N |

| Region | FW3 | | | | | | | | | | | | | | | | | | | | |
|---|---|---|---|---|---|---|---|---|---|---|---|---|---|---|---|---|---|---|---|---|---|
| Kabat | 61 | 62 | 63 | 64 | 65 | 66 | 67 | 68 | 69 | 70 | 71 | 72 | 73 | 74 | 75 | 76 | 77 | 78 | 79 | 80 | 81 |
| anti CD52 | P | S | V | K | G | R | V | T | M | L | V | D | T | S | K | N | Q | F | S | L | R |
| anti-Her2 | D | S | V | K | G | R | F | T | I | S | A | D | T | S | K | N | T | A | Y | L | Q |
| anti-VEGF | A | D | F | K | R | R | F | T | F | S | L | D | T | S | K | S | T | A | Y | L | Q |
| anti-EGFR | T | P | F | T | S | R | L | S | I | N | K | D | N | S | K | S | Q | V | F | F | K |

Fig. 23A

| Region | | | | | | | | | | | | | | | | | | | CDR3 | | | | |
|---|---|---|---|---|---|---|---|---|---|---|---|---|---|---|---|---|---|---|---|---|---|---|---|
| Kabat | 82 | 82a | 82b | 82c | 83 | 84 | 85 | 86 | 87 | 88 | 89 | 90 | 91 | 92 | 93 | 94 | 95 | 96 | 97 | 98 | 99 |
| anti-CD52 | L | S | S | V | T | A | A | D | T | A | V | Y | Y | C | A | R | E | G | H | T | A |
| anti-Her2 | M | N | S | L | R | A | E | D | T | A | V | Y | Y | C | S | R | W | G | G | D | G |
| anti-VEGF | M | N | S | L | R | A | E | D | T | A | V | Y | Y | C | A | K | Y | P | H | Y | Y |
| anti-EGFR | M | N | S | L | Q | S | N | D | T | A | I | Y | Y | C | A | R | A | L | T | Y | Y |

| Region | | | | | | | | FW4 | | | | | | | | | |
|---|---|---|---|---|---|---|---|---|---|---|---|---|---|---|---|---|---|
| Kabat | 100 | 100a | 100b | 100c | 100d | 100e | 100f | 101 | 102 | 103 | 104 | 105 | 106 | 107 | 108 | 109 | 110 | 111 | 112 | 113 |
| anti-CD52 | A | P | F | - | - | - | - | D | Y | W | G | Q | G | S | L | V | T | V | S | S |
| anti-Her2 | F | Y | A | M | - | - | - | D | Y | W | G | Q | G | T | L | V | T | V | S | S |
| anti-VEGF | G | S | H | W | Y | F | - | D | V | W | G | Q | G | T | L | V | T | V | S | S |
| anti-EGFR | D | Y | E | F | - | - | - | A | Y | W | G | Q | G | T | L | V | T | V | S | A | anti-CD52   see for example US 7923538
anti-Her2 see or example US 6719971
anti-VEGF see for example US7117096
anti-EGFR  see for example US 7060808

‡ May include additional CDR residues 35a, 35b, 35c, etc.

Fig. 23B

| EU | 118 | 119 | 120 | 121 | 122 | 123 | 124 | 125 | 126 | 127 | 128 | 129 | 130 | 131 | 132 | 133 | 134 | 135 | 136 | 137 |
|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G |
| IgG2 | A | S | T | K | G | P | S | V | F | P | L | A | P | C | S | R | S | T | S | E |
| IgG3 | A | S | T | K | G | P | S | V | F | P | L | A | P | C | S | R | S | T | S | G |
| IgG4 | A | S | T | K | G | P | S | V | F | P | L | A | P | C | S | R | S | T | S | E |

| EU | 138 | 139 | 140 | 141 | 142 | 143 | 144 | 145 | 146 | 147 | 148 | 149 | 150 | 151 | 152 | 153 | 154 | 155 | 156 | 157 |
|---|---|---|---|---|---|---|---|---|---|---|---|---|---|---|---|---|---|---|---|---|
| IgG1 | G | T | A | A | L | G | C | L | V | K | D | Y | F | P | E | P | V | T | V | S |
| IgG2 | S | T | A | A | L | G | C | L | V | K | D | Y | F | P | E | P | V | T | V | S |
| IgG3 | G | T | A | A | L | G | C | L | V | K | D | Y | F | P | E | P | V | T | V | S |
| IgG4 | S | T | A | A | L | G | C | L | V | K | D | Y | F | P | E | P | V | T | V | S |

| EU | 158 | 159 | 160 | 161 | 162 | 163 | 164 | 165 | 166 | 167 | 168 | 169 | 170 | 171 | 172 | 173 | 174 | 175 | 176 | 177 |
|---|---|---|---|---|---|---|---|---|---|---|---|---|---|---|---|---|---|---|---|---|
| IgG1 | W | N | S | G | A | L | T | S | G | V | H | T | F | P | A | V | L | Q | S | S |
| IgG2 | W | N | S | G | A | L | T | S | G | V | H | T | F | P | A | V | L | Q | S | S |
| IgG3 | W | N | S | G | A | L | T | S | G | V | H | T | F | P | A | V | L | Q | S* | S |
| IgG4 | W | N | S | G | A | L | T | S | G | V | H | T | F | P | A | V | L | Q | S | S |

| EU | 178 | 179 | 180 | 181 | 182 | 183 | 184 | 185 | 186 | 187 | 188 | 189 | 190 | 191 | 192 | 193 | 194 | 195 | 196 | 197 |
|---|---|---|---|---|---|---|---|---|---|---|---|---|---|---|---|---|---|---|---|---|
| IgG1 | G | L | Y | S | L | S | S | V | V | T | V | P | S | S | S | L | G | T | Q | T |
| IgG2 | G | L | Y | S | L | S | S | V | V | T | V | P* | S | S | N* | F* | G | T | Q | T |
| IgG3 | G | L | Y | S | L | S | S | V | V | T | V | P | S | S | S* | L* | G | T | Q | T |
| IgG4 | G | L | Y | S | L | S | S | V | V | T | V | P | S | S | S | L | G | T | K | T |

*site of known allelic variation

Fig. 24A

| EU | 198 | 199 | 200 | 201 | 202 | 203 | 204 | 205 | 206 | 207 | 208 | 209 | 210 | 211 | 212 | 213 | 214 | 215 | 216 | 217 |
|---|---|---|---|---|---|---|---|---|---|---|---|---|---|---|---|---|---|---|---|---|
| IgG1 | Y | I | C | N | V | N | H | K | P | S | N | T | K | V | D | K | K* | V | E | P |
| IgG2 | Y | T | C | N | V | D | H | K | P | S | N | T | K | V | D | K | T | V | E | R |
| IgG3 | Y | T | C | N | V | N | H | K | P | S | N | T | K | V | D | K | R | V | E | L |
| IgG4 | Y | T | C | N | V | D | H | K | P | S | N | T | K | V | D | K | R | V | E | S |

| EU | 218 | 219 | 220 | 221 | 222 | 223 | 224 | 225 | 226 | 227 | 228 |
|---|---|---|---|---|---|---|---|---|---|---|---|
| IgG1 | K | S | C | D | K | T | H | T | C | P | P |
| IgG2 | K |   | C | C | V | E | C | P | P | C | P |
| IgG3 | K | T | P | L | G | D | T | T | H | T | C |
| IgG4 | K | Y | G |   |   |   |   |   |   | P | S |

| EU |   |   |   |   |   |   |   |   |   |   |   |
|---|---|---|---|---|---|---|---|---|---|---|---|
| IgG1 |   |   |   |   |   |   |   |   |   |   |   |
| IgG2 |   |   |   |   |   |   |   |   |   |   |   |
| IgG3 | D | T | P | P | P | C | P | R | C | P | K |
| IgG4 |   |   |   |   |   |   |   |   |   |   |   |

| EU |   |   |   |   |   |   |   |   |   |   |   |
|---|---|---|---|---|---|---|---|---|---|---|---|
| IgG1 |   |   |   |   |   |   |   |   |   |   |   |
| IgG2 |   |   |   |   |   |   |   |   |   |   |   |
| IgG3 | E | P | K | S | C | D | T | P | P | P | C |
| IgG4 |   |   |   |   |   |   |   |   |   |   |   |

| EU |   |   | 229 | 230 |
|---|---|---|---|---|
| IgG1 |   |   | C | P |
| IgG2 |   |   | C | P |
| IgG3 | C | P | R | C | P |
| IgG4 |   |   | C | P |

Fig. 24B

*site of known allelic variation

| EU | 231 | 232 | 233 | 234 | 235 | 236 | 237 | 238 | 239 | 240 | 241 | 242 | 243 | 244 | 245 | 246 | 247 | 248 | 249 | 250 | 251 | 252 |
|---|---|---|---|---|---|---|---|---|---|---|---|---|---|---|---|---|---|---|---|---|---|---|
| IgG1 | A | P | E | L | L | G | G | P | S | V | F | L | F | P | P | K | P | K | D | T | L | M |
| IgG2 | A | P | P | V | A | G | G | P | S | V | F | L | F | P | P | K | P | K | D | T | L | M |
| IgG3 | A | P | E | L | L | G | G | P | S | V | F | L | F | P | P | K | P | K | D | T | L | M |
| IgG4 | A | P | E | F | L | G | G | P | S | V | F | L | F | P | P | K | P | K | D | T | L | M |

| EU | 253 | 254 | 255 | 256 | 257 | 258 | 259 | 260 | 261 | 262 | 263 | 264 | 265 | 266 | 267 | 268 | 269 | 270 | 271 | 272 | 273 | 274 |
|---|---|---|---|---|---|---|---|---|---|---|---|---|---|---|---|---|---|---|---|---|---|---|
| IgG1 | – | S | R | T | P | E | V | T | C | V | V | V | D | V | S | H | E | D | P | E | V | K |
| IgG2 | – | S | R | T | P | E | V | T | C | V | V | V | D | V | S | H | E | D | P | E | V | Q |
| IgG3 | – | S | R | T | P | E | V | T | C | V | V | V | D | V | S | H | E | D | P | E | V | Q |
| IgG4 | – | S | R | T | P | E | V | T | C | V | V | V | D | V | S | Q | E | D | P | E | V | Q |

| EU | 275 | 276 | 277 | 278 | 279 | 280 | 281 | 282 | 283 | 284 | 285 | 286 | 287 | 288 | 289 | 290 | 291 | 292 | 293 | 294 | 295 | 296 |
|---|---|---|---|---|---|---|---|---|---|---|---|---|---|---|---|---|---|---|---|---|---|---|
| IgG1 | F | N | W | Y | V | D | G | V | E | V | H | N | A | K | T | K | P | R | E | E | Q | Y |
| IgG2 | F | N | W | Y | V | D | G | V* | E | V | H | N | A | K | T | K | P | R | E | E | Q | F |
| IgG3 | F | K | W | Y | V | D | G | V | E | V | H | N | A | K | T | K | P* | R* | E | E | Q | Y* |
| IgG4 | F | N | W | Y | V | D | G | V | E | V | H | N | A | K | T | K | P | R | E | E | Q | F |

| EU | 297 | 298 | 299 | 300 | 301 | 302 | 303 | 304 | 305 | 306 | 307 | 308 | 309 | 310 | 311 | 312 | 313 | 314 | 315 | 316 | 317 | 318 |
|---|---|---|---|---|---|---|---|---|---|---|---|---|---|---|---|---|---|---|---|---|---|---|
| IgG1 | N | S | T | Y | R | V | V | S | V | L | T | V | L | H | Q | D | W | L | N | G | K | E |
| IgG2 | N | S | T | F | R | V | V | S | V | L | T | V | V | H | Q | D | W | L | N | G | K | E |
| IgG3 | N | S | T | F | R | V | V | S | V | L | T | V | L* | H | Q | D | W | L | N | G | K | E |
| IgG4 | N | S | T | Y | R | V | V | S | V | L | T | V | L | H | Q | D | W | L | N | G | K | E |

| EU | 319 | 320 | 321 | 322 | 323 | 324 | 325 | 326 | 327 | 328 | 329 | 330 | 331 | 332 | 333 | 334 | 335 | 336 | 337 | 338 | 339 | 340 |
|---|---|---|---|---|---|---|---|---|---|---|---|---|---|---|---|---|---|---|---|---|---|---|
| IgG1 | Y | K | C | K | V | S | N | K | A | L | P | A | P | I | E | K | T | I | S | K | A | K |
| IgG2 | Y | K | C | K | V | S | N | K | G | L | P | A | P | I | E | K | T | – | S | K | T | K |
| IgG3 | Y | K | C | K | V | S | N | K | A | L | P | A | P | I | E | K | T | – | S | K | T* | K |
| IgG4 | Y | K | C | K | V | S | N | K | G | L | P | S | S | I | E | K | T | – | S | K | A | K |

Fig. 24C

*site of known allelic variation

| EU   | 341 | 342 | 343 | 344 | 345 | 346 | 347 | 348 | 349 | 350 | 351 | 352 | 353 | 354 | 355 | 356 | 357 | 358 | 359 | 360 | 361 | 362 |
|------|-----|-----|-----|-----|-----|-----|-----|-----|-----|-----|-----|-----|-----|-----|-----|-----|-----|-----|-----|-----|-----|-----|
| IgG1 | G   | Q   | P   | R   | E   | P   | Q   | V   | Y   | T   | L   | P   | P   | S   | R   | D*  | E   | L*  | T   | K   | N   | Q   |
| IgG2 | G   | Q   | P   | R   | E   | P   | Q   | V   | Y   | T   | L   | P   | P   | S   | R   | E   | E   | M   | T   | K   | N   | Q   |
| IgG3 | G   | Q   | P   | R   | E   | P   | Q   | V   | Y   | T   | L   | P   | P   | S   | R   | E   | E   | M   | T   | K   | N   | Q   |
| IgG4 | G   | Q   | P   | R   | E   | P   | Q   | V   | Y   | T   | L   | P   | P   | S   | Q   | E   | E   | M   | T   | K   | S*  | Q   |

| EU   | 363 | 364 | 365 | 366 | 367 | 368 | 369 | 370 | 371 | 372 | 373 | 374 | 375 | 376 | 377 | 378 | 379 | 380 | 381 | 382 | 383 | 384 |
|------|-----|-----|-----|-----|-----|-----|-----|-----|-----|-----|-----|-----|-----|-----|-----|-----|-----|-----|-----|-----|-----|-----|
| IgG1 | V   | S   | L   | T   | C   | L   | V   | K   | G   | F   | Y   | P   | S   | D   | I   | A   | V   | E   | W   | E   | S   | N   |
| IgG2 | V   | S   | L   | T   | C   | L   | V   | K   | G   | F   | Y   | P   | S   | D   | I   | S*  | V   | E   | W   | E   | S   | N   |
| IgG3 | V   | S   | L   | T   | C   | L   | V   | K   | G   | F   | Y   | P   | S   | D   | I   | A   | V*  | E   | W   | E   | S   | S*  |
| IgG4 | V   | S   | L   | T   | C   | L   | V   | K   | G   | F   | Y   | P   | S   | D   | I   | A   | V   | E   | W   | E   | S   | N   |

| EU   | 385 | 386 | 387 | 388 | 389 | 390 | 391 | 392 | 393 | 394 | 395 | 396 | 397 | 398 | 399 | 400 | 401 | 402 | 403 | 404 | 405 | 406 |
|------|-----|-----|-----|-----|-----|-----|-----|-----|-----|-----|-----|-----|-----|-----|-----|-----|-----|-----|-----|-----|-----|-----|
| IgG1 | G   | Q   | P   | E   | N   | N   | Y   | K   | T   | T   | P   | P   | V   | L   | D   | S   | D   | G   | S   | F   | F   | L   |
| IgG2 | G   | Q   | P   | E   | N   | N   | Y   | K   | T   | T   | P   | P   | M   | L   | D   | S   | D   | G   | S   | F   | F   | L   |
| IgG3 | G   | Q   | P   | E   | N   | N*  | Y   | N   | T   | T   | P   | P   | M*  | L   | D   | S   | D   | G   | S   | F   | F   | L   |
| IgG4 | G   | Q   | P   | E   | N   | N   | Y   | K   | T   | T   | P   | P   | V   | L   | D   | S   | D   | G   | S   | F   | F   | L   |

| EU   | 407 | 408 | 409 | 410 | 411 | 412 | 413 | 414 | 415 | 416 | 417 | 418 | 419 | 420 | 421 | 422 | 423 | 424 | 425 | 426 | 427 | 428 |
|------|-----|-----|-----|-----|-----|-----|-----|-----|-----|-----|-----|-----|-----|-----|-----|-----|-----|-----|-----|-----|-----|-----|
| IgG1 | Y   | S   | K   | L   | T   | V   | D   | K   | S   | R   | W   | Q   | Q   | G   | N   | V   | F   | S   | C   | S   | V   | M   |
| IgG2 | Y   | S   | K   | L   | T   | V   | D   | K   | S   | R   | W   | Q   | Q   | G   | N   | V   | F   | S   | C   | S   | V   | M   |
| IgG3 | Y   | S   | K*  | L   | T   | V   | D   | K   | S   | R   | W   | Q   | Q*  | G   | N   | I*  | F   | S   | C   | S   | V   | M   |
| IgG4 | Y   | S   | R*  | L   | T   | V   | D   | K   | S   | R   | W   | Q   | E   | G   | N   | V   | F   | S   | C   | S   | V   | M   |

| EU   | 429 | 430 | 431 | 432 | 433 | 434 | 435 | 436 | 437 | 438 | 439 | 440 | 441 | 442 | 443 | 444 | 445 | 446 | 447 |
|------|-----|-----|-----|-----|-----|-----|-----|-----|-----|-----|-----|-----|-----|-----|-----|-----|-----|-----|-----|
| IgG1 | H   | E   | A   | L   | H   | N   | H   | Y   | T   | Q   | K   | S   | L   | S   | L   | S   | P   | G   | K   |
| IgG2 | H   | E   | A   | L   | H   | N   | H   | Y   | T   | Q   | K   | S   | L   | S   | L   | S   | P   | G   | K   |
| IgG3 | H   | E   | A   | L   | H   | N   | R*  | F*  | T   | Q   | K   | S   | L   | S   | L   | S   | P   | G   | K   |
| IgG4 | H   | E   | A   | L   | H   | N   | H   | Y   | T   | Q   | K   | S   | L   | S   | L   | S   | L   | G   | K   |

*site of known allelic variation

Fig. 24D

SEQUENCE LISTING

<160> NUMBER OF SEQ ID NOS: 6

<210> SEQ ID NO 1
<211> LENGTH: 330
<212> TYPE: PRT
<213> ORGANISM: Homo sapiens
<220> FEATURE:
<221> NAME/KEY: MISC_FEATURE
<222> LOCATION: (97)..(97)
<223> OTHER INFORMATION: Xaa is Lys or Arg
<220> FEATURE:
<221> NAME/KEY: MISC_FEATURE
<222> LOCATION: (239)..(239)
<223> OTHER INFORMATION: Xaa is Asp or Glu
<220> FEATURE:
<221> NAME/KEY: MISC_FEATURE
<222> LOCATION: (241)..(241)
<223> OTHER INFORMATION: Xaa is Leu or Met
<220> FEATURE:
<221> NAME/KEY: MISC_FEATURE
<222> LOCATION: (314)..(314)
<223> OTHER INFORMATION: Xaa is Ala or Gly

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Xaa Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Xaa Glu
225                 230                 235                 240

Xaa Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
        290                 295                 300

Val Phe Ser Cys Ser Val Met His Glu Xaa Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens
<220> FEATURE:
<221> NAME/KEY: MISC_FEATURE
<222> LOCATION: (72)..(72)
<223> OTHER INFORMATION: Xaa is Pro or Thr
<220> FEATURE:
<221> NAME/KEY: MISC_FEATURE
<222> LOCATION: (75)..(75)
<223> OTHER INFORMATION: Xaa is Asn or Ser
<220> FEATURE:
<221> NAME/KEY: MISC_FEATURE
<222> LOCATION: (76)..(76)
<223> OTHER INFORMATION: Xaa is Phe or Leu
<220> FEATURE:
<221> NAME/KEY: MISC_FEATURE
<222> LOCATION: (161)..(161)
<223> OTHER INFORMATION: Xaa is Val or Met
<220> FEATURE:
<221> NAME/KEY: MISC_FEATURE
<222> LOCATION: (257)..(257)
<223> OTHER INFORMATION: Xaa is Ala or Ser

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Xaa Ser Ser Xaa Xaa Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Xaa Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

-continued

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Xaa Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 3
<211> LENGTH: 377
<212> TYPE: PRT
<213> ORGANISM: Homo sapiens
<220> FEATURE:
<221> NAME/KEY: MISC_FEATURE
<222> LOCATION: (59)..(59)
<223> OTHER INFORMATION: Xaa is Ser or Thr
<220> FEATURE:
<221> NAME/KEY: MISC_FEATURE
<222> LOCATION: (75)..(75)
<223> OTHER INFORMATION: Xaa is Asn or Ser
<220> FEATURE:
<221> NAME/KEY: MISC_FEATURE
<222> LOCATION: (76)..(76)
<223> OTHER INFORMATION: Xaa is Phe or Leu

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Xaa Ser Gly Leu Tyr Ser
    50                  55                  60

Leu Ser Ser Val Val Thr Val Pro Ser Ser Xaa Xaa Gly Thr Gln Thr
65                  70                  75                  80

Tyr Thr Cys Asn Val Asn His Lys Pro Ser Asn Thr Lys Val Asp Lys
            85                  90                  95

Arg Val Glu Leu Lys Thr Pro Leu Gly Asp Thr Thr His Thr Cys Pro
        100                 105                 110

Arg Cys Pro Glu Pro Lys Ser Cys Asp Thr Pro Pro Pro Cys Pro Arg
    115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
        180                 185                 190

Val Val Asp Val Ser His Glu Asp Pro Glu Val Gln Phe Lys Trp Tyr

```
                195                 200                 205
Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 4
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 107
<212> TYPE: PRT
<213> ORGANISM: Homo sapiens
<220> FEATURE:
<221> NAME/KEY: MISC_FEATURE
<222> LOCATION: (46)..(46)
<223> OTHER INFORMATION: Xaa is Ala or Val
<220> FEATURE:
<221> NAME/KEY: MISC_FEATURE
<222> LOCATION: (84)..(84)
<223> OTHER INFORMATION: Xaa is Val or Leu

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Xaa Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Xaa Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 6
<211> LENGTH: 104
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Ala or Asn
<220> FEATURE:
<221> NAME/KEY: MISC_FEATURE
<222> LOCATION: (7)..(7)
<223> OTHER INFORMATION: Xaa is Ser or Thr
<220> FEATURE:
<221> NAME/KEY: MISC_FEATURE
```

```
<222> LOCATION: (45)..(45)
<223> OTHER INFORMATION: Xaa is Ser of Gly
<220> FEATURE:
<221> NAME/KEY: MISC_FEATURE
<222> LOCATION: (55)..(55)
<223> OTHER INFORMATION: Xaa is Thr or Lys
<220> FEATURE:
<221> NAME/KEY: MISC_FEATURE
<222> LOCATION: (82)..(82)
<223> OTHER INFORMATION: Xaa is Arg or Lys

<400> SEQUENCE: 6

Gln Pro Lys Ala Xaa Pro Xaa Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Xaa Ser Pro Val
            35                  40                  45

Lys Ala Gly Val Glu Thr Xaa Thr Pro Ser Lys Gln Ser Asn Asn Lys
50                      55                  60

Tyr Ala Ala Ser Ser Tyr Leu Ser Leu Thr Pro Glu Gln Trp Lys Ser
65                  70                  75                  80

His Xaa Ser Tyr Ser Cys Gln Val Thr His Glu Gly Ser Thr Val Glu
            85                  90                  95

Lys Thr Val Ala Pro Thr Glu Cys
            100
```

MODIFIED POLYPEPTIDES FOR BISPECIFIC ANTIBODY SCAFFOLDS

CROSS-REFERENCE TO RELATED APPLICATIONS

This application is a U.S. National Stage application of International Application No. PCT/US2012/070310, filed on Dec. 18, 2012, said International Application No. PCT/US2012/070310 claims benefit under 35 U.S.C. § 119(e) of the U.S. Provisional Application No. 61/577,956, filed Dec. 20, 2011. Each of the above listed applications is incorporated by reference herein in its entirety for all purposes.

REFERENCE TO SEQUENCE LISTING SUBMITTED ELECTRONICLY

This application incorporates by reference a Sequence Listing submitted with this application as text file entitled AEMS_110WO_SL created on Dec. 17, 2012 and having a size of 15.0 kilobytes.

FIELD

The technology relates in part to engineered antibodies. Such antibodies can be utilized for diagnostic and therapeutic applications in some aspects.

BACKGROUND

Antibodies, which also are referred to as immunoglobulins (Ig) are proteins that naturally occur in blood or other bodily fluids of vertebrates. Antibodies are immune system agents that bind to and neutralize foreign objects, such as bacteria and viruses.

Naturally occurring antibodies generally include two larger heavy chains and two smaller light chains. In the case of native full-length antibodies, these chains join together to form a "Y-shaped" protein. Heavy chains and light chains include cysteine amino acids that can be joined to one another via disulphide linkages. Such disulphide linkages generally are formed between thiol side chain moieties of the free cysteine amino acids. The heavy chains are joined to one another by disulphide linkages between cysteine amino acids in each chain. Each light chain is joined to a heavy chain also by disulphide linkages between cysteine amino acids in the chains. Particular cysteine amino acids in each heavy chain and light chain sometimes are referred to as "interchain cysteines" as they generally participate in disulphide linkages between antibody chains.

Each heavy chain (HC) has at one end a variable domain (VH) followed by a number of constant domains (CH). Each light chain (LC) has a variable domain (VL) at one end and a constant domain (CL) at its other end; the constant domain of the light chain is aligned with the first constant domain (CH1) of the heavy chain, and the light chain variable domain is aligned with the variable domain of the heavy chain. In certain full-length antibodies, the variable domains are located at the ends of each arm of the "Y-shaped" protein. The variable domains within a native antibody typically have the same polypeptide sequence for each variable heavy chain component and the same polypeptide sequence for each variable light chain component, and, when fully assembled, each arm can each bind to the same antigen species. In some cases, an antibody can be engineered such that it has variable domains with different polypeptide sequences and different antigen and/or epitope specificities. Such molecules are often referred to as "bispecific" antibodies and can be useful for diagnostic or therapeutic applications.

SUMMARY

Provided herein are antibodies comprising a modified heavy chain, where the modified heavy chain comprises (i) a substitution of a native cysteine to a non-cysteine amino acid, and (ii) a substitution of a native non-cysteine amino acid to a cysteine amino acid; and a modified light chain, where the modified light chain comprises (i) a substitution of a native cysteine to a non-cysteine amino acid, and (ii) a substitution of a native non-cysteine amino acid to a cysteine amino acid. In certain aspects substituted cysteine of the heavy chain and the substituted cysteine of the light chain can form a disulphide bond. In certain aspects the antibodies further comprise a second heavy chain and second light chain, wherein the second heavy and light chains do not comprise a substitution of a native cysteine to a non-cysteine amino acid. In still other aspects, the first and/or the second heavy chains comprise a modification in the Fc region. In some aspects, the Fc region of both the first and the second heavy chains comprise different modifications that favor the interchain pairing of the first heavy chain with the second heavy chain.

Provided herein are antibodies comprising: (i) a first modified heavy chain comprising the substitution of at least one amino acid resulting in a protrusion and/or a cavity, and a first modified light chain comprising the substitution of at least one amino acid resulting in a compensatory cavity and/or protrusion; and (ii) a second modified heavy chain comprising the substitution of at least one amino acid resulting in a cavity and/or protrusion, and a second modified light chain comprising the substitution of at least one amino acid resulting in a compensatory protrusion and/or cavity, wherein the modifications favor the interchain pairing of the first heavy chain with the first light chain and the second heavy chain with the second light chain. In certain aspects the amino acid substitution(s) in the first heavy chain are different from those in the second heavy chain and the amino acid substitution(s) in the first light chain are different from those in the second light chain. In certain aspects the first heavy and light chains and/or the second heavy and light chains further comprise a substitution of a native cysteine to a non-cysteine amino acid. In still other aspects, the first and/or the second heavy chains comprise a modification in the Fc region. In some aspects, the Fc region of both the first and the second heavy chains comprise different modifications that favor the interchain pairing of the first heavy chain with the second heavy chain.

Also provided are compositions comprising any of the above antibodies and methods of using the same.

Also provided are nucleic acids encoding a modified heavy chain polypeptide, where the modified heavy chain comprises (i) a substitution of a native cysteine to a non-cysteine amino acid, and (ii) a substitution of a native non-cysteine amino acid to a cysteine amino acid; and nucleic acids encoding a modified light chain polypeptide, where the modified light chain comprises (i) a substitution of a native cysteine to a non-cysteine amino acid, and (ii) a substitution of a native non-cysteine amino acid to a cysteine amino acid. In certain aspects the substituted cysteine of the heavy chain and the substituted cysteine of the light chain can form a disulphide bond. In certain aspects the nucleic acids further encode a second heavy chain and second light chain, wherein the second heavy and light chains do not comprise a substitution of a native cysteine to a non-cysteine amino acid.

In still other aspects, the first and/or the second heavy chains comprise a modification in the Fc region. In some aspects, the Fc region of both the first and the second heavy chains comprise different modifications that favor the interchain pairing of the first heavy chain with the second heavy chain.

Also provided are nucleic acids encoding a first modified heavy chain comprising the substitution of at least one amino acid resulting in a protrusion and/or a cavity, nucleic acids encoding a first modified light chain comprising the substitution of at least one amino acid resulting in a compensatory cavity and/or protrusion; nucleic acids encoding a second modified heavy chain comprising the substitution of at least one amino acid resulting in a cavity and/or protrusion, and nucleic acids encoding a second modified light chain comprising the substitution of at least one amino acid resulting in a compensatory protrusion and/or cavity, wherein the modifications favor the interchain pairing of the first heavy chain with the first light chain and the second heavy chain with the second light chain. In certain aspects the amino acid substitution(s) in the first heavy chain are different from those in the second heavy chain and the amino acid substitution(s) in the first light chain are different from those in the second light chain. In certain aspects the first heavy and light chains and/or the second heavy and light chains further comprise a substitution of a native cysteine to a non-cysteine amino acid. In still other aspects, the first and/or the second heavy chains comprise a modification in the Fc region. In some aspects, the Fc region of both the first and the second heavy chains comprise different modifications that favor the interchain pairing of the first heavy chain with the second heavy chain.

Also provided are vectors and cells comprising any of the above nucleic acids and methods of expressing any of the above nucleic acids.

Certain aspects are described further in the following description, examples, embodiments, claims and drawings.

BRIEF DESCRIPTION OF THE DRAWINGS

The drawings illustrate aspects of the technology and are not limiting. For clarity and ease of illustration, the drawings are not made to scale and, in some instances, various aspects may be shown exaggerated or enlarged to facilitate an understanding of particular aspects.

FIGS. 3A and 3B show vectors for expression of two kappa or lambda light chains and FIG. 3C shows a vector for expression of two heavy chains. Another light chain vector expressing one lambda chain and one kappa chain could be readily generated. Using such vectors numerous combinations can be generated, including for example; Kappa WT/Kappa V12, Lambda WT/Lambda V12, Kappa WT/Lambda V12 and Lambda WT/Kappa V12. Each vector can express either two different light chains or two different heavy chains. Each chain is separately expressed using its own promoter. Each vector comprises a number of restriction sites that facilitate the rapid cloning of different variable regions. Each vector also comprises both bacterial and mammalian selection markers in addition to a bacterial origin of replication and an oriP sequence which can be useful in combination with EBNA sequences to enhance plasmid maintenance and expression in mammalian systems. Expression of the two light chains from a first vector and two the heavy chains from a second vector minimizes the production of homodimerized heavy chains and other undesired products that could result from the transformation of cells with a single vector. For example, heavy chains typically are not secreted efficiently without light chains and light chains typically can not be purified by protein A chromatography without heavy chains. Therefore any cell secreting protein A binding antibodies will be carrying both the first and the second plasmids that express the two light chains and the two heavy chains.

FIG. 6A and FIG. 6B show SEC and light scattering analysis of anti-IL6 WT/anti-RAGE variant 12 (V12) monovalent bispecific antibody (MBab) and parental antibodies. FIG. 6A shows SEC UV traces for SEC purified parental antibodies (upper left and right) and SEC purified anti-IL6 WT/anti-RAGE V12 MBab (lower middle). Each trace showed that the purified material was largely monomeric. The anti-RAGE and anti-IL6 parent antibodies had retention times of 24.61 and 26.27 minutes, respectively, while the anti-IL6 WT/anti-RAGE V12 MBab had an intermediate retention time of 25.85, which showed that the MBab exhibited a monomeric profile and displayed properties of the two parental MAbs. FIG. 6B shows a SEC UV trace for protein A purified anti-IL6 WT/anti-RAGE V12 MBab (left panel) and the corresponding light scattering trace (right panel), which showed that the protein A purified material was composed of about 85% intact IgG having 2H2L, about 10% IgG having 1H1L (Half IgG), and about 5% aggregates.

FIG. 7A-C show analysis of a MBab-RF construct comprising a lambda light chain for antigenA binding (antigenA heavy chain comprises "Hole" in addition to the "RF" substitution) and a kappa light chain for antigenB binding (antigen heavy chain comprise "Knob"). FIG. 7A shows SDS-PAGE (left) analysis, Lane 1: protein A purified MBab-RF non-reducing, Lane 2: protein A purified MBab-RF reducing and SEC UV trace (right) for protein A purified MBab-RF. FIG. 7B shows the migration profile of protein A purified parental and MBab-RF antibodies under non-reducing conditions. FIG. 7C shows the migration profile of protein A purified MBab-RF under reducing conditions, antigenA light chain (LC-A), antigenB light chain (LC-B), antigenA heavy chain (HC-A), antigenB heavy chain (HC-B), the migration times are indicated.

FIG. 8A shows SDS-PAGE (left) analysis, Lanes 1, 5: protein A purified MBab-RF, Lanes 2, 6: protein A+LambdaSelect purified MBab-RF, Lanes 3, 7: LambdaSelect flow through, Lanes 4, 8: protein A purified parent B; and SEC UV trace (right) for protein A+LambdaSelect purified MBab-RF. FIG. 8B shows the migration profile of LambdaSelect flow through under reducing conditions. FIG. 8C shows the migration profile of protein A+LambdaSelect purified MBab-RF under reducing conditions, antigenA light chain (LC-A), antigenB light chain (LC-B), antigenA heavy chain (HC-A), antigenB heavy chain (HC-B), the migration times are indicated.

FIG. 9A and FIG. 9 show bispecificity of the anti-IL6 WT/anti-RAGE variant 12 monovalent bispecific antibody (IL6/RAGE V12 MBab), as determined by Octet analysis. FIG. 9A shows full traces including an antibody capture (10 micrograms/ml) portion, baseline, and RAGE binding and IL6 binding portions.

FIG. 11A shows SDS-PAGE analysis under non-reducing conditions of EGFR/HER2V12 MBab on the right and a schematic illustration of EGFR/HER2V12 MBab on the left. The arrows indicate 2H2L (about 150 kDa)—IgG with 2 heavy chains and 2 light chains, and 1H1L (about 75 kDa)—half IgG with 1 heavy chain and 1 light chain. FIG. 11B shows SEC analysis of EGFR/HER2V12 MBab. Before SEC, protein A purified material had a SEC profile of about 90% monomer, about 10% half IgG and less than 3% aggregates (upper panel). Following preparative SEC, the monomeric EGFR/HER2V12 MBab represented greater than 99% of the sample (lower panel). FIG. 9C shows SEC UV traces for SEC purified parental antibody (upper left and right) and SEC purified anti-EGFR WT/anti-HER2V12 MBab (lower middle). All were largely monomeric. The anti-EGFR and anti-HER2 parent antibodies had retention times of 8.745 and 8.899 minutes, respectively, while the anti-EGFR WT/anti-HER2 V12 MBab had an intermediate retention time of 8.857, which showed that the MBab displayed properties intermediate of the two parents. FIG. 9D shows an overlay of the light scattering traces for the anti-EGFR WT/anti-HER2V12 MBab and the parental antibodies, which showed that the anti-EGFR WT/anti-HER2V12 MBab had the expected molecular mass of about 150 kDa for a monomeric antibody.

FIG. 12A shows full traces including an antibody capture (20 micrograms/ml) portion, baseline, and HER2 binding and EGFR binding portions. FIG. 12B shows an expansion of the baseline, HER2 and EGFR binding portions of the traces. The two parent antibodies showed a single increase in signal in response to binding their specific antigen, while the EGFR/HER2V12 MBab showed an increase in signal in response to both HER2 and EGFR, which demonstrated bispecificity and simultaneous antigen binding. NMGC, which does not bind either HER2 or EGFR, was used as a negative control antibody.

FIG. 13A shows full traces including an antibody capture on the EGFR antigen, baseline, and HER2 antigen binding portions. FIG. 13B shows full traces including an antibody capture on the HER2 antigen, baseline, and EGFR antigen binding portions. The two parent antibodies showed a single increase in signal in response to binding their specific antigen, while the EGFR/HER2V12 MBab showed an increase in signal in response to both HER2 and EGFR, which demonstrated bispecificity and simultaneous antigen binding.

FIG. 14A shows thermograms for Anti-HER2 (anti-HER2; upper left) and Anti-EGFR (anti-EGFR; lower right). The anti-HER2 thermogram displayed two transitions; the Fab was very stable and its TM overlapped with the CH3 TM at about 81° C., and the CH2 had a TM of about 69° C. The anti-EGFR thermogram displayed four transitions. FIG. 11B shows thermograms for the anti-EGFR WT/anti-HER2 variant 12 monovalent bispecific antibody (EGFR/HER2V12 MBab). Deconvolution of the EGFR/HER2V12 MBab thermogram (upper left) revealed 4 transitions; the transition at about 60° C. corresponded to the Cetuximabanti-EGFR variable domains, the transition at about 73° C. corresponded to the Cetuximabanti-EGFR CH1 and Ck domains, the transition at about 70° C. corresponded with the CH2 and CH3 (knob-into-hole) domains, the transition at about 81° C. corresponded to the engineered anti-HER2Fab in the MBab having an alternative disulfide bond. The correspondence also is shown by overlay of the thermograms (lower right).

FIG. 15A shows binding to A431 epidermal cells (left) and BxPC-3 pancreas cells (right). These cells express higher levels of EGFR, and express lower levels of HER2. FIG. 15B shows binding to SKBR-3 breast cells (left) and SK-OV-3 Ovarian cells (right). These cells express higher levels of HER2, and express lower levels of EGFR. Anti-Hu IgG Fc FITC was used as the secondary antibody for detection. NMGC, which does not bind HER2 or EGFR, was used as a negative control antibody. The levels of target expression are shown in the tables.

FIGS. 16A to 16C show cytotoxicity properties of the anti-EGFR WT/anti-HER2 variant 12 monovalent bispecific antibody (anti-EGFR/HER2V12 MBab), as determined by growth inhibition assays. Anti-EGFR/HER2V12 MBab inhibited cell growth to the same extent that a combination of parental antibodies inhibited cell growth in a number of cell types. An additive killing effect was achieved when EGFR levels were similar or higher than those of HER2, as seen for A431 and BxPC-3 cells. FIG. 16A shows growth inhibition of A431 epidermal cells (upper) and BxPC-3 pancreas cells (lower). These cells express higher levels of EGFR, and express lower levels of HER2. FIG. 16B shows growth inhibition of SK-OV-3 Ovarian cells (lower) and SKBR-3 breast cells (upper). These cells express higher levels of HER2, and express low levels of EGFR. Anti-Hu IgG Fc FITC was used as the secondary antibody for detection. NMGC, which does not bind HER2 or EGFR, was used as a negative control antibody. The levels of target expression are shown in the tables. FIG. 16C shows inhibition data for A431 cells, replotted as a line graph.

FIG. 17A shows binding of purified anti-EGFR WT/anti-HER2 variant 12 monovalent bispecific antibody (Anti-EGFR/HER2V12 MBab) and parental antibodies to FcγRIIIa (top left) and C1q (bottom right), using direct ELISA. FIG. 17B shows Antibody Dependent Cell Cytotoxicity (ADCC) studies using A431 cells. The MBab elicited specific ADCC activity to the same level as combination treatment with parental antibodies. The control antibody NMGC and parental anti-HER2 demonstrated no ADCC activity, while the parental anti-EGFR demonstrated strong ADCC activity. The -KC assays included all assay components except for Killer Cells.

FIG. 19 shows a diagram depicting an application for MBabs where homodimerization or receptor cross-linking is undesirable and/or where both antigens are selectively restricted to the target cells/tissue. The left panel shows low avidity monovalent binding of the MBab to non-target cells which is insufficient to elicit homodimerization. The right panel shows higher avidity bivalent binding of the MBab to both antigens at the same time on target cells. Bivalent binding can enhance preferential binding to target cells by binding the two targets simultaneously and may enhance receptor dimerization.

FIG. 20A shows a diagram of the biological detection assay used to demonstrate concurrent binding of a C/D-specific MBab to cells expressing cell surface antigens C and D. FIG. 20B, left panel shows the binding curves of the parental anti-C (open symbols) and anti-D (closed symbols) antibodies to cells expressing the C antigen (C-cells, triangles), the D antigen (D-cells, squares) or both C and D antigens (C/D-cells, circles). FIG. 20B, right panel shows the binding curves of the C/D-MBab to cells expressing the C antigen (C-cells, triangles), the D antigen (D-cells, squares) or both C and D antigens (C/D-cells, circles). FIG. 20C shows the binding curves of C/D-MBab binding to cells expressing the C antigen (C-cells, triangles), the D antigen (D-cells, squares) or both C and D antigens (C/D-cells, circles) followed by binding of labeled recombinant D protein (rD, left panel) or labeled recombinant C protein (rC, right panel).

FIG. 21A and FIG. 21B show the amino acid sequences and numbering for several representative light chain variable regions known in the art (anti-CD52; anti-HER2; anti-VEGF; and anti-EGFR) according the Kabat index as set forth in Kabat (Kabat et al., Sequences of Proteins of Immunological Interest, 5th Ed. Public Health Service, National Institutes of Health, Bethesda, Md. (1991)). The CDR regions are shaded and the location of possible insertions into the numbering scheme, as described below, are indicated by a dagger (†) and a double dagger (‡). See FIG. 23A and FIG. 23B for corresponding heavy chain variable regions.

FIG. 22 shows the amino acid sequences and numbering for the IgG light chain constant regions (kappa and lambda) according to the EU index as set forth in Kabat (ibid.).

Figure 1A:
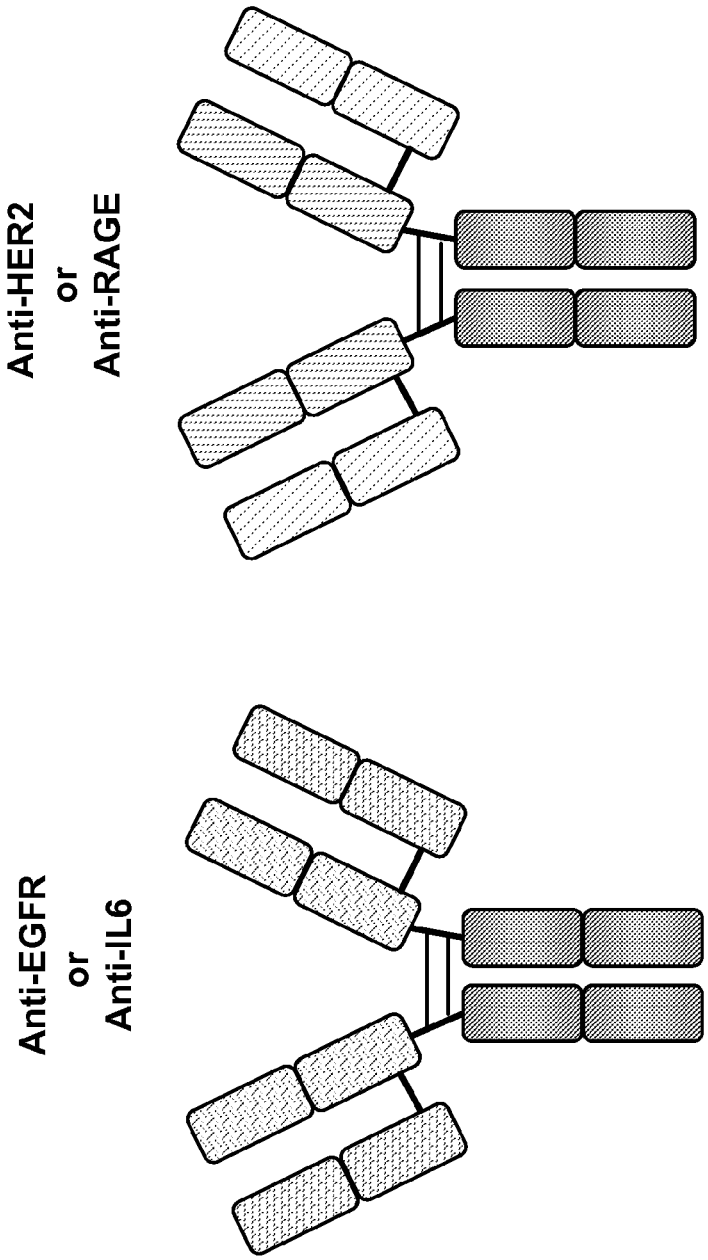
FIG. 1 shows antibody illustrations. Parental bivalent monospecific parent antibodies are illustrated in panel A. Representative monovalent bispecific antibodies (MBab) are illustrated in panel B. The star on the heavy chain comprising the "Hole" represents engineering to ablate protein A binding of the "Hole" chain. Additional MBab constructs are contemplated and described below. The MBab on the left comprises a wild type HC-LC interface on one arm and a cysteine engineered HC-LC interface on the other arm to relocate the interchain disulphide linkage. The disulphide linkage may be relocated within the CH1-CL interface as shown, or may be relocated to the VL-VH interface as described herein. The MBab on the right comprises an engineered HC-LC interface on each arm, wherein the interface regions have been engineered to promote specific HC-LC interface interactions, which may include substitution of the native cysteine residues involved in forming disulfide bonds between the CL and CH1 regions (indicated by dashed lines). Both MBabs have been engineered in the Fc region (e.g. CH3) to promote heavy chain heterodimerization. The binding specificities of the Fab regions may be directed to any desired target. The binding specificities denoted are for the antibodies utilized in the examples herein. Parent antibodies can bind one of four antigens: IL-6, RAGE, EGFR or HER2. The monovalent bispecific antibody (MBab) can bind both IL-6 and RAGE or both EGFR and HER2.

Lambda chain residues which differ from kappa are shaded and sites of known allelic variation are indicated by an asterisk (*).

FIG. 23A and FIG. 23B show the amino acid sequences and numbering for several representative heavy chain variable regions known in the art (anti-CD52; anti-HER2; anti-VEGF; and anti-EGFR) according the Kabat index as set forth in forth in Kabat (ibid). The CDR regions are shaded and the location of additional possible insertions into the numbering scheme, as described below, are indicated by a double dagger (‡). See FIG. 21A and FIG. 21B for corresponding light chain variable regions.

FIGS. 24A to 24D show the amino acid sequences and numbering for the IgG heavy chains (IgG1, IgG2, IgG3 and IgG4) according to the EU index as set forth in Kabat (ibid). FIG. 24A-B shows the amino acid sequences and numbering for the CH1 and hinge regions. FIG. 24C shows the amino acid sequences and numbering for the CH2 region. FIG. 24D shows the amino acid sequence and numbering for the CH3 region. Residues which differ from IgG are shaded and sites of known allelic variation are indicated by an asterisk (*).

DETAILED DESCRIPTION

Provided herein, as more fully discussed below, are engineered antibodies in which one or more interchain cysteines have been relocated which, in some aspects, results in the relocation of an interchain disulphide linkage at the HC-LC interface. In some aspects, this involves modification of one heavy chain and the corresponding light chain within an antibody whereby a native cysteine is substituted by a non-cysteine amino acid, and a native non-cysteine amino acid is substituted by a cysteine amino acid. In some aspects, the antibodies provided herein are bispecific which means they contain variable domains with different antigen and/or epitope specificities. In certain aspects, the modified heavy and light chain duplex for a given antibody contains a variable domain with a certain antigen specificity and the unmodified heavy and light chain duplex within the same antibody contains a variable domain with a different antigen specificity. Methods are known for generating bispecific antibodies. Such methods, however, are often limited by a multitude of possible antibody formations which can include several combinations of incorrect pairings of heavy and light chains. Such mispairings can decrease production efficiency. Other methods require the use of a common light chain, which can impact affinity of one or both variable domains or rely on the use of scFvs which similarly can impact affinity and further are less stable and potentially immunogenic structures. Other methods require the removal of all disulfide bonds and the introduction of numerous mutations in both the heavy and light chains to alter the electrostatic interaction of the chains, which may reduce the stability and increase the immunogenicity of the resulting molecule. The modified heavy chains and modified light chains provided herein overcome these limitations by preferentially hybridizing with each other generating the preferred bispecific monovalent antibody assembly. The BMabs provided herein are readily produced, stable and likely to be non-immunogenic or less immunogenic because of the limited number of mutations involved.

Terminology

Methods provided herein often are not limited to specific compositions or process steps, as such may vary. Also, as used herein, the singular form "a", "an" and "the" include plural referents unless the context clearly dictates otherwise.

The terms "a" (or "an"), as well as the terms "one or more," and "at least one" can be used interchangeably herein.

The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%).

Furthermore, "and/or" where used herein is intended as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood in the art to which this technology is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide a general dictionary of many of the terms used herein.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the technology herein, which can be had by reference to the specification as a whole. Accordingly, the terms defined immediately below are more fully defined by reference to the specification in its entirety.

It is understood that wherever aspects or embodiments are described herein with the language "comprising," otherwise analogous aspects or embodiments described in terms of "consisting of" and/or "consisting essentially of" are also provided.

Amino acids often are referred to herein by commonly known three letter symbols or by the one-letter symbols recommended by the IUPAC-IUB Biochemical Nomenclature Commission. Nucleotides, likewise, often are referred to by commonly accepted single-letter codes.

The term "antibody" means an immunoglobulin molecule that recognizes and specifically binds to a target, such as a protein, polypeptide, peptide, carbohydrate, polynucleotide, lipid, other haptens, or combinations of the foregoing through at least one antigen recognition site within the variable region of the immunoglobulin molecule. As used herein, the terms "antibody" and "antibodies", also known as immunoglobulins, encompass monoclonal antibodies (including full-length monoclonal antibodies), polyclonal antibodies, multispecific antibodies comprising at least two different epitope binding domains (e.g., bispecific antibodies), human antibodies, humanized antibodies, camelised antibodies, chimeric antibodies, fusion proteins comprising an antigen determination portion of an antibody, and any other modified immunoglobulin molecule comprising an antigen recognition site so long as the antibodies exhibit the desired biological activity. In particular, antibodies include immunoglobulin molecules and immunologically active fragments of immunoglobulin molecules, i.e., molecules that contain at least one antigen-binding site. Immunoglobulin molecules can be of any isotype/class (e.g., IgG, IgE, IgM, IgD, IgA and IgY), subisotype/subclass (e.g., IgG1, IgG2, IgG3, IgG4, IgA1 and IgA2) or allotype (e.g., Gm, e.g., G1m (f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, and the like, or other animals such as birds (e.g. chickens). Antibodies can be naked or conjugated to other molecules such as toxins, radioisotopes, etc.

A "variable region" of an antibody refers to the variable region of the antibody light chain or the variable region of the antibody heavy chain, either alone or in combination. The variable regions of the heavy and light chain each consist of four framework regions (FW) connected by three complementarity determining regions (CDRs) also known as hypervariable regions. The CDRs in each chain are held together in close proximity by the FW regions and, with the CDRs from the other chain, contribute to the formation of the antigen-binding site of antibodies. The numbering of amino acids in the variable domain, complementarity determining region (CDRs) and framework regions (FR), of an antibody follow, unless otherwise indicated, the Kabat definition (also referred to herein as the "Kabat Index" or "Kabat numbering") as set forth in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include an amino acid insertion (residue 52a according to Kabat) after residue 52 of H2 and inserted residues (e.g. residues 82a, 82b, and 82c, etc according to Kabat) after heavy chain FR residue 82.

The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, as used for the Fv region. In addition, the identity of certain individual residues at any given Kabat site number may vary from antibody chain to antibody chain due to interspecies or allelic divergence. As used throughout the specification the VL and VH CDR sequences described correspond to the classical Kabat numbering locations as provided in Table 1, with the intervening framework regions being numbered accordingly. FIGS. 15A, 15B, 17A and 17B provide the Kabat numbering of variable regions (Frameworks and CDRs) from several representative antibodies.

TABLE 1

| CDR | L1 | L2 | L3 | H1 | H2 | H3 |
|---|---|---|---|---|---|---|
| Kabat Location | L24-L34 | L50-L56 | L89-L97 | H31-H35 | H50-H65 | H95-H102 |

As used herein, the Fc region (also referred to herein simply as "Fc") includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and may also include the flexible hinge N-terminal to these domains. For IgA and IgM Fc may include the J chain. For IgG, Fc comprises immunoglobulin domains Cgamma2 and Cgamma3 (Cγ2 and Cγ3) and at least a portion of the hinge between Cgamma1 (Cγ1) and Cgamma2 (Cγ2). Fc may refer to this region in isolation, or this region in the context of an antibody, antibody fragment, or Fc fusion protein. Although the boundaries of the Fc region may vary, the human IgG heavy chain Fc region is usually defined to comprise residues C226 or P230 to its carboxyl-terminus, where the numbering is according to the EU index as set forth in Kabat (Kabat et al., Sequences of Proteins of Immunological Interest, 5th Ed. Public Health Service, National Institutes of Health, Bethesda, Md. (1991)). See FIG. 22 for the numbering of the kappa and lambda light chain constant regions and FIGS. 24A-24D for the numbering of the heavy chain constant regions of IgG1, IgG2, IgG3 and IgG4, all the constant region numbering is according to the EU index as set forth in Kabat. Polymorphisms have been observed at a number of different Fc positions, including but not limited to positions 270, 272, 312, 315, 356, and 358 as numbered by the EU index, and thus slight differences between the presented sequence and sequences in the prior art may exist.

Antibodies

Antibodies are immunological proteins that bind a specific antigen. In most mammals, including humans and mice, antibodies are constructed from paired heavy and light polypeptide chains. Each chain is made up of two distinct regions, referred to as the variable (Fv) and constant (Fc) regions. The light and heavy chain Fv regions contain the antigen binding determinants of the molecule and are responsible for binding the target antigen. The Fc regions define the class (or isotype) of antibody (IgG for example) and are responsible for binding a number of natural proteins to elicit important biochemical events. Each light chain is linked to a heavy chain by one covalent disulphide bond. The two light chain-heavy chain dimers are linked via disulphide bridges between the heavy chains, forming a Y-shaped molecule. The number of disulphide linkages between the heavy chains can vary among different immunoglobulin isotypes. The region in which the arms of the Y meet the stem is called the hinge region, and exhibits some flexibility.

Each chain includes constant regions that are representative of the antibody class and variable regions specific to each antibody. The constant region determines the mechanism used to destroy antigen. Antibodies are divided into five major classes, IgM, IgG, IgA, IgD, and IgE, based on their constant region structure and immune function. The variable and constant regions of both the light and the heavy chains are structurally folded into functional units called domains. Each light chain consists of one variable domain (VL) at one end and one constant domain (CL) at its other end. Each heavy chain has at one end a variable domain (VH) followed by three or four constant domains (CH1, CH2, CH3, CH4).

The arms of the Y contain the site that bind antigen and is called the Fab (fragment, antigen binding) region. It is composed of one constant and one variable domain from each heavy and light chain of the antibody. The constant domain of the light chain is aligned with the first constant domain of the heavy chain, and the light chain variable domain is aligned with the variable domain of the heavy chain. Light chains are classified as lambda chains or kappa chains based on the amino acid sequence of the light chain constant region. The variable domain of a kappa light chain may also be denoted herein as VK.

The Fc region of an antibody interacts with a number of ligands including Fc receptors and other ligands, imparting an array of important functional capabilities referred to as effector functions. An important family of Fc receptors for the IgG class is the Fc gamma receptors (FcγRs). These receptors mediate communication between antibodies and the cellular arm of the immune system. In humans this protein family includes FcγRI (CID64), including isoforms FcγRIA, FcγRIB, and FcγRIC; FcγRII (CD32), including isoforms FcγRIIA, FcγRIIB, and FcγRIIC; and FcγRIII (CD16), including isoforms FcγRIIIA and FcγRIIB. These receptors typically have an extracellular domain that mediates binding to Fc, a membrane spanning region, and an intracellular domain that may mediate some signaling event within the cell. These different FcγR subtypes are expressed on different cell types. For example, in humans, FcγRIIIB is found only on neutrophils, whereas FcγRIIIA is found on macrophages, monocytes, natural killer (NK) cells, and a subpopulation of T-cells. Formation of the Fc/FcγR complex recruits effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell mediated reaction where nonspecific cytotoxic cells that express FcγR5 recognize bound antibody on a target cell and subsequently cause lysis of the target cell is referred to as antibody dependent cell-mediated cytotoxicity (ADCC). The primary cells for mediating ADCC, NK cells, express only FcγRIIIA, whereas monocytes express FcγRI, FcγRII and FcγRIII.

Another important Fc ligand is the complement protein C1q. Fc binding to C1q mediates a process called complement dependent cytotoxicity (CDC). C1q is capable of binding six antibodies, although binding to two IgGs is sufficient to activate the complement cascade. C1q forms a complex with the C1r and C1s serine proteases to form the C1 complex of the complement pathway.

Several key features of antibodies including but not limited to, specificity for target, ability to mediate immune effector mechanisms, and long half-life in serum, make antibodies and related immunoglobulin molecules powerful therapeutics. There are a number of possible mechanisms by which antibodies destroy tumor cells, including anti-proliferation via blockage of needed growth pathways, intracellular signaling leading to apoptosis, enhanced down regulation and/or turnover of receptors, ADCC, CDC, and promotion of an adaptive immune response.

Antibodies provided herein include full length or intact antibody, antibody fragments, native sequence antibody or amino acid variants, human, humanized, post-translationally modified, chimeric or fusion antibodies, immunoconjugates, and functional fragments thereof. In some aspects, the antibodies can be modified in the Fc region, and certain modifications can provide desired effector functions or serum half-life. As discussed in more detail in the sections below, with the appropriate Fc regions, a naked antibody bound on the cell surface can induce cytotoxicity, e.g., via antibody-dependent cellular cytotoxicity (ADCC) or by recruiting complement in complement dependent cytotoxicity (CDC), or by recruiting nonspecific cytotoxic cells that express one or more effector ligands that recognize bound antibody on a target cell and subsequently cause phagocytosis of the target cell in antibody dependent cell-mediated phagocytosis (ADCP), or some other mechanism. Where it is desirable to eliminate or reduce effector function, so as to minimize side effects or therapeutic complications, certain other Fc regions may be used. The Fc region of antibodies can be modified to increase the binding affinity for FcRn and thus increase serum half-life. Alternatively, the Fc region can be conjugated to PEG or albumin to increase the serum half-life, or some other conjugation that results in a desired effect.

In certain aspects, an antibody herein is an isolated and/or purified and/or pyrogen free antibody. The term "purified" as used herein, refers to a molecule of interest that has been identified and separated and/or recovered from a component of its natural environment. Thus, in some aspects, an antibody provided herein is a purified antibody where it has been separated from one or more components of its natural environment. The term "isolated antibody" as used herein refers to an antibody which is substantially free of other antibody molecules having different structure or antigenic specificities. A bi- or multi-specific antibody molecule is an isolated antibody when substantially free of other antibody molecules. Thus, in some aspects, antibodies provided are isolated antibodies which have been separated from antibodies with a different specificity. An isolated antibody may be a monoclonal antibody. An isolated antibody that specifically binds to an epitope, isoform or variant of a target may, however, have cross-reactivity to other related antigens, e.g., from other species (e.g., species homologs). An isolated antibody as provided may be substantially free of one or more other cellular materials. In some aspects, a combination of "isolated" monoclonal antibodies is provided, and pertains to antibodies having different specificities and combined in a defined composition. Methods of production and purification/isolation of an antibody are described elsewhere herein.

Isolated antibodies presented comprise antibody amino acid sequences disclosed herein, which can be encoded by any suitable polynucleotide. Isolated antibodies sometimes are provided in formulated form. In some aspects, an antibody binds to one or more proteins and, thereby partially or substantially alters at least one biological activity of at least one protein, for example, cellular proliferation activity.

Humanized Antibodies

A humanized antibody is an antibody or its variant or fragment thereof which is capable of binding to a predetermined antigen and which comprises a framework region having substantially the amino acid sequence of a human immunoglobulin and a complementarity determining region (CDR) having substantially the amino acid sequence of a non-human immunoglobulin. Complementarity determining regions (CDRs) are often the most variable regions within an antibody that determine the antibody's affinity and specificity for specific antigens. A humanized antibody comprises substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. A humanized antibody may also comprise at least a portion of an immunoglobulin constant region (Fc), typically that of a human immunoglobulin. The antibody may contain both the light chain as well as at least the variable domain of a heavy chain. The antibody also may include the CH1, hinge, CH2, CH3, and CH4 regions of the heavy chain.

The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 or IgG4 class. The humanized antibody may comprise sequences from more than one class or isotype, and methods for selecting particular constant domains to optimize desired effector functions are known in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, may not be extensive. At least 75% of the humanized antibody residues may correspond to those of the parental framework region (FR) and CDR sequences, with the correspondence sometimes being 90% or greater or 95% or greater, for example.

Humanization can essentially be performed following methods known in the art, by substituting hypervariable region sequences for the corresponding sequences of a human antibody. Specifically, humanized antibodies may be prepared by methods known in the art including CDR grafting approaches, veneering or resurfacing, chain shuffling strategies, molecular modeling strategies, and the like. These general approaches may be combined with standard mutagenesis and recombinant synthesis techniques to produce antibodies herein with desired properties.

CDR grafting is performed by replacing one or more CDRs of an acceptor antibody (e.g., a human antibody) with one or more CDRs of a donor antibody (e.g., a non-human antibody). Acceptor antibodies may be selected based on similarity of framework residues between a candidate acceptor antibody and a donor antibody and may be further modified to introduce similar residues. Following CDR grafting, additional changes may be made in the donor and/or acceptor sequences to optimize antibody binding and functionality.

Grafting of abbreviated CDR regions is a related approach. Abbreviated CDR regions include the specificity-determining residues and adjacent amino acids, including those at positions 27d-34, 50-55 and 89-96 in the light chain, and at positions 31-35b, 50-58, and 95-101 in the heavy chain. Grafting of specificity-determining residues (SDRs) is premised on the understanding that the binding specificity and affinity of an antibody combining site is determined by the most highly variable residues within each of the CDR regions. Analysis of the three-dimensional structures of antibody-antigen complexes, combined with analysis of the available amino acid sequence data was used to model sequence variability based on structural dissimilarity of amino acid residues that occur at each position within the CDR. Minimally immunogenic polypeptide sequences consisting of contact residues, which are referred to as SDRs, are identified and grafted onto human framework regions.

Framework residues in the framework regions may be substituted with the corresponding residue from the CDR donor antibody to alter, and potentially improve, antigen binding. These framework substitutions are identified by methods known in the art, e.g., by modeling of the interactions of the CDR and framework residues to identify framework residues important for antigen binding and sequence comparison to identify unusual framework residues at particular positions.

Veneering or resurfacing is based on the concept of reducing potentially immunogenic amino acid sequences in a rodent or other non-human antibody by resurfacing the solvent accessible exterior of the antibody with human amino acid sequences. Thus, veneered antibodies appear less foreign to human cells. A non-human antibody is veneered by (1) identifying exposed exterior framework region residues in the non-human antibody, which are different from those at the same positions in framework regions of a human antibody, and (2) replacing the identified residues with amino acids that typically occupy these same positions in human antibodies.

By definition, humanized antibodies are chimeric antibodies. Chimeric antibodies are antibodies in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity. Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences.

Human Antibodies

For some uses, including in vivo use of antibodies in humans and in vitro detection assays, it may be appropriate to use human or chimeric antibodies. Completely human antibodies may be desirable for therapeutic treatment of human subjects. Human antibodies can be made by a variety of methods known in the art including phage display methods described below using antibody libraries derived from human immunoglobulin sequences.

Human antibodies also can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of an antibody herein.

Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. In addition, companies such as Medarex (Princeton, N.J.) provide human antibodies directed against a selected antigen.

Also known in the art is a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and usually a second constant region (sometimes a gamma constant region) are formed into a construct for insertion into an animal.

The generation of human antibodies from mice in which, through microcell fusion, large pieces of chromosomes, or entire chromosomes, have been introduced, is also known in the art. For example, cross-breeding of Kirin's Tc mice with Medarex's minilocus (Humab) mice has generated mice possessing the human IgH transchromosome of the Kirin mice and the kappa chain transgene of the Genpharm mice.

Human antibodies also can be derived by in vitro methods. Suitable examples include but are not limited to phage display (MedImmune (formerly CAT), Morphosys, Dyax, Biosite/Medarex, Xoma, Symphogen, Alexion (formerly Proliferon), Affimed) ribosome display (MedImmune (formerly CAT)), yeast display, and the like. The phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats as known in the art. A diverse array of anti-oxazolone antibodies has been isolated from a small random combinatorial library of V genes derived from the spleens of immunized mice. A repertoire of V genes from unimmunized human donors can be constructed and antibodies to a diverse array of antigens (including self-antigens) can be isolated essentially following the techniques known in the art. Human antibodies may also be generated by in vitro activated B cells.

Multivalent Antibodies

Antibodies typically are characterized as bivalent, meaning that they contain two antigen binding sites (i.e. one on each arm of the F(ab')2 fragment). Antibodies with more than two valencies are also contemplated (e.g. more than one antigen binding site on one or both arms of the F(ab')2 fragment). For example, trispecific antibodies can be prepared. Thus, the antibodies herein presented can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In one aspect a dimerization domain comprises (or consists of) an Fc region or a hinge region. In this scenario, the antibody may comprise an Fc region and three or more antigen binding sites amino-terminal and/or carboxyl-terminal to the Fc region. In certain aspects the multivalent antibody herein comprises (or consists of) three to about eight antigen binding sites. The multivalent antibody comprises at least one polypeptide chain where the polypeptide chain(s) comprise two or more variable domains. For instance, the polypeptide chain(s) may comprise VD1-(X1) n-VD2-(X2)n-Fc, where VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two light chain variable domain polypeptides. The multivalent antibody herein may, for instance, comprise from about two to about eight light chain variable domain polypeptides. The light chain variable domain polypeptides contemplated herein comprise a light chain variable domain and, optionally, further comprise a $C_L$ domain.

Bispecific Antibodies

In some aspects, the antibodies provided herein are bispecific. As used herein, bispecific antibodies are antibodies that have binding specificities for at least two independent antigens (or targets) or different epitopes within the same antigen. Exemplary bispecific antibodies may bind to two different epitopes of a target, or may bind two different targets. Other such antibodies may combine a first target binding site with a second binding site for another target. A target binding arm may sometimes be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the target protein-expressing cell. Bispecific antibodies may also be used to localize cytotoxic agents to cells which express the antigen. Such antibodies may possess a target binding arm and an arm which binds the cytotoxic agent (e.g. saporin, anti-interferon-α, vinca alkaloid, ricin A chain, methotrexate or radioactive isotope hapten).

In some cases, bispecific antibodies provide additive and/or synergistic therapeutic effects derived from targeting two antigens simultaneously, with the administration of a single manufactured molecule. For example, a cancer patient having breast carcinoma with moderate expression of HER2, who could not be treated with anti-HER2 mAb therapy, might benefit from the synergic treatment with a bispecific targeting both HER2 and EGFR, provided that the tumor also expresses EGFR. However, treatment with two bivalent mAb or the bivalent bispecific derivative of these two mAbs might pose a severe therapeutic and/or toxic risk. Given that the two mAbs or the bivalent bispecific antibodies react with two receptors that are associated with malignant transformation should increase the tumor specificity of the treatment. However, because the combined mAb treatment or the bivalent bispecific antibody is active against tumor cells with moderate expression of the antigen, some new side effects may arise, due to the presence of some normal tissues with low antigen expression. These tissues may not be sensitive to the single mAb, but may become sensitive to the combined mAb treatment or bivalent bispecific derivative. This potential risk can be more significant with bivalent or multivalent molecules that display enhanced antigen-cell binding due to avidity effects.

In some aspects, the antibodies provided herein are monovalent bispecific antibodies (MBab). The monovalent bispecific antibody scaffolds described herein provide a superior platform for the generation of bispecific antibodies that fulfill all the benefits associated with bispecific antibodies while reducing the potential therapeutic risks mentioned above due to their monovalent nature. Furthermore, the MBabs provided herein are readily expressed, stable and are likely to have low immunogenicity. As used herein, the term "monovalent bispecific," which may be abbreviated "MBab," refers to bispecific antibodies, where each arm can specifically bind to a different target antigen, and for a given pair of different target antigens (A and B), the MBab can bind to one of each. In certain aspects, monovalent bispecific antibodies can specifically bind to two independent antigens (or targets) or two independent epitopes on the same antigen. Typically, monovalent bispecific antibodies comprise two different variable regions. In some aspects, the binding affinity for the two independent antigens is about the same. In some aspects, the binding affinities for the two independent antigens are different. In some aspects, the binding affinity for two independent epitopes on the same antigen is about the same. In some aspects, the binding affinity for two independent epitopes on the same antigen is different. In still other aspects, each arm has the same specificity (e.g., binds the same, or an overlapping epitope) but binds with a different affinity. In some aspects, the affinities may differ by 3 fold or more. It may be particularly desirable to have one arm with higher affinity and one arm with lower affinity when combining variable regions from antibodies having different in vivo potencies to prevent the over or under dosing of one of the arms.

Figure 18:
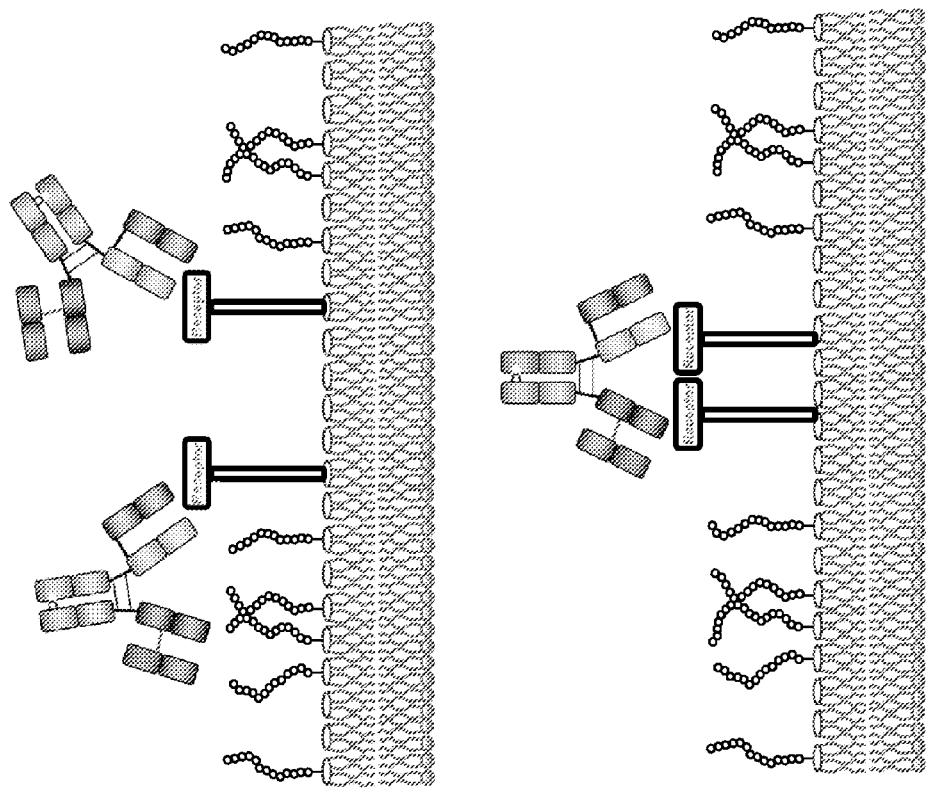
FIG. 18 shows a diagram depicting the role of affinity/avidity regulating MBab activity. The top panel shows that at high MBab concentration avidity effects do not come to play, therefore, the binding to the receptor will be mediated through the high affinity binding domain, hence no receptor cross-linking/activation. The bottom panel shows that at low MBab concentration avidity effects do come to play, therefore, the binding to the receptor will be mediated through both binding domains, leading to receptor cross-linking/activation.

In certain aspects, an MBab binds the same epitopes or an overlapping epitopes on the same antigen (e.g. a receptor), with different affinities. In particular, same epitopes or overlapping epitopes, which are in close proximity when the antigen is dimerized. Such an antibody will have a dual characteristic depending on the relative concentration. For example, at high concentration, where the MBab concentration is saturating the antigen concentration, the high affinity binding domain will compete out the low affinity binding domain and little to no avidity effect will take place. That is the antibody will function primarily as a monovalent binding entity and little to no antigen cross-linking/signalling will take place (see FIG. 18). However, at low concentration avidity effects will come into play and the MBab can concurrently bind both binding sites, preferably on two antigen molecules, leading to antigen cross-linking/signaling (see FIG. 18). In this manner antigen signaling can be regulated by MBab concentration.

In certain aspects, a, MBab binds two different antigens (e.g. different receptors) where homodimerization of the antigens is undesirable and/or both antigens are present separately on non-targets cells/tissues and are present together on target cells/tissue. Such an antibody will bind with only one arm on non-target cells, this low avidity monovalent binding of only one arm of the MBab to non-target cells/tissues is insufficient to elicit homodimerization (see FIG. 19, left side). In contrast the MBab can bind to both antigens on the target cells/tissue, binding to both antigens on the target cells simultaneously will result in a higher avidity bivalent binding that can enhance preferential binding to target cells and may enhance receptor dimerization (see FIG. 19, right side).

In some aspects, the monovalent bispecific antibodies further comprise additional binding sites. The additional binding sites can be specific for one or both target antigens (A and B) of the monoclonal bispecific antibody (MBab) and/or can be specific for additional target antigens. In some aspects, one or more-single chain variable fragments (scFv) are added to the N- or C-terminus of one or both heavy chains and/or one or both light chains, where the one or more scFvs specifically bind to one or more additional target antigens. For example, a monovalent trispecific antibody can be generated by the addition of a scFv (specific for antigen C) to one chain (e.g., heavy or light) of a monovalent bispecific antibody (specific for antigens A and B). In this case, the antibody would be monovalent for antigens A, B, and C. If a scFv (specific for antigen C) is added to two chains (e.g. both heavy chains, both light chains, one heavy chain and one light chain), the trispecific antibody would be monovalent for antigens A and B and bivalent for antigen C. Any possible combination of additional binding sites is contemplated for the monovalent bispecific antibodies herein (see e.g., Dimasi et al. J. Mol. Biol. (2009) 393: 672-692). It is contemplated that the binding affinity of the additional binding sites may be about the same as one or both arms of the MBab or may be different from one or both arms of the MBab. As described above, the relative affinities may be selected or tailored depending on the antigens and the intended use of the molecule.

Bispecific antibodies can be prepared as full length antibodies or antibody fragments (e.g. F(ab')2 bispecific antibodies). Traditional production of full length bispecific antibodies is based on the co-expression of two immunoglobulin heavy chain-light chain pairs, where the two chains have different specificities. Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields can be low.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. This method, however, typically requires the use of non-human proteins, which can carry high immunogenicity potential. Further, the antibody fragments sometimes have little or no effector function and a short half-life.

Bispecific antibodies can be prepared using chemical linkage. In one procedure intact antibodies are proteolytically cleaved to generate F(ab')2 fragments. These fragments are reduced in the presence of the dithiol complexing agent, sodium arsenite, to stabilize vicinal dithiols and prevent intermolecular disulphide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. This method, however, often leads to poor yield, is difficult to control, and the products can carry high immunogenicity potential. Further, the antibody fragments sometimes have little or no effector function and a short half-life.

Fab'-SH fragments can be directly recovered from E. coli, which can be chemically coupled to form bispecific antibodies. A fully humanized bispecific antibody F(ab')2 molecule may be created by secreting each Fab' fragment separately from E. coli and subjecting to directed chemical coupling in vitro to form the bispecific antibody. This method, however, often leads to poor yield and is difficult to control. Further, the antibody fragments sometimes have little or no effector function and a short half-life.

Bispecific antibodies may also be produced using leucine zippers. The leucine zipper peptides from the Fos and Jun proteins are linked to the Fab' portions of two different antibodies by gene fusion. The antibody homodimers are reduced at the hinge region to form monomers and then re-oxidized to form the antibody heterodimers. This method can also be utilized for the production of antibody homodimers. The "diabody" technology described has provided an additional mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers is also known in the art. This method, however, often leads to poor yield, is difficult to control, and the products can carry high immunogenicity potential. Further, the antibody fragments sometimes have little or no effector function and a short half-life.

Bispecific antibodies may also be produced using heavy chain heterodimerization methods. Such methods include "knob in hole" and strand-exchanged engineered domain (SEED) methods, and those which alter the charge polarity across the Fc dimer interface. Such methods are described in further detail herein and in e.g., U.S. Pat. No. 7,183,076; Merchant et al. (1998) Nat. Biotech 16:677-681; Ridgway et al. (1996) Protein Engineering 9:617-621; Davis et al. (2010) Prot. Eng. Design & Selection 23:195-202; WO 2007/110205; WO 2007/147901; Gunasekaran et al. (2010) JBC 285:19637-46. In these methods, the interface between a pair of antibody molecules may be engineered to maximize the percentage of heterodimers which are recovered from recombinant cell culture. In the "knob in hole" method, a "protrusion" is generated by replacing one or more small amino acid side chains from the interface of the first antibody molecule with larger side chains (e.g. tyrosine or tryptophan). Compensatory "cavities" of identical or similar size to the large side chain(s) are created on the interface of the second antibody molecule by replacing amino acid having large side chains with amino acids having smaller ones (e.g. alanine or threonine). This provides a mechanism for increasing the yield of the heterodimer over other unwanted end-products such as homodimers. In the SEED method, Fc homodimers are converted into heterodimers by interdigitating beta-strand segments of human IgG and IgA CH3 domains. These derivatives of human IgG and IgA CH3 domains create complementary human SEED CH3 heterodimers that are composed of alternating segments of human IgA and IgG CH3 sequences. The resulting pair of SEED CH3 domains preferentially associates to form heterodimers when expressed in mammalian cells. Other methods include introducing modifications which alter the charge polarity across the Fc dimer interface such that co-expression of electrostatically matched Fc regions results in heterodimerization. These methods improve heavy chain heterodimerization, but do not address the light-heavy chain mispairings formed during bispecific antibody formation. In some cases use of a common light chain can decrease the number of possible mispairings, as described in WO 98/50431, but often results in the loss or reduction of binding specificity and/or affinity.

Duel specific antibodies are another type of bispecific antibody that can be produced (see e.g. Bostrum et al. (2009) Science 323:1610-1614). Such antibodies can be produced by generating variants with mutations in the light chain (LC) complementarity determining regions (CDR) such that they can bind a new antigen target while maintaining binding specificity for its native target antigen. The antigen binding sites often overlap, however, preventing the antibody from binding both antigens at the same time. Additionally, these antibodies are difficult to generate and may not possess the desired affinities for each of the two antigens.

The modified polypeptides provided herein can be useful for the generation of bispecific antibodies and overcome the limitations and technical difficulties noted above. In some aspects, one heavy chain and one light chain within an antibody are modified whereby a native cysteine is substituted by a non-cysteine amino acid, and a native non-cysteine amino acid is substituted by a cysteine amino acid. Such modifications provided herein are generated in the HC and LC domains and result in the relocation of an HC-LC interchain disulphide bridge. When generating a bispecific antibody from four separate polypeptides, for example, where the modified arm has a binding specificity for one target and the unmodified arm has a binding specificity for a different target, the four polypeptides will assemble such that the modified heavy chain properly hybridizes with the modified light chain and the unmodified heavy chain properly hybridizes with the unmodified light chain. As used herein, the term "unmodified" refers to heavy and light chains that do not contain the HC-LC modifications introduced for the relocation of cysteines and/or disulphide bridges, as described herein. Such "unmodified" heavy and light chains may comprise other modifications, such as, for example, heterodimerization modifications in the CH2 and/or CH3 regions described herein and/or known in the art. The HC-LC modifications provided herein can be combined with further modifications of the heavy chain, particularly in the CH2 and/or CH3 regions to ensure proper heavy chain heterodimerization and/or to enhance purification of the a heavy chain heterodimer and are described in detail below.

Assays for Bispecificity

Any assay known in the art for determining bispecificity can be used to characterize the antibodies provided herein. Non-limiting examples of assays for bispecificity include immunoassays, direct binding assays, and crosslinking assays. For example, an AlphaLISA assay (Perkin Elmer) is an immunoassay can be used to determine bispecificity of an antibody. An APLHLISA assay is based on bringing a donor and acceptor bead into close proximity, resulting in a recordable signal. For a bispecific antibody, the simultaneous binding of an antibody to two antigens brings the donor and acceptor bead into close proximity and generates a signal. The first antigen can be engineered to contain a tag, such as a FLAG tag, which can bind to acceptor beads conjugated to an anti-tag antibody (e.g., anti-FLAG). The second antigen can be biotinylated and can bind to strepavidin-coated donor beads. An antibody that is bispecific for the first and second antigens will bring the donor and acceptor beads into close proximity and generate a signal. Additional assays for determining bispecificity are exemplified in the examples herein.

Antibody Function

Antibodies can effect several functions, such as antigen binding and inducing an immune response, for example.

Antigen Binding

The term "antigen" as used herein refers to a molecule that causes an immune response when introduced into an organism and that is capable of binding with specific antibodies. Antibody-antigen binding is mediated by the sum of many weak interactions between the antigen and antibody including, for example, hydrogen bonds, van der Waals forces, and ionic and/or hydrophobic interactions.

An antigen binds to the complementarity regions on an antibody. The corresponding region(s) of the antigen is referred to as an "antigenic determinant" or "epitope". Most antigens have multiple determinants; if 2 or more are identical, the antigen is multivalent.

The affinity of an antibody reflects the fit between the antigenic determinant and the antibody binding site and is independent of the number of binding sites. The avidity of the binding reflects the overall stability of the antibody-antigen complex. Avidity is defined as the total binding strength of all binding sites. Thus, both affinity of the antibody for its antigen and the valencies of both the antibody and the antigen can influence avidity. Engagement of both, rather than only one, multivalent binding sites may strengthen binding by a factor of as much as 10,000 in a typical IgG molecule.

The multivalent nature of many antibodies and antigens may give rise to secondary reactions such as precipitation, cell clumping, and complement fixation in an organism. Such reactions can be useful in techniques such as western blotting, ELISA, immunoprecipitation, and the like. However, these reactions may be undesirable in a molecule intended for therapeutic and/or diagnostic use. The monovalent nature of the bispecific antibodies provided herein thus provides an advantage for therapeutic and/or diagnostic purposes.

Examples of Targets

In some aspects, specific pairs of molecules are targeted by antibodies as provided herein. Antibodies of the disclosure may be capable of binding pairs of cytokines selected from, for example, IL-1alpha and IL-1beta; IL-12 and IL-18; TNFalpha and IL-23; TNFalpha and IL-13; TNF and IL-18; TNF and IL-12; TNF and IL-1beta; TNF and MIF; TNF and IL-17; TNF and IL-15; TNF and VEGF; VEGFR and EGFR; IL-13 and IL-9; IL-13 and IL-4; IL-13 and IL-5; IL-13 and IL-25; IL-13 and TARC; IL-13 and MDC; IL-13 and MIF; IL-13 and TGF-beta; IL-13 and LHR agonist; IL-13 and CL25; IL-13 and SPRR2a; IL-13 and SPRR2b; IL-13 and ADAMS; TNFalpha and PGE4; IL-13 and PED2; TNF and PEG2; HER2 and HER3; HER1 and HER2; HER1 and HER3.

In certain aspects, antibodies as provided herein may be capable of binding pairs of targets selected from, for example, CD138 and CD20; CD138 and CD40; CD19 and CD20; CD20 and CD3; CD38 and CD138; CD38 and CD20; CD38 and CD40; CD40 and CD20; CD-8 and IL-6; CSPGs and RGM A; CTLA4 and BTNO2; IGF1 and IGF2; IGF1/2 and ErbB2; IGFR and EGFR; ErbB2 and ErbB3; ErbB2 and CD64; IL-12 and TWEAK; IL-13 and IL-1 beta; MAG and RGM A; NgR and RGM A; NogoA and RGM A; OMGp and RGM A; PDL-1 and CTLA4; RGM A and RGM B; Te38 and TNFalpha; TNFalpha and Blys; TNFalpha and CD-22; TNFalpha and CTLA-4; TNFalpha and GP130; TNFalpha and IL-12p40; and TNFalpha and RANK ligand.

In some aspects, antibodies as provided herein may be capable of binding one, two or more growth factors, cytokines, cytokine-related proteins, and receptors selected from among, for example, BMP1, BMP2, BMP3B (GDF10), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, FGFR, FGFR1, FGFR2, FGFR3, FGFR4, FGFRL1, FGFR6, IGF1, IGF2, IGF1R, IGF2R, IFNA1, IFNA2, IFNA4, IFNA5, IFNA6, IFNA7, IFNAR1, IFNAR2, IFNB1, IFNG, IFNW1, FIL1, FIL1 (EPSILON), FIL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, IL2RA, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL17RA, IL17RB, IL17RC, IL17RD, IL18R1, IL20RA, IL20RB, IL21R, IL22R, IL22RA1, IL23R, IL27RA, IL28RA, PDGFA, PDGFB, PDGFRA, PDGFRB, TGFA, TGFB1, TGFB2, TGFB3, TGFBR1, TGFBR2, TGFBR3, ACVRL1, GFRA1, LTA (TNF-beta), LTB, TNF (TNF-alpha), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, TNFRSF1A, TNFRSF1B, TNFRSF10A (Trail-receptor), TNFRSF10B (Trail-receptor 2), TNFRSF10C (Trail-receptor 3), TNFRSF10D (Trail-receptor 4), FIGF (VEGFD), VEGF, VEGFB, VEGFC, KDR, FLT1, FLT4, NRP1, IL1HY1, IL1RAP, IL1RAPL1, IL1RAPL2, URN, IL6ST, IL18BP, IL18RAP, IL22RA2, AIF1, HGF, LEP (leptin), PTN, ALK and THPO.

In further aspects, antibodies as provided herein may be capable of binding one or more chemokines, chemokine receptors, and chemokine-related proteins selected from among, for example, CCL1 (I-309), CCL2 (MCP-1/MCAF), CCL3 (MIP-1a), CCL4 (MIP-1b), CCL5 (RANTES), CCL7 (MCP-3), CCL8 (mcp-2), CCL11 (eotaxin), CCL13 (MCP-4), CCL15 (MIP-1d), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL10 (IP 10), CXCL11 (1-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR -L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10 (C10), EPO, FY (DARC), GDF5, HIF1A, IL8, PRL, RGS3, RGS13, SDF2, SLIT2, TLR2, TLR4, TREM1, TREM2, and VHL.

Other antibodies as provided herein may be capable of binding cell surface proteins selected from among, for example, integral membrane proteins including ion channels, ion pumps, G-protein coupled receptors, structural proteins, adhesion proteins such as integrins, transporters, membrane-bound enzymes, proteins involved in accumulation and transduction of energy and lipid-anchored proteins including G proteins and some membrane-anchored kinases. Antibodies as provided herein may also be capable of binding enzymes such as kinases, proteases, lipases, phosphatases, fatty acid synthetases, digestive enzymes such as pepsin, trypsin, and chymotrypsin, lysozyme, and polymerases. Antibodies as provided herein may also be capable of binding to receptors such as hormone receptors, lymphokine receptors, monokine receptors, growth factor receptors, G-protein coupled receptors, and more.

In some aspects, the multimeric nature of the antibodies as provided herein confers the ability to target labels or therapeutics to a specific cell type or molecular target. For example, one antigen binding domain of an antibody as provided herein may bind to a target at the surface of a cell, while another antigen binding domain in the same antibody binds to a hapten or labeling agent useful for detection. Similarly, one functional domain may bind to a cellular target while a second functional domain binds to a toxin. Because both binding reactions are mediated through a single molecule, the toxin may be placed in the proximity of the cellular target, where it effects a cytotoxic function.

Immune Function

Antibodies bind and inactivate pathogens, can stimulate removal of pathogens by macrophages and other cells by coating the pathogen, and trigger destruction of pathogens by stimulating other immune responses such as the complement pathway. Antibodies activate the complement pathway by binding to surface antigens on, for example, a bacterium or cancer cell. The Fc region of the antibody then interacts with the complement cascade. The binding of the antibody and of complement cascade molecules attracts phagocytes and marks the microbe or cell for ingestion. Complement system components may form a membrane attack complex to assist antibodies to kill the bacterium or cell directly.

Antibody binding may cause pathogens to agglutinate. Antibody coated pathogens stimulate effector functions in cells that recognize the antibody Fc region. The effector function ultimately results in destruction of the invading microbe or pathogenic cell, e.g. phagocytes will phagocytose, mast cells and neutrophils will degranulate, and natural killer cells will release cytokines and cytotoxic molecules.

Transformed tumor cells express abnormal antigens from several sources, including oncogenic viruses, abnormally high levels of the organism's own proteins, and cancer inducing oncogenes. Tumor antigens are presented on major histo-compatiblity (MHC) class 1 molecules in a manner similar to viral antigens. Antigens activate killer T-Cells and also generate antibodies that trigger the complement system.

An antibody herein may bind to a tumor or other pathogenic cell antigen and trigger cell destruction through an antibody function. In certain aspects, an antibody herein may be conjugated to a therapeutic molecule, including a diagnostic molecule or toxin, and carry the conjugated molecule to selected site by means of antibody-antigen affinity.

Epitopes

The term "epitope" as used herein refers to a molecular determinant capable of binding to an antibody. Epitopes generally include chemically active surface groupings of molecules such as amino acids and/or sugar side chains and generally have specific three dimensional structural characteristics, as well as specific chemical characteristics (e.g., charge, polarity, basic, acidic, hydrophobicity and the like). Conformational and non-conformational epitopes are distinguished in that the binding to the former but not the latter is lost in the presence of denaturing solvents.

In certain aspects, an epitope is comprised of at least one extracellular, soluble, hydrophilic, external or cytoplasmic portion of a target protein. A specified epitope can comprise any combination of at least one amino acid sequence from of at least 3 amino acid residues to the entire specified portion of contiguous amino acids of the target protein. In some aspects, the epitope is at least 4 amino acid residues, at least 5 amino acid residues, at least 6 amino acid residues, at least 7 amino acid residues, at least 8 amino acid residues or at least 9 amino acid residues to the entire specified portion of contiguous amino acids of the target protein.

Antibody Fragments

In certain aspects, the present antibodies are antibody fragments or antibodies comprising these fragments. The antibody fragment comprises a portion of the full length antibody, which generally is the antigen binding or variable region thereof. Examples of antibody fragments include Fab, Fab', F(ab')2, Fd and Fv fragments. Diabodies; linear antibodies; single-chain antibody molecules; and multispecific antibodies are antibodies formed from these antibody fragments.

Traditionally, these fragments were derived via proteolytic digestion of intact antibodies using techniques known in the art. However, these fragments can now be produced directly by recombinant host cells. Fab, Fv and scFv antibody fragments can all be expressed in and secreted from E. coli, thus allowing the facile production of large amounts of these fragments. In one aspect, the antibody fragments can be isolated from the antibody phage libraries discussed elsewhere herein. Fab'-SH fragments can also be directly recovered from E. coli and chemically coupled to form F(ab')2 fragments. F(ab')2 fragments can also be isolated directly from recombinant host cell culture. Other techniques for the production of antibody fragments are known in the art. In certain aspects, antibodies provided herein comprise a single-chain Fv fragment (scFv) or other antigen binding domain.

In certain aspects, the antibodies herein comprise domain antibodies, e.g., antibodies containing the small functional binding units of antibodies, corresponding to the variable regions of the heavy (VH) or light (VL) chains of human antibodies. Examples of domain antibodies include, but are not limited to, those available from Domantis that are specific to therapeutic targets. Commercially available libraries of domain antibodies can be used to identify antigen domain antibodies. In certain aspects, antibodies herein comprise a functional binding unit and an Fc gamma receptor functional binding unit.

In certain aspects, the antibodies herein comprise vaccibodies. Vaccibodies are dimeric polypeptides. Each monomer of a vaccibody consists of a scFv with specificity for a surface molecule on APC connected through a hinge region and a Cγ3 domain to a second scFv. In some aspects, vaccibodies containing as one of the scFv's an antibody lacking interchain cysteines fragment may be used to juxtapose those cells for destruction and an effector cell that mediates ADCC.

In certain aspects, the antibodies herein are linear antibodies. Linear antibodies comprise a pair of tandem Fd segments (VH-CH1-VH-CH1) which form a pair of antigen-binding regions. Linear antibodies can be bispecific, in certain aspects.

HC and LC Modifications

Provided herein, in some aspects, are engineered antibodies in which one or more interchain cysteines have been relocated which, in some aspects, results in the relocation of an interchain disulphide linkage. In some aspects, this involves modification of one heavy chain and one light chain within an antibody whereby a native cysteine in the heavy chain and a native cysteine in the light chain are each substituted by a non-cysteine amino acid, and a native non-cysteine amino acid in the heavy chain and a native non-cysteine amino acid in the light chain are each substituted by a cysteine amino acid. In some aspects, the relocated disulphide bridge is on one of the two CH1-CL interfaces of an antibody (i.e., on one arm of the antibody). Often, the HC and LC regions are modified such that each contain a substitution of a native cysteine to a non-cysteine amino acid, and a substitution of a native non-cysteine amino acid to a cysteine amino acid, such that the resulting disulphide bridge that forms between the modified HC and LC regions is at a location along the interface that is different from the disulphide bridge that forms between the unmodified HC and LC regions. In certain aspects, each heavy chain further comprises a modification that favors heavy chain heterodimerization. In other aspects, one heavy chain further comprises a modification that facilitates purification of the heterodimer, this modification may be in addition to or as an alternative to a modification that favors heavy chain heterodimerization.

Also provided herein, in some aspects, are engineered antibodies in which the heavy chain(s) and corresponding light chain(s) have been engineered to favor the interchain pairing of a first heavy chain with a first light chain and a second heavy chain with a second light chain. In some aspects, this involves modification of a first heavy chain and a first light chain whereby the first heavy chain comprises protrusion and/or a cavity and the first light chain comprises a compensatory cavity and/or protrusion which favors the interchain pairing of the first heavy and first light chain. In some aspects, this further involves the modification of a second heavy chain and a second light chain whereby the second heavy chain comprises protrusion and/or a cavity and the second light chain comprises a compensatory cavity and/or protrusion which favors the interchain pairing of the second heavy and second light chain. In some aspects, the first heavy and light chains and/or the second heavy and light chains further comprise a substitution of a native cysteine to a non-cysteine amino acid. In certain aspects, each heavy chain further comprises a modification that favors heavy chain heterodimerization. In other aspects, one heavy chain further comprises a modification that facilitates purification of the heterodimer, this modification may be in addition to or as an alternative to a modification that favors heavy chain heterodimerization.

Examples of positions, numbered according to the EU index as set forth in Kabat, containing a substitution within the constant region of an IgG heavy or light chain and the corresponding positions within the sequences set forth in Table 8 and the sequence listing herein are presented in Table 2 below. FIGS. 22 and 24 show the numbering of the light and heavy chain constant regions, respectively, according to the EU index as set forth in Kabat.

TABLE 2

Modified Constant Region Amino Acid Positions

| Antibody Isotype - CH region | SEQ ID NO | Numbering according to EU index | Corresponding position for each SEQ ID NO |
|---|---|---|---|
| Constant Region - Heavy Chain | | | |
| IgG1-CH1 | 1 | 126 | 9 |
| | | 128 | 11 |
| | | 141 | 24 |
| | | 145 | 28 |
| | | 147 | 30 |
| | | 168 | 51 |
| | | 170 | 53 |
| | | 183 | 66 |
| | | 185 | 68 |
| | | 220 | 103 |
| IgG1-CH2-CH3 | 1 | 349 | 232 |
| | | 354 | 237 |
| | | 366 | 249 |
| | | 368 | 251 |
| | | 407 | 290 |
| | | 435 | 318 |
| | | 436 | 319 |
| IgG2-CH1 | 2 | 126 | 9 |
| | | 128 | 11 |
| | | 131 | 14 |
| | | 141 | 24 |
| | | 145 | 28 |
| | | 147 | 30 |
| | | 168 | 51 |
| | | 170 | 53 |
| | | 183 | 66 |
| | | 185 | 68 |
| | | 219 | 102 |
| | | 220 | 103 |
| IgG2-CH2-CH3 | 2 | 349 | 229 |
| | | 354 | 234 |
| | | 366 | 246 |
| | | 368 | 248 |
| | | 407 | 286 |
| | | 435 | 314 |
| | | 436 | 315 |
| IgG3-CH1 | 3 | 126 | 9 |
| | | 128 | 11 |
| | | 131 | 14 |
| | | 141 | 24 |
| | | 145 | 28 |
| | | 147 | 30 |
| | | 168 | 51 |
| | | 170 | 53 |
| | | 183 | 66 |
| | | 185 | 68 |
| IgG3-CH2-CH3 | 3 | 349 | 379 |
| | | 354 | 384 |
| | | 366 | 296 |
| | | 368 | 298 |
| | | 407 | 337 |
| | | 435 | 365 |
| | | 436 | 366 |
| IgG4-CH1 | 4 | 126 | 9 |
| | | 128 | 11 |
| | | 131 | 14 |
| | | 141 | 24 |
| | | 145 | 28 |
| | | 147 | 30 |
| | | 168 | 51 |
| | | 170 | 53 |
| | | 183 | 66 |
| | | 185 | 68 |
| IgG4-CH2-CH3 | 4 | 349 | 229 |
| | | 354 | 234 |
| | | 366 | 246 |
| | | 368 | 248 |
| | | 407 | 287 |
| | | 435 | 315 |
| | | 436 | 316 |
| Light Chain | | | |
| Kappa | 5 | 116 | 9 |
| | | 118 | 11 |
| | | 121 | 14 |
| | | 131 | 24 |
| | | 135 | 28 |
| | | 164 | 57 |
| | | 176 | 69 |
| | | 178 | 71 |
| | | 214 | 107 |

TABLE 2-continued

Modified Constant Region Amino Acid Positions

| Antibody Isotype - CH region | SEQ ID NO | Numbering according to EU index | Corresponding position for each SEQ ID NO |
|---|---|---|---|
| Lambda | 6 | 116 | 9 |
|  |  | 118 | 11 |
|  |  | 121 | 14 |
|  |  | 131 | 24 |
|  |  | 135 | 28 |
|  |  | 164 | 56 |
|  |  | 176 | 68 |
|  |  | 178 | 70 |
|  |  | 214 | 104 |

Examples of positions, numbered according to the Kabat definition, containing a substitution within the variable region of an IgG heavy or light chain are presented in Table 3 below.

TABLE 3

Modified Variable Region Amino Acid Positions

| Antibody Chain | Numbering according to Kabat definition‡ | Antibody Chain | Numbering according to Kabat definition‡ |
|---|---|---|---|
| Heavy Chain Variable Region | 44 | Light Chain Variable Region | 100 |
|  | 44 |  | 105 |
|  | 45 |  | 87 |
|  | 55 |  | 101 |
|  | 100 |  | 50 |
|  | 98 |  | 46 |
|  | 101 |  | 46 |
|  | 105 |  | 43 |
|  | 106 |  | 57 |

‡Table 3 provides the numbering of the variable regions according to the Kabat definition. FIGS. 15A, 15B, 17A and 17B provide the Kabat numbering of variable regions (Frameworks and CDRS) from several representative antibodies.

Native Cysteines Substituted by Non-Cysteine Amino Acids

In some aspects, native cysteines are replaced by non-cysteine amino acids. In some aspects, interchain cysteines within the HC-LC interface are replaced by non-cysteine amino acids. In some aspects, one or more interchain cysteines are replaced by non-cysteine amino acids in an IgG1, IgG2, IgG3 or IgG4 heavy chain. In some aspects, an IgG1 heavy chain has a substitution of a native cysteine to a non-cysteine amino acid at position 220, where numbering is according to the EU index. In some aspects, an IgG2 heavy chain has a substitution of a native cysteine to a non-cysteine amino acid at position 131 and/or 219 and/or 220, where numbering is according to the EU index. In some aspects, an IgG3 or IgG4 heavy chain has a substitution of a native cysteine to a non-cysteine amino acid at position 131, where numbering is according to the EU index. In some aspects, an interchain cysteine is replaced by a non-cysteine amino acid in an IgG light chain. In some aspects, the light chain is a kappa light chain and in some aspects the light chain is a lambda light chain. In some aspects, an IgG light chain has a substitution of a native cysteine to a non-cysteine amino acid at position 214, where numbering is according to the EU index. Such non-cysteine amino acids include, in some aspects, naturally occurring and/or non-classical amino acids.

Naturally occurring non-cysteine amino acids include glycine, alanine, valine, leucine, isoleucine, proline, serine, threonine, methionine, histidine, lysine, arginine, glutamate, aspartate, glutamine, asparagine, phenylalanine, tyrosine and tryptophan. Non-classical amino acids can sometimes be incorporated via cellular expression systems (e.g., pro-karyotic and/or eukaryotic expression systems). Examples of non-classical amino acids include ornithine, diaminobutyric acid, norleucine, pyrylalanine, thienylalanine, naphthylalanine and phenylglycine. Other examples of non-classical amino acids are alpha and alpha-disubstituted amino acids, N-alkyl amino acids, lactic acid*, halide derivatives of natural amino acids such as trifluorotyrosine*, p-X-phenylalanine (where X is a halide such as F, Cl, Br, or I)*, allylglycine*, 7-aminoheptanoic acid*, methionine sulfone*, norleucine*, norvaline*, p-nitrophenylalanine*, hydroxyproline#, thioproline*, methyl derivatives of phenylalanine (Phe) such as 4-methyl-Phe*, pentamethyl-Phe*, Phe (4-amino)#, Tyr (methyl)*, Phe (4-isopropyl)*, Tic (1,2,3,4-tetrahydroisoquinoline-3-carboxyl acid)*, diaminopropionic acid, Phe (4-benzyl)*, 4-aminobutyric acid (gamma-Abu)*, 2-aminobutyric acid (alpha-Abu)*, 6-aminohexanoic acid (epsilon-Ahx)*, 2-aminoisobutyric acid (Aib)*, 3-aminopropionic acid*, norvaline*, hydroxyproline, sarcosine, citrulline, homocitrulline, cysteic acid, t-butylglycine*, t-butylalanine*, phenylglycine*, cyclohexylalanine*, fluoroamino acids, designer amino acids such as beta-methyl amino acids, and the like. The notation * indicates a derivative having hydrophobic characteristics and # indicates a derivative having hydrophilic characteristics.

In certain aspects, HC-LC interchain cysteines are replaced by valine or alanine. In some aspects, the amino acid at position 220 in an IgG1 heavy chain is replaced by valine or alanine. In some aspects, the amino acid at position 131 and/or 219 and/or 220 in an IgG2 heavy chain is replaced by valine or alanine. In some aspects, the amino acid at position 131 in an IgG3 or IgG4 heavy chain is replaced by valine or alanine. In some aspects, the amino acid at position 214 in an IgG light chain is replaced by valine.

Native Non-Cysteine Amino Acids Substituted by Cysteine

In some aspects, native non-cysteine amino acids are replaced by cysteine amino acids. In some aspects, native non-cysteine amino acids are replaced by cysteine amino acids within the HC and LC regions. Native non-cysteine amino acids can be replaced by cysteine amino acids at any position within the CH1 region and the CL region that contains a native non-cysteine amino acid. Such positions, in some aspects, are permissive to interchain disulphide bond formation when the native amino acid is substituted by a cysteine amino acid. In some aspects, a native non-cysteine amino acid is replaced by a cysteine amino acid in an IgG1, IgG2, IgG3 or IgG4 heavy chain. In some aspects, an IgG1, IgG2, IgG3 or IgG4 heavy chain has a substitution of a native non-cysteine amino acid to a cysteine amino acid at position 141, where numbering is according to the EU index. In some aspects, an IgG1, IgG2, IgG3 or IgG4 heavy chain has a substitution of a native non-cysteine amino acid to a cysteine amino acid at position 168, where numbering is according to the EU index. In some aspects, an IgG1, IgG2, IgG3 or IgG4 heavy chain has a substitution of a native non-cysteine amino acid to a cysteine amino acid at position 126, where numbering is according to the EU index. In some aspects, an IgG1, IgG2, IgG3 or IgG4 heavy chain has a substitution of a native non-cysteine amino acid to a cysteine amino acid at position 128, where numbering is according to the EU index.

In some aspects, a native non-cysteine amino acid is replaced by a cysteine amino acid in an IgG light chain. In some aspects, the light chain is a kappa light chain and in some aspects the light chain is a lambda light chain. In some aspects, an IgG light chain has a substitution of a native non-cysteine amino acid to a cysteine amino acid at position 116, where numbering is according to the EU index. In some aspects, an IgG light chain has a substitution of a native non-cysteine amino acid to a cysteine amino acid at position 164, where numbering is according to the EU index. In some aspects, an IgG light chain has a substitution of a native non-cysteine amino acid to a cysteine amino acid at position 121, where numbering is according to the EU index. In some aspects, an IgG light chain has a substitution of a native non-cysteine amino acid to a cysteine amino acid at position 118, where numbering is according to the EU index.

In some aspects, the alanine at position 141 is substituted by a cysteine in an IgG1, IgG2, IgG3 or IgG4 heavy chain. In some aspects, the histidine at position 168 is substituted by a cysteine in an IgG1, IgG2, IgG3 or IgG4 heavy chain. In some aspects, the phenylalanine at position 126 is substituted by a cysteine in an IgG1, IgG2, IgG3 or IgG4 heavy chain. In some aspects, the leucine at position 128 is substituted by a cysteine in an IgG1, IgG2, IgG3 or IgG4 heavy chain. In some aspects, the phenylalanine or threonine at position 116 is substituted by a cysteine in an IgG light chain. In some aspects, the threonine or lysine at position 164 is substituted by a cysteine in an IgG light chain. In some aspects, the serine at position 121 is substituted by a cysteine in an IgG light chain. In some aspects, the phenylalanine at position 118 is substituted by a cysteine in an IgG light chain.

In some aspects, native non-cysteine amino acids are replaced by cysteine amino acids within the VH and VL regions. Native non-cysteine amino acids can be replaced by cysteine amino acids at any position within the VH region and the VL region that contains a native non-cysteine amino acid. Such positions, in some aspects, are permissive to interchain disulphide bond formation when the native amino acid is substituted by a cysteine amino acid. In some aspects, a native non-cysteine amino acid is replaced by a cysteine amino acid in an IgG1, IgG2, IgG3 or IgG4 heavy chain variable region. In some aspects, a native non-cysteine amino acid is replaced by a cysteine amino acid within the variable region of the VH and VL at a position known in the art, see for example Brinkmann et al., 1993, PNAS, 90:7538-42; Zhu et al., 1997, Prot. Sci. 6:781-8; Reiter et al., 1994, Biochem. 33:5451-9; Reiter et al., 1996, Nature 14: 1239-45; Luo et al., 1995, J. Biochem. 118:825-31; Young et al., 1995, FEBS Let. 377:135-9; Glockshuber et al., 1990, Biochem. 29:1362-7. In some aspects, an IgG1, IgG2, IgG3 or IgG4 heavy chain has a substitution of a native non-cysteine amino acid to a cysteine amino acid at position 37 of the variable region, where numbering is according to the Kabat index. In some aspects, an IgG1, IgG2, IgG3 or IgG4 heavy chain has a substitution of a native non-cysteine amino acid to a cysteine amino acid at position 44 of the variable region, where numbering is according to the Kabat index. In some aspects, an IgG1, IgG2, IgG3 or IgG4 heavy chain has a substitution of a native non-cysteine amino acid to a cysteine amino acid at position 45 of the variable region, where numbering is according to the Kabat index. In some aspects, an IgG1, IgG2, IgG3 or IgG4 heavy chain has a substitution of a native non-cysteine amino acid to a cysteine amino acid at position 55 of the variable region, where numbering is according to the Kabat index. In some aspects, an IgG1, IgG2, IgG3 or IgG4 heavy chain has a substitution of a native non-cysteine amino acid to a cysteine amino acid at position 98 of the variable region, where numbering is according to the Kabat index. In some aspects, an IgG1, IgG2, IgG3 or IgG4 heavy chain has a substitution of a native non-cysteine amino acid to a cysteine amino acid at position 100 of the variable region, where numbering is according to the Kabat index. In some aspects, an IgG1, IgG2, IgG3 or IgG4 heavy chain has a substitution of a native non-cysteine amino acid to a cysteine amino acid at position 101 of the variable region, where numbering is according to the Kabat index. In some aspects, an IgG1, IgG2, IgG3 or IgG4 heavy chain has a substitution of a native non-cysteine amino acid to a cysteine amino acid at position 105 of the variable region, where numbering is according to the Kabat index. In some aspects, an IgG1, IgG2, IgG3 or IgG4 heavy chain has a substitution of a native non-cysteine amino acid to a cysteine amino acid at position 106 of the variable region, where numbering is according to the Kabat index.

In some aspects, a native non-cysteine amino acid is replaced by a cysteine amino acid in an IgG light chain variable region. In some aspects, an IgG light chain has a substitution of a native non-cysteine amino acid to a cysteine amino acid at position 43 of the variable region, where numbering is according to the Kabat index. In some aspects, an IgG light chain has a substitution of a native non-cysteine amino acid to a cysteine amino acid at position 46 of the variable region, where numbering is according to the Kabat index. In some aspects, an IgG light chain has a substitution of a native non-cysteine amino acid to a cysteine amino acid at position 50 of the variable region, where numbering is according to the Kabat index. In some aspects, an IgG light chain has a substitution of a native non-cysteine amino acid to a cysteine amino acid at position 57 of the variable region, where numbering is according to the Kabat index. In some aspects, an IgG light chain has a substitution of a native non-cysteine amino acid to a cysteine amino acid at position 87 of the variable region, where numbering is according to the Kabat index. In some aspects, an IgG light chain has a substitution of a native non-cysteine amino acid to a cysteine amino acid at position 95 of the variable region, where numbering is according to the Kabat index. In some aspects, an IgG light chain has a substitution of a native non-cysteine amino acid to a cysteine amino acid at position 100 of the variable region, where numbering is according to the Kabat index. In some aspects, an IgG light chain has a substitution of a native non-cysteine amino acid to a cysteine amino acid at position 101 of the variable region, where numbering is according to the Kabat index. In some aspects, an IgG light chain has a substitution of a native non-cysteine amino acid to a cysteine amino acid at position 105 of the variable region, where numbering is according to the Kabat index.

Protrusions and Cavities

In some aspects substitution of at least one amino acid generates a protrusion and/or a cavity. Amino acid substitutions which generate a protrusion and/or a cavity may be at any positions within the CH1 region and/or the CL region. In some aspects, the substitution of at least one amino acid generates a protrusion and/or a cavity within the CH1 region and generates a compensatory cavity and/or protrusion within the CL region. Such substitutions, in certain aspects, favor the interchain pairing of the CH1 comprising the cavity and/or protrusion and the CL comprising the compensatory cavity and/or protrusion. In certain aspects, in addition to the substitution(s) generating a protrusion and/or a cavity, the CH1 and CL comprise further substitutions replacing the interchain cysteines within the HC-LC interface with non-cysteine amino acids as described above.

In some aspects substitution of at least one amino acid generates a protrusion and/or a cavity in an IgG1, IgG2, IgG3 or IgG4 heavy chain. In some aspects, position 145 of an IgG1, IgG2, IgG3 or IgG4 heavy chain is substituted with an amino acid having a large side chain where numbering is according to the EU index. In some aspects, position 183 of an IgG1, IgG2, IgG3 or IgG4 heavy chain is substituted with an amino acid having a large side chain where numbering is according to the EU index. In some aspects, position 185 of an IgG1, IgG2, IgG3 or IgG4 heavy chain is substituted with an amino acid having a large side chain where numbering is according to the EU index. In some aspects, position 147 of an IgG1, IgG2, IgG3 or IgG4 heavy chain is substituted with an amino acid having a small side chain where numbering is according to the EU index. In some aspects, position 170 of an IgG1, IgG2, IgG3 or IgG4 heavy chain is substituted with an amino acid having a small side chain where numbering is according to the EU index. In some aspects, position 147 is substituted with an amino acid having a small side chain and position 185 is substituted with an amino acid having a large side chain in an IgG1, IgG2, IgG3 or IgG4 heavy chain where numbering is according to the EU index. In some aspects, position 145 is substituted with an amino acid having a large side chain, position 170 is substituted with an amino acid having a small side chain, position 183 is substituted with an amino acid having a large side chain, and position 185 is substituted with an amino acid having a large side chain in an IgG1, IgG2, IgG3 or IgG4 heavy chain where numbering is according to the EU index. In certain aspects, in addition to the substitution(s) generating a protrusion and/or a cavity, the IgG1, IgG2, IgG3 or IgG4 heavy chain further comprises the substitution of the interchain cysteines with non-cysteine amino acids as described above.

In some aspects substitution of at least one amino acid generates a protrusion and/or a cavity in an IgG light chain. In some aspects, the light chain is a kappa light chain and in some aspects the light chain is a lambda light chain. In some aspects, position 131 of an IgG light chain is substituted with an amino acid having a large side chain where numbering is according to the EU index. In some aspects, position 176 of an IgG light chain is substituted with an amino acid having a large side chain where numbering is according to the EU index. In some aspects, position 135 of an IgG light chain is substituted with an amino acid having a small side chain where numbering is according to the EU index. In some aspects, position 178 of an IgG light chain is substituted with an amino acid having a small side chain where numbering is according to the EU index. In some aspects, position 131 is substituted with an amino acid having a large side chain and position 135 is substituted with an amino acid having a small side chain in an IgG light chain where numbering is according to the EU index. In some aspects, position 176 is substituted with an amino acid having a large side chain and position 178 is substituted with an amino acid having a small side chain in an IgG light chain where numbering is according to the EU index. In certain aspects, in addition to the substitution(s) generating a protrusion and/or a cavity, the IgG light chain further comprises the substitution of the interchain cysteines with non-cysteine amino acids as described above.

In one aspect, the leucine at position 145 is substituted with a phenylalanine in an IgG1, IgG2, IgG3 or IgG4 heavy chain where numbering is according to the EU index, In one aspect, the lysine at position 147 is substituted with an alanine in an IgG1, IgG2, IgG3 or IgG4 heavy chain where numbering is according to the EU index. In one aspect, the phenylalanine position 170 is substituted with valine in an IgG1, IgG2, IgG3 or IgG4 heavy chain where numbering is according to the EU index, In one aspect, the serine at position 183 is substituted with phenylalanine in an IgG1, IgG2, IgG3 or IgG4 heavy chain where numbering is according to the EU index. In one aspect, the valine at position 185 is substituted with a tryptophan or phenylalanine in an IgG1, IgG2, IgG3 or IgG4 heavy chain where numbering is according to the EU index. In one aspect, the valine at position 185 is substituted with a tryptophan and the lysine at position 147 is substituted with an alanine in an IgG1, IgG2, IgG3 or IgG4 heavy chain where numbering is according to the EU index. In one aspect, the leucine at position 145 is substituted with a phenylalanine, the phenylalanine at position 170 is substituted with valine, the serine at position 183 is substituted with phenylalanine, and the valine at position 185 is substituted with a phenylalanine in an IgG1, IgG2, IgG3 or IgG4 heavy chain where numbering is according to the EU index. In certain aspects, in addition to the substitutition(s) generating a protrusion and/or a cavity, the IgG1, IgG2, IgG3 or IgG4 heavy chain further comprises the substitution of the interchain cysteines with non-cysteine amino acids as described above.

In one aspect, the serine at position 131 of a kappa light chain or the threonine at position 131 of a lambda light chain is substituted with tryptophan where numbering is according to the EU index. In one aspect, the serine at position 176 of a kappa or lambda light chain is substituted with a phenylalanine where numbering is according to the EU index. In one aspect, the leucine at position 135 of a kappa or lambda light chain is substituted with a glycine where numbering is according to the EU index. In one aspect, the threonine at position 178 of an kappa light chain or the tyrosine at position 178 of a lambda light chain is substituted with an alanine where numbering is according to the EU index. In some aspects, the serine at position 131 is substituted with an tryptophane and the leucine at position 135 is substituted with an alanine in a kappa light chain where numbering is according to the EU index. In some aspects, the serine at position 176 is substituted with phenylalanine and the threonine at position 178 is substituted with alanine in a kappa light chain where numbering is according to the EU index.

In some aspects, the threonine at position 131 is substituted with a tryptophane and the leucine at position 135 is substituted with an alanine in a lambda light chain where numbering is according to the EU index. In some aspects, the serine at position 176 is substituted with phenylalanine and the tyrosine at position 178 is substituted with alanine in a lambda light chain where numbering is according to the EU index. In certain aspects, in addition to the substitutition(s) generating a protrusion and/or a cavity, the IgG light chain further comprises the substitution of the interchain cysteines with non-cysteine amino acids as described above.

HC-LC Amino Acid Substitution Combinations

In certain aspects, combinations of substitutions are made in an IgG heavy chain and corresponding light chain. Often, such combinations of substitutions result in the removal of native cysteines that typically form a disulphide bridge between the heavy and light chain within HC and LC regions and the generation of a new pair of cysteines capable of forming a disulphide bridge at a different location within the HC-LC interface. The new pair of cysteines may be located within the variable regions and/or the CH1-LC of the heavy and light chains. Such combinations of substitutions are summarized in Table 4 below. Position numbering is according to the EU index for the constant regions and according to the Kabat index for the variable regions. Although not specifically indicated in Table 4, the light chain may be a kappa (κ) or lambda (λ) light chain.

In certain aspects, a bispecific antibody of the invention will comprise two different heavy chains of the same Ig type (e.g., two IgG1 heavy chains, one with a modification of a cysteine residue and one without such a modification) and two different light chains (e.g., one with a modification of a cysteine residue and one without such a modification), which may be any combination of kappa and/or lambda (i.e. two kappa light chains, two lambda light chain, or one lambda and one kappa light chain). In a particular aspect, a bispecific antibody of the invention will comprise two different heavy chains of the same Ig type and one lambda light chain and one kappa light chain.

While the use of the various modifications described herein greatly enhances the formation of bivalent antibodies, some mis-paired antibodies may arise due to mis-pairing of the heavy and light chains or due to homo-dimerization of the heavy chains. The presence of two different light chain constant regions provides a convenient means of removing any mis-paired antibodies having the same light chain through the use of affinity chromatography media (e.g., resins) specific for the kappa or lambda type light chains. Affinity chromatography media that specifically interact with the kappa or lambda light chain constant domains are known in the art (e.g., CaptureSelect Kappa and CaptureSelect Lambda affinity matrices (BAC BV, Holland)). In certain aspects, only one type of LC-mispaired byproduct is formed due to excess of only one light chain. Therefore, if the excess light chain is kappa the LC-byproduct will be removed using an affinity chromatography media specific for the lambda light chain and if the excess light chain is lambda the byproduct will be removed using an affinity chromatography media specific for the kappa light chain.

Alternatively, or optionally light chain specific affinity media can be used in multi-step process to purify antibodies having one kappa light chain and one lambda light chain. A representative three step process is provided by way of example: (1) protein A and/or G resin, as appropriate, is used capture IgG (all IgG including mis-paired product will bind to protein A and/or G); (2) the antibodies from the protein A and/or G media are passed over a kappa specific media to capture IgG containing kappa light chain(s) (all IgG comprises one or two kappa light chains will bind a kappa specific media while antibodies comprising two lambda chains will flow through), (3) the antibodies from the kappa specific media are passed over a lambda specific media to capture IgG containing a lambda light chain (antibodies comprising two kappa chains will flow through). It should be noted that the order of the steps can be altered and further that certain steps can be eliminated and/or replaced with other chromatography methods useful in the purification of antibodies from contaminates (e.g., host cell proteins). A representative two step process is exemplified in the Examples provided herein. Also see, International Patent Publication WO 2012/023053 and the Examples provided herein.

Amino acid substitutions as described herein (e.g., of native amino acid residues, cysteine and/or non-cysteine amino acid residues) can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbor Laboratory Press, Cold Spring Harbour, N.Y., 1989; Ausbel et al., Current Protocols in Molecular Biology, Greene Publishing & Wiley-Interscience, NY, 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

TABLE 4

Amino acid substitution combinations

| Variant | Ig Type | Position(s) in VH† | Position(s) in CH1‡ | Position(s) in VL† | Position(s) in CL‡ |
|---|---|---|---|---|---|
| V1 | IgG1 | | 147 to small side chain<br>185 to large side chain<br>Optional: 220 native Cys to non-Cys | | 131 to large side chain<br>135 to small side chain<br>Optional: 214 native Cys to non-Cys |
| V1-2a | IgG2 | | 147 to small side chain<br>185 to large side chain<br>Optional: 131 native Cys to non-Cys; 219 native Cys to non-Cys; 220 native Cys to non-Cys | | 131 to large side chain<br>135 to small side chain<br>Optional: 214 native Cys to non-Cys |
| V1-2b | IgG2 | | 147 to small side chain<br>185 to large side chain<br>Optional: 131 native Cys to non-Cys; 220 native Cys to non-Cys | | 131 to large side chain<br>135 to small side chain<br>Optional: 214 native Cys to non-Cys |
| V1-3 | IgG3 | | 147 to small side chain<br>185 to large side chain<br>Optional: 131 native Cys to non-Cys | | 131 to large side chain<br>135 to small side chain<br>Optional: 214 native Cys to non-Cys |
| V1-4 | IgG4 | | 147 to small side chain<br>185 to large side chain<br>Optional: 131 native Cys to non-Cys | | 131 to large side chain<br>135 to small side chain<br>Optional: 214 native Cys to non-Cys |
| V3 | IgG1 | | 145 to large side chain<br>170 to small side chain<br>183 to large side chain<br>185 to large side chain<br>Optional: 220 native Cys to non-Cys | | 176 to large side chain<br>178 to small side chain<br>Optional: 214 native Cys to non-Cys |

TABLE 4-continued

| | | Amino acid substitution combinations | | | |
|---|---|---|---|---|---|
| Variant | Ig Type | Position(s) in VH† | Position(s) in CH1‡ | Position(s) in VL† | Position(s) in CL‡ |
| V3-2a | IgG2 | | 145 to large side chain<br>170 to small side chain<br>183 to large side chain<br>185 to large side chain<br>Optional: 131 native Cys to non-Cys; 219 native Cys to non-Cys; 220 native Cys to non-Cys | | 176 to large side chain<br>178 to small side chain<br>Optional: 214 native Cys to non-Cys |
| V3-2b | IgG2 | | 145 to large side chain<br>170 to small side chain<br>183 to large side chain<br>185 to large side chain<br>Optional: 131 native Cys to non-Cys; 220 native Cys to non-Cys | | 176 to large side chain<br>178 to small side chain<br>Optional: 214 native Cys to non-Cys |
| V3-3 | IgG3 | | 145 to large side chain<br>170 to small side chain<br>183 to large side chain<br>185 to large side chain<br>Optional: 131 native Cys to non-Cys | | 176 to large side chain<br>178 to small side chain<br>Optional: 214 native Cys to non-Cys |
| V3-4 | IgG4 | | 145 to large side chain<br>170 to small side chain<br>183 to large side chain<br>185 to large side chain<br>Optional: 131 native Cys to non-Cys | | 176 to large side chain<br>178 to small side chain<br>Optional: 214 native Cys to non-Cys |
| V10 | IgG1 | | 141 native non-Cys to Cys<br>220 native Cys to non-Cys | | 116 native non-Cys to Cys<br>214 native Cys to non-Cys |
| V10-2a | IgG2 | | 141 native non-Cys to Cys<br>131 native Cys to non-Cys<br>219 native Cys to non-Cys<br>220 native Cys to non-Cys | | 116 native non-Cys to Cys<br>214 native Cys to non-Cys |
| V10-2b | IgG2 | | 141 native non-Cys to Cys<br>131 native Cys to non-Cys<br>220 native Cys to non-Cys | | 116 native non-Cys to Cys<br>214 native Cys to non-Cys |
| V10-3 | IgG3 | | 141 native non-Cys to Cys<br>131 native Cys to non-Cys | | 116 native non-Cys to Cys<br>214 native Cys to non-Cys |
| V10-4 | IgG4 | | 141 native non-Cys to Cys<br>131 native Cys to non-Cys | | 116 native non-Cys to Cys<br>214 native Cys to non-Cys |
| V11 | IgG1 | | 168 native non-Cys to Cys<br>220 native Cys to non-Cys | | 164 native non-Cys to Cys<br>214 native Cys to non-Cys |
| V11-2a | IgG2 | | 168 native non-Cys to Cys<br>131 native Cys to non-Cys<br>219 native Cys to non-Cys<br>220 native Cys to non-Cys | | 164 native non-Cys to Cys<br>214 native Cys to non-Cys |
| V11-2b | IgG2 | | 168 native non-Cys to Cys<br>131 native Cys to non-Cys<br>220 native Cys to non-Cys | | 164 native non-Cys to Cys<br>214 native Cys to non-Cys |
| V11-3 | IgG3 | | 168 native non-Cys to Cys<br>131 native Cys to non-Cys | | 164 native non-Cys to Cys<br>214 native Cys to non-Cys |
| V11-4 | IgG4 | | 168 native non-Cys to Cys<br>131 native Cys to non-Cys | | 164 native non-Cys to Cys<br>214 native Cys to non-Cys |
| V12 | IgG1 | | 126 native non-Cys to Cys<br>220 native Cys to non-Cys | | 121 native non-Cys to Cys<br>214 native Cys to non-Cys |
| V12-2a | IgG2 | | 126 native non-Cys to Cys<br>131 native Cys to non-Cys<br>219 native Cys to non-Cys<br>220 native Cys to non-Cys | | 121 native non-Cys to Cys<br>214 native Cys to non-Cys |
| V12-2b | IgG2 | | 126 native non-Cys to Cys<br>131 native Cys to non-Cys<br>220 native Cys to non-Cys | | 121 native non-Cys to Cys<br>214 native Cys to non-Cys |
| V12-3 | IgG3 | | 126 native non-Cys to Cys<br>131 native Cys to non-Cys | | 121 native non-Cys to Cys<br>214 native Cys to non-Cys |
| V12-4 | IgG4 | | 126 native non-Cys to Cys<br>131 native Cys to non-Cys | | 121 native non-Cys to Cys<br>214 native Cys to non-Cys |
| VN | IgG1 | | 128 native non-Cys to Cys<br>220 native Cys to non-Cys | | 118 native non-Cys to Cys<br>214 native Cys to non-Cys |
| VN-2a | IgG2 | | 128 native non-Cys to Cys<br>131 native Cys to non-Cys<br>219 native Cys to non-Cys<br>220 native Cys to non-Cys | | 118 native non-Cys to Cys<br>214 native Cys to non-Cys |
| VN-2b | IgG2 | | 128 native non-Cys to Cys<br>131 native Cys to non-Cys<br>220 native Cys to non-Cys | | 118 native non-Cys to Cys<br>214 native Cys to non-Cys |

TABLE 4-continued

Amino acid substitution combinations

| Variant | Ig Type | Position(s) in VH† | Position(s) in CH1‡ | Position(s) in VL† | Position(s) in CL‡ |
|---|---|---|---|---|---|
| VN-3 | IgG3 | | 128 native non-Cys to Cys<br>131 native Cys to non-Cys | | 118 native non-Cys to Cys<br>214 native Cys to non-Cys |
| VN-4 | IgG4 | | 128 native non-Cys to Cys<br>131 native Cys to non-Cys | | 118 native non-Cys to Cys<br>214 native Cys to non-Cys |
| VVa-1 | IgG1 | 37 native non-Cys to Cys | 220 native Cys to non-Cys | 95 native non-Cys to Cys | 214 native Cys to non-Cys |
| VVa-2a | IgG2 | 37 native non-Cys to Cys | 131 native Cys to non-Cys<br>219 native Cys to non-Cys<br>220 native Cys to non-Cys | 95 native non-Cys to Cys | 214 native Cys to non-Cys |
| VVa-2b | IgG2 | 37 native non-Cys to Cys | 131 native Cys to non-Cys<br>220 native Cys to non-Cys | 95 native non-Cys to Cys | 214 native Cys to non-Cys |
| VVa-3 | IgG3 | 37 native non-Cys to Cys | 131 native Cys to non-Cys | 95 native non-Cys to Cys | 214 native Cys to non-Cys |
| VVa-4 | IgG4 | 37 native non-Cys to Cys | 131 native Cys to non-Cys | 95 native non-Cys to Cys | 214 native Cys to non-Cys |
| VVb-1 | IgG1 | 44 native non-Cys to Cys | 220 native Cys to non-Cys | 100 native non-Cys to Cys | 214 native Cys to non-Cys |
| VVb-2a | IgG2 | 44 native non-Cys to Cys | 131 native Cys to non-Cys<br>219 native Cys to non-Cys<br>220 native Cys to non-Cys | 100 native non-Cys to Cys | 214 native Cys to non-Cys |
| VVb-2b | IgG2 | 44 native non-Cys to Cys | 131 native Cys to non-Cys<br>220 native Cys to non-Cys | 100 native non-Cys to Cys | 214 native Cys to non-Cys |
| VVb-3 | IgG3 | 44 native non-Cys to Cys | 131 native Cys to non-Cys | 100 native non-Cys to Cys | 214 native Cys to non-Cys |
| VVb-4 | IgG4 | 44 native non-Cys to Cys | 131 native Cys to non-Cys | 100 native non-Cys to Cys | 214 native Cys to non-Cys |
| VVc-1 | IgG1 | 44 native non-Cys to Cys | 220 native Cys to non-Cys | 105 native non-Cys to Cys | 214 native Cys to non-Cys |
| VVc-2a | IgG2 | 44 native non-Cys to Cys | 131 native Cys to non-Cys<br>219 native Cys to non-Cys<br>220 native Cys to non-Cys | 105 native non-Cys to Cys | 214 native Cys to non-Cys |
| VVc-2b | IgG2 | 44 native non-Cys to Cys | 131 native Cys to non-Cys<br>220 native Cys to non-Cys | 105 native non-Cys to Cys | 214 native Cys to non-Cys |
| VVc-3 | IgG3 | 44 native non-Cys to Cys | 131 native Cys to non-Cys | 105 native non-Cys to Cys | 214 native Cys to non-Cys |
| VVc-4 | IgG4 | 44 native non-Cys to Cys | 131 native Cys to non-Cys | 105 native non-Cys to Cys | 214 native Cys to non-Cys |
| VVd-1 | IgG1 | 45 native non-Cys to Cys | 220 native Cys to non-Cys | 87 native non-Cys to Cys | 214 native Cys to non-Cys |
| VVd-2a | IgG2 | 45 native non-Cys to Cys | 131 native Cys to non-Cys<br>219 native Cys to non-Cys<br>220 native Cys to non-Cys | 87 native non-Cys to Cys | 214 native Cys to non-Cys |
| VVd-2b | IgG2 | 45 native non-Cys to Cys | 131 native Cys to non-Cys<br>220 native Cys to non-Cys | 87 native non-Cys to Cys | 214 native Cys to non-Cys |
| VVd-3 | IgG3 | 45 native non-Cys to Cys | 131 native Cys to non-Cys | 87 native non-Cys to Cys | 214 native Cys to non-Cys |
| VVd-4 | IgG4 | 45 native non-Cys to Cys | 131 native Cys to non-Cys | 87 native non-Cys to Cys | 214 native Cys to non-Cys |
| VVe-1 | IgG1 | 55 native non-Cys to Cys | 220 native Cys to non-Cys | 101 native non-Cys to Cys | 214 native Cys to non-Cys |
| VVe-2a | IgG2 | 55 native non-Cys to Cys | 131 native Cys to non-Cys<br>219 native Cys to non-Cys<br>220 native Cys to non-Cys | 101 native non-Cys to Cys | 214 native Cys to non-Cys |
| VVe-2b | IgG2 | 55 native non-Cys to Cys | 131 native Cys to non-Cys<br>220 native Cys to non-Cys | 101 native non-Cys to Cys | 214 native Cys to non-Cys |
| VVe-3 | IgG3 | 55 native non-Cys to Cys | 131 native Cys to non-Cys | 101 native non-Cys to Cys | 214 native Cys to non-Cys |
| VVe-4 | IgG4 | 55 native non-Cys to Cys | 131 native Cys to non-Cys | 101 native non-Cys to Cys | 214 native Cys to non-Cys |
| VVf-1 | IgG1 | 100 native non-Cys to Cys | 220 native Cys to non-Cys | 50 native non-Cys to Cys | 214 native Cys to non-Cys |
| VVf-2a | IgG2 | 100 native non-Cys to Cys | 131 native Cys to non-Cys<br>219 native Cys to non-Cys<br>220 native Cys to non-Cys | 50 native non-Cys to Cys | 214 native Cys to non-Cys |
| VVf-2b | IgG2 | 100 native non-Cys to Cys | 131 native Cys to non-Cys<br>220 native Cys to non-Cys | 50 native non-Cys to Cys | 214 native Cys to non-Cys |
| VVf-3 | IgG3 | 100 native non-Cys to Cys | 131 native Cys to non-Cys | 50 native non-Cys to Cys | 214 native Cys to non-Cys |
| VVf-4 | IgG4 | 100 native non-Cys to Cys | 131 native Cys to non-Cys | 50 native non-Cys to Cys | 214 native Cys to non-Cys |
| VVg-1 | IgG1 | 98 native non-Cys to Cys | 220 native Cys to non-Cys | 46 native non-Cys to Cys | 214 native Cys to non-Cys |
| VVg-2a | IgG2 | 98 native non-Cys to Cys | 131 native Cys to non-Cys<br>219 native Cys to non-Cys<br>220 native Cys to non-Cys | 46 native non-Cys to Cys | 214 native Cys to non-Cys |
| VVg-2b | IgG2 | 98 native non-Cys to Cys | 131 native Cys to non-Cys<br>220 native Cys to non-Cys | 46 native non-Cys to Cys | 214 native Cys to non-Cys |
| VVg-3 | IgG3 | 98 native non-Cys to Cys | 131 native Cys to non-Cys | 46 native non-Cys to Cys | 214 native Cys to non-Cys |
| VVg-4 | IgG4 | 98 native non-Cys to Cys | 131 native Cys to non-Cys | 46 native non-Cys to Cys | 214 native Cys to non-Cys |
| VVh-1 | IgG1 | 101 native non-Cys to Cys | 220 native Cys to non-Cys | 46 native non-Cys to Cys | 214 native Cys to non-Cys |
| VVh-2a | IgG2 | 101 native non-Cys to Cys | 131 native Cys to non-Cys<br>219 native Cys to non-Cys<br>220 native Cys to non-Cys | 46 native non-Cys to Cys | 214 native Cys to non-Cys |
| VVh-2b | IgG2 | 101 native non-Cys to Cys | 131 native Cys to non-Cys<br>220 native Cys to non-Cys | 46 native non-Cys to Cys | 214 native Cys to non-Cys |
| VVh-3 | IgG3 | 101 native non-Cys to Cys | 131 native Cys to non-Cys | 46 native non-Cys to Cys | 214 native Cys to non-Cys |
| VVh-4 | IgG4 | 101 native non-Cys to Cys | 131 native Cys to non-Cys | 46 native non-Cys to Cys | 214 native Cys to non-Cys |
| VVi-1 | IgG1 | 105 native non-Cys to Cys | 220 native Cys to non-Cys | 43 native non-Cys to Cys | 214 native Cys to non-Cys |
| VVi-2a | IgG2 | 105 native non-Cys to Cys | 131 native Cys to non-Cys<br>219 native Cys to non-Cys<br>220 native Cys to non-Cys | 43 native non-Cys to Cys | 214 native Cys to non-Cys |

TABLE 4-continued

Amino acid substitution combinations

| Variant | Ig Type | Position(s) in VH† | Position(s) in CH1‡ | Position(s) in VL† | Position(s) in CL‡ |
|---|---|---|---|---|---|
| VVi-2b | IgG2 | 105 native non-Cys to Cys | 131 native Cys to non-Cys<br>220 native Cys to non-Cys | 43 native non-Cys to Cys | 214 native Cys to non-Cys |
| VVi-3 | IgG3 | 105 native non-Cys to Cys | 131 native Cys to non-Cys | 43 native non-Cys to Cys | 214 native Cys to non-Cys |
| VVi-4 | IgG4 | 105 native non-Cys to Cys | 131 native Cys to non-Cys | 43 native non-Cys to Cys | 214 native Cys to non-Cys |
| VVj-1 | IgG1 | 106 native non-Cys to Cys | 220 native Cys to non-Cys | 57 native non-Cys to Cys | 214 native Cys to non-Cys |
| VVj-2a | IgG2 | 106 native non-Cys to Cys | 131 native Cys to non-Cys<br>219 native Cys to non-Cys<br>220 native Cys to non-Cys | 57 native non-Cys to Cys | 214 native Cys to non-Cys |
| VVj-2b | IgG2 | 106 native non-Cys to Cys | 131 native Cys to non-Cys<br>220 native Cys to non-Cys | 57 native non-Cys to Cys | 214 native Cys to non-Cys |
| VVj-3 | IgG3 | 106 native non-Cys to Cys | 131 native Cys to non-Cys | 57 native non-Cys to Cys | 214 native Cys to non-Cys |
| VVj-4 | IgG4 | 106 native non-Cys to Cys | 131 native Cys to non-Cys | 57 native non-Cys to Cys | 214 native Cys to non-Cys |

†Numbering the variable regions is as per the Kabat index
‡Numbering of the constant region is as per the EU index Fc Region Modifications Provided herein are antibodies with HC and LC modifications in the variable and/or CH1 and/or CL regions. Also provided, in some aspects, are modified antibodies that further comprise one or more modifications in the Fc region described hereafter. Fc regions comprising one or more modifications are referred to herein as "variant Fc regions."

The interface between a pair of antibody molecules may be engineered to maximize the percentage of heterodimers which are recovered from recombinant cell culture. An appropriate interface comprises at least a part of the CH3 domain. In this method, a "protrusion" (also referred here in as a "Knob") is generated by replacing one or more small amino acid side chains from the interface of the first antibody molecule with larger side chains (e.g. tyrosine or tryptophan). Compensatory "cavities" (also referred to herein as "Holes") of identical or similar size to the large side chain(s) are created on the interface of the second antibody molecule by replacing large amino acid side chains with smaller ones (e.g. alanine or threonine). Alternatively, or additionally, the CH3 region may be modified to include mutations that introduce cysteine residues capable of forming a disulphide bond. These modifications provide a mechanism for increasing the yield of the heterodimer over other unwanted end-products such as homodimers. CH3 modifications to enhance heterodimerization include, for example, Y407V/T366S/L368A on one heavy chain and T366W on the other heavy chain; S354C/T366W on one heavy chain and Y349C/Y407V/T366S/L368A on the other heavy chain. Additional modifications resulting in a protrusion on one chain and a cavity on the other are provided in Table 5 and described in U.S. Pat. No. 7,183,076; and Merchant et al., 1998, Nat. Biotech 16:677-681. Other modifications which may be used to generate heterodimers include but are not limited to those which alter the charge polarity across the Fc dimer interface such that co-expression of electrostatically matched Fc regions results in heterodimerization. Modifications which alter the charge polarity include, but are not limited to, those presented in Table 6 (also see, WO 2007/147901; Gunasekaran et al., 2010, JBC 285:19637-46). In addition, Davis et al. (2010, Prot. Eng. Design & Selection 23:195-202) describe a heterodimeric Fc platform using strand-exchanged engineered domain (SEED) CH3 regions which are derivatives of human IgG and IgA CH3 domains (also, see WO 2007/110205).

TABLE 5

CH3 modifications for heterodimerization‡

| Modification(s) one heavy chain | Modification(s) other heavy chain |
|---|---|
| T366Y | Y407T |
| T366W | Y407A |
| T366Y | Y407T |
| T394W | F405A |
| T366Y/F405A | T394W/Y407T |
| T366W/F405W | T394S/Y407A |
| F405W | T394S |
| D399C | K392C |
| T366W | T366S/L368A/Y407V |
| T366W/D399C | T366S/L368A/K392C/Y407V |
| T366W/K392C | T366S/D399C/L368A/Y407V |
| S354C/T366W | Y349C/T366S/L368A/Y407V |
| Y349C/T366W | S354C/T366S/L368A/Y407V |
| E356C/T366W | Y349C/T366S/L368A/Y407V |
| Y349C/T366W | E356C/T366S/L368A/Y407V |
| E357C/T366W | Y349C/T366S/L368A/Y407V |
| Y349C/T366W | E357C/T366S/L368A/Y407V |

‡Numbering of the constant region is as per the EU index

TABLE 6

CH3 modifications for heterodimerization‡

| Modification(s) one heavy chain | Modification(s) other heavy chain |
|---|---|
| K370E/D399K/K439D | D356K/E357K/K409D |
| K409D | D399K |
| K409E | D399K |
| K409E | D399R |
| K409D | D399R |
| D339K | E356K |
| D399K/E356K | K409D/K392D |
| D399K/E356K | K409D/K439D |
| D399K/E357K | K409D/K370D |
| D399K/E356K/E357K | K409D/K392D/K370D |
| D399K/E357K | K409D/K392D |
| K392D/K409D | D399K |
| K409D/K360D | D399K |

‡Numbering of the constant region is as per the EU index

Any of the CH3 modifications to enhance heterodimerization described herein can be on either chain of the antibodies provided herein so long as one chain has one set of modifications and the other chain has the compensatory modifications. For example, the Y407V/T366S/L368A modifications described above can be in the same heavy chain that contains the CH1 modifications described herein if the T366W modification is in the heavy chain with an unmodified CH1 region. Conversely, the Y407V/T366S/L368A modifications can be in the heavy chain with an unmodified CH1 region if the T366W modification is in the heavy chain that contains the CH1 modifications described herein. In certain aspects, additional mutations useful for increasing/stabilizing heterodimer formation are introduced into the CH2 and/or CH3 regions. In some aspects, one or more residues in the CH2 and/or CH3 region are mutated to cysteine residues capable of forming interchain disulphide linkages between the two heavy chains.

It will be understood by one of skill in the art that antibodies having different variable regions may be expressed at different levels. Therefore, the heavy and/or light chains having different variable regions which make up the MBabs provided herein may be expressed at different levels. Such uneven expression may result in the production of antibodies having a loosely paired homodimeric heavy chains which may be secreted as half antibodies, or may be secreted and subsequently form half antibodies. Provided herein are methods to minimize the production of half antibodies. Specifically, in certain aspects a first heavy chain which is expressed at a higher level than a second heavy chain is engineered to comprise a mutation in the CH2 and/or CH3 region which strongly destabilizes homodimeric pairing. Without being bound by any particular theory, the presence of a mutation which strongly destabilize homodimeric pairs result in the degradation of such pairs rather than secretion, thus minimizing the production of half antibodies. For example, in certain aspects, the T366W mutation is incorporated into the CH3 region of whichever heavy chain is expressed at higher levels and the compensatory Y407V/T366S/L368A modifications are introduced into the other heavy chain. As described herein, additional mutations may be further incorporated into the Fc region to further increase/stabilize heterodimer formation and/or alter effector function and/or alter half-life. In other methods known in the art may also be used to balance the expression levels of the two heavy chains, such as the use of strong/weak promoters.

Residue 435, numbered per the EU index, in the Fc region of IgG is located at the site of interaction with staphylococcal protein A (Deisenhofer, 1981, Biochem. 20:2361-2370) and IgGs comprising H435 and Y436 bind protein A while IgGs comprising R435 and F436 do not bind protein A (Jendeberg et al., 1997, J Immunol Methods 201:25-34). In addition, antibodies comprising H435/Y436 on one heavy chain and R435/F436 on the other heavy chain can be separated from antibodies comprising two heavy chains comprising H435/Y436 on protein A media (see, e.g., WO2010/151792 and Examples provided herein.). Thus, the incorporation of the appropriate mutation into one heavy chain CH3 region provides a mechanism to facilitate the removal of homodimers using protein A chromatography. Accordingly, in some aspects, the antibodies provided herein are IgG1, IgG2 or IgG4 and comprise one heavy chain CH3 region having a mutation that reduces or eliminates protein A binding and one heavy chain that maintains binding to protein A. In other aspects, the antibodies provided herein are IgG3 and comprise one heavy chain CH3 region having a mutation that restores protein A binding and one heavy chain that does not bind to protein A. In certain aspects, the antibodies provided herein comprise one heavy chain CH3 region having H435 and one heavy chain CH3 having R435. In other aspects, the antibodies provided herein comprise one heavy chain CH3 region having H435/Y436 and one heavy chain CH3 having R435/F436.

It is known that the VH3 family variable domain binds protein A. Accordingly, in certain aspects, to prevent the binding of Hole heavy chains carrying a mutation to ablate protein A binding but comprised of VH3 family variable domain a form of protein A that doesn't bind VH3 variable domains is used (e.g., MabSelect SuRe LX protein A, GE Healthcare).

The modifications to alter protein A binding described herein can be on either chain of the antibodies provided herein so long as only one heavy chain is modified at residue 435 alone or in combination with 436 the other chain is wild type at 435. As shown in FIG. 24D, wild type human IgG1, IgG2 and IgG4 each comprise H435/Y436 while wild type human IgG3 comprises R435/F436. Thus, the nature of the mutation will depend on the type of IgG. Specifically, for an IgG1, IgG2 or IgG4 H435R/Y436F mutations will be introduced into one heavy chain CH3, while for an IgG3 435H/F436Y mutations will be introduced into one heavy chain CH3. In certain aspects, an alternative mutation that reduces or eliminates protein A binding is introduced into only one heavy chain of an IgG1, IgG2 or IgG4. In certain other aspects an alternative mutation that restores protein A binding is introduced into only one heavy chain of an IgG3. Alternative substitutions at positions 435 and/or 436 that reduce or ablate protein A binding can be identified, by introducing any of the other 18 standard amino acid residues into the heavy chain CH3 region of a conventional IgG1, IgG2 or IgG4 antibody and screening for loss of protein A binding. Alternative substitutions at positions 435 and/or 436 that restore protein A binding can be identified, by introducing any of the other 18 standard amino acid residues into the heavy chain CH3 region of a conventional IgG3 antibody and screening for protein A binding.

Although certain Fc mutations provided herein enhance the formation of bivalent antibodies (e.g., those provided in Table 5) some mis-paired antibodies may still arise due to homo-dimerization of the heavy chains. In particular, heavy chains having mutation(s) resulting in the formation of a cavity (also referred to herein as a "Hole") are known to form homodimers, especially when in excess (Merchant, et al., 1998, Nat. Biotech. 16:677-681). Accordingly, in some aspects, the Fc mutations useful for increasing heterodimer formation may be combined with Fc mutations useful to alter binding to affinity medias to enhance purification of heavy chain heterodimers. In certain aspects, the antibodies provided herein comprise one heavy chain having Fc mutations resulting in the formation of a "cavity" and CH3 residues R435/F436; and one heavy chain having Fc mutations resulting in the formation of a "protrusion" and CH3 residues H435/Y436. It will be understood from the instant disclosure that depending on the type of IgG one chain or the other will comprise mutations at positions 435 and 436. In a specific aspect, an Mbab is an IgG1, IgG2 or IgG4 and comprises one heavy chain having Fc mutations Y407V/T366S/L368A/H435R and optionally Y436F and one heavy chain having the Fc mutation T366W. In another specific aspect, an Mbab is an IgG3 and comprises one heavy chain having Fc mutations Y407V/T366S/L368A and one heavy chain having the Fc mutation T366W/R435H and optionally F436Y. In another specific aspect, an Mbab is an IgG1, IgG2 or IgG4 and comprises one heavy chain having the Fc mutation Y349C/Y407V/T366S/L368A/H435R and optionally Y436F and one heavy chain having the Fc mutation S354C/T366W. In another specific aspect, an Mbab is an IgG3 and comprises one heavy chain having the Fc mutation Y349C/Y407V/T366S/L368A and one heavy chain having the Fc mutation S354C/T366W/R435H and optionally F436Y.

In certain aspects, the Fc modifications useful for increasing heterodimer formation may be combined with other known Fc modifications useful to alter effector function such as those disclosed in Ghetie et al., 1997, Nat. Biotech. 15:637-40; Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164: 4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; 2004/0002587; and WO 99/58572. Other modifications (e.g., substitutions and/or additions and/or deletions) of the Fc will be readily apparent to one skilled in the art.

In some cases, certain modifications to the Fc region (e.g., amino acid substitutions and/or additions and/or deletions) can enhance or diminish effector function. In certain aspects, variant Fc regions of antibodies exhibit a similar level of inducing effector function as compared to native Fc. In various aspects, an antibody with a variant Fc region exhibits a higher induction of effector function as compared to the same antibody with the native Fc. An antibody with a variant Fc region sometimes exhibits lower induction of effector function as compared to the same antibody with the native Fc. In some aspects, an antibody with a variant Fc region exhibits higher induction of antibody-dependent cell-mediated cytotoxicity (ADCC) as compared to the same antibody with the native Fc. In certain aspects, an antibody with a variant Fc region exhibits lower induction of ADCC as compared to the same antibody with the native Fc. In some aspects, an antibody with a variant Fc region exhibits higher induction of complement-dependent cytotoxicity (CDC) as compared to the same antibody with the native Fc. In some aspects, an antibody with a variant Fc region exhibits lower induction of CDC as compared to the same antibody with the native Fc.

The ability of any particular antibody with a variant Fc region to mediate lysis of a target cell by ADCC can be assayed. To assess ADCC activity, an antibody with a variant Fc region of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Effector cells for such assays may include peripheral blood mononuclear cells (PBMC) and Natural Killer (NK) cells. Specific examples of in vitro ADCC assays are known in the art.

In certain aspects the effector functions elicited by IgG antibodies strongly depend on the carbohydrate moiety linked to the Fc region of the protein (Claudia Ferrara et al., 2006, Biotechnology and Bioengineering 93:851-861). Thus, glycosylation of the Fc region of an antibody described herein can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277: 26733-26740; Shinkawa et al., 2003, J Biol Chem 278:3466-3473; U.S. Pat. Nos. 6,602,684; 6,946,292; 7,064,191; 7,214,775; 7,393,683; 7,425,446; 7,504,256; U.S. Publication. Nos. 2003/0157108; 2003/0003097; 2009/0010921; Potelligent® technology (Biowa, Inc. Princeton, N.J.); GlycoMAb® glycosylation engineering technology (GLYCART biotechnology AG, Zurich, Switzerland)). Accordingly, in one aspect the Fc regions of an antibody described herein comprises altered glycosylation of amino acid residues. In another aspect, the altered glycosylation of the amino acid residues results in lowered effector function. In another aspect, the altered glycosylation of the amino acid residues results in increased effector function. In a specific aspect, the Fc region has reduced fucosylation. In another aspect, the Fc region is afucosylated (see for examples, U.S. Patent Application Publication No. 2005/0226867). In one aspect, these antibodies with increased effector function, specifically ADCC, as generated in host cells (e.g., CHO cells, Lemna minor) engineered to produce highly defucosylated antibody with over 100-fold higher ADCC compared to antibody produced by the parental cells (Mon et al., 2004, Biotechnol Bioeng 88:901-908; Cox et al., 2006, Nat. Biotechnol., 24:1591-7).

The addition of sialic acid to the oligosaccharides on IgG molecules may enhances their anti-inflammatory activity and alter their cytotoxicity (e.g., Keneko et al., Science, 2006, 313:670-673; Scallon et al., Mol. Immuno. 2007 March; 44(7):1524-34). Thus, the efficacy of antibody therapeutics may be optimized by selection of a glycoforra that is best suited to the intended application. The two oligosaccharide chains interposed between the two CH2 domains of antibodies are involved in the binding of the Fc region to its receptors. IgG molecules with increased sialylation exhibit anti-inflammatory properties whereas IgG molecules with reduced sialylation show increased immunostimulatory properties. Therefore, an antibody therapeutic can be "tailor-made" with an appropriate sialylation profile for a particular application. Methods for modulating the sialylation state of antibodies are known in the art (e.g., US Publication No. 2009/0004179 and International Publication No. WO 2007/005786).

In some aspects, the Fc modifications useful for increasing heterodimer formation may be combined with other modifications which are useful to alter the binding properties for an Fc ligand (e.g., an Fc receptor, C1q) relative to a comparable molecule (e.g., a protein having the same amino acid sequence except having a wild type Fc region). Examples of binding properties include but are not limited to, binding specificity, equilibrium dissociation constant ($K_D$), dissociation and association rates ($k_{off}$ and $k_{on}$ respectively), binding affinity and/or avidity. It is generally understood that a binding molecule, such as an antibody, with a low $K_{on}$ may be preferable to a binding molecule with a high $k_{off}$. However, in some instances the value of the $k_{on}$ or $k_{off}$ may be more relevant than the value of the $K_D$. One skilled in the art can determine which kinetic parameter is most important for a given antibody application.

The affinities and binding properties of an Fc region for its ligand may be determined by a variety of in vitro assay methods (biochemical or immunological based assays) known in the art for determining Fc-FcγR interactions, i.e., specific binding of an Fc region to an FcR including but not limited to, equilibrium methods (e.g. enzyme-linked immunoabsorbent assay (ELISA), or radioimmunoassay (RIA)), or kinetics (e.g. BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to colorimetric, spectrometric, spectrophotometric, fluorescent, luminescent, or isotopic labels.

In some aspects, an antibody with a variant Fc region has enhanced binding to one or more Fc ligands relative to the same antibody with the native Fc. In various aspects, the antibody with a variant Fc region has enhanced binding to an Fc receptor. In some aspects, the antibody with a variant Fc region has enhanced binding to the Fc receptor FcγRIIIA. In certain aspects, the antibody with a variant Fc region has enhanced biding to the Fc receptor FcγR IIB The antibody with a variant Fc region sometimes has enhanced binding to C1q relative to the same antibody with the native Fc. In various aspects, the antibody with a variant Fc region has enhanced binding to the Fc receptor FcRn.

In some aspects, an antibody with a variant Fc region has enhanced ADCC activity relative to the same antibody with the native Fc. In certain aspects, an antibody with a variant Fc region has enhanced binding to the Fc receptor FcγRIIIA and has enhanced ADCC activity relative to the same antibody with the native Fc. In some aspects, the antibody with a variant Fc region has both enhanced ADCC activity and enhanced serum half life relative to the same antibody with the native Fc.

In certain aspects, an antibody with a variant Fc region has reduced ADCC activity relative to the same antibody with the native Fc. In various aspects, an antibody with a variant Fc region has reduced binding to the Fc receptor FcγRIIIA and has reduced ADCC activity relative to the same antibody with the native Fc. The antibody with a variant Fc region sometimes has both reduced ADCC activity and enhanced serum half life relative to the same antibody with the native Fc.

In some aspects, an antibody with a variant Fc region has enhanced CDC activity relative to the same antibody with the native Fc. In certain aspects, the antibody with a variant Fc region has both enhanced CDC activity and enhanced serum half life relative to the same antibody with the native Fc. In some aspects, the antibody with a variant Fc region has reduced binding to one or more Fc ligand relative to the same antibody with the native Fc.

In some aspects, the antibody with a variant Fc region has reduced binding to an Fc receptor relative to the same antibody with the native Fc. In certain aspects, the antibody with a variant Fc region has reduced binding to the Fc receptor FcγRIIIA relative to the same antibody with the native Fc. The antibody with a variant Fc region sometimes has reduced binding to the Fc receptor FcRn relative to the same antibody with the native Fc. In some aspects, the antibody with a variant Fc region has reduced binding to C1q relative to the same antibody with the native Fc.

The Fc region can also be modified to increase the half-lives of proteins. An increase in half-life can allow for the reduction in amount of drug given to a patient as well as reducing the frequency of administration. Accordingly, antibodies herein with increased half-lives may be generated by modifying (for example, substituting, deleting, or adding) amino acid residues identified as being involved in the interaction between the Fc and the FcRn receptor (U.S. Pat. No. 7,083,784). In certain aspects, a methionine at position 252, and/or a serine at position 254 and/or a threonine at position 256 of an IgG1 isotype antibody can be changed to tyrosine, threonine and glutamate, respectively, such that the resulting antibody includes tyrosine-252, threonine-254 and glutamate-256 (i.e., M252Y, S254T, T256E). Such an Fc region of an IgG1 antibody includes a YTE modification and counterpart positions can be similarly modified in IgG2, IgG3 and IgG4 antibodies. In addition, the half-life of antibodies herein may be increased by conjugation to PEG or Albumin by techniques known in the art. In certain aspects, the Fc modifications useful for increasing heterodimer formation may be combined with other modifications useful to alter the half-life of the antibody, including but not limited to M252Y and/or S254T and/or T256E and/or with other known Fc modifications useful to alter effector function and/or alter binding to one or more Fc ligand including those described herein.

Antibody Synthesis

An antibody containing relocated interchain cysteines may be produced by any method known in the art for the synthesis of antibodies, in particular, by chemical synthesis or by recombinant expression techniques.

Any antigen can be used to synthesize an antibody. Examples of antigens, or "targets," are described herein. Cells expressing the desired antigen at their cell surface or membranes prepared from such cells can also be used to generate antibodies. Antigens can be produced recombinantly and isolated from in bacterial or eukaryotic cells using standard recombinant DNA methodology. Antigen can be expressed as a tagged (e.g., epitope tag) or other fusion protein to facilitate isolation as well as identification in various assays.

Monoclonal antibodies are highly specific, being directed against a single antigenic site or multiple antigenic sites in the case of multispecific engineered antibodies. Furthermore, in contrast to polyclonal antibody preparations which include different antibodies directed against different determinants (epitopes), each monoclonal antibody is directed against the same determinant on the antigen. In addition to their specificity, the monoclonal antibodies are advantageous in that they may be synthesized uncontaminated by other antibodies.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. In some aspects, an antibody herein is 90% or more monoclonal. Following is a description of representative methods for producing monoclonal antibodies which is not limiting and may be used to produce, for example, monoclonal mammalian, chimeric, humanized, human, domain, diabodies, vaccibodies, linear and multispecific antibodies.

Methods for producing and screening for specific antibodies using hybridoma technology are known in the art. Briefly, mice can be immunized with a target antigen (either the full length protein or a domain thereof, e.g., the extracellular domain or the ligand binding domain) and once an immune response is detected, e.g., antibodies specific for the target antigen are detected in the mouse serum, the mouse spleen is harvested and splenocytes isolated. The splenocytes are then fused by known techniques to any suitable myeloma cells, for example cells from cell line SP20 available from the ATCC. Hybridomas are selected and cloned by limited dilution. Hybridoma clones are then assayed by methods known in the art for cells that secrete antibodies capable of binding a polypeptide of an antibody herein. Ascites fluid, which generally contains high levels of antibodies, can be generated by immunizing mice with positive hybridoma clones.

Accordingly, monoclonal antibodies can be generated by culturing a hybridoma cell secreting an antibody, where the hybridoma is generated by fusing splenocytes isolated from a mouse immunized with a target antigen with myeloma cells and then screening the hybridomas resulting from the fusion for hybridoma clones that secrete an antibody able to bind to a specific target antigen.

Additionally, lymphocytes may be immunized in vitro. After immunization, lymphocytes are isolated and then fused with a myeloma cell line using a suitable fusing agent or fusion partner, such as polyethylene glycol, to form a hybridoma cell. In certain aspects, the selected myeloma cells are those that fuse efficiently, support stable high-level production of antibody by the selected antibody-producing cells, and are sensitive to a selective medium that selects against the unfused parental cells. In one aspect, the myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines for the production of human monoclonal antibodies are also known in the art.

Once hybridoma cells that produce antibodies of the desired specificity, affinity, and/or activity are identified, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal, e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose or Kappa) or ion-exchange chromatography, affinity tags, hydroxylapatite chromatography, gel electrophoresis, dialysis, etc. Exemplary purification methods are described in more detail below.

Antibody fragments which recognize specific target antigen epitopes may be generated by any technique known in the art. For example, Fab and F(ab')2 fragments herein may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies herein can also be generated using various phage display methods known in the art and more fully discussed below, including using antibody libraries derived from human immunoglobulin sequences.

Phage Display Techniques

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to an epitope of interest can be selected or identified with antigen, e.g., using labeled antigen or antigen bound or captured to a solid surface or bead. Phage display methods are known in the art.

After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab') 2 fragments can also be employed using methods known in the art.

To generate whole antibodies, PCR primers including VH or VL nucleotide sequences, a restriction site, and a flanking sequence to protect the restriction site can be used to amplify the VH or VL sequences in scFv clones. Utilizing cloning techniques known in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The vectors for expressing the VH or VL domains sometimes comprise a promoter (e.g., an EF-1α promoter), a secretion signal (e.g. a pelB signal), a cloning site for the variable domain, constant domains, and a selection marker such as neomycin. The VH and/or VL domains may also be cloned into one vector expressing the necessary constant regions. As detailed in the Examples below, the two VL domains may be cloned into one vector expressing the necessary CL regions such that the two light chains may be expressed from a single vector (see, e.g., FIGS. 3A and 3B), and the two VH domains may be cloned into one vector expressing the necessary constant regions such that the two heavy chains may be expressed from a single vector (see, e.g., FIG. 3C). The heavy chain vectors and light chain vectors are then co-transfected into cell lines to generate stable or transient cell lines that express full-length antibodies, e.g., IgG, using techniques known in the art. Non-limiting examples of cloning and expression of monovalent bispecific antibody chains are described in Example 1.

Nucleic Acids

A polynucleotide may be obtained, and the nucleotide sequence of the polynucleotide determined, by any method known in the art. Since the amino acid sequences of antibodies are known, nucleotide sequences encoding these antibodies can be determined using methods known in the art, e.g., nucleotide codons known to encode particular amino acids are assembled in such a way to generate a nucleic acid that encodes the antibody or fragment thereof herein. Such a polynucleotide encoding the antibody may be assembled from chemically synthesized oligonucleotides which, briefly, involves the synthesis of overlapping oligonucleotides containing portions of the sequence encoding the antibody, annealing and ligating of those oligonucleotides, and then amplification of the ligated oligonucleotides by PCR.

In some aspects, a polynucleotide encoding an antibody may be generated from nucleic acid from a suitable source. If a clone containing a nucleic acid encoding a particular antibody is not available, but the sequence of the antibody is known, a nucleic acid encoding the immunoglobulin may be chemically synthesized or obtained from a suitable source (e.g., an antibody cDNA library, or a cDNA library generated from, or nucleic acid, sometimes poly A+ RNA, isolated from, any tissue or cells expressing the antibody by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method known in the art.

Once the nucleotide sequence of the antibody is determined, the nucleotide sequence of the antibody may be manipulated using methods known in the art for the manipulation of nucleotide sequences, e.g., recombinant DNA techniques, site directed mutagenesis, PCR, etc. to generate antibodies having a different amino acid sequence, for example to create amino acid substitutions, deletions, and/or insertions, including, for example, the amino acid substitutions provided herein.

In certain aspects, one or more of the CDRs is inserted within framework regions using recombinant DNA techniques. The framework regions may be naturally occurring or consensus framework regions, and sometimes human framework regions. The polynucleotide generated by the combination of the framework regions and CDRs may encode an antibody that specifically binds to a selected antigen or antigens or epitopes. In some aspects, one or more amino acid substitutions may be made within the framework regions, and the amino acid substitutions may improve binding of the antibody to its antigen. Other alterations to the polynucleotide are encompassed by the present disclosure and/or are known in the art.

Expression Systems

Recombinant expression of an antibody herein, antibody heavy chain, antibody light chain, derivative, analog or fragment thereof, requires construction of an expression vector containing a polynucleotide or polynucleotides that encode the antibody or portion thereof. Once a polynucleotide encoding an antibody or a heavy or light chain of an antibody, or portion thereof, herein has been obtained, the vector for the production of the antibody may be produced by recombinant DNA technology using techniques known in the art. Thus, methods for preparing a protein by expressing a polynucleotide containing an antibody encoding nucleotide sequence are described herein. Methods which are known in the art can be used to construct expression vectors containing antibody coding sequences and appropriate transcriptional and translational control signals. These methods include, for example, in vitro recombinant DNA techniques, synthetic techniques, and in vivo genetic recombination.

Herein provided, thus, are replicable vectors comprising a nucleotide sequence encoding an antibody herein, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody and the variable domain of the antibody may be cloned into such a vector for expression of the entire heavy chain, the entire light chain, or both the entire heavy and light chains. In particular, vectors comprising nucleotides sequences encoding two different light chains which may be any combination of kappa and/or lambda (i.e. two kappa light chains, two lambda light chain, or one lambda and one kappa light chain) are provided. Also provided are vectors comprising nucleotides sequences encoding two different heavy chains both of which may be IgG1, IgG2, IgG3 or IgG4. It is specifically contemplated that these vectors are used in combination for the expression of an antibody as provided herein comprising two different heavy chains and two different light chains.

The expression vector is transferred to a host cell by conventional techniques and the transfected cells are then cultured by conventional techniques to produce an antibody herein. Thus, provided herein are host cells containing a polynucleotide encoding an antibody herein or fragments thereof, or a heavy or light chain thereof, or portion thereof, or a single chain antibody herein, operably linked to a heterologous promoter. In certain aspects for the expression of double-chained antibodies, vectors encoding both the heavy and light chains may be co-expressed in the host cell for expression of the entire immunoglobulin molecule, as detailed below.

A variety of host-expression vector systems may be utilized to express the antibodies herein. Such host-expression systems represent vehicles by which the coding sequences of interest may be produced and subsequently purified, but also represent cells which may, when transformed or transfected with the appropriate nucleotide coding sequences, express an antibody herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Bacterial cells such as *Escherichia coli*, and eukaryotic cells, may be used for the expression of a recombinant antibody. For non-limiting example, mammalian cells such as Chinese hamster ovary cells (CHO), in conjunction with a vector such as the major intermediate early gene promoter element from human cytomegalovirus can be an effective expression system for antibodies.

In bacterial systems, a number of expression vectors may be advantageously selected depending upon the use intended for the antibody being expressed. For example, when a large quantity of such a protein is produced, for the generation of pharmaceutical compositions of an antibody, vectors which direct the expression of high levels of fusion protein products that are readily purified may be desirable. Such vectors include, but are not limited to, the *E. coli* expression vector pUR278, in which the antibody coding sequence may be ligated individually into the vector in frame with the lac Z coding region so that a fusion protein is produced; pIN vectors and the like. PGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis In an insect system, *Autographa californica* nuclear polyhedrosis virus (AcNPV) is used as a vector to express foreign genes. The virus grows in *Spodoptera frugiperda* cells. The antibody coding sequence may be cloned individually into nonessential regions of the virus and placed under control of an AcNPV promoter.

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1or E3) may result in a recombinant virus that is viable and capable of expressing the antibody in infected hosts. Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc.

In some aspects, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, BT483, Hs578T, HTB2, BT2O, NS1 and T47D, NS0 (a murine myeloma cell line that does not endogenously produce any immunoglobulin chains), CRL7O3O and HsS78Bst cells.

For long-term, high-yield production of recombinant proteins, stable expression is appropriate. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may be used to engineer cell lines which express the antibody. Such engineered cell lines may be useful in screening and evaluation of compositions that interact directly or indirectly with the antibody.

In certain aspects, antibodies presented herein are expressed in a cell line with transient expression of the antibody. Transient transfection is a process in which the nucleic acid introduced into a cell does not integrate into the genome or chromosomal DNA of that cell but is maintained as an extrachromosomal element, e.g. as an episome, in the cell. Transcription processes of the nucleic acid of the episome are not affected and a protein encoded by the nucleic acid of the episome is produced.

The cell line, either stable or transiently transfected, is maintained in cell culture medium and conditions known in the art resulting in the expression and production of antibody proteins. In certain aspects, the mammalian cell culture media is based on commercially available media formulations, including, for example, DMEM or Ham's F12. In some aspects, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

In various aspects, the cell lines are maintained using a fed batch method. As used herein, "fed batch method," refers to a method by which a fed batch cell culture is supplied with additional nutrients after first being incubated with a basal medium. For example, a fed batch method may comprise adding supplemental media according to a determined feeding schedule within a given time period. Thus, a "fed batch cell culture" refers to a cell culture where the cells, typically mammalian, and culture medium are supplied to the culturing vessel initially and additional culture nutrients are fed, continuously or in discrete increments, to the culture during culturing, with or without periodic cell and/or product harvest before termination of culture.

The cell culture medium used and the nutrients contained therein are known in the art. In some aspects, the cell culture medium comprises a basal medium and at least one hydrolysate, e.g., soy-based, hydrolysate, a yeast-based hydrolysate, or a combination of the two types of hydrolysates resulting in a modified basal medium. The additional nutrients may sometimes include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the technology herein include BME Basal Medium (Gibco-Invitrogen; Dulbecco's Modified Eagle Medium (DMEM, powder) (Gibco-Invitrogen (#31600)).

In certain aspects, the basal medium may be is serum-free, meaning that the medium contains no serum (e.g., fetal bovine serum (FBS), horse serum, goat serum, or any other animal-derived serum known in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. In certain aspects, the cell culture medium contains a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. In some aspects, the modified basal medium further contains glutamine, e.g., L-glutamine, and/or methotrexate.

In some aspects, antibody production is conducted in large quantity by a bioreactor process using fed-batch, batch, perfusion or continuous feed bioreactor methods known in the art. Large-scale bioreactors have at least 1000 liters of capacity, sometimes about 1,000 to 100,000 liters of capacity. These bioreactors may use agitator impellers to distribute oxygen and nutrients. Small scale bioreactors refers generally to cell culturing in no more than approximately 100 liters in volumetric capacity, and can range from about 1 liter to about 100 liters. Alternatively, single-use bioreactors (SUB) may be used for either large-scale or small scale culturing.

Temperature, pH, agitation, aeration and inoculum density may vary depending upon the host cells used and the recombinant protein expressed. For example, a recombinant protein cell culture may be maintained at a temperature between 30 and 45 degrees Celsius. The pH of the culture medium may be monitored during the culture process such that the pH stays at an optimum level, which may be for certain host cells, within a pH range of 6.0 to 8.0. An impellor driven mixing may be used for such culture methods for agitation. The rotational speed of the impellor may be approximately 50 to 200 cm/sec tip speed, but other airlift or other mixing/aeration systems known in the art may be used, depending on the type of host cell being cultured. Sufficient aeration is provided to maintain a dissolved oxygen concentration of approximately 20% to 80% air saturation in the culture, again, depending upon the selected host cell being cultured. Alternatively, a bioreactor may sparge air or oxygen directly into the culture medium. Other methods of oxygen supply exist, including bubble-free aeration systems employing hollow fiber membrane aerators.

A number of selection systems may be used, including but not limited to, the herpes simplex virus thymidine kinase, glutamine synthetase, hypoxanthine guanine phosphoribosyltransferase, and adenine phosphoribosyltransferase genes can be employed in tk-, gs-, hgprt- or aprt-cells, respectively. Also, antimetabolite resistance can be used as the basis of selection for the following genes: dhfr, which confers resistance to methotrexate gpt, which confers resistance to mycophenolic acid, neo, which confers resistance to the aminoglycoside G-418, and hygro, which confers resistance to hygromycin.

Methods known in the art of recombinant DNA technology may be applied to select the desired recombinant clone including but not limited to, the herpes simplex virus thymidine kinase, glutamine synthetase, hypoxanthine guanine phosphoribosyltransferase, and adenine phosphoribosyltransferase genes can be employed in tk-, gs-, hgprt- or aprt-cells, respectively.

Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods known in the art of recombinant DNA technology may be applied to select the desired recombinant clone.

The expression levels of antibody proteins can be increased by vector amplification. When a marker in the vector system expressing antibody proteins is amplifiable, increase in the level of inhibitor present in culture of host cell may increase the number of copies of the marker gene. Since the amplified region is associated with the antibody gene, production of the antibody protein may also increase.

For production of the monovalent bispecific antibodies provided herein the host cell may be co-transfected with two expression vectors of the antibodies herein; wherein, each vector encodes a heavy chain and a light chain, such that between the two vectors all four chains (i.e. the two heavy and the two light chains) are encoded. When each vector encodes a heavy and a light chain it is preferable that each vector comprises a different mammalian selection marker. The use of two different selection markers ensures that both vectors are present in a host cell. Alternatively, the first vector encodes two heavy chain polypeptides (see, e.g., FIG. 3C) and the second vector encodes two light chain polypeptides (see, e.g., FIGS. 3A and 3B). When each vector expresses only heavy or light chains the two vectors may contain identical selectable markers, as only host cells comprising both plasmids will express IgG and they are highly likely to be predominately MBabs. Alternatively, a single vector may be used which encodes, and is capable of expressing, all the heavy and light chain polypeptides. In such situations, the light chains may be placed before the heavy chains to avoid an excess of toxic free heavy chain. As described herein, a number of methods may be utilized to enable equal expression of heavy and light chain polypeptides. The coding sequences for the heavy and light chains may comprise cDNA or genomic DNA.

Figure 3A:
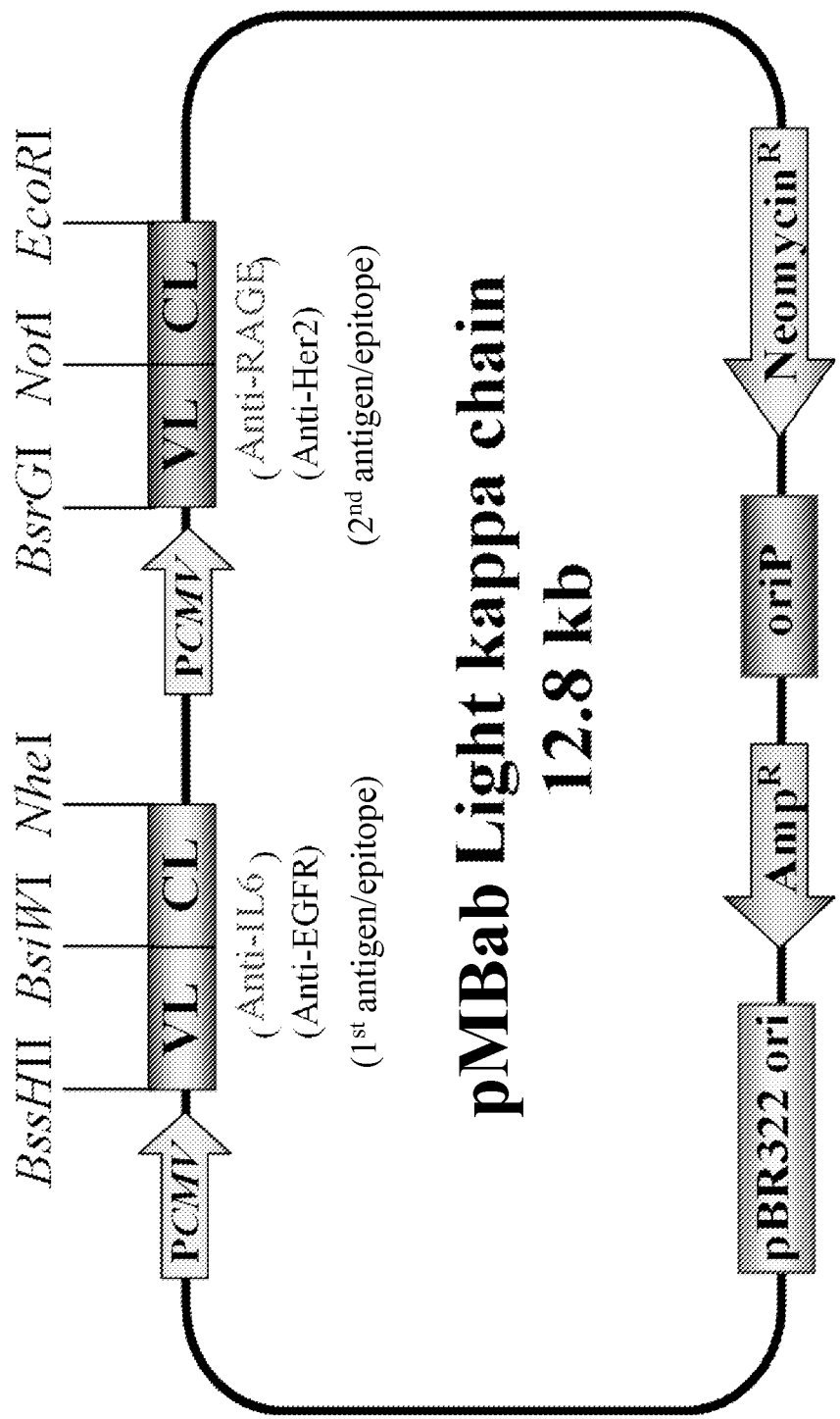
FIG. 3A to 3C illustrate representative MBab expression vectors which make use of a single mammalian selection marker.
Figure 3B:
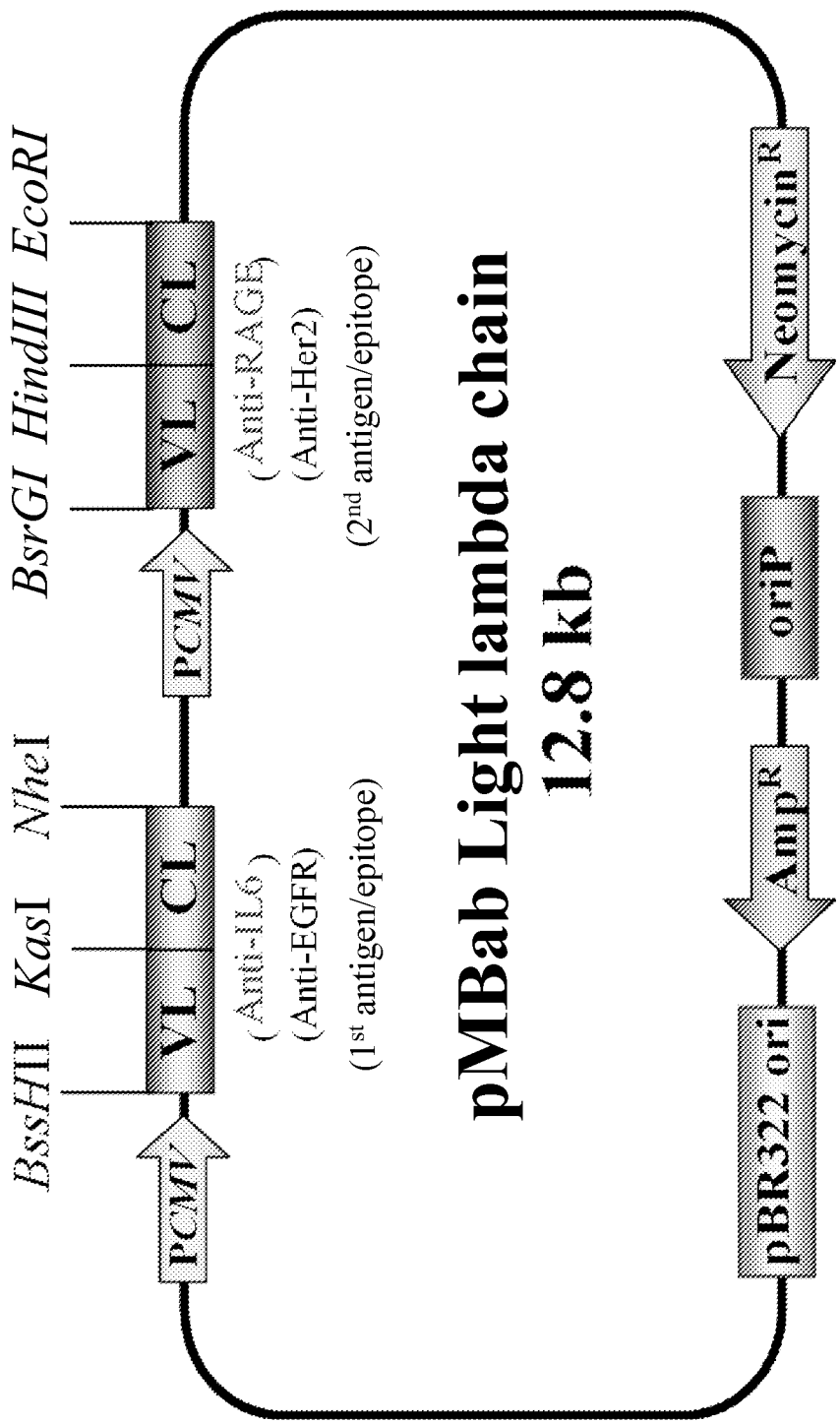
Figure 3C:
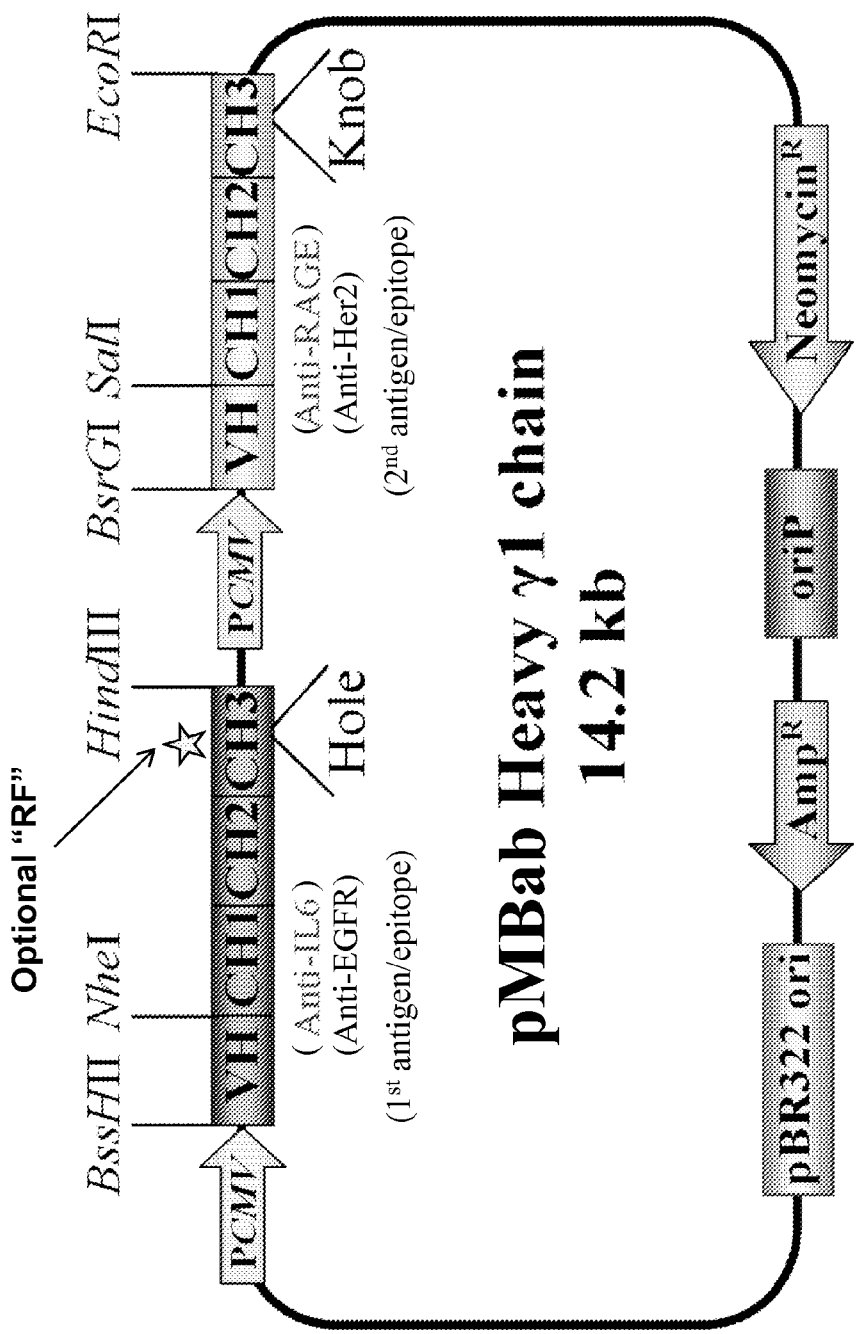

In some aspects, the host cell is co-transfected with two expression vectors; the first vector encoding a first heavy chain polypeptide comprising any of the modifications described herein and a second heavy chain polypeptide without modifications or with compensatory Fc modifications (see, e.g., FIG. 3C); and the second vector encoding a first modified light chain polypeptide which corresponds to the first heavy chain and a second unmodified light chain polypeptide (see, e.g., FIGS. 3A and 3B). In some aspects, each chain is individually expressed using its own promoter. Expression of two light chains from a single vector and two heavy chains from a single can be particularly useful for generating antibodies with different heavy and light chains. Furthermore, as described herein, selection of which mutations to introduce into the Fc region of each heavy chain can be used to minimize production of half antibodies.

Once an antibody with one modified HC-LC interface and one unmodified HC-LC interface has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies herein or fragments thereof may be fused to heterologous polypeptide sequences described herein or otherwise known in the art to facilitate purification.

Antibody Purification and Isolation

Once an antibody protein herein has been produced by recombinant expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present technology or fragments thereof may be fused to heterologous polypeptide sequences (referred to herein as "tags") described above or otherwise known in the art to facilitate purification. In some aspects, the antibodies provided herein are purified by a multiple step process comprising two or more affinity medias. Medias useful for the purification of the antibodies provided herein include medias specific for the Fc portion, e.g., Protein A or Protein G; resins specific for the light chain constant region, e.g., CaptureSelect Kappa and CaptureSelect Lambda; resins specific for the antigen binding domain, e.g., resins that incorporate all or a portion of the antigen, or comprise an anti-id antibody binding domain.

When using recombinant techniques, the antibody protein can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. For example, procedures for isolating antibodies which are secreted into the periplasmic space of *E. coli* are known in the art. Where the antibody protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc region that is present in the antibody and will be understood by one of skill in the art. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody protein comprises a CH3 domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody protein recovered.

Following any preliminary purification step(s), the mixture comprising the antibody of interest and contaminants may be subjected to low pH hydrophobic interaction chromatography using an elution buffer at a pH between about 2.5-4.5, and performed at low salt concentrations (e.g., from about 0-0.25 M salt).

Thus, in certain aspects, antibodies as provided herein are substantially purified/isolated. In an aspect, these isolated/purified recombinantly expressed antibodies may be administered to a patient to mediate a prophylactic or therapeutic effect. In some aspects these isolated/purified antibodies may be used to diagnose a disease.

Diagnostic Methods of Use

In certain aspects, antibodies with a modified HC-LC interface and compositions herein may be used in vivo and/or in vitro for diagnosing diseases associated with the antibody molecule. This can be achieved, for example, by contacting a sample for testing, optionally along with a control sample, with the antibody under conditions that allow for formation of a complex between the antibody and the molecule of interest. Complex formation is then detected (e.g., using an ELISA). When using a control sample along with the test sample, complex is detected in both samples and any statistically significant difference in the formation of complexes between the samples is indicative of the presence of the molecule of interest in the test sample.

In some aspects, the technology herein provides a method of determining the presence of a molecule of interest in a sample suspected of containing such a molecule, the method comprising exposing the sample to an antibody provided herein, and determining binding of the antibody to the molecule of interest in the sample where binding of the antibody to the molecule of interest in the sample is indicative of the presence of the molecule of interest in the sample. In some aspects, the sample is a biological sample. In certain aspects, the biological sample is from a mammal experiencing or suspected of experiencing disease or disorder associated with the molecule of interest.

In certain aspects, an antibody provided herein may be used to detect the overexpression or amplification of a molecule of interest using an in vivo diagnostic assay. In some aspects, an antibody provided herein is added to a sample where the antibody binds the molecule of interest for detection and is tagged with a detectable label (e.g. a radioactive isotope or a fluorescent label) and externally scanning the patient for localization of the label.

FISH assays such as the INFORM™ (sold by Ventana, Ariz.) or PATHVISION™ (Vysis, Ill.) may be carried out on formalin-fixed, paraffin-embedded tissue to determine the extent (if any) of overexpression of a molecule of interest in the tumor.

In certain aspects, an antibody provided herein may be used in a method of diagnosing a cell proliferative disorder associated with an increase in cells expressing a molecule of interest. In some aspects, the method comprises contacting test cells in a biological sample with an antibody provided herein; determining the level of a molecule of interest in test cells in the sample by detecting binding of an antibody provided herein; and comparing the level of antibody bound to cells in a control sample, where the level of antibody bound is normalized to the number molecule of interest expressing cells in the test and control samples, and where a higher level of antibody bound in the test sample as compared to the control sample indicates the presence of a cell proliferative disorder associated with cells expressing the molecule of interest.

In certain aspects, an antibody provided herein may be used in a method of detecting a soluble molecule of interest in blood or serum. In some aspects, the method comprises contacting a test sample of blood or serum from a mammal suspected of experiencing a disorder associated with a molecule of interest with an antibody provided herein and detecting an increase in soluble molecule of interest in the test sample relative to a control sample of blood or serum from a normal mammal. In some aspects, the method of detecting is useful as a method of diagnosing a disorder associated with an increase in soluble molecule of interest in blood or serum of a mammal.

Treatment Methods of Use

In various aspects an antibody provided herein is administered to cells, for example cancer cells. The biological effect of the antibody provided herein may be observed, including but not limited to cell, death, cell proliferation inhibition, lack of effect, changes in cell morphology, and changes in cellar growth pattern. In some aspects the antibody provided herein comprises a detectable label and/or carries a drug or toxin to a tumor antigen. In certain aspects the label indicates the location of the tumor antigen within the cell.

Examples of conditions or hyperproliferative disorders include benign or malignant tumors, leukemia and lymphoid malignancies. Others include neuronal, glial, astrocytal, hypothalamic, glandular, macrophagal, epithelial, endothelial, and stromal malignancies. Other cancers or hyperproliferative disorders include: cancers of the head, neck, eye, mouth, throat, esophagus, chest, skin, bone, lung, colon, rectum, colorectal, stomach, spleen, kidney, skeletal muscle, subcutaneous tissue, metastatic melanoma, endometrial, prostate, breast, ovaries, testicles, thyroid, blood, lymph nodes, kidney, liver, pancreas, brain, or central nervous system. Examples of cancers that can be prevented, managed, treated or ameliorated in accordance with the methods herein include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple mycloma, nonsecretory myeloma, osteosclerotic myeloma, plasma cell leukemia, solitary plasmacytoma and extramedullary plasmacytoma, Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

It is also contemplated that cancers caused by aberrations in apoptosis can also be treated by the methods and compositions herein. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

The antibody proteins and compositions herein are useful for many purposes, for example, as therapeutics against a wide range of chronic and acute diseases and disorders including, but not limited to, autoimmune and/or inflammatory disorders, which include Sjogren's syndrome, rheumatoid arthritis, lupus psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection.

Examples of autoimmune and/or inflammatory disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, Sjogren's syndrome, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitisherpetiformis vasculitis, vitiligo, and Wegener's granulomatosis.

Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections.

The compositions and methods herein can be used with one or more conventional therapies that are used to prevent, manage or treat the above diseases. Also provided, in some aspects are methods of using antibodies to inactivate various infectious agents such as viruses, fungi, eukaryotic microbes, and bacteria. In some aspects the antibodies herein may be used to inactivate RSV, hMPV, PIV, or influenza viruses. In some aspects, the antibodies herein may be used to inactivate fungal pathogens, such as, but not limited to members of *Naegleria, Aspergillus, Blastomyces, Histoplasma, Candida* or *Tinea* genera. In some aspects, the antibodies herein may be used to inactivate eukaryotic microbes, such as, but not limited to members of *Giardia, Toxoplasma, Plasmodium, Trypanosoma*, and *Entamoeba* genera. In some aspects, the antibodies herein may be used to inactivate bacterial pathogens, such as but not limited to members of *Staphylococcus, Streptococcus, Pseudomonas, Clostridium, Borrelia, Vibro* and *Neiserria* genera.

The antibodies and compositions herein are useful for many purposes, for example, as therapeutics against a wide range of chronic and acute diseases and disorders including, but not limited to, infectious disease, including viral, bacterial and fungal diseases. Examples of viral pathogens include but are not limited to: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., mparamyxovirus, parainfluenza virus 1, mobillivirus (e.g., measles virus), rubulavirus (e.g., mumps virus), pneumonovirinae (e.g., pneumovirus, human respiratory syncitial virus), and metapneumovirus (e.g., avian pneumovirus and human metapneumovirus)), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLVHTLV retroviruses, lentivirus (e.g. human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Examples of bacterial pathogens include but are not limited to: the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species,

*Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens,* and *Shigella flexneri*), Gardinella family, *Haemophilus influenzae,* Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcuss* (e.g., methicillin resistant *Staphylococcus aureus* and *Staphylococcus pyrogenes*), *Streptococcus* (e.g., *Streptococcus enteritidis, Streptococcus fasciae,* and *Streptococcus pneumoniae*), Vampirovibr Helicobacter family, and Vampirovibrio family.

Examples of fungal pathogens include, but are not limited to: *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger,* and *Aspergillus terreus*), *Basidiobolus ranarum, Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea,* and *Candida tropicalis*), *Coccidioides immitis, Conidiobolus* species, *Cryptococcus neoforms, Cunninghamella* species, *dermatophytes, Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae,* and *Rhizopus microsporus*), *Saccharomyces* species, *Sporothrix schenckii, zygomycetes,* and classes such as Zygomycetes, Ascomycetes, the Basidiomycetes, Deuteromycetes, and Oomycetes.

Provided also, in some aspects, are methods of using antibodies to deplete a cell population. In an aspect, methods herein may be used in the depletion of the following cell types: eosinophil, basophil, neutrophil, T cell, B cell, mast cell, monocytes, endothelial cell and tumor cell.

In certain aspects, the antibodies herein may also be useful in the diagnosis and detection of diseases of symptoms thereof. In some aspects, the compositions herein may be useful in the monitoring of disease progression. In various aspects, the compositions herein may be useful in the monitoring of treatment regimens. In certain aspects, the compositions herein are useful for diagnosis in an ex vivo application, such as a diagnostic kit.

The compositions herein may be useful in the visualization of target antigens. In some aspects, the target antigens are cell surface receptors that internalize. In certain aspects, the target antigen is an intracellular antigen. In some aspects the target is an intranuclear antigen. In some aspects, some of the antibodies herein once bound, internalize into cells Conjugates The antibodies provided herein can be used in non-conjugated form or conjugated to at least one of a variety of heterologous moieties to facilitate target detection or for imaging or therapy. The Tn3 scaffolds of the can be labeled or conjugated either before or after purification, when purification is performed.

Many heterologous moieties lack suitable functional groups to which the antibodies herein can be linked. Thus, in some aspects, the effector molecule is attached to the scaffold through a linker, where the linker contains reactive groups for conjugation. In some aspects, the heterologous moiety conjugated to an antibody herein can function as a linker. In other aspects, the moiety is conjugated to an antibody herein via a linker that can be cleavable or non-cleavable. In one aspect, the cleavable linking molecule is a redox cleavable linking molecule, such that the linking molecule is cleavable in environments with a lower redox potential, such as the cytoplasm and other regions with higher concentrations of molecules with free sulfhydryl groups. Examples of linking molecules that may be cleaved due to a change in redox potential include those containing disulfides.

In some aspects, an antibody herein is engineered to provide reactive groups for conjugation. In such antibodies, the N-terminus and/or C-terminus can also serve to provide reactive groups for conjugation. In other aspects, the N-terminus can be conjugated to one moiety (such as, but not limited to PEG) while the C-terminus is conjugated to another moiety (such as, but not limited to biotin), or vice versa.

The term "polyethylene glycol" or "PEG" means a polyethylene glycol compound or a derivative thereof, with or without coupling agents, coupling or activating moieties (e.g., with thiol, triflate, tresylate, aziridine, oxirane, N-hydroxysuccinimide or a maleimide moiety). The term "PEG" is intended to indicate polyethylene glycol of a molecular weight between 500 and 150,000 Da, including analogues thereof, where for instance the terminal OH-group has been replaced by a methoxy group (referred to as mPEG).

The antibodies herein can be derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a specific aspect, the PEGs employed have molecular weights ranging from 5,000 daltons to about 20,000 daltons. PEGs coupled to the scaffolds herein can be either branched or unbranched. See, for example, Monfardini, C. et al. 1995 Bioconjugate Chem 6:62-69. PEGs are commercially available from Nektar Inc., Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

Briefly, the hydrophilic polymer which is employed, for example, PEG, is capped at one end by an unreactive group such as a methoxy or ethoxy group. Thereafter, the polymer is activated at the other end by reaction with a suitable activating agent, such as cyanuric halides (for example, cyanuric chloride, bromide or fluoride), carbonyldiimidazole, an anhydride reagent (for example, a dihalo succinic anhydride, such as dibromosuccinic anhydride), acyl azide, p-diazoniumbenzyl ether, 3-(p-diazoniumphenoxy)-2-hydroxypropylether) and the like. The activated polymer is then reacted with a polypeptide as described herein to produce a polypeptide derivatized with a polymer. Alternatively, a functional group in an antibody herein can be activated for reaction with the polymer, or the two groups can be joined in a concerted coupling reaction using known coupling methods. It will be readily appreciated that the polypeptides herein can be derivatized with PEG using a myriad of other reaction schemes known in the art. A PEG can be coupled to a scaffold herein at one or more functional groups at either end of the antibody or within the antibody. In certain aspects, the PEG is coupled at either the N-terminus or the C-terminus.

In other aspects, an antibody herein, analogs or derivatives thereof may be conjugated to a diagnostic or detectable agent. Such antibodies can be useful for monitoring or prognosing the development or progression of a disease as part of a clinical testing procedure, such as determining the efficacy of a particular therapy.

The technology herein further encompasses uses of an antibody herein conjugated to a therapeutic moiety. An antibody herein may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Compositions

In certain aspects, the disclosure provides compositions. Such compositions may be compositions comprising a nucleic acid molecule that encodes an antibody provided herein. Such pharmaceutical compositions may also be compositions comprising an antibody provided herein, or a combination of antibodies herein, and a pharmaceutically acceptable excipient. In certain aspects, the compositions of the disclosure are used as a medicament.

In certain aspects, antibodies herein or a combination of antibodies herein (or nucleic acid molecules encoding one or more antibodies herein) may be formulated with a pharmaceutically acceptable carrier, excipient or stabilizer, as pharmaceutical compositions. In certain aspects, such pharmaceutical compositions are suitable for administration to a human or non-human animal via any one or more route of administration using methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also contain compatible solid or liquid fillers, diluents or encapsulating substances which are suitable for administration into a human. Other contemplated carriers, excipients, and/or additives, which may be utilized in the formulations described herein include, for example, flavoring agents, antimicrobial agents, sweeteners, antioxidants, antistatic agents, lipids, protein excipients such as serum albumin, gelatin, casein, salt-forming counterions such as sodium and the like. These and additional known pharmaceutical carriers, excipients and/or additives suitable for use in the formulations described herein are known in the art, e.g., as listed in "Remington: The Science & Practice of Pharmacy", 21$^{st}$ ed., Lippincott Williams & Wilkins, (2005), and in the "Physician's Desk Reference", 60$^{th}$ ed., Medical Economics, Montvale, N.J. (2005). Pharmaceutically acceptable carriers can be routinely selected that are suitable for the mode of administration, solubility and/or stability desired or required.

In one aspect, the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). In certain specific aspects, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

When used for in vivo administration, the formulations of the disclosure should be sterile. The formulations of the disclosure may be sterilized by various sterilization methods, including sterile filtration, radiation, etc. In one aspect, the formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005).

Therapeutic compositions of the present disclosure can be formulated for particular routes of administration, such as oral, nasal, pulmonary, topical (including buccal and sublingual), rectal, vaginal and/or parenteral administration. The phrases "parenteral administration" and "administered parenterally" as used herein refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Formulations of the present disclosure which are suitable for topical or transdermal administration include powders, sprays, ointments, pastes, creams, lotions, gels, solutions, patches and inhalants. The iMers may be mixed under sterile conditions with a pharmaceutically acceptable carrier, and with any preservatives, buffers, or propellants which may be required (U.S. Pat. Nos. 7,378,110; 7,258,873; 7,135,180; US Publication No. 2004-0042972; and 2004-0042971).

The formulations may conveniently be presented in unit dosage form and may be prepared by any method known in the art of pharmacy. Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient (e.g., "a therapeutically effective amount"). The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. Suitable dosages may range from about 0.0001 to about 100 mg/kg of body weight or greater, for example about 0.1, 1, 10, or 50 mg/kg of body weight, with about 1 to about 10 mg/kg of body weight being suitable.

Note that the disclosure similarly contemplates that formulations suitable for diagnostic and research use may also be made. The concentration of active agent in such formulations, as well as the presence or absence of excipients and/or pyrogens can be selected based on the particular application and intended use.

Embodiments

Provided hereafter are non-limiting examples of certain embodiments of the technology.

A1. An antibody comprising a modified heavy chain, wherein the modified heavy chain comprises (i) a substitution of a native cysteine to a non-cysteine amino acid, and (ii) a substitution of a native non-cysteine amino acid to a cysteine amino acid.

A2. The antibody of embodiment A1, wherein the CH1 region comprises (i) the substitution of a native cysteine to a non-cysteine amino acid, and (ii) the substitution of a native non-cysteine amino acid to a cysteine amino acid.

A3. The antibody of embodiment A1 wherein the CH1 region comprises the substitution of a native cysteine to a non-cysteine amino acid and the VH region comprises the substitution of a native non-cysteine amino acid to a cysteine amino acid.

A4. The antibody of embodiment A1, A2, or A3, wherein the heavy chain native cysteine is capable of forming an interchain disulphide bond.

A5. The antibody of any one of embodiments A1 to A4, further comprising a modified light chain, wherein the modified light chain comprises (i) a substitution of a native cysteine to a non-cysteine amino acid, and (ii) a substitution of a native non-cysteine amino acid to a cysteine amino acid.

A6. The antibody of embodiment A5, wherein the CL region comprises (i) the substitution of a native cysteine to a non-cysteine amino acid, and (ii) the substitution of a native non-cysteine amino acid to a cysteine amino acid.

A7. The antibody of embodiment A5, wherein the CL region comprises the substitution of a native cysteine to a non-cysteine amino acid, and the VL region comprises the substitution of a native non-cysteine amino acid to a cysteine amino acid.

A8. The antibody of embodiment A5, A6 or A7, wherein the light chain native cysteine is capable of forming an interchain disulphide bond.

A9. The antibody of embodiment A5, A6, A7, or A8, wherein the substituted cysteine of the modified heavy chain, resulting from the substitution of the native non-cysteine amino acid to the cysteine amino acid, and the substituted cysteine of the modified light chain, resulting from the substitution of the native non-cysteine amino acid to the cysteine amino acid, can form a disulphide bond.

A10. The antibody of any one of embodiments A1 to A9, comprising two heavy chains and two light chains.

A11. The antibody of embodiment A10, wherein the two heavy chains and two light chains are four separate polypeptides.

A12. The antibody of embodiment A10, wherein the two heavy chains and two light chains are a single polypeptide.

A13. The antibody of any one of embodiments A1 to A12, which is a full-length antibody.

A14. The antibody of any one of embodiments A10 to A13, wherein the two heavy chains each comprise a VH domain, a CH1 domain and an Fc region, wherein the VH domains have the same or different amino acid sequences, the CH1 domains have the same or different amino acid sequences, and the Fc regions have different amino acid sequences.

A15. The antibody of embodiment A14, wherein the two heavy chains form a heterodimer.

A16. The antibody of any one of embodiments A10 to A15, wherein the two light chains each comprise a VL domain and a CL domain, wherein the VL domains have the same or different amino acid sequences and the CL domains have different amino acid sequences.

A17. The antibody of any one of embodiments A1 to A16, that specifically binds to two independent antigens or to two independent epitopes on the same antigen.

A18. The antibody of embodiment A17, wherein the binding affinity for the two independent antigens is the same or different.

A19. The antibody of embodiment A17, wherein the binding affinity for the two independent epitopes on the same antigen is the same or different.

A20. The antibody of embodiment A17, that specifically binds to the same epitope with two different binding affinities.

A21. The antibody of any one of embodiments A5 to A20, wherein the light chain is a kappa light chain or a lambda light chain.

A22. The antibody of any one of embodiments A10 to A20, wherein one light chain is a kappa light chain and one light chain is a lambda light chain.

A23. The antibody of any one of embodiments A1 to A22, comprising (i) one modified heavy chain comprising a modification in the CH1 region and one modified corresponding light chain comprising a modification in the CL region, and (ii) a second heavy chain and corresponding light chain, wherein the CH1 and CL regions are not modified.

A24. The antibody of any one of embodiments A1 to A23, which is an immunoglobulin G (IgG).

A25. The antibody of any one of embodiments A1 to A24, wherein the modified heavy chain is an IgG1 heavy chain comprising the substitution of a native cysteine to a non-cysteine amino acid at position 220 of the CH1 region, wherein numbering is according to the EU index.

A26. The antibody of any one of embodiments A1 to A24, wherein the modified heavy chain is an IgG2 heavy chain comprising the substitution of a native cysteine to a non-cysteine amino acid at positions 131 and/or 219 and/or 220 of the CH1 region, wherein numbering is according to the EU index.

A27. The antibody of any one of embodiments A1 to A24, wherein the modified heavy chain is an IgG2 heavy chain comprising the substitution of a native cysteine to a non-cysteine amino acid at each of positions 131 and 219 and 220 of the CH1 region, wherein numbering is according to the EU index.

A28. The antibody of any one of embodiments A1 to A24, wherein the modified heavy chain is an IgG2 heavy chain comprising the substitution of a native cysteine to a non-cysteine amino acid at each of positions 131 and 220 of the CH1 region, wherein numbering is according to the EU index.

A29. The antibody of any one of embodiments A1 to A24, wherein the modified heavy chain is an IgG3 or IgG4 heavy chain comprising the substitution of a native cysteine to a non-cysteine amino acid at position 131 of the CH1 region, wherein numbering is according to the EU index.

A30. The antibody of embodiment A29, wherein the modified corresponding light chain comprises the substitution of a native cysteine to a non-cysteine amino acid at position 214 of the CL region, wherein numbering is according to the EU index.

A31. The antibody of any one of embodiments A24 to A30, wherein the non-cysteine amino acid is a valine or alanine.

A32. The antibody of any one of embodiments A24 to A31, wherein the modified heavy chain comprises the substitution of a native non-cysteine amino acid to a cysteine amino acid at position 141 of the CH1 region, wherein numbering is according to the EU index.

A33. The antibody of embodiment A32, wherein the modified heavy chain is an IgG1 heavy chain comprising amino acid substitutions whereby the alanine at position 141 of the CH region is substituted by a cysteine, and the cysteine at position 220 of the CH region is substituted by an amino acid that is not cysteine, wherein numbering is according to the EU index.

A34. The antibody of embodiment A32, wherein the modified heavy chain is an IgG2 heavy chain comprising amino acid substitutions whereby the alanine at position 141 of the CH1 region is substituted by a cysteine, and the cysteine at each of positions 131 and 220 of the CH1 region is substituted by an amino acid that is not cysteine, wherein numbering is according to the EU index.

A35. The antibody of embodiment A32, wherein the modified heavy chain is an IgG3 or IgG4 heavy chain comprising amino acid substitutions whereby the alanine at position 141 of the CH1 region is substituted by a cysteine, and the cysteine at position 131 of the CH1 region is substituted by an amino acid that is not cysteine, wherein numbering is according to the EU index.

A36. The antibody of embodiment A32, A33, or A34, wherein the modified heavy chain comprises amino acid substitutions whereby the alanine at position 141 of the CH1 region is substituted by a cysteine, and the cysteine at position 220 of the CH1 region is substituted by a valine, wherein numbering is according to the EU index.

A37. The antibody of embodiment A32, A34, A35 or A36, wherein the modified heavy chain comprises amino acid substitutions whereby the alanine at position 141 of the CH1 region is substituted by a cysteine, and the cysteine at position 131 of the CH1 region is substituted by a valine, wherein numbering is according to the EU index.

A38. The antibody of any one of embodiments A32 to A37, wherein the modified corresponding light chain comprises the substitution of a native non-cysteine amino acid to a cysteine amino acid at position 116 of the CL region and the substitution of a native cysteine to a non-cysteine amino acid at position 214 of the CL region, wherein numbering is according to the EU index.

A39. The antibody of any one of embodiments A32 to A38, wherein the modified corresponding light chain comprises amino acid substitutions whereby the phenylalanine or threonine at position 116 of the CL region is substituted by a cysteine, and the cysteine at position 214 of the CL region is substituted by an amino acid that is not cysteine, wherein numbering is according to the EU index.

A40. The antibody of any one of embodiments A32 to A39, wherein the modified corresponding light chain comprises amino acid substitutions whereby the phenylalanine at position 116 of the CL region is substituted by a cysteine, and the cysteine at position 214 of the CL region is substituted by a valine, wherein numbering is according to the EU index.

A41. The antibody of any one of embodiments A32 to A39, wherein the modified corresponding light chain comprises amino acid substitutions whereby the threonine at position 116 of the CL region is substituted by a cysteine, and the cysteine at position 214 of the CL region is substituted by a valine, wherein numbering is according to the EU index.

A42. The antibody of any one of embodiments A24 to A31, wherein the modified heavy chain comprises the substitution of a native non-cysteine amino acid to a cysteine amino acid at position 168 of the CH1 region, wherein numbering is according to the EU index.

A43. The antibody of embodiment A42, wherein the modified heavy chain is an IgG1 heavy chain comprising amino acid substitutions whereby the histidine at position 168 of the CH 1 region is substituted by a cysteine, and the cysteine at position 220 of the CH1 region is substituted by an amino acid that is not cysteine, wherein numbering is according to the EU index.

A44. The antibody of embodiment A42, wherein the modified heavy chain is an IgG2 heavy chain comprising amino acid substitutions whereby the histidine at position 168 of the CH 1 region is substituted by a cysteine, and the cysteine at each of positions 131 and 220 of the CH1 region is substituted by an amino acid that is not cysteine, wherein numbering is according to the EU index.

A45. The antibody of embodiment A42, wherein the modified heavy chain is an IgG3 or IgG4 heavy chain comprising amino acid substitutions whereby the histidine at position 168 of the CH1 region is substituted by a cysteine, and the cysteine at position 131 of the CH1 region is substituted by an amino acid that is not cysteine, wherein numbering is according to the EU index.

A46. The antibody of any one of embodiments A42 to A44, wherein the modified heavy chain comprises amino acid substitutions whereby the histidine at position 168 of the CH1 region is substituted by a cysteine, and the cysteine at position 220 of the CH1 region is substituted by a valine, wherein numbering is according to the EU index.

A47. The antibody of embodiment A42, A44 or A45, wherein the modified heavy chain comprises amino acid substitutions whereby the histidine at position 168 of the CH1 region is substituted by a cysteine, and the cysteine at position 131 of the CH1 region is substituted by a valine, wherein numbering is according to the EU index.

A48. The antibody of any one of embodiments A42 to A47, wherein the modified corresponding light chain comprises the substitution of a native non-cysteine amino acid to a cysteine at position 164 of the CL region and the substitution of a native cysteine to a non-cysteine amino acid at position 214 of the CL region, wherein numbering is according to the EU index.

A49. The antibody of any one of embodiments A42 to A48, wherein the modified corresponding light chain comprises amino acid substitutions whereby the threonine at position 164 of the CL region is substituted by a cysteine, and the cysteine at position 214 of the CL region is substituted by a non-cysteine amino acid, wherein numbering is according to the EU index.

A50. The antibody of any one of embodiments A42 to A49, wherein the modified corresponding light chain comprises amino acid substitutions whereby the threonine at position 164 of the CL region is substituted by a cysteine, and the cysteine at position 214 of the CL region is substituted by a valine, wherein numbering is according to the EU index.

A51. The antibody of any one of embodiments A24 to A31, wherein the modified heavy chain comprises the substitution of a native non-cysteine amino acid to cysteine amino acid at position 126 of the CH1 region, wherein numbering is according to the EU index.

A52. The antibody of embodiment A51, wherein the modified heavy chain is an IgG1 heavy chain comprising amino acid substitutions whereby the phenylalanine at position 126 of the CH1 region is substituted by a cysteine, and the cysteine at position 220 of the CH1 region is substituted by an amino acid that is not cysteine, wherein numbering is according to the EU index.

A53. The antibody of embodiment A51, wherein the modified heavy chain is an IgG2 heavy chain comprising amino acid substitutions whereby the phenylalanine at position 126 of the CH1 region is substituted by a cysteine, and the cysteine at each of positions 131 and 220 of the CH1 region is substituted by an amino acid that is not cysteine, wherein numbering is according to the EU index.

A54. The antibody of embodiment A51, wherein the modified heavy chain is an IgG3 or IgG4 heavy chain comprising amino acid substitutions whereby the phenylalanine at position 126 of the CH1 region is substituted by a cysteine, and the cysteine at position 131 of the CH1 region is substituted by an amino acid that is not cysteine, wherein numbering is according to the EU index.

A55. The antibody of any one of embodiments A51 to A53, wherein the modified heavy chain comprises amino acid substitutions whereby the phenylalanine at position 126 of the CH1 region is substituted by a cysteine, and the cysteine at position 220 of the CH1 region is substituted by a valine, wherein numbering is according to the EU index.

A56. The antibody of embodiment A51 or A53 to A55, wherein the modified heavy chain comprises amino acid substitutions whereby the phenylalanine at position 126 of the CH1 region is substituted by a cysteine, and the cysteine at position 131 of the CH1 region is substituted by a valine, wherein numbering is according to the EU index.

A57. The antibody of any one of embodiments A51 to A56, wherein the modified corresponding light chain comprises the substitution of a native non-cysteine amino acid to a cysteine amino acid at position 121 of the CL region, and the substitution of a native cysteine to a non-cysteine amino acid at position 214 of the CL region, wherein numbering is according to the EU index.

A58. The antibody of any one of embodiments A51 to A57, wherein the modified corresponding light chain comprises amino acid substitutions whereby the serine at position 121 of the CL region substituted by a cysteine, and the cysteine at position 214 of the CL region is substituted by an amino acid that is not cysteine, wherein numbering is according to the EU index.

A59. The antibody of any one of embodiments A51 to A48, wherein the modified corresponding light chain comprises amino acid substitutions whereby the serine at position 121 of the CL region substituted by a cysteine, and the cysteine at position 214 of the CL region is substituted by a valine, wherein numbering is according to the EU index.

A60. The antibody of any one of embodiments A24 to A31, wherein the modified heavy chain comprises the substitution of a native non-cysteine amino acid to a cysteine amino acid at position 128 of the CH1 region, wherein numbering is according to the EU index.

A61. The antibody of embodiment A60, wherein the modified heavy chain is an IgG1 heavy chain comprising amino acid substitutions whereby the leucine at position 128 of the CH1 region is substituted by a cysteine, and the cysteine at position 220 of the CH1 region is substituted by an amino acid that is not cysteine, wherein numbering is according to the EU index.

A62. The antibody of embodiment A60, wherein the modified heavy chain is an IgG2 heavy chain comprising amino acid substitutions whereby the leucine at position 128 of the CH1 region is substituted by a cysteine, and the cysteine at each of positions 131 and 220 of the CH1 region is substituted by an amino acid that is not cysteine, wherein numbering is according to the EU index.

A63. The antibody of embodiment A60, wherein the modified heavy chain is an IgG3 or IgG4 heavy chain comprising amino acid substitutions whereby the leucine at position 128 of the CH1 region is substituted by a cysteine, and the cysteine at position 131 of the CH1 region is substituted by an amino acid that is not cysteine, wherein numbering is according to the EU index.

A64. The antibody of any one of embodiments A60 to A62, wherein the modified heavy chain comprises amino acid substitutions whereby the leucine at position 128 of the CH1 region is substituted by a cysteine, and the cysteine at position 220 of the CH1 region is substituted by a valine, wherein numbering is according to the EU index.

A65. The antibody of embodiment A60 or A62 to A64, wherein the modified heavy chain comprises amino acid substitutions whereby the leucine at position 128 of the CH1 region is substituted by a cysteine, and the cysteine at position 131 of the CH1 region is substituted by a valine, wherein numbering is according to the EU index.

A66. The antibody of any one of embodiments A60 to A65, wherein the modified corresponding light chain comprises the substitution of a native non-cysteine amino acid to a cysteine amino acid at position 118 of the CL region and the substitution of a native cysteine to a non-cysteine amino acid at position 214 of the CL region, wherein numbering is according to the EU index.

A67. The antibody of any one of embodiments A60 to A66, wherein the modified corresponding light chain comprises amino acid substitutions whereby the phenylalanine at position 118 of the CL region is substituted by a cysteine, and the cysteine at position 214 of the CL region is substituted by an amino acid that is not cysteine, wherein numbering is according to the EU index.

A68. The antibody of any one of embodiments A60 to A67, wherein the modified corresponding light chain comprises amino acid substitutions whereby the phenylalanine at position 118 of the CL region is substituted by a cysteine, and the cysteine at position 214 of the CL region is substituted by a valine, wherein numbering is according to the EU index.

A69. The antibody of any one of embodiments A24 to A31, wherein the modified heavy chain comprises the substitution of a native non-cysteine amino acid to a cysteine amino acid at position 44 of the variable region, wherein numbering is according to the Kabat index.

A70. The antibody of embodiment A69, wherein the modified heavy chain is an IgG1 heavy chain comprising the substitution of a native non-cysteine amino acid to a cysteine amino acid at position 44 of the variable region, wherein numbering is according to the Kabat index, and wherein the cysteine at position 220 of the CH region is substituted by an amino acid that is not cysteine, wherein numbering is according to the EU index.

A71. The antibody of embodiment A69, wherein the modified heavy chain is an IgG2 heavy chain comprising the substitution of a native non-cysteine amino acid to a cysteine amino acid at position 44 of the variable region, wherein numbering is according to the Kabat index, and wherein the cysteine at each of positions 131 and 220 of the CH1 region is substituted by an amino acid that is not cysteine, wherein numbering is according to the EU index.

A72. The antibody of embodiment A69, wherein the modified heavy chain is an IgG3 or IgG4 heavy chain comprising the substitution of a native non-cysteine amino acid to a cysteine amino acid at position 44 of the variable region, wherein numbering is according to the Kabat index, and wherein the cysteine at position 131 of the CH1 region is substituted by an amino acid that is not cysteine, wherein numbering is according to the EU index.

A73. The antibody of any one of embodiments A69 to A72, wherein the modified corresponding light chain comprises the substitution of a native non-cysteine amino acid to a cysteine amino acid at position 100 of the variable region wherein numbering is according to Kabat, and the substitution of a native cysteine to a non-cysteine amino acid at position 214 of the CL region, wherein numbering is according to the EU index.

A74. The antibody of any one of embodiments A14 to A73, wherein the Fc region of either or both heavy chains comprises one or more modifications.

A75. The antibody of embodiment A74, wherein the modifications in the Fc region facilitate heterodimerization of the heavy chains.

A76. The antibody of embodiment A74, wherein the modifications in the Fc region alter protein A binding and are only present in one heavy chain.

A77. The antibody of embodiment A75, further comprising modifications in the Fc region that alter protein A binding and are only present in one heavy chain.

A78. The antibody of embodiment A76 or A77, wherein the antibody is an IgG1, an IgG2 or an IgG4 and the Fc region modifications that alter protein A binding is the amino acid substitution H435R/Y436F, wherein numbering is according to the EU index.

A79. The antibody of embodiment A76 or A77, wherein the antibody is IgG3 and the Fc region modifications that alter protein A binding is the amino acid substitution R435H/F436Y, wherein numbering is according to the EU index.

A80. The antibody of any one of embodiments A14 to A75, wherein the modified heavy chain Fc region comprises the amino acid substitution T366W, and the second heavy chain Fc region comprises the amino acid substitution Y407V/T366S/L368A, wherein numbering is according to the EU index.

A81. The antibody of embodiment A80, wherein the antibody is an IgG1, an IgG2 or an IgG4 and the second heavy chain Fc region further comprises the amino acid substitution H435R/Y436F, wherein numbering is according to the EU index.

A82. The antibody of embodiment A80, wherein the antibody is IgG3 and the modified heavy chain Fc region further comprises the amino acid substitution R435H/F436Y, wherein numbering is according to the EU index.

A83. The antibody of any one of embodiments A14 to A75, wherein the modified heavy chain Fc region comprises the amino acid substitution Y407V/T366S/L368A, and the second heavy chain comprises a Fc(b) region comprising the amino acid substitution T366W, wherein numbering is according to the EU index.

A84. The antibody of embodiment A83, wherein the antibody is an IgG1, an IgG2 or an IgG4 and the modified heavy chain Fc region further comprises the amino acid substitution H435R/Y436F, wherein numbering is according to the EU index.

A85. The antibody of embodiment A83, wherein the antibody is IgG3 and the second heavy chain Fc region further comprises the amino acid substitution R435H/F436Y, wherein numbering is according to the EU index.

A86. The antibody of any one of embodiments A80 to A85, wherein the modified heavy chain Fc region further comprises the amino acid substitution S354C, and the second heavy chain Fc region further comprises the amino acid substitution Y349C, wherein numbering is according to the EU index.

A87. The antibody of any one of embodiments A80 to A85, wherein the modified heavy chain Fc region further comprises the amino acid substitution Y349C, and the second heavy chain Fc region further comprises a the amino acid substitution S354C, wherein numbering is according to the EU index.

A88. The antibody of embodiment A74, wherein the modifications in the Fc region alter the half-life of the antibody, wherein the half-life depends on FcRn binding affinity.

A89. The antibody of any one of embodiments A57b to A59d, further comprising modifications in the Fc region that alter the half-life of the antibody, wherein the half-life depends on FcRn binding affinity A90. The antibody of any one of embodiments A74, wherein the modifications in the Fc region that alter the effector function, wherein the binding affinity for the Fc gamma receptor or C1q complement protein is increased or decreased.

A91. The antibody of any one of embodiments A77 to A89, further comprising modifications in the Fc region that alter the effector function, wherein the binding affinity for the Fc gamma receptor or C1q complement protein is increased or decreased.

A92. The antibody of any one of embodiments A1 to A91, which is a human antibody.

A93. The antibody of any one of embodiments A1 to A91, which is a humanized antibody.

A94. The antibody of any one of embodiments A1 to A91, which is a chimeric antibody.

B1. An antibody comprising a modified heavy chain, wherein the modified heavy chain comprises the substitution of at least one amino acid in the CH1 region resulting in a protrusion and/or a cavity.

B2. The antibody of embodiment B1, wherein the modified heavy chain further comprises a substitution of a native cysteine to a non-cysteine amino acid.

B3. The antibody of embodiment B2, wherein the heavy chain native cysteine is capable of forming an interchain disulphide bond.

B4. The antibody of any one of embodiments B1 to B3, further comprising a modified light chain, wherein the modified light chain comprises the substitution of at least one amino acid in the CL region resulting in a compensatory cavity and/or protrusion.

B5. The antibody of embodiment B4, wherein the modifications favor the interchain pairing of the modified heavy chain with the modified light chain.

B6. The antibody of embodiment B4 or B5, wherein the modified light chain further comprises a substitution of a native cysteine to a non-cysteine amino acid.

B7. The antibody of embodiment B6, wherein the light chain native cysteine is capable of forming an interchain disulphide bond.

B8. The antibody of any one of embodiments B1 to B7, further comprising a second heavy chain and a second light chain.

B9. The antibody of embodiment B8, wherein two heavy chains and light chains are four separate polypeptides.

B10. The antibody of embodiment B8, wherein the two heavy chains and two light chains are a single polypeptide.

B11. The antibody of any one of embodiments B1 to B10, which is a full-length antibody.

B12. The antibody of any one of embodiments B8 to B11, wherein the first and second heavy chains each comprise a VH domain, a CH1 domain and an Fc region, wherein the VH domains have the same or different amino acid sequences, the CH1 domains have different amino acid sequences, and the Fc regions have different amino acid sequences.

B13. The antibody of embodiment B12, wherein the first and second heavy chains form a heterodimer.

B14. The antibody of any one of embodiments B8 to B13, wherein the first and second light chains each comprise a VL domain and a CL domain, wherein the VL domains have the same or different amino acid sequences and the CL domains have different amino acid sequences.

B15. The antibody of any one of embodiments B1 to B14, that specifically binds to two independent antigens or to two independent epitopes on the same antigen.

B16. The antibody of embodiment B15, wherein the binding affinity for the two independent antigens is the same or different.

B17. The antibody of embodiment B15, wherein the binding affinity for the two independent epitopes on the same antigen is the same or different.

B18. The antibody of any one of embodiments B1 to B14, that specifically binds to the same epitope with two different binding affinities.

B19. The antibody of any one of embodiments B8 to B18, wherein the first and the second light chain are kappa light chains or are lambda light chains.

B20. The antibody of any one of embodiments B8 to B18, wherein one light chain is a kappa light chain and one light chain is a lambda light chain.

B21. The antibody of any one of embodiments B1 to B20, comprising (i) one modified heavy chain comprising a modification in the CH1 region and one modified corresponding light chain comprising a modification in the CL region, and (ii) a second heavy chain and corresponding light chain, wherein the CH1 and CL regions are not modified.

B22. The antibody of any one of embodiments B8 to B20, wherein the second heavy chain is a modified heavy chain comprising the substitution of at least one amino acid in the CH1 region resulting in a protrusion and/or a cavity.

B23. The antibody of embodiment B22, wherein the second modified heavy chain further comprised a substitution of a native cysteine to a non-cysteine amino acid.

B24. The antibody of embodiment B23, wherein the heavy chain native cysteine is capable of forming an interchain disulphide bond.

B25. The antibody of any one of embodiments B22 to B24, wherein the second light chain is a modified light chain comprising the substitution of at least one amino acid in the CL region resulting in a compensatory cavity and/or protrusion.

B26. The antibody of embodiment B20, wherein the modifications favor the interchain pairing of the second modified heavy chain with the second modified light chain.

B27. The antibody of embodiment B25 or B26, wherein the second modified light chain further comprises a substitution of a native cysteine to a non-cysteine amino acid.

B28. The antibody of embodiment B27, wherein the light chain native cysteine is capable of forming an interchain disulphide bond.

B29. The antibody of any one of embodiments B2 to B28, wherein the first and/or second modified heavy chain is an IgG1 heavy chain comprising the substitution of a native cysteine to a non-cysteine amino acid at position 220 of the CH1 region, wherein numbering is according to the EU index.

B30. The antibody of any one of embodiments B2 to B28, wherein the first and/or second modified heavy chain is an IgG2 heavy chain comprising the substitution of a native cysteine to a non-cysteine amino acid at each of positions 131 and 219 and 220 of the CH1 region, wherein numbering is according to the EU index.

B31. The antibody of any one of embodiments B2 to B28, wherein the first and/or second modified heavy chain is an IgG2 heavy chain comprising the substitution of a native cysteine to a non-cysteine amino acid at each of positions 131 and 220 of the CH1 region, wherein numbering is according to the EU index.

B32. The antibody of any one of embodiments B2 to B28, wherein the first and/or second modified heavy chain is an IgG3 or IgG4 heavy chain comprising the substitution of a native cysteine to a non-cysteine amino acid at position 131 of the CH1 region, wherein numbering is according to the EU index.

B33. The antibody of any one of embodiments B6 to B32, wherein the first and/or second modified light chain comprises the substitution of a native cysteine to a non-cysteine amino acid at position 214 of the CL region, wherein numbering is according to the EU index.

B34. The antibody of any one of embodiments B2 to B33, wherein the non-cysteine amino acid is a valine or alanine.

B35. The antibody of any of embodiments B1 to B34, wherein the substitution of at least one amino acid in the CH1 region resulting in a protrusion and/or a cavity is a substitution of the amino acid at position 145 with an amino acid having a large side chain, a substitution of the amino acid at position 170 is with an amino acid having a small side chain, a substitution of the amino acid at position 183 with an amino acid having a large side chain, and a substitution of the amino acid at position 185 with an amino acid having a large side chain, wherein numbering is according to the EU index.

B36. The antibody of embodiment B35, wherein the leucine at position 145 is substituted with phenylalanine, the phenylalanine at position 170 is substituted with valine, the serine at position 183 is substituted with phenylalanine and the valine at position 185 is substituted with phenylalanine, wherein numbering is according to the EU index.

B37. The antibody of embodiment B35 or B36, wherein the substitution of at least one amino acid in the CL region resulting in a compensatory cavity and/or protrusion is a substitution of the amino acid at position 176 with an amino acid having a large side chain and a substation of the amino acid at position 178 with an amino acid having a small side chain, wherein numbering is according to the EU index.

B38. The antibody of embodiment B37, wherein the serine at position 176 is substituted with phenylalanine and the threonine or tyrosine at position 178 is substituted with alanine wherein numbering is according to the EU index.

B39. The antibody of any of embodiments B1 to B28, wherein the substitution of at least one amino acid in the CH1 region resulting in a protrusion and/or a cavity is a substitution of the amino acid at position 147 with an amino acid having a small side chain and a substitution of the amino acid at position 185 with an amino acid having a large side chain, wherein numbering is according to the EU index.

B40. The antibody of embodiment B39, wherein the lysine at position 147 is substituted with alanine and the valine at position 185 is substituted with tryptophan, wherein numbering is according to the EU index.

B41. The antibody of embodiment B39 or B40, wherein the substitution of at least one amino acid in the CL region resulting in a compensatory cavity and/or protrusion is a substitution of the amino acid at position 131 with an amino acid having a large side chain and a substitution of the amino acid at position 135 with an amino acid having a small side chain, wherein numbering is according to the EU index.

B42. The antibody of embodiment B41, wherein the serine or threonine at position 131 is substituted with tryptophan and the leucine at position 135 is substituted with glycine, wherein numbering is according to the EU index.

B43. The antibody of any one of embodiments B24 to B34, wherein
- (a) the modified heavy chain comprises a substitution of the amino acid at position 145 with an amino acid having a large side chain, a substitution of the amino acid at position 170 is with an amino acid having a small side chain, a substitution of the amino acid at position 183 with an amino acid having a large side chain, and a substitution of the amino acid at position 185 with an amino acid having a large side chain; and
- (b) the modified light chain comprises a substitution of the amino acid at position 176 with an amino acid having a large side chain and a substitution of the amino acid at position 178 with an amino acid having a small side chain, wherein numbering is according to the EU index.

B44. The antibody of any one of embodiments B24 to B34, wherein
- (a) the modified heavy chain comprises a substitution of the amino acid at position 147 with an amino acid having a small side chain and a substitution of the amino acid at position 185 with an amino acid having a large side chain; and
- (b) the modified light chain comprises a substitution of the amino acid at position 131 with an amino acid having a large side chain and a substitution of the amino acid at position 135 with an amino acid having a small side chain, wherein numbering is according to the EU index.

B45. The antibody of any one of embodiments B25 to B34, wherein
- (a) the first modified heavy chain comprises a substitution of the amino acid at position 145 with an amino acid having a large side chain, a substitution of the amino acid at position 170 is with an amino acid having a small side chain, a substitution of the amino acid at position 183 with an amino acid having a large side chain, and a substitution of the amino acid at position 185 with an amino acid having a large side chain;
- (b) the first modified light chain comprises a substitution of the amino acid at position 176 with an amino acid having a large side chain and a substitution of the amino acid at position 178 with an amino acid having a small side chain;
- (c) the second modified heavy chain comprises a substitution of the amino acid at position 147 with an amino acid having a small side chain and a substitution of the amino acid at position 185 with an amino acid having a large side chain; and
- (d) the second modified light chain comprises a substitution of the amino acid at position 131 with an amino acid having a large side chain and a substitution of the amino acid at position 135 with an amino acid having a small side chain, wherein numbering is according to the EU index.

B46. The antibody of embodiment B43, wherein
- (a) the modified heavy chain comprises amino acid substitutions whereby the leucine at position 145 is substituted with phenylalanine, the phenylalanine at position 170 is substituted with valine, the serine at position 183 is substituted with phenylalanine and the valine at position 185 is substituted with phenylalanine;
- (b) the modified light chain comprises amino acid substitutions whereby the serine at position 176 is substituted with phenylalanine and the threonine or tyrosine at position 178 is substituted with alanine, wherein numbering is according to the EU index.

B47. The antibody of embodiment B44. wherein
- (a) the modified heavy chain comprises amino acid substitutions whereby the lysine at position 147 is substituted with alanine and the valine at position 185 is substituted with tryptophan; and
- (b) the modified light chain comprises amino acid substitutions whereby he serine or threonine at position 131 is substituted with tryptophan and the leucine at position 135 is substituted with glycine, wherein numbering is according to the EU index.

B48. The antibody of embodiment B45, wherein
- (a) the first modified heavy chain comprises amino acid substitutions whereby the leucine at position 145 is substituted with phenylalanine, the phenylalanine at position 170 is substituted with valine, the serine at position 183 is substituted with phenylalanine and the valine at position 185 is substituted with phenylalanine;
- (b) the first modified light chain comprises amino acid substitutions whereby the serine at position 176 is substituted with phenylalanine and the threonine or tyrosine at position 178 is substituted with alanine:
- (c) the second modified heavy chain comprises amino acid substitutions whereby the lysine at position 147 is substituted with alanine and the valine at position 185 is substituted with tryptophan; and
- (d) the second modified light chain comprises amino acid substitutions whereby he serine or threonine at position 131 is substituted with tryptophan and the leucine at position 135 is substituted with glycine, wherein numbering is according to the EU index.

B49. The antibody of any one of embodiments B25 to B34, wherein
- (a) the first modified heavy chain comprises a substitution of the amino acid at position 147 with an amino acid having a small side chain and a substitution of the amino acid at position 185 with an amino acid having a large side chain; and
- (b) the first modified light chain comprises a substitution of the amino acid at position 131 with an amino acid having a large side chain and a substitution of the amino acid at position 135 with an amino acid having a small side chain
- (c) the second modified heavy chain comprises a substitution of the amino acid at position 145 with an amino acid having a large side chain, a substitution of the amino acid at position 170 is with an amino acid having a small side chain, a substitution of the amino acid at position 183 with an amino acid having a large side chain, and a substitution of the amino acid at position 185 with an amino acid having a large side chain;

(d) the second modified light chain comprises a substitution of the amino acid at position 176 with an amino acid having a large side chain and a substitution of the amino acid at position 178 with an amino acid having a small side chain, wherein numbering is according to the EU index.

B50. The antibody of embodiment B49, wherein (a) the first modified heavy chain comprises amino acid substitutions whereby the lysine at position 147 is substituted with alanine and the valine at position 185 is substituted with tryptophan; and (b) the first modified light chain comprises amino acid substitutions whereby he serine or threonine at position 131 is substituted with tryptophan and the leucine at position 135 is substituted with glycine:

(c) the second modified heavy chain comprises amino acid substitutions whereby the leucine at position 145 is substituted with phenylalanine, the phenylalanine at position 170 is substituted with valine, the serine at position 183 is substituted with phenylalanine and the valine at position 185 is substituted with phenylalanine;

(d) the second modified light chain comprises amino acid substitutions whereby the serine at position 176 is substituted with phenylalanine and the threonine or tyrosine at position 178 is substituted with alanine, wherein numbering is according to the EU index.

B51. The antibody of any one of embodiments B11 to B50, wherein the Fc region comprises one or more modifications.

B52. The antibody of embodiment B51, wherein the modifications in the Fc region facilitate heterodimerization of the heavy chains.

B53. The antibody of embodiment B51, wherein the modifications in the Fc region alter protein A binding and are only present in one heavy chain.

B54. The antibody of embodiment B52, further comprising modifications in the Fc region that alter protein A binding and are only present in one heavy chain.

B55. The antibody of embodiment B53 or B54, wherein the antibody is an IgG1, an IgG2 or an IgG4 and the Fc region modifications that alter protein A binding is the amino acid substitution H435R/Y436F, wherein numbering is according to the EU index.

B56. The antibody of embodiment B53 or B54, wherein the antibody is IgG3 and the Fc region modifications that alter protein A binding is the amino acid substitution R435H/F436Y, wherein numbering is according to the EU index.

B57. The antibody of any one of embodiments B11 to B52, wherein the modified heavy chain Fc region comprises the amino acid substitution T366W, and the second heavy chain the amino acid substitution Y407V/T366S/L368A, wherein numbering is according to the EU index.

B58. The antibody of embodiment B57, wherein the antibody is an IgG1, an IgG2 or an IgG4 and the second heavy chain Fc region further comprises the amino acid substitution H435R/Y436F, wherein numbering is according to the EU index.

B59. The antibody of embodiment B57, wherein the antibody is IgG3 and the modified heavy chain Fc region further comprises the amino acid substitution R435H/F436Y, wherein numbering is according to the EU index.

B60. The antibody of any one of embodiments B11 to B52, wherein the modified heavy chain Fc region comprises the amino acid substitution Y407V/T366S/L368A, and the second heavy chain comprises the amino acid substitution T366W, wherein numbering is according to the EU index.

B61. The antibody of embodiment B60, wherein the antibody is an IgG1, an IgG2 or an IgG4 and the modified heavy chain Fc region further comprises the amino acid substitution H435R/Y436F, wherein numbering is according to the EU index.

B62. The antibody of embodiment B60, wherein the antibody is IgG3 and the second heavy chain Fc region further comprises the amino acid substitution R435H/F436Y, wherein numbering is according to the EU index.

B63. The antibody of any one of embodiments B57 to B62, wherein the modified heavy chain Fc region further comprises the amino acid substitution S354C, and the second heavy chain Fc region further comprises a the amino acid substitution Y349C, wherein numbering is according to the EU index.

B64. The antibody of any one of embodiments B57 to B62, wherein the first modified heavy chain Fc region further comprises the amino acid substitution of Y349C, and the second heavy chain Fc region further comprises a the amino acid substitution S354C, wherein numbering is according to the EU index.

B65. The antibody of embodiment B51, wherein the modifications in the Fc region which alter the half-life of the antibody, wherein the half-life depends on FcRn binding affinity.

B66. The antibody of any one of embodiments B52 to B64, further comprising modifications in the Fc region that alter the half-life of the antibody, wherein the half-life depends on FcRn binding affinity.

B67. The antibody of any one of embodiments B51 to B65, wherein the one or more modifications alter the effector function, wherein the binding affinity for the Fc gamma receptor or C1q complement protein is increased or decreased.

B68. The antibody of any one of embodiments B52 to B66, further comprising modifications in the Fc region that alter the effector function, wherein the binding affinity for the Fc gamma receptor or C1q complement protein is increased or decreased.

B69. The antibody of any one of embodiments B1 to B68, which is a human antibody.

B70. The antibody of any one of embodiments B1 to B468, which is a humanized antibody.

B71. The antibody of any one of embodiments B1 to B68, which is a chimeric antibody.

C1. An isolated nucleic acid comprising a nucleotide sequence that encodes a modified heavy chain polypeptide, wherein the modified heavy chain comprises (i) a substitution of a native cysteine to a non-cysteine amino acid, and (ii) a substitution of a native non-cysteine amino acid to a cysteine amino acid.

C2. The nucleic acid of embodiment C1, wherein the CH1 region of the modified heavy chain polypeptide comprises (i) the substitution of a native cysteine to a non-cysteine amino acid, and (ii) the substitution of a native non-cysteine amino acid to a cysteine amino acid.

C3. The nucleic acid of embodiment C1 wherein the CH1 region of the modified heavy chain polypeptide comprises the substitution of a native cysteine to a non-cysteine amino acid and the VH region of the modified heavy chain comprises the substitution of a native non-cysteine amino acid to a cysteine amino acid.

C4. An isolated nucleic acid comprising a nucleotide sequence that encodes a modified heavy chain polypeptide, wherein the modified heavy chain comprises the substitution of at least one amino acid in the CH1 region resulting in a protrusion and/or a cavity.

C5. The nucleic acid of embodiment C2, wherein the modified heavy chain further comprises a substitution of a native cysteine to a non-cysteine amino acid.

C6. The nucleic acid of embodiment C1, C2, C3, or C5, wherein the heavy chain native cysteine is capable of forming an interchain disulphide bond.

C7. The nucleic acid of any one of embodiments C1 to C6, which encodes a modified immunoglobulin G (IgG) heavy chain.

C8. The nucleic acid of embodiment C7, wherein the modified heavy chain is an IgG1 heavy chain comprising the substitution of a native cysteine to a non-cysteine amino acid at position 220 of the CH1 region, wherein numbering is according to the EU index.

C9. The nucleic acid of embodiment C7, wherein the modified heavy chain is an IgG2 heavy chain comprising the substitution of a native cysteine to a non-cysteine amino acid at positions 131 and/or 219 and/or 220 of the CH1 region, wherein numbering is according to the EU index.

C10. The nucleic acid of embodiment C7, wherein the modified heavy chain is an IgG2 heavy chain comprising the substitution of a native cysteine to a non-cysteine amino acid at each of positions 131 and 219 and 220 of the CH1 region, wherein numbering is according to the EU index.

C11. The nucleic acid of embodiment C7, wherein the modified heavy chain is an IgG2 heavy chain comprising the substitution of a native cysteine to a non-cysteine amino acid at each of positions 131 and 220 of the CH1 region, wherein numbering is according to the EU index.

C12. The nucleic acid of embodiment C7, wherein the modified heavy chain is an IgG3 or IgG4 heavy chain comprising the substitution of a native cysteine to a non-cysteine amino acid at position 131 of the CH1 region, wherein numbering is according to the EU index.

C13. The nucleic acid of any one of embodiments C7 to C12, wherein the non-cysteine amino acid is a valine or alanine.

C14. The nucleic acid of any one of embodiments C7 to C13, wherein the modified heavy chain comprises the substitution of a native non-cysteine amino acid to a cysteine amino acid at position 141 of the CH1 region, wherein numbering is according to the EU index.

C15. The nucleic acid of embodiment C14, wherein the modified heavy chain is an IgG1 heavy chain comprising amino acid substitutions whereby the alanine at position 141 of the CH1 region is substituted by a cysteine, and the cysteine at position 220 of the CH1 region is substituted by an amino acid that is not cysteine, wherein numbering is according to the EU index.

C16. The nucleic acid of embodiment C14, wherein the modified heavy chain is an IgG2 heavy chain comprising amino acid substitutions whereby the alanine at position 141 of the CH1 region is substituted by a cysteine, and the cysteine at each of positions 131 and 220 of the CH1 region is substituted by an amino acid that is not cysteine, wherein numbering is according to the EU index.

C17. The nucleic acid of embodiment C14, wherein the modified heavy chain is an IgG3 or IgG4 heavy chain comprising amino acid substitutions whereby the alanine at position 141 of the CH1 region is substituted by a cysteine, and the cysteine at position 131 of the CH1 region is substituted by an amino acid that is not cysteine, wherein numbering is according to the EU index.

C18. The nucleic acid of any one of embodiments C14 to C16, wherein the modified heavy chain comprises amino acid substitutions whereby the alanine at position 141 of the CH1 region is substituted by a cysteine, and the cysteine at position 220 of the CH1 region is substituted by a valine, wherein numbering is according to the EU index.

C19. The nucleic acid of embodiment C14, or C16 to C18, wherein the modified heavy chain comprises amino acid substitutions whereby the alanine at position 141 of the CH1 region is substituted by a cysteine, and the cysteine at position 131 of the CH1 region is substituted by a valine, wherein numbering is according to the EU index.

C20. The nucleic acid of any one of embodiments C7 to C13, wherein the modified heavy chain comprises the substitution of a native non-cysteine amino acid to a cysteine amino acid at position 168 of the CH1 region, wherein numbering is according to the EU index.

C21. The nucleic acid of embodiment C20, wherein the modified heavy chain is an IgG1 heavy chain comprising amino acid substitutions whereby the histidine at position 168 of the CH1 region is substituted by a cysteine, and the cysteine at position 220 of the CH1 region is substituted by an amino acid that is not cysteine, wherein numbering is according to the EU index.

C22. The nucleic acid of embodiment C20, wherein the modified heavy chain is an IgG2 heavy chain comprising amino acid substitutions whereby the histidine at position 168 of the CH1 region is substituted by a cysteine, and the cysteine at each of positions 131 and 220 of the CH1 region is substituted by an amino acid that is not cysteine, wherein numbering is according to the EU index.

C23. The nucleic acid of embodiment C20, wherein the modified heavy chain is an IgG3 or IgG4 heavy chain comprising amino acid substitutions whereby the histidine at position 168 of the CH1 region is substituted by a cysteine, and the cysteine at position 131 of the CH1 region is substituted by an amino acid that is not cysteine, wherein numbering is according to the EU index.

C24. The nucleic acid of any one of embodiments C20 to C22, wherein the modified heavy chain comprises amino acid substitutions whereby the histidine at position 168 of the CH1 region is substituted by a cysteine, and the cysteine at position 220 of the CH1 region is substituted by a valine, wherein numbering is according to the EU index.

C25. The nucleic acid of any one of embodiments C20, or C22 to C24, wherein the modified heavy chain comprises amino acid substitutions whereby the histidine at position 168 of the CH1 region is substituted by a cysteine, and the cysteine at position 131 of the CH1 region is substituted by a valine, wherein numbering is according to the EU index.

C26. The nucleic acid of any one of embodiments C7 to C13, wherein the modified heavy chain comprises the substitution of a native non-cysteine amino acid to cysteine amino acid at position 126 of the CH1 region, wherein numbering is according to the EU index.

C27. The nucleic acid of embodiment C26, wherein the modified heavy chain is an IgG1 heavy chain comprising amino acid substitutions whereby the phenylalanine at position 126 of the CH1 region is substituted by a cysteine, and the cysteine at position 220 of the CH1 region is substituted by an amino acid that is not cysteine, wherein numbering is according to the EU index.

C28. The nucleic acid of embodiment C26, wherein the modified heavy chain is an IgG2 heavy chain comprising amino acid substitutions whereby the phenylalanine at position 126 of the CH1 region is substituted by a cysteine, and the cysteine at each of positions 131 and 220 of the CH1 region is substituted by an amino acid that is not cysteine, wherein numbering is according to the EU index.

C29. The nucleic acid of embodiment C26, wherein the modified heavy chain is an IgG3 or IgG4 heavy chain comprising amino acid substitutions whereby the phenylalanine at position 126 of the CH1 region is substituted by a cysteine, and the cysteine at position 131 of the CH1 region is substituted by an amino acid that is not cysteine, wherein numbering is according to the EU index.

C30. The nucleic acid of any one of embodiments C26 to C28, wherein the modified heavy chain comprises amino acid substitutions whereby the phenylalanine at position 126 of the CH1 region is substituted by a cysteine, and the cysteine at position 220 of the CH1 region is substituted by a valine, wherein numbering is according to the EU index.

C31. The nucleic acid of any one of embodiments C26 or C28 to C30, wherein the modified heavy chain comprises amino acid substitutions whereby the phenylalanine at position 126 is substituted by a cysteine, and the cysteine at position 131 is substituted by a valine, wherein numbering is according to the EU index.

C32. The nucleic acid of any one of embodiments C7 to C13, wherein the modified heavy chain comprises the substitution of a native non-cysteine amino acid to a cysteine amino acid at position 128 of the CH1 region, wherein numbering is according to the EU index.

C33. The nucleic acid of embodiment C32, wherein the modified heavy chain is an IgG1 heavy chain comprising amino acid substitutions whereby the leucine at position 128 of the CH1 region is substituted by a cysteine, and the cysteine at position 220 of the CH1 region is substituted by an amino acid that is not cysteine, wherein numbering is according to the EU index.

C34. The nucleic acid of embodiment C32, wherein the modified heavy chain is an IgG2 heavy chain comprising amino acid substitutions whereby the leucine at position 128 of the CH1 region is substituted by a cysteine, and the cysteine at each of positions 131 and 220 of the CH1 region is substituted by an amino acid that is not cysteine, wherein numbering is according to the EU index.

C35. The nucleic acid of embodiment C32, wherein the modified heavy chain is an IgG3 or IgG4 heavy chain comprising amino acid substitutions whereby the leucine at position 128 of the CH1 region is substituted by a cysteine, and the cysteine at position 131 of the CH1 region is substituted by an amino acid that is not cysteine, wherein numbering is according to the EU index.

C36. The nucleic acid of embodiment C32 to C34, wherein the modified heavy chain comprises amino acid substitutions whereby the leucine at position 128 of the CH1 region is substituted by a cysteine, and the cysteine at position 220 of the CH1 region is substituted by a valine, wherein numbering is according to the EU index.

C37. The nucleic acid of any one of embodiments C32 or C34 to C36, wherein the modified heavy chain comprises amino acid substitutions whereby the leucine at position 128 of the CH1 region is substituted by a cysteine, and the cysteine at position 131 of the CH1 region is substituted by a valine, wherein numbering is according to the EU index.

C38. The nucleic acid of any one of embodiments C7 to C13, wherein the modified heavy chain comprises the substitution of a native non-cysteine amino acid to a cysteine amino acid at position 44 of the variable region, wherein numbering is according to the Kabat index.

C39. The nucleic acid of embodiment C38, wherein the modified heavy chain is an IgG1 heavy chain comprising the substitution of a native non-cysteine amino acid to a cysteine amino acid at position 44 of the variable region, wherein numbering is according to the Kabat index, and wherein the cysteine at position 220 of the CH region is substituted by an amino acid that is not cysteine, wherein numbering is according to the EU index.

C40. The nucleic acid of embodiment C38, wherein the modified heavy chain is an IgG2 heavy chain comprising the substitution of a native non-cysteine amino acid to a cysteine amino acid at position 44 of the variable region, wherein numbering is according to the Kabat index, and wherein the cysteine at each of positions 131 and 220 of the CH1 region is substituted by an amino acid that is not cysteine, wherein numbering is according to the EU index.

C41. The nucleic acid of embodiment C38, wherein the modified heavy chain is an IgG3 or IgG4 heavy chain comprising the substitution of a native non-cysteine amino acid to a cysteine amino acid at position 44 of the variable region, wherein numbering is according to the Kabat index, and wherein the cysteine at position 131 of the CH1 region is substituted by an amino acid that is not cysteine, wherein numbering is according to the EU index.

C42. The nucleic acid of any one of embodiments C2, C3, or C7 to C12, wherein the modified heavy chain comprises a substitution of the amino acid at position 145 with an amino acid having a large side chain, a substitution of the amino acid at position 170 is with an amino acid having a small side chain, a substitution of the amino acid at position 183 with an amino acid having a large side chain, and a substitution of the amino acid at position 185 with an amino acid having a large side chain, wherein numbering is according to the EU index.

C43. The nucleic acid of embodiment C42, wherein the modified heavy chain comprises amino acid substitutions whereby the leucine at position 145 is substituted with phenylalanine, the phenylalanine at position 170 is substituted with valine, the serine at position 183 is substituted with phenylalanine and the valine at position 185 is substituted with phenylalanine, wherein numbering is according to the EU index.

C44. The nucleic acid of embodiment C2, C3, or C7 to C12, wherein the modified heavy chain comprises a substitution of the amino acid at position 147 with an amino acid having a small side chain and a substitution of the amino acid at position 185 with an amino acid having a large side chain, wherein numbering is according to the EU index.

C45. The nucleic acid of embodiment C44, wherein the modified heavy chain comprises amino acid substitutions whereby the lysine at position 147 is substituted with alanine and the valine at position 185 is substituted with tryptophan, wherein numbering is according to the EU index.

C46. The nucleic acid of any one of embodiments C1 to C45, wherein the modified heavy chain comprises an Fc region.

C47. The nucleic acid of embodiment C46, wherein the modified heavy chain Fc region comprises one or more modifications.

C48. The nucleic acid of embodiment C47, wherein the modifications in the modified heavy chain Fc region facilitate heterodimerization of two heavy chains.

C49. The nucleic acid of embodiment C47, wherein the modifications in the modified heavy chain Fc region alter protein A binding.

C50. The nucleic acid of embodiment C48, wherein the modified heavy chain Fc region further comprises modifications that alter protein A binding.

C51. The nucleic acid of embodiment C49 or C50, wherein the modified heavy chain is an IgG1, an IgG2 or an IgG4 and the modifications that alter protein A binding is the amino acid substitution H435R/Y436F, wherein numbering is according to the EU index.

C52. The nucleic acid of embodiment C49 or C50, wherein the modified heavy chain is an IgG3 and the modifications that alter protein A binding is the amino acid substitution R435H/F436Y, wherein numbering is according to the EU index.

C53. The nucleic acid of embodiment C47 or C48, wherein the modified heavy chain Fc region comprises an amino acid substitution T366W, wherein numbering is according to the EU index.

C54. The nucleic acid of embodiment C53, wherein the modified heavy chain is an IgG3 heavy chain and further comprises the amino acid substitution R435H/F436Y, wherein numbering is according to the EU index.

C55. The nucleic acid of embodiment C47 or C48, wherein the modified heavy chain Fc region comprises an amino acid substitution Y407V/T366S/L368A, wherein numbering is according to the EU index.

C56. The nucleic acid of embodiment C55, wherein the modified heavy chain is an IgG1, IgG2 or IgG4 heavy chain and further comprises an amino acid substitution H435R/Y436F, wherein numbering is according to the EU index.

C57. The nucleic acid of any one of embodiments C53 to C56, wherein the modified heavy chain Fc region further comprises an amino acid substitution of S354C or Y349C, wherein numbering is according to the EU index.

C58. The nucleic acid of embodiment C47, wherein the modifications in the modified heavy chain Fc region alter the half-life of the antibody, wherein the half-life depends on FcRn binding affinity.

C59. The nucleic acid of any one of embodiments C48 to C57, further comprising modifications in the modified heavy chain Fc region that alter the half-life of the antibody, wherein the half-life depends on FcRn binding affinity C60. The nucleic acid of embodiment C47, wherein the modifications in the modified heavy chain Fc region alter the effector function, wherein the binding affinity for the Fc gamma receptor or C1q complement protein is increased or decreased.

C61. The nucleic acid of any one of embodiments C48 to C59, further comprising modifications in the modified heavy chain Fc region that alter the effector function, wherein the binding affinity for the Fc gamma receptor or C1q complement protein is increased or decreased.

C62. The nucleic acid of any one of embodiments C1 to C61, which is in an expression vector.

C63. The nucleic acid of embodiment C62, wherein the expression vector further comprises a second nucleic acid which encodes a second heavy chain, wherein the second heavy chain comprises a CH1 region that is unmodified.

C64. The nucleic acid of embodiment C63, wherein the expression vector further comprises a third and fourth nucleic acid which each encode a first and second light chain wherein:
  (a) the first light chain is a modified light chain comprising (i) a substitution of a native cysteine to a non-cysteine amino acid, and (ii) a substitution of a native non-cysteine amino acid to a cysteine amino acid; and
  (b) the second light chain is unmodified.

C65. The nucleic acid of embodiment C62, wherein the expression vector further comprises a second nucleic acid which encodes a second heavy chain, wherein the second heavy chain comprises a CH1 region that is modified.

C66. The nucleic acid of embodiment C65, wherein the second modified heavy chain comprises the substitution of at least one amino acid in the CH1 region resulting in a protrusion and/or a cavity.

C67. The nucleic acid of embodiment C65 or C66, wherein the expression vector further comprises a third and fourth nucleic acid which each encode a first and second light chain wherein:
  (a) the first light chain is a modified light chain comprising the substitution of at least one amino acid in the CL region resulting in a compensatory cavity and/or protrusion; and
  (b) the second light chain is a modified light chain comprising the substitution of at least one amino acid in the CL region resulting in a compensatory cavity and/or protrusion,
  wherein the modifications favor the interchain pairing of the first heavy chain with the first light chain and the second heavy chain with the second light chain.

C68. The nucleic acid of any one of embodiments C63 to C67, wherein the second heavy chain comprises a, Fc region.

C69. The nucleic acid of embodiment C68, wherein the Fc region of the second heavy chain comprises one or more modifications.

C70. The nucleic acid of embodiment C69, wherein the modifications in the second heavy chain Fc region facilitate heterodimerization of two heavy chains.

C71. The nucleic acid of embodiment C69, wherein the modifications in the second heavy chain Fc region alter protein A binding.

C72. The nucleic acid of embodiment C70, wherein the second heavy chain Fc region further comprises modifications that alter protein A binding.

C73. The nucleic acid of embodiment C50a or C50b, wherein the second heavy chain is an IgG1, an IgG2 or an IgG4 and the modifications that alter protein A binding is the amino acid substitution H435R/Y436F, wherein numbering is according to the EU index.

C74. The nucleic acid of embodiment C71 or C72, wherein the second heavy chain is IgG3 and the modifications that alter protein A binding is the amino acid substitution R435H/F436Y, wherein numbering is according to the EU index.

C75. The nucleic acid of embodiment C69 or C70, wherein the modified heavy chain Fc region comprises the amino acid substitution Y407V/T366S/L368A, and the second heavy chain Fc region comprises the amino acid substitution T366W, wherein numbering is according to the EU index.

C76. The nucleic acid of embodiment C75, wherein the heavy chains are IgG1, an IgG2 or an IgG4 and the modified heavy chain Fc region further comprises the amino acid substitution H435R/Y436F, wherein numbering is according to the EU index.

C77. The nucleic acid of embodiment C75, wherein the heavy chains are IgG3 and the second heavy chain Fc region further comprises the amino acid substitution R435H/F436Y, wherein numbering is according to the EU index.

C78. The nucleic acid of embodiment C69 or C70, wherein the modified heavy chain Fc region comprises the amino acid substitution T366W, and the second heavy chain Fc region comprises the amino acid substitution Y407V/T366S/L368A, wherein numbering is according to the EU index.

C79. The nucleic acid of embodiment C78, wherein the heavy chains are IgG1, IgG2 or IgG4 and the second heavy chain Fc region further comprises an amino acid substitution H435R/Y436F, wherein numbering is according to the EU index.

C80. The nucleic acid of embodiment C78, wherein the heavy chains are IgG3 and the second heavy chain Fc region further comprises the amino acid substitution R435H/F436Y, wherein numbering is according to the EU index.

C81. The nucleic acid of any one of embodiments C75 to C80, wherein the second heavy chain Fc region further comprises an amino acid substitution of S354C or Y349C, wherein numbering is according to the EU index.

C82. The nucleic acid of embodiment C69, wherein the modifications in second heavy chain Fc region alter the half-life of the antibody, wherein the half-life depends on FcRn binding affinity.

C83. The nucleic acid of any one of embodiments C69 to C80, further comprising modifications in second heavy chain Fc region alter the half-life of the antibody, wherein the half-life depends on FcRn binding affinity.

C84. The nucleic acid of embodiment C49, wherein the modifications in the second heavy chain Fc region alter the effector function, wherein the binding affinity for the Fc gamma receptor or C1q complement protein is increased or decreased.

C85. The nucleic acid of any one of embodiments C69 to C83, further comprising modifications in the second heavy chain Fc region alter the effector function, wherein the binding affinity for the Fc gamma receptor or C1q complement protein is increased or decreased.

D1. An antibody comprising a modified light chain wherein the modified light chain comprises (i) a substitution of a native cysteine to a non-cysteine amino acid, and (ii) a substitution of a native non-cysteine amino acid to a cysteine amino acid.

D2. The antibody of embodiment D1, wherein the CL region comprises (i) the substitution of a native cysteine to a non-cysteine amino acid, and (ii) the substitution of a native non-cysteine amino acid to a cysteine amino acid.

D3. The antibody of embodiment D1 wherein the CL region comprises the substitution of a native cysteine to a non-cysteine amino acid and the VL region comprises the substitution of a native non-cysteine amino acid to a cysteine amino acid.

D4. The antibody of any one of embodiments D1 to D3, wherein the light chain native cysteine is capable of forming an interchain disulphide bond.

D5. The antibody of any one of embodiments D1 to D4, further comprising a modified heavy chain wherein the modified heavy chain comprises (i) a substitution of a native cysteine to a non-cysteine amino acid, and (ii) a substitution of a native non-cysteine amino acid to a cysteine amino acid.

D6. The antibody of embodiment D5, wherein the CH1 region comprises (i) the substitution of a native cysteine to a non-cysteine amino acid, and (ii) the substitution of a native non-cysteine amino acid to a cysteine amino acid.

D7. The antibody of embodiment D5, wherein the CH1 region comprises the substitution of a native cysteine to a non-cysteine amino acid, and the VH region comprises the substitution of a native non-cysteine amino acid to a cysteine amino acid.

D8. The antibody of embodiment D5, D6 or D7, wherein the heavy chain native cysteine is capable of forming an interchain disulphide bond.

D9. The antibody of embodiment D5, D6, D7 or D8 wherein the substituted cysteine of the modified heavy chain, resulting from the substitution of the native non-cysteine amino acid to the cysteine amino acid, and the substituted cysteine of the modified light chain, resulting from the substitution of the native non-cysteine amino acid to the cysteine amino acid, can form a disulphide bond.

D10. The antibody of any one of embodiments D1 to D9, comprising two heavy chains and two light chains.

D11. The antibody of embodiment D10, wherein the two heavy chains and two light chains are four separate polypeptides.

D12. The antibody of embodiment D10, wherein the two heavy chains and two light chains are a single polypeptide.

D13. The antibody of any one of embodiments D1 to D12, which is a full-length antibody.

D14. The antibody of any one of embodiments D10 to D13, wherein the two heavy chains each comprise a VH domain, a CH1 domain and an Fc region, wherein the VH domains have the same or different amino acid sequences, the CH1 domains have different amino acid sequences, and the Fc regions have different amino acid sequences.

D15. The antibody of embodiment D14, wherein the two heavy chains form a heterodimer.

D16. The antibody of any one of embodiments D10 to D15, wherein the two light chains each comprise a VL domain and a CL domain, wherein the VL domains have the same or different amino acid sequences and the CL domains have different amino acid sequences.

D17. The antibody of any one of embodiments D1 to D16, that specifically binds to two independent antigens or to two independent epitopes on the same antigen.

D18. The antibody of embodiment D17, wherein the binding affinity for the two independent antigens is the same or different.

D19. The antibody of embodiment D17, wherein the binding affinity for the two independent epitopes on the same antigen is the same or different.

D20. The antibody of any one of embodiments D1 to D16, that specifically binds to the same epitope with two different binding affinities.

D21. The antibody of any one of embodiments D1 to D20, wherein the light chain is a kappa light chain or a lambda light chain.

D22. The antibody of any one of embodiments D6 to D20, wherein one light chain is a kappa light chain and one light chain is a lambda light chain.

D23. The antibody of any one of embodiments D1 to D22, comprising (i) one modified heavy chain comprising a modification in the CH1 region and one modified corresponding light chain comprising a modification in the CL region, and (ii) a second heavy chain and corresponding light chain, wherein the CH1 and CL regions are not modified.

D24. The antibody of any one of embodiments D1 to D23, which is an immunoglobulin G (IgG).

D25. The antibody of any one of embodiments D5 to D24, wherein the modified heavy chain is an IgG1 heavy chain comprising the substitution of a native cysteine to a non-cysteine amino acid at position 220 of the CH1 region, wherein numbering is according to the EU index.

D26. The antibody of any one of embodiments D5 to D24, wherein the modified heavy chain is an IgG2 heavy chain comprising the substitution of a native cysteine to a non-cysteine amino acid at positions 131 and/or 219 and/or 220 of the CH1 region, wherein numbering is according to the EU index.

D27. The antibody of any one of embodiments D5 to D24, wherein the modified heavy chain is an IgG2 heavy chain comprising the substitution of a native cysteine to a non-cysteine amino acid at each of positions 131 and 219 and 220 of the CH1 region, wherein numbering is according to the EU index.

D28. The antibody of any one of embodiments D5 to D24, wherein the modified heavy chain is an IgG2 heavy chain comprising the substitution of a native cysteine to a non-cysteine amino acid at each of positions 131 and 220 of the CH1 region, wherein numbering is according to the EU index.

D29. The antibody of any one of embodiments D5 to D24, wherein the modified heavy chain is an IgG3 or IgG4 heavy chain comprising the substitution of a native cysteine to a non-cysteine amino acid at position 131 of the CH1 region, wherein numbering is according to the EU index.

D30. The antibody of embodiment D29, wherein the modified corresponding light chain comprises the substitution of a native cysteine to a non-cysteine amino acid at position 214 of the CL region, wherein numbering is according to the EU index.

D31. The antibody of any one of embodiments D25 to D30, wherein the non-cysteine amino acid is a valine or alanine.

D32. The antibody of any one of embodiments D25 to D31, wherein the modified heavy chain comprises the substitution of a native non-cysteine amino acid to a cysteine amino acid at position 141 of the CH1 region, wherein numbering is according to the EU index.

D33. The antibody of embodiment D32, wherein the modified heavy chain is an IgG1 heavy chain comprising amino acid substitutions whereby the alanine at position 141 of the CH1 region is substituted by a cysteine, and the cysteine at position 220 of the CH1 region is substituted by an amino acid that is not cysteine, wherein numbering is according to the EU index.

D34. The antibody of embodiment D32, wherein the modified heavy chain is an IgG2 heavy chain comprising amino acid substitutions whereby the alanine at position 141 of the CH1 region is substituted by a cysteine, and the cysteine at each of positions 131 and 220 of the CH1 region is substituted by an amino acid that is not cysteine, wherein numbering is according to the EU index.

D35. The antibody of embodiment D32, wherein the modified heavy chain is an IgG3 or IgG4 heavy chain comprising amino acid substitutions whereby the alanine at position 141 of the CH1 region is substituted by a cysteine, and the cysteine at position 131 of the CH1 region is substituted by an amino acid that is not cysteine, wherein numbering is according to the EU index.

D36. The antibody of embodiment D32, D33, or D34, wherein the modified heavy chain comprises amino acid substitutions whereby the alanine at position 141 of the CH1 region is substituted by a cysteine, and the cysteine at position 220 of the CH1 region is substituted by a valine, wherein numbering is according to the EU index.

D37. The antibody of embodiment D32, D33, D34 or D35, wherein the modified heavy chain comprises amino acid substitutions whereby the alanine at position 141 of the CH1 region is substituted by a cysteine, and the cysteine at position 131 of the CH1 region is substituted by a valine, wherein numbering is according to the EU index.

D38. The antibody of any one of embodiments D32 to D37, wherein the modified corresponding light chain comprises the substitution of a native non-cysteine amino acid to a cysteine amino acid at position 116 of the CL region and the substitution of a native cysteine to a non-cysteine amino acid at position 214 of the CL region, wherein numbering is according to the EU index.

D39. The antibody of any one of embodiments D32 to D38, wherein the modified corresponding light chain comprises amino acid substitutions whereby the phenylalanine or threonine at position 116 of the CL region is substituted by a cysteine, and the cysteine at position 214 of the CL region is substituted by an amino acid that is not cysteine, wherein numbering is according to the EU index.

D40. The antibody of any one of embodiments D32 to D39, wherein the modified corresponding light chain comprises amino acid substitutions whereby the phenylalanine at position 116 of the CL region is substituted by a cysteine, and the cysteine at position 214 of the CL region is substituted by a valine, wherein numbering is according to the EU index.

D41. The antibody of any one of embodiments D32 to D39, wherein the modified corresponding light chain comprises amino acid substitutions whereby the threonine at position 116 of the CL region is substituted by a cysteine, and the cysteine at position 214 of the CL region is substituted by a valine, wherein numbering is according to the EU index.

D42. The antibody of any one of embodiments D25 to D33, wherein the modified heavy chain comprises the substitution of a native non-cysteine amino acid to a cysteine amino acid at position 168 of the CH1 region, wherein numbering is according to the EU index.

D43. The antibody of embodiment D42, wherein the modified heavy chain is an IgG1 heavy chain comprising amino acid substitutions whereby the histidine at position 168 of the CH1 region is substituted by a cysteine, and the cysteine at position 220 of the CH1 region is substituted by an amino acid that is not cysteine, wherein numbering is according to the EU index.

D44. The antibody of embodiment D42, wherein the modified heavy chain is an IgG2 heavy chain comprising amino acid substitutions whereby the histidine at position 168 of the CH1 region is substituted by a cysteine, and the cysteine at each of positions 131 and 220 of the CH1 region is substituted by an amino acid that is not cysteine, wherein numbering is according to the EU index.

D45. The antibody of embodiment D42, wherein the modified heavy chain is an IgG3 or IgG4 heavy chain comprising amino acid substitutions whereby the histidine at position 168 of the CH1 region is substituted by a cysteine, and the cysteine at position 131 of the CH1 region is substituted by an amino acid that is not cysteine, wherein numbering is according to the EU index.

D46. The antibody of any one of embodiments D42 to D44, wherein the modified heavy chain comprises amino acid substitutions whereby the histidine at position 168 of the CH1 region is substituted by a cysteine, and the cysteine at position 220 of the CH1 region is substituted by a valine, wherein numbering is according to the EU index.

D47. The antibody of embodiment D42, D44 or D45, wherein the modified heavy chain comprises amino acid substitutions whereby the histidine at position 168 of the CH1 region is substituted by a cysteine, and the cysteine at position 131 of the CH1 region is substituted by a valine, wherein numbering is according to the EU index.

D48. The antibody of any one of embodiments D42 to D47, wherein the modified corresponding light chain comprises the substitution of a native non-cysteine amino acid to a cysteine at position 164 of the CL region and the substitution of a native cysteine to a non-cysteine amino acid at position 214 of the CL region, wherein numbering is according to the EU index.

D49. The antibody of any one of embodiments D42 to D48, wherein the modified corresponding light chain comprises amino acid substitutions whereby the threonine at position 164 of the CL region is substituted by a cysteine, and the cysteine at position 214 of the CL region is substituted by a non-cysteine amino acid, wherein numbering is according to the EU index.

D50. The antibody of any one of embodiments D42 to D49, wherein the modified corresponding light chain comprises amino acid substitutions whereby the threonine at position 164 of the CL region is substituted by a cysteine, and the cysteine at position 214 of the CL region is substituted by a valine, wherein numbering is according to the EU index.

D51. The antibody of any one of embodiments D25 to D31, wherein the modified heavy chain comprises the substitution of a native non-cysteine amino acid to cysteine amino acid at position 126 of the CH1 region, wherein numbering is according to the EU index.

D52. The antibody of embodiment D51, wherein the modified heavy chain is an IgG1 heavy chain comprising amino acid substitutions whereby the phenylalanine at position 126 of the CH1 region is substituted by a cysteine, and the cysteine at position 220 of the CH1 region is substituted by an amino acid that is not cysteine, wherein numbering is according to the EU index.

D53. The antibody of embodiment D51, wherein the modified heavy chain is an IgG2 heavy chain comprising amino acid substitutions whereby the phenylalanine at position 126 of the CH1 region is substituted by a cysteine, and the cysteine at each of positions 131 and 220 of the CH1 region is substituted by an amino acid that is not cysteine, wherein numbering is according to the EU index.

D54. The antibody of embodiment D51, wherein the modified heavy chain is an IgG3 or IgG4 heavy chain comprising amino acid substitutions whereby the phenylalanine at position 126 of the CH1 region is substituted by a cysteine, and the cysteine at position 131 of the CH1 region is substituted by an amino acid that is not cysteine, wherein numbering is according to the EU index.

D55. The antibody of any one of embodiments D51 to D53, wherein the modified heavy chain comprises amino acid substitutions whereby the phenylalanine at position 126 of the CH1 region is substituted by a cysteine, and the cysteine at position 220 of the CH1 region is substituted by a valine, wherein numbering is according to the EU index.

D56. The antibody of any one of embodiments D51 or D53 to D55, wherein the modified heavy chain comprises amino acid substitutions whereby the phenylalanine at position 126 of the CH1 region is substituted by a cysteine, and the cysteine at position 131 of the CH1 region is substituted by a valine, wherein numbering is according to the EU index.

D57. The antibody of any one of embodiments D51 to D56, wherein the modified corresponding light chain comprises the substitution of a native non-cysteine amino acid to a cysteine amino acid at position 121 of the CL region, and the substitution of a native cysteine to a non-cysteine amino acid at position 214 of the CL region, wherein numbering is according to the EU index.

D58. The antibody of any one of embodiments D51 to D57, wherein the modified corresponding light chain comprises amino acid substitutions whereby the serine at position 121 of the CL region substituted by a cysteine, and the cysteine at position 214 of the CL region is substituted by an amino acid that is not cysteine, wherein numbering is according to the EU index.

D59. The antibody of any one of embodiments D51 to D58, wherein the modified corresponding light chain comprises amino acid substitutions whereby the serine at position 121 of the CL region substituted by a cysteine, and the cysteine at position 214 of the CL region is substituted by a valine, wherein numbering is according to the EU index.

D60. The antibody of any one of embodiments D25 to D31, wherein the modified heavy chain comprises the substitution of a native non-cysteine amino acid to a cysteine amino acid at position 128 of the CH1 region, wherein numbering is according to the EU index.

D61. The antibody of embodiment D60, wherein the modified heavy chain is an IgG1 heavy chain comprising amino acid substitutions whereby the leucine at position 128 of the CH1 region is substituted by a cysteine, and the cysteine at position 220 of the CH1 region is substituted by an amino acid that is not cysteine, wherein numbering is according to the EU index.

D62. The antibody of embodiment D60, wherein the modified heavy chain is an IgG2 heavy chain comprising amino acid substitutions whereby the leucine at position 128 of the CH1 region is substituted by a cysteine, and the cysteine at each of positions 131 and 220 of the CH1 region is substituted by an amino acid that is not cysteine, wherein numbering is according to the EU index.

D63. The antibody of embodiment D60, wherein the modified heavy chain is an IgG3 or IgG4 heavy chain comprising amino acid substitutions whereby the leucine at position 128 of the CH1 region is substituted by a cysteine, and the cysteine at position 131 of the CH1 region is substituted by an amino acid that is not cysteine, wherein numbering is according to the EU index.

D64. The antibody of any one of embodiments D60 to D62, wherein the modified heavy chain comprises amino acid substitutions whereby the leucine at position 128 of the CH1 region is substituted by a cysteine, and the cysteine at position 220 of the CH1 region is substituted by a valine, wherein numbering is according to the EU index.

D65. The antibody of any one of embodiments D60 or D62 to D64, wherein the modified heavy chain comprises amino acid substitutions whereby the leucine at position 128 of the CH1 region is substituted by a cysteine, and the cysteine at position 131 of the CH1 region is substituted by a valine, wherein numbering is according to the EU index.

D66. The antibody of any one of embodiments D60 to D65, wherein the modified corresponding light chain comprises the substitution of a native non-cysteine amino acid to a cysteine amino acid at position 118 of the CL region and the substitution of a native cysteine to a non-cysteine amino acid at position 214 of the CL region, wherein numbering is according to the EU index.

D67. The antibody of any one of embodiments D60 to D66, wherein the modified corresponding light chain comprises amino acid substitutions whereby the phenylalanine at position 118 of the CL region is substituted by a cysteine, and the cysteine at position 214 of the CL region is substituted by an amino acid that is not cysteine, wherein numbering is according to the EU index.

D68. The antibody of any one of embodiments D60 to D67, wherein the modified corresponding light chain comprises amino acid substitutions whereby the phenylalanine at position 118 of the CL region is substituted by a cysteine, and the cysteine at position 214 of the CL region is substituted by a valine, wherein numbering is according to the EU index.

D69. The antibody of any one of embodiments D23 to D31, wherein the modified heavy chain comprises the substitution of a native non-cysteine amino acid to a cysteine amino acid at position 44 of the variable region, wherein numbering is according to the Kabat index.

D70. The antibody of embodiment D69, wherein the modified heavy chain is an IgG1 heavy chain comprising the substitution of a native non-cysteine amino acid to a cysteine amino acid at position 44 of the variable region, wherein numbering is according to the Kabat index, and wherein the cysteine at position 220 of the CH region is substituted by an amino acid that is not cysteine, wherein numbering is according to the EU index.

D71. The antibody of embodiment D69, wherein the modified heavy chain is an IgG2 heavy chain comprising the substitution of a native non-cysteine amino acid to a cysteine amino acid at position 44 of the variable region, wherein numbering is according to the Kabat index, and wherein the cysteine at each of positions 131 and 220 of the CH1 region is substituted by an amino acid that is not cysteine, wherein numbering is according to the EU index.

D72. The antibody of embodiment D69, wherein the modified heavy chain is an IgG3 or IgG4 heavy chain comprising the substitution of a native non-cysteine amino acid to a cysteine amino acid at position 44 of the variable region, wherein numbering is according to the Kabat index, and wherein the cysteine at position 131 of the CH1 region is substituted by an amino acid that is not cysteine, wherein numbering is according to the EU index.

D73. The antibody of any one of embodiments D69 to D72, wherein the modified corresponding light chain comprises the substitution of a native non-cysteine amino acid to a cysteine amino acid at position 100 of the variable region wherein numbering is according to Kabat, and the substitution of a native cysteine to a non-cysteine amino acid at position 214 of the CL region, wherein numbering is according to the EU index.

D74. The antibody of embodiment D14, wherein the Fc region comprises one or more modifications.

D75. The antibody of embodiment D74, wherein the modifications in the Fc region facilitate heterodimerization of the heavy chains.

D76. The antibody of embodiment D74, wherein the modifications in the Fc region alter protein A binding and are only present in one heavy chain.

D77. The antibody of embodiment D75, further comprising modifications in the Fc region that alters protein A binding and are only present in one heavy chain.

D78. The antibody of embodiment D76 or D77, wherein the antibody is an IgG1, an IgG2 or an IgG4 and the Fc region modifications that alter protein A binding is the amino acid substitution H435R/Y436F, wherein numbering is according to the EU index.

D79. The antibody of embodiment D76 or D77, wherein the antibody is IgG3 and the Fc region modifications that alter protein A binding is the amino acid substitution R435H/F436Y, wherein numbering is according to the EU index.

D80. The antibody of any one of embodiments D23-D75, wherein the modified heavy chain Fc region comprises the amino acid substitution T366W, and the second heavy chain Fc region comprises the amino acid substitution Y407V/T366S/L368A, wherein numbering is according to the EU index.

D81. The antibody of embodiment D80, wherein the antibody is an IgG1, an IgG2 or an IgG4 and the second heavy chain Fc region further comprises the amino acid substitution H435R/Y436F, wherein numbering is according to the EU index.

D82. The antibody of embodiment D80, wherein the antibody is IgG3 and the first heavy chain Fc region further comprises the amino acid substitution R435H/F436Y, wherein numbering is according to the EU index.

D83. The antibody of any one of embodiments D23-D75, wherein the modified heavy chain Fc region comprises the amino acid substitution Y407V/T366S/L368A, and the second heavy chain comprises a CH3 region comprising the amino acid substitution T366W, wherein numbering is according to the EU index.

D84. The antibody of embodiment D83, wherein the antibody is an IgG1, an IgG2 or an IgG4 and the modified heavy chain Fc region further comprises the amino acid substitution H435R/Y436F, wherein numbering is according to the EU index.

D85. The antibody of embodiment D83, wherein the antibody is IgG3 and the second heavy chain Fc region further comprises the amino acid substitution R435H/F436Y, wherein numbering is according to the EU index.

D86. The antibody of any one of embodiments D80-D85, wherein the modified heavy chain Fc region further the amino acid substitution of S354C, and the second heavy chain Fc region further comprises the amino acid substitution Y349C, wherein numbering is according to the EU index.

D87. The antibody of any one of embodiments D80-D85, wherein the modified heavy chain Fc region further comprises the amino acid substitution of Y349C, and the second heavy Fc region chain further comprises the amino acid substitution S354C, wherein numbering is according to the EU index.

D88. The antibody of embodiment D74, wherein the modifications in the Fc region alter the half-life of the antibody, wherein the half-life depends on FcRn binding affinity.

D89. The antibody of any one of embodiments D74 to D88, further comprising modifications in the Fc region that alter the half-life of the antibody, wherein the half-life depends on FcRn binding affinity.

D90. The antibody of embodiment D74, wherein the modifications in the Fc region alter the effector function, wherein the binding affinity for the Fc gamma receptor or C1q complement protein is increased or decreased.

D91. The antibody of any one of embodiments D74-D89, further comprising modifications in the Fc region that alter the effector function, wherein the binding affinity for the Fc gamma receptor or C1q complement protein is increased or decreased.

D92. The antibody of any one of embodiments D1 to D91, which is a human antibody.

D93. The antibody of any one of embodiments D1 to D91, which is a humanized antibody.

D94. The antibody of any one of embodiments D1 to D91, which is a chimeric antibody.

E1. A composition comprising the antibody of any one of embodiments A1 to A94.

E2. A composition comprising the antibody of any one of embodiments B1 to B71.

E3. A composition comprising the antibody of any one of embodiments D1 to D94

F1. An isolated nucleic acid comprising a nucleotide sequence that encodes a modified light chain polypeptide, wherein the modified light chain comprises (i) a substitution of a native cysteine to a non-cysteine amino acid, and (ii) a substitution of a native non-cysteine amino acid to a cysteine amino acid.

F2. The nucleic acid of embodiment F1, wherein the CL region of the modified light chain polypeptide comprises (i) the substitution of a native cysteine to a non-cysteine amino acid, and (ii) the substitution of a native non-cysteine amino acid to a cysteine amino acid.

F3. The nucleic acid of embodiment F1 wherein the CL region of the modified light chain polypeptide comprises the substitution of a native cysteine to a non-cysteine amino acid and the VL region of the modified light chain polypeptide comprises the substitution of a native non-cysteine amino acid to a cysteine amino acid.

F4. An isolated nucleic acid comprising a nucleotide sequence that encodes a modified light chain polypeptide, wherein the modified light chain comprises a substitution of at least one amino acid in the CL region resulting in a cavity and/or a protrusion.

F5. The nucleic acid of embodiment F4, wherein the modified light chain further comprises a substitution of a native cysteine to a non-cysteine amino acid.

F6. The nucleic acid of embodiment F1, F2, F3, or F5, wherein the light chain native cysteine is capable of forming an interchain disulphide bond.

F7. The nucleic acid of any one of embodiments F1 to F6, wherein the modified light chain is a kappa light chain.

F8. The nucleic acid of any one of embodiments F1 to F6, wherein the modified light chain is a lambda light chain.

F9. The nucleic acid of any one of embodiments F1 to F8, which encodes a modified immunoglobulin G (IgG) light chain.

F10. The nucleic acid of embodiment F9, wherein the modified light chain comprises the substitution of a native cysteine to a non-cysteine amino acid at position 214 of the CL region, wherein numbering is according to the EU index.

F11. The nucleic acid of embodiment F9, wherein the modified light chain comprises the substitution of a native non-cysteine amino acid to a cysteine amino acid at position 116 of the CL region and the substitution of a native cysteine to a non-cysteine amino acid at position 214 of the CL region, wherein numbering is according to the EU index.

F12. The nucleic acid of embodiment F11, wherein the modified light chain comprises amino acid substitutions whereby the phenylalanine or threonine at position 116 of the CL region is substituted by a cysteine, and the cysteine at position 214 of the CL region is substituted by an amino acid that is not cysteine, wherein numbering is according to the EU index.

F13. The nucleic acid of embodiment F12, wherein the modified light chain comprises amino acid substitutions whereby the phenylalanine at position 116 of the CL region is substituted by a cysteine, and the cysteine at position 214 of the CL region in is substituted by a valine, wherein numbering is according to the EU index.

F14. The nucleic acid of any one of embodiments F12, wherein the modified light chain comprises amino acid substitutions whereby the threonine at position 116 of the CL region is substituted by a cysteine, and the cysteine at position 214 of the CL region in is substituted by a valine, wherein numbering is according to the EU index.

F15. The nucleic acid of embodiment F5, wherein the modified light chain comprises amino acid substitutions whereby the threonine at position 164 of the CL region is substituted by a cysteine, and the cysteine at position 214 of the CL region is substituted by a valine, wherein numbering is according to the EU index.

F16. The nucleic acid of embodiment F9, wherein the modified light chain comprises amino acid substitutions whereby the serine at position 121 of the CL region substituted by a cysteine, and the cysteine at position 214 of the CL region is substituted by a valine, wherein numbering is according to the EU index.

F17. The nucleic acid of embodiment F9, wherein the modified light chain comprises amino acid substitutions whereby the phenylalanine at position 118 of the CL region is substituted by a cysteine, and the cysteine at position 214 of the CL region is substituted by a valine, wherein numbering is according to the EU index.

F18. The nucleic acid of embodiment F9, wherein the modified light chain comprises the substitution of a native non-cysteine amino acid to a cysteine amino acid at position 100 of the variable region wherein numbering is according to Kabat.

F19. The nucleic acid of embodiment F9 or F10, wherein the modified light chain comprises a substitution of the amino acid at position 131 with an amino acid having a large side chain and a substitution of the amino acid at position 135 with an amino acid having a small side chain, wherein numbering is according to the EU index.

F20. The nucleic acid of embodiment F19, wherein the modified light chain comprises amino acid substitutions whereby the serine or threonine at position 131 is substituted with a tryptophan and the leucine at position 135 of the CL region is substituted by a glycine, wherein numbering is according to the EU index.

F21. The nucleic acid of embodiment F9 or 10, wherein the modified light chain comprises a substitution of the amino acid at position 176 with an amino acid having a large side chain and a substitution of the amino acid at position 178 with an amino acid having a small side chain chain, wherein numbering is according to the EU index.

F22. The nucleic acid of embodiment F2, wherein the modified light chain comprises amino acid substitutions whereby the serine at position 176 is substituted with a phenylalanine and the threonine or tyrosine at position 178 is substituted with alanine, wherein numbering is according to the EU index.

F23. The nucleic acid of any one of embodiments F1 to F22, which is in an expression vector.

F24. The nucleic acid of embodiment F23, wherein the expression vector further comprises a second nucleic acid which encodes a second light chain that is unmodified.

F25. The nucleic acid of embodiment F23, wherein the expression vector further comprises a third and fourth nucleic acid which each encode a first and second heavy chain wherein:
(a) the first heavy chain is a modified heavy chain comprising (i) a substitution of a native cysteine to a non-cysteine amino acid, and (ii) a substitution of a native non-cysteine amino acid to a cysteine amino acid; and
(b) the second heavy chain is unmodified.

F26. The nucleic acid of embodiment F23, wherein the expression vector further comprises a second nucleic acid which encodes a second light chain that is modified.

F1. The nucleic acid of embodiment F26, wherein the second modified light chain comprises the substitution of at least one amino acid in the CL region resulting in a cavity and/or a protrusion.

F27. The nucleic acid of embodiment F26 or F27, wherein the expression vector further comprises a third and fourth nucleic acid which each encode a first and second heavy chain wherein:

(a) the first heavy chain is a modified heavy chain comprising the substitution of at least one amino acid in the CH1 region resulting in a compensatory protrusion and/or cavity; and (b) the second heavy chain is a modified heavy chain comprising the substitution of at least one amino acid in the CH1 region resulting in a compensatory protrusion and/or cavity, wherein the modifications favor the interchain pairing of the first light chain with the first heavy chain and the second light chain with the second heavy chain.

G1. A cell comprising the nucleic acid of any one of embodiments C62 to C85.

G2. A cell comprising the nucleic acid of any one of embodiments F23 to F28

G3. A cell comprising the nucleic acid of any one of embodiments C62, C63, C65, C66 or C68-C85, and the nucleic acid of embodiment F23, F24, F26 or F27.

H1. A method of producing a modified heavy chain polypeptide and corresponding modified light chain polypeptide, comprising contacting a plurality of cells comprising the nucleic acid of embodiment C62, C63, C65, C66 or C68-C85 and the nucleic acid of embodiment F23, F24, F26 or F27 to conditions under which the polypeptides are expressed.

H2. The method of embodiment H1, wherein the cells further comprise a nucleic acid encoding a second heavy chain polypeptide that is unmodified and a nucleic acid encoding a corresponding second light chain polypeptide that is unmodified.

H3. The method of embodiment H1, wherein the cells further comprise a nucleic acid encoding a second heavy chain polypeptide that is modified and a nucleic acid encoding a corresponding second light chain polypeptide that is modified.

H4. A method of producing (a) a modified heavy chain polypeptide, (b) a corresponding modified light chain polypeptide, (c) a second heavy chain polypeptide that is unmodified and (d) a corresponding light chain polypeptide that is unmodified, comprising contacting a plurality of cells comprising the nucleic acid of embodiment C63 or C68 to C85 and the nucleic acid of embodiment F24 to conditions under which the polypeptides are expressed.

H5. A method of producing (a) a modified heavy chain polypeptide, (b) a corresponding modified first light chain polypeptide, (c) a second modified heavy chain polypeptide that and (d) a corresponding second modified light chain polypeptide, comprising contacting a plurality of cells comprising the nucleic acid of embodiment C65, C66, or C68 to C85 and the nucleic acid of embodiment F26 to conditions under which the polypeptides are produced.

H5. A method of producing (a) a modified heavy chain polypeptide, (b) a corresponding modified light chain polypeptide, (c) a second heavy chain polypeptide comprising a CH1 region that is unmodified and (d) a corresponding light chain polypeptide that is unmodified, comprising contacting a plurality of cells comprising the nucleic acid of embodiment C64 or C68 to C85 or the nucleic acid of embodiment F25 to conditions under which the polypeptides are expressed.

H6. A method of producing (a) a first modified heavy chain polypeptide, (b) a corresponding modified light chain polypeptide, (c) a second heavy chain polypeptide that is modified and (d) a corresponding light chain polypeptide that is modified, comprising contacting a plurality of cells comprising the nucleic acid of embodiment C67 or C68 to C85 or the nucleic acid of embodiment F28 to conditions under which the polypeptides are expressed.

EXAMPLES

The examples set forth below illustrate certain aspects and do not limit the technology.

Example 1

Materials and Methods

The materials and methods set forth in this Example were used to perform the experiments described in subsequent examples. All reagents were from Invitrogen, Carlsbad, Calif., unless stated otherwise.

Construction of pMBab-Heavy and pMBab-Light Mammalian Expression Vectors and Cloning of Immunoglobulin Genes Expressed as MBab IgG1

Plasmids pMBab-Heavy and pMBab-Light (kappa and lambda) were designed for production of monovalent bispecific human IgG1 antibodies (MBab) in mammalian cell culture. The pMBab-Heavy vector contained two human gamma1 heavy chain (HC) cassettes to support HC heterodimerization, the former heavy chain carries the "Hole" set of mutations in CH3 domain while the latter carries the complement "Knob" mutation in CH3, although the order of the cassettes could readily be reversed. To circumvent mispairing of heavy and light chains, the native cysteine in the CH1 domain of the "Knob" heavy chain forming the interface disulfide with the light chain is removed and an alternative interface cysteine is inserted elsewhere in the CH1 domain or elsewhere in the VH region to support homodimerization of cognate (also referred to herein as "corresponding) light and heavy chains. Alternatively, the native cysteine in the CH1 domain of the "Hole" heavy chain forming the interface disulfide with the light chain may be removed and an alternative interface cysteine was inserted elsewhere in the CH1 domain or elsewhere in the VH domain to support dimerization of cognate light and heavy chains. Optionally, instead of an alternative interface cysteine one or more substitutions are introduced into each CH1 which generate a cavity and/or protrusion to support dimerization of cognate light and heavy chains, VH domains are introduced into the "Hole" and "Knob" HC cassettes in pMBab-Heavy vector as BssHII/NheI and BsrGI/SalI restriction fragments, respectively. The pMBab-Light-kappa vector contains two human kappa light chain (LC) cassettes. Vk domains are introduced into the LC cassettes in pMBab-Light-kappa vector as BssHII/BsiWI and BsrGI/NotI restriction fragments, respectively. A pMBab-Light-lambda vector is prepared using similar methods. VA domains are introduced into the LC cassettes in pMBab-Light-Lambda vector as BssHII/KasI and BsrGI/HindIII restriction fragments, respectively. Similarly, a pMBab-light vector could be constructed having one cassette with a kappa domain and one cassette with a lambda domain. To circumvent mispairings of the heavy and light chains the native cysteine in one of the CL (Ck or Cλ) domains forming the interface disulfide with the heavy chain is removed and instead an alternative interface cysteine is inserted elsewhere in the CL (Ck or Cλ) domain or elsewhere in the VL that complements with the alternative cysteine in the CH1 domain or VH domain for supporting dimerization of cognate light and heavy chains. Optionally, instead of an alternative interface cysteine in the CL domain one or more substitutions are introduced into each CL which generate a compensatory protrusion and/or cavity that complement with the cavity and/or protrusions in the CH1 domains to support the dimerization of cognate light and heavy chains. Using these vectors a MBab may be generated having two heavy chains and (i) two kappa chains; (ii) two lambda chains; or (iii) one lambda and one kappa chain, wherein substitutions have been introduced into at least one of the heavy chains and one of the light chains to circumvent mispairing and support dimerization of cognate light and heavy chains.

Plasmids pMBab-Heavy and pMBab-Light (kappa and lambda) were constructed on the backbone of an in-house mammalian expression vector used for production of mammalian human IgG1 antibodies. For construction of the pMBab-Heavy vector, a PmlI site was introduced into the hinge-region sequence by site-directed mutagenesis using overlap-extension PCR techniques to facilitate convenient cloning of engineered constant domains. The "Knob" mutation, T366W, and a stabilizing mutation, S354C, were introduced into the CH3 domain by site-directed mutagenesis using overlap-extension PCR techniques. The resulting "Knob" CH2-CH3 PCR product was cloned back into the vector as PmlI/EcoRI restriction fragment resulting in the removal of an internal NotI site in the vector. To construct the V12 variant two mutations, C220V and F126C. were introduced into the CH1 domain of the "Knob" heavy chain by site-directed mutagenesis using overlap-extension PCR techniques, where the former mutated the native Cysteine in CH1 forming the interface disulfide with light chain and the latter introduced an alternative interface Cysteine in CH1 to support homodimerization of cognate light and heavy chains. To construct the V10, V11, or VN variants, a C220V mutation, is combined with a A141C mutation, or a H168C mutation, or a L128C mutation. To construct the V1 variant, V185W and K147A mutations are optionally combined with a C220V mutation. To construct the V3 variant L145F, F170V, S183F and V185F mutations are optionally combined with the C220V. In the examples detailed below, the V1 or the V3 variant was combined with the C220V mutation via generation of synthetic gene fragments and inserted into the "Knob" heavy chain cassette in different vectors and subsequently paired with the alternate variant (i.e., V1 in the Knob cassette was paired with V3 in the hole cassette) in the "Hole" heavy chain cassette (see below). To facilitate removal of undesirable "Hole-Hole" homodimers additional mutations are introduced into the "Knob" CH3 domain of IgG3 Fc regions to introduce protein A binding. For example the R435H, F436Y mutations are known to introduce protein A binding into IgG3 antibodies and may be introduced using methods similar to those detailed below.

The "Hole" set of mutations, T366S, L368A, Y407V, and a stabilizing mutation, Y349C, were introduced into the CH3 domain of a second vector by site-directed mutagenesis using overlap-extension PCR techniques. The resulting "Hole" VH-CH1-CH2-CH3 PCR product was digested with BssHII/XbaI and inserted back into the vector carrying the "Knob" heavy chain following linearization of the vector with BssHII/NheI. Consequently the "Hole" heavy chain fragment had replaced the Light chain segment in the vector and further introduced a silent mutation that knocked out an internal NheI site and inserted a new HindIII site. For convenient cloning of VH domains into the "Hole" heavy chain segment, the internal SalI site at the 5' of CH1 domain was mutated to NheI by site-directed mutagenesis using overlap-extension PCR techniques. After sequence validation, the resulting plasmid was named pMBab-Heavy. To construct the V1 variant, V185W and K147A mutations are optionally combined with a C220V mutation. To construct the V3 variant L145F, F170V, S183F and V185F mutations are optionally combined with the C220V. In the examples detailed below, the V1 and V3 variants were generated as synthetic gene fragments without the C220V mutation and inserted into the "Hole" heavy chain cassette of the pMBab-Heavy vectors comprising the alternate variant in the "Knob" cassette, respectively. To facilitate removal of undesirable "Hole-Hole" homodimers additional mutations are introduced into the "Hole" CH3 domain of IgG1, IgG2 or IgG4 Fc regions to reduce or ablate protein A binding. For example the H435R, Y436F mutations known to eliminate protein A binding were introduced as described below.

For the construction of the pMBab-Light vector comprising the V12 variant, two mutations, C214V and S121C, were introduced into the light chain cassette in the vector by site-directed mutagenesis using overlap-extension PCR techniques. The former mutated the native Cysteine in the Ck domain forming the interface disulfide with heavy chain and the latter introduced an alternative interface Cysteine in Ck to complement with the alternative Cysteine in the CH1 domain for supporting homodimerization of cognate light and heavy chains. The resulting V-Ck PCR product was introduced back into the vector as BsrGI/EcoRI restriction fragment, replacing the existing heavy chain cassette. This further resulted in the removal of an internal NotI site in the vector. For convenient cloning of Vk domains into the Cysteine mutated light chain, the internal SalI site at the 5' of the Ck domain was mutated to NheI by site-directed mutagenesis using overlap-extension PCR techniques. After sequence validation the resulting vector was named pMBab-Light kappa chain. A similar vector made using the Vλ region comprises an engineered HindIII site replacing the NotI site in the second light chain cassette and a KasI site replacing the BsiWI in the first light chain cassette. The resulting vector was named pMBab-Light lambda chain. To construct the V10, V11, or VN variants a C214V mutation is combined with a F116C mutation (κ)/T116C mutation (λ), or a T164C mutation (κ or λ), or a F118C mutation (κ or λ), To construct the V1 variant, a S131W (κ)/T131W (κ) mutation and a L135G (κ or λ) mutation are optionally combined with a C220V mutation. To construct the V3 variant a S176F (κ or λ) mutation and a T178A (κ)/Y178A (λ) mutation are optionally combined with the C220V. In the examples detailed below, either the V1 or the V3 variant was combined with the C214V mutation via generation of synthetic gene fragments and inserted into the pMab-Light vector. The C214V mutation was included on only the VL paired with the corresponding CH1 having the C220V mutation.

Expression, Affinity Purification and Protein Quantification

All constructs indicated below were transiently expressed in HEK293F cells in suspension using 293Fectin™ (Invitrogen) as a transfection reagent and grown in Invitrogen's serum-free Freestyle™ medium. The following combinations of vectors were used for the expression of the antibodies used in these studies:

1. pMBab-Heavy anti-IL6 WT+anti-RAGE WT+pMBab-Light anti-IL6 WT+anti-RAGE WT;
2. pMBab-Heavy anti-IL6 WT+anti-RAGE (−Cys)+pMBab-Light anti-IL6 WT+anti-RAGE (−Cys);
3. pMBab-Heavy anti-IL6 WT+anti-RAGE V10+pMBab-Light anti-IL6 WT+anti-RAGE V10;
4. pMBab-Heavy anti-IL6 WT+anti-RAGE V11+pMBab-Light anti-IL6 WT+anti-RAGE V11;
5. pMBab-Heavy anti-IL6 WT+anti-RAGE V12+pMBab-Light anti-IL6 WT+anti-RAGE V12;

5. pMBab-Heavy anti-EGFR WT+anti-HER2V12+ pMBab-Light anti-EGFR WT+anti-HER2 V12;
6. pMBab-Heavy anti-IL6 V1+anti-RAGE V3 (–Cys)+ pMab-Light anti-IL6 V1+anti-RAGE V3 (–Cys);
7. pMBab-Heavy anti-IL6 V3+anti-RAGE V1 (–Cys)+ pMab-Light anti-IL6 V3+anti-RAGE V1 (–Cys);
8. pMBab-Heavy anti-IL6 V1+anti-RAGE V3+pMab-Light anti-IL6 V1+anti-RAGE V3; and
9. pMBab-Heavy anti-IL6 V3+anti-RAGE V1+pMab-Light anti-IL6 V3+anti-RAGE V1.

The culture medium was collected 10 days after transfection, and all antibody formats were purified by standard protein A affinity chromatography in accordance with the manufacturer's protocol (GE Healthcare, Piscataway, N.J.) and were subsequently buffer exchanged in PBS (pH 7.4). The purity of the constructs was analyzed using SDS-PAGE under reducing and nonreducing conditions and using analytical size-exclusion chromatography (see method below). The concentrations of the purified antibodies were determined by reading the absorbance at 280 nm using theoretically determined extinction coefficients.

Engineering, Production and Analysis of a pMBab-Heavy Construct Carrying "RF" Mutations in "Hole" Heavy Chain.

For ablation of protein A binding of the "Hole" heavy chain, hIgG1 residues H435 and Y436 in CH3 domain were mutated to the corresponding R435 and F436 respectively (H435R/Y436F), as found in human IgG3 by site-directed mutagenesis using overlap-extension PCR techniques. The resulting human IgG1 "Hole" heavy chain carrying mutations H435R and Y436F referred to "RF" mutation lack the ability of binding to protein A. pMBab constructs carrying the RF mutation were transiently expressed in HEK293F cells in suspension using 293Fectin™ (Invitrogen) as a transfection reagent and grown in Invitrogen's serum-free Freestyle™ medium. Culture supernatants were purified by standard protein A affinity chromatography in accordance with the manufacturer's protocol (GE Healthcare, Piscataway, N.J.) and were subsequently buffer exchanged in PBS (pH 7.4). Protein samples were analyzed and characterized by SDS-PAGE under reducing and non-reducing conditions, by analytical size-exclusion chromatography (SEC) and by reverse phase-high-pressure liquid-chromatography (RP-HPLC) under reducing and non-reducing conditions. Light-chain mispaired by-products (i.e., heavy chain heterodimers comprising mispaired light chains) were removed by CaptureSelect LC-Kappa or LC-Lambda affinity chromatography in accordance with the manufacturer's protocol (GE Healthcare, Piscataway, N.J.) and were subsequently buffer exchanged in PBS (pH 7.4). The concentrations of the purified antibodies were determined by reading the absorbance at 280 nm using the determined extinction coefficients.

SEC-HPLC and Light Scattering Detection Analysis

Preparative SEC-HPLC was carried out using a Superdex 200 column (GE Healthcare), at a flow rate of 1 ml/min. Analytical SEC-HPLC (Agilent 1100 Capillary LC System) coupled in-line with a light scattering detector was used to determine the absolute molecular masses of parental antibodies and the monovalent bispecific antibody (MBab).

ELISA Binding

ELISA plates were coated with antigens diluted in PBS (pH 7.4) at 4° C. for 20 hours and blocked with 2% (v/v) non-fat milk+0.05% (v/v) TWEEN 20 in PBS for two hours at room temperature. All subsequent steps were done at room temperature. Antibodies were applied to the plates at various concentrations and incubated for 1 hour. HRP-conjugated goat anti-human was used as a secondary antibody. The ELISA plates were developed using the chromogenic HRP substrate TMB and color development was terminated with 1 M $H_2SO_4$ and the signal obtained was read at A450 nm.

AlphaLISA Binding

All AlphaLISA reagents were from PerkinElmer. Incubation steps with AlphaLISA beads were performed under subdued lighting conditions at room temperature. Assays were performed in white 96-well half-area OPTIPLATES. Antibodies at various concentrations were incubated with AlphaLISA anti-FLAG acceptor beads at 40 micrograms/ml and 10 nM of biotinylated IL6 and RAGE-FLAG antigens in 1× AlphaLISA Immunoassay Buffer for 1 hour at room temperature. AlphaLISA (SA) donor beads at 400 micrograms/ml were added for 30 min and subsequently the assay plates were read in an ENVISION plate reader.

Kinetics and Concurrent Binding

Binding kinetics were measured by biolayer interferometry on an Octet384 instrument (ForteBio) using two different capture formats.

Format I: Anti-hIgG-Fc capture (AHC) biosensors were loaded with antibodies in PBS pH 7.4, 1 mg/ml BSA, 0.05% (v/v) TWEEN (Kinetic buffer). The loaded biosensors were washed in the same buffer before carrying out association and dissociation measurements with various antigens for the indicated times. Kinetic parameters (kon and koff) and affinities (KD) were calculated from a non-linear fit of the data using the OCTET software v.6.1.

Format II: Streptavidin High Binding Capacity (Kinetics Grade) Biosensors were loaded with biotinylated antigens in PBS pH 7.4, 1 mg/ml BSA, 0.05% (v/v) Tween (Kinetic buffer). The loaded biosensors were washed in the same buffer before carrying out association and dissociation measurements with antibodies and antigens for the indicated times. Data analysis was done using the Octet software v.6.1.

Differential Scanning Calorimetry Analysis

DSC experiments were carried out using a MICROCAL VP-DSC scanning microcalorimeter (Microcal, Northampton, Mass.). All solutions and samples used for DSC were filtered using a 0.22-micrometer filter and degassed prior to loading into the calorimeter. Antibodies used for the DSC studies were greater than 95% monomeric as judged by analytical gel filtration chromatography. Prior to DSC analysis, all samples were exhaustively dialyzed (at least three buffer exchanges) in 25 mM histidine-HCl (pH 6). Buffer from this dialysis was then used as reference buffer for subsequent DSC experiments. Prior to sample measurement, baseline measurements (buffer-versus-buffer) were obtained for subtraction from the sample measurement. Dialyzed samples (at a concentration of 1 mg/ml) were added to the sample well and DSC measurements were performed at a 1° C./min scan rate. Data analysis and deconvolution were carried out using the Origin™ DSC software provided by Microcal. Deconvolution analysis was performed using a non-two-state model and best fits were obtained using 100 iteration cycles. The interpretation of the DSC deconvolution results was based on the fact that the different domains in the oligospecific antibody formats unfold independently with cooperative transitions.

Peptide Mapping

Free thiol groups in the sample were initially capped using 1 mM N-ethylmaleimide. The sample was then denatured in a solution of 5 mM disodium hydrogen phosphate, 100 mM sodium chloride and 6 M guanidine, pH 7.0 at 37° C. for 30 minutes. The denatured solution was then diluted 2.5-fold with 100 mM phosphate buffer which contains 0.06 mM EDTA at pH 7.0. Endoproteinase Lys-C was added at a 1:10 enzyme:protein ratio and the reaction mixture was incubated at 37° C. for 16 hours. Additional LysC was added at 1:10 enzyme:protein ratio and further incubated for 4 hours at 37° C. Following Lys-C digestion, half of each reaction mixture was reduced by adding DTT to a final concentration of 30 mM and incubating at 37° C. for 15 minutes. The other half of the reaction mixture was prepared without reduction. The digested peptides were separated by UPLC reverse phase chromatographic analysis (Waters ACCQUITY UPLC BEH RP C18 column; 1.7 micrometers 100×2.1 mm) and analyzed by a UV-detector and an on-line LTQ ORBITRAP mass spectrometer (ThermoElectron). The RP-UPLC mobile phase A was 0.02% TFA in water and the mobile phase B is 0.02% TFA in acetonitrile; samples were eluted using a gradient of increasing buffer B. Peptides were identified and analyzed by comparing the results from the non-reduced (containing disulphide bonded peptides) and reduced (containing peptides in reduced form) peptide maps. The sequence of each peptide was identified using MS (mass) and confirmed using MS/MS (peptide mass sequencing) data, based on the known sequence of the protein. Disulphide bonded peptides were confirmed by MS data and also as peptides which were present only in the non-reduced sample.

Papain Digested Q-TOF LC-MS Analysis

For Papain digestion, antibodies at 1 mg/ml were treated with 0.4 micrograms of Papain working solution and incubated in a 37±1° C. water bath for 4 hours. Q-TOF MS was performed with one of the Q-TOF (quadrupole and orthogonal acceleration time-of-flight) type mass spectrometers in conjunction with a Waters ACQUITY UPLC™ system. Reverse-phase chromatography separation was performed on a BEH C4 1.7 micrometers 2.1×50 mm column using mobile phase A of 0.1% FA, 0.01% TFA in water and mobile phase B of 0.1% FA, 0.01% TFA in acetonitrile. Samples were eluted using a 25 minute linear gradient of increasing mobile phase B. Fab and Fc mAb fragments were identified using MS (mass) data, based on the known sequences of the proteins.

Cellular Binding

Cellular binding by the monovalent bispecific IgG1 antibody (MBab) and parental mAbs were tested by flow cytometry. Cell lines used were the human Epidermoid carcinoma A431 cell line, the human Breast carcinoma cell line SKBR3, the human Pancreas carcinoma cell line BxPC-3 and the human Ovarian carcinoma cell line SK-OV-3. Approximately $5\times10^5$ cells were used in each experiment. After trypsinization, cells were washed twice with FACS buffer (1% BSA in D-PBS ($Ca^{++}$, $mg^{++}$ free)). Antibodies at 10 micrograms/ml were added to the cell tubes for 1 hour at 4° C. After washing twice with FACS buffer, FITC-labeled goat anti-human was added for 45 min at 4° C. Detection of bound antibodies was performed by means of flow cytometry on a SLR II (Becton Dickinson, Calif.) and results were analyzed with the FLOWJO program.

Cell-Viability Assays

Cell-killing activities were measured by the CellTiter-Glo® Luminescent Cell Viability Assay (Promega). Cell lines used were the human Epidermoid carcinoma A431 cell line, the human Breast carcinoma cell line SKBR3, the human Pancreas carcinoma cell line BxPC-3 and the human Ovarian carcinoma cell line SK-OV-3. Cells were seeded in 96-well plates at a density of $5\times10^3$ cells/well in DMEM supplemented with 10% FCS. Antibodies at various concentrations were added to quadruplicate samples, and the cells were incubated for 96 hours at 37° C. in 5% CO2 atmosphere. After treatment, the cells were exposed to the CellTiter-Glo® reagent for 20 min and the luminescent was measured using an ENVISION plate reader.

Binding Kinetics to Fc Receptors

The binding affinity of MBab antibodies and human IgG1 isotypes to a variety of human Fc receptors was on ProteOn using steady state equilibrium binding assay. Antibodies at 50 ug/ml were immobilized on a GLC chip surface in ProteOn Acetate buffer at pH 5.0. Analytes were passed over the immobilized surface at 5 concentrations in 1:3 serial dilutions using the same buffer. Binding studies were performed at room temperature and equilibrium binding rates of each analyte were determined and used to calculate equilibrium dissociation constants (KD).

ADCC studies

ADCC were measured by the CYTOTOX 96 Non-Radioactive Cytotoxicity Assay (Promega). The human Epidermoid carcinoma A431 cell line was used in this assay. Cells were seeded in 96-well plates at a density of or $4\times10^4$ cells/well in RPMI 1640 without phenol red supplemented with 3% FCS. Human NK cell line from a malignant non-Hodgkin's lymphoma transgenic for human CD16 (FcγRIIIA) and FcεRIγ were mixed with target cells at a ratio of 1:1. Antibodies at various concentrations were added to quadruplicate samples, and the cells were incubated for 5 hours at 37° C. in 5% CO2 atmosphere. After treatment, the cells were exposed to the CYTOTOX 96 reagent for 15 min and OD at 409 nm was measured using a SPECTRAMAX 340PC plate reader.

Preferential Binding Studies

For preferential binding studies a MBab comprised of an anti-cell surface antigen C (anti-C) and an anti-cell surface antigen D (anti-D) was generated (C/D-MBab). Preferential binding of the MBab to cells expressing both target antigens (C and D) was measured using a combined population culture system that mixed cell expressing antigen C only (C cells), cells expressing antigen D (D cells) and cells expressing both C and D (C/D cells) in a single well for antibody staining. Briefly, C and C/D cells were each stained with a unique identifying tracer dye prior to their combination in culture: C cells with eFluor® 670 (eBioscience, Cat#65-0840-90) C/D cells with CellTrace™ Violet (Invitrogen, Cat# C34557), while D cells were left unstained. In this way each population could be distinguished during flow cytometric analysis after antibody staining. Cells were combined at 1:1:1 ratio and incubated with serial dilutions of the C/D-MBab and the two bivalent parental IgGs (anti-C and anti-D). Primary antibody incubations were carried out at 4° C. for 1 hour, excess antibody was removed and cell-bound antibody was detected using a PE-labeled anti-human IgG. Analysis was carried out on a BD LSR II, with doublets excluded based on physical properties (height, width and density).

Concurrent binding of each C/D-MBab arm to its target antigen on the same cell was determined using recombinant target protein labeled with Alexa Fluor® 647 (Invitrogen, A30009) and flow cytometric analysis. C/D cells (expressing both target antigens) were incubated with serial dilations of C/D-MBab (from 5-0.01 nM) for 1 hour, after which unbound C/D-MBab was removed by 2 washes with FACS buffer (PBS+1% fetal calf serum). Cell-bound C/D-MBab was detected using PE-labeled anti-human IgG and unbound C/D-MBab arm could be detected using recombinant target protein (C or D) labeled with fluorescent Alexa Fluor® 647 microscale protein labeling kit (Invitrogen, A30009) dye. To ensure concurrent binding on a single cell is being measured, doublets (two or more cells that pass through the flow cytometer together), are rigorously excluded based on the physical properties of height, width and density of the each cell included in analysis.

Example 2

Monovalent Bispecific Antibody (MBab) Design

Figure 2:
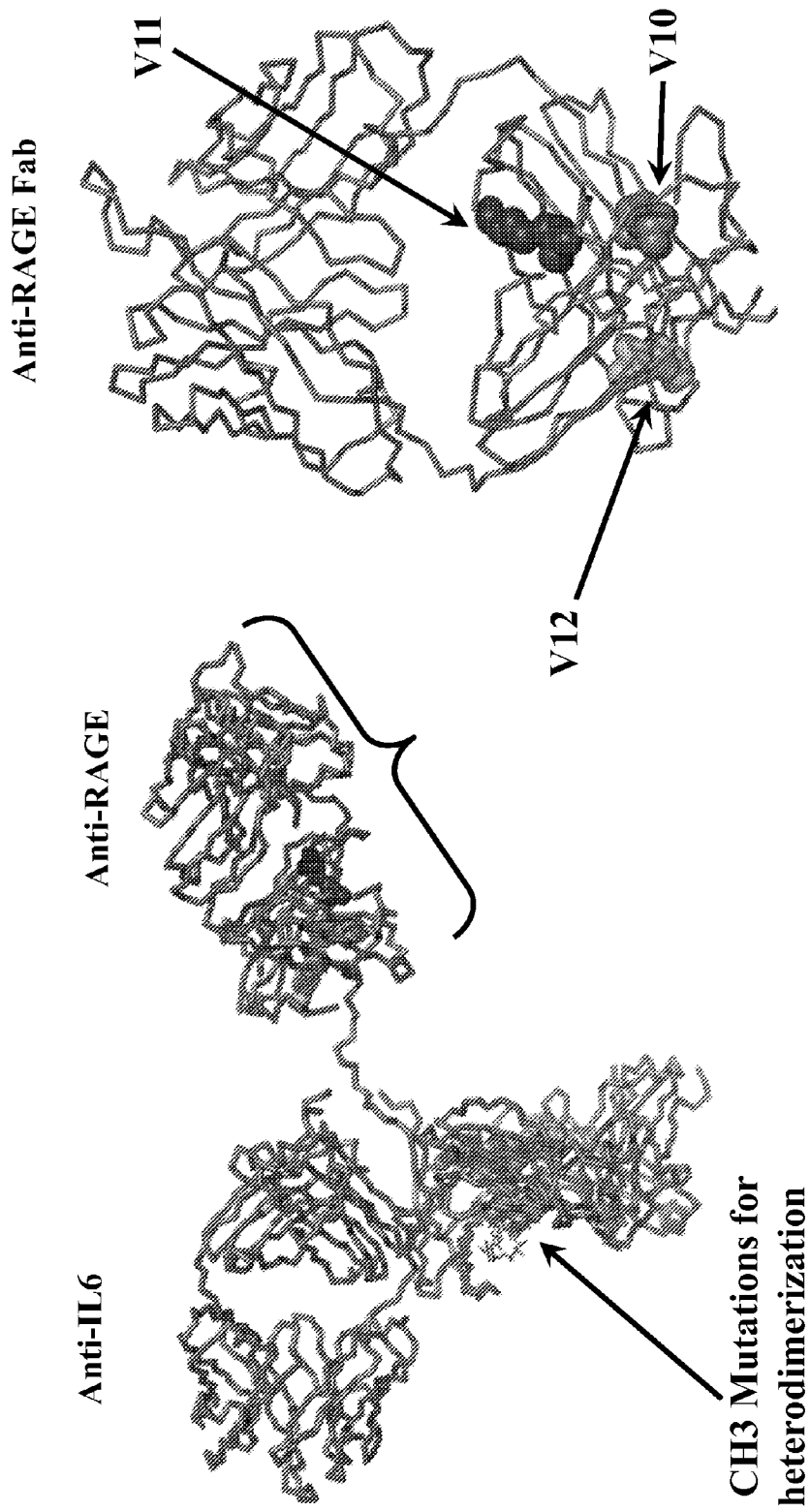
FIG. 2 shows a three dimensional representation of a monovalent bispecific antibody (MBab) having one arm that binds IL-6 and a second arm that binds RAGE. The arrow indicates the location of the heavy chain mutations in the heavy chain constant region that facilitate heterodimerization. The bracketed Fab region is show enlarged on the right. The arrows indicate the locations of the modifications in variant 10 (V10; HC: A141C-LC: F116C); the modifications in variant 11 (V11; HC: H168C-LC: T164C); and the modifications in variant 12 (V12; HC: F126C-LC: S121C). Additional modifications that remove native cysteines (-Cys; e.g., HC: C220V-LC: C214V) are not shown but are present in variants 10-12 (V10-V12).

A schematic representation of a Monovalent Bispecific IgG format (MBab) is presented in FIG. 1B. The MBab is a bispecific antibody with a monovalent binding site for each antigen in an IgG format. For heterodimerization of two distinct heavy chains the platform harnessed the classical "knob-into-hole" concept in the CH3 domain as described in Ridgway et al. (1996) Protein Eng. 9(7):617-21, and also the incorporation of an interchain disulfide in CH3 domain that further enhanced the stability and heterodimerization of the two heavy chains, as described in Merchant et. al. (1998) Nat. Biotech 16:677-681. Additionally or alternatively, the CH3 domain is engineered to comprise amino acid residues H435 and Y436 on one heavy chain and amino acid residues R435 and F436 on the other heavy chain to ablate protein A binding on one chain. As described above, where the "knob-into-hole" platform is used, the heavy chain comprising the "Hole" can comprise the acid residues R435 and F436 (indicated by a star in FIG. 1B). The location of the CH3 domain is indicated by the arrow in the structure presented in the left panel of FIG. 2. For correct pairing of cognate heavy and light chains in the monovalent bispecific antibodies, the native interchain Cysteines forming the disulfide linkage between the heavy and light of one of the two antibodies in the MBab construct were removed and instead an alternative interchain disulfide was inserted elsewhere in the CL-CH1 interface to support homodimerization of cognate heavy and light chains.

Example 3

Design of Variants with Alternative Cysteines in the LC-HC Interface

Several methods may be implemented to generate alternative LC-HC interfaces to enforce correct pairing of only cognate heavy and light chains, including remodling the interchain disulfides in one of the two antibodies in the MBab construct. Initially, the native interchain Cysteines forming the disulfide linkage between the heavy and light chain were replaced by a non-Cysteine amino acid residue, e.g., Valine. Next, three criteria were used to identify pairs of amino acids in LC-HC interface suitable for substitution to Cysteine. First, the distance between corresponding alpha carbons should be similar to those found in naturally occurring disulfide linkages (6.0-7.0 Å). Second, the beta carbons should be pointing towards each other with a distance of (4.0-5.0 Å). Third, the residue pairs should belong to different chains. Seven pairs of residues in the LC-HC interface meeting these criteria are provided in Table 7.

TABLE 7

| LC-HC interface pairs* | |
|---|---|
| HC: F126 | LC (κ): S121 or LC (λ): S121 |
| HC: L128 | LC (κ): F118 or LC (λ): F118 |
| HC: A141 | LC (κ): F116 or LC (λ): T116 |
| HC: H168 | LC (κ): T164 or LC (λ): T164 |

TABLE 7-continued

| LC-HC interface pairs* | |
|---|---|
| HC: F170 | LC (κ): S176 or LC (λ): S176 |
| HC: P171 | LC (κ): S162 or LC (λ): T162 |
| HC: V173 | LC (κ): Q160 or LC (λ): V160 |

*Numbering in Table 6 is according to the EU index as set forth in Kabat et al. (Sequences of Proteins of Immunological Interest, 5th Ed. Public Health Service, National Institutes of Health, Bethesda, MD. (1991)). The corresponding residues at the indicated positions for both the lambda (λ) and kappa (κ) chain are provided. It will be understood that, due to allotype and allelic variations present in the population, the wild type amino acid residue at these positions may vary from that listed above. Regardless of the wild type amino acid residue, each position of a given pair will be substituted with a Cysteine. A number of allotype and allelic variations are provided herein.

Three variants were tested; HC: A141/LC: F116, HC: H168/LC: T164 and HC: F126/LC: S121 corresponding to variants 10, 11 and 12 (V10, V11 and V12), respectively. The location of these positions is indicated by arrows on the structure presented in the right panel of FIG. 2.

In an another approach, an alternative interchain disulfide may be engineered in the variable region of the antibody between the VH and VL regions. In particular, such a disulfide may be introduced in the framework regions such that the VL and VH regions are linked via the alternative disulfide. In this approach the native interchain Cysteines forming the disulfide linkage between the heavy and light chain are replaced with a non-cysteine amino acid residue (e.g., Valine, Alanine, Glycine, etc.) and certain non-Cysteine amino acids in the VH and VL regions, generally in the Framework regions, are replaced with Cysteine. The positions are selected such that the Cysteine residues can form a disulfide bond. The position of residues in the VH and VL regions meeting these criteria are provided in Table 8.

TABLE 8

| VH-VL pairs‡ |
|---|
| VH44 + VL100 |
| VH44 + VL105 |
| VH45 + VL87 |
| VH55 + VL101 |
| VH100 + VL50 |
| VH98 + VL 46 |
| VH101 + VL46 |
| VH105 + VL43 |
| VH106 + VL57 |

‡Numbering in Table 7 is according to the Kabat index as set forth in Kabat et al. (Sequences of Proteins of Immunological Interest, 5th Ed. Public Health Service, National Institutes of Health, Bethesda, MD. (1991)). It will be understood that the wild type amino acid residue at these positions will vary. Regardless of the wild type amino acid residue each position of a given pair will be substituted with a Cysteine. Table 1, provides the numbering of several representative variable regions according to the Kabat index.

In still another approach, the CH1 region may be engineered to generate a protrusion and/or a cavity while the cognate light chain is engineered to generate a compensatory cavity and/or protrusion. To further enforce correct pairing of only congnate heavy and light chains the CH1 and CL region may be further modified to remove the native interchain cysteines forming the disulfide linkage between the heavy and light chain.

Bispecific antibodies may be generated in which the LC-HC interface of just one arm is modified as described above, or alternatively, both arms may be modified. It will be understood based on the teaching herein that, the LC-HC interface of each arm will be modified differently to enforce the correct pairing of the cognate heavy and light chains while minimizing incorrect pairing. For example, but not by way of limitation, one arm may modified to relocate the native disulfide bond to a different position within the LC and CH1 regions, and the other arm may be engineered to relocate the native disulfide bond to the VL-VH region. or both arms may modified to relocate the native disulfide bonds to a different position within the LC and CH1 interface, or both arm may be modified to incorporate a cavity and/or protrusion at different positions within the LC and CH1 interface.

Example 4

Development of the pMBab Vector System for Production of Monovalent Bispecific Antibodies in Mammalian Cells Plasmids pMBab-Heavy and pMBab-Light were designed for production of monovalent bispecific human IgG1 antibodies in mammalian cell culture. The pMBab-Heavy vector (FIG. 3C) contained two human gamma1 heavy chain cassettes to support HC heterodimerization, the former heavy chain carried the "Hole" set of mutations in the CH3 domain while the latter carried the complement "Knob" mutation in the CH3 domain and the alternative Cysteine in the CH1 domain. VH domains were introduced into the "Hole" and "Knob" HC cassettes in pMBab-Heavy vector as BssHII/NheI and BsrGI/SalI restriction fragments, respectively. The pMBab-Light kappa vector (FIG. 3A) contained two human kappa light chain (LC) cassettes, the latter carried the alternative interface Cysteine in Ck domain that complemented with the alternative Cysteine in the CH1 domain. Vk domains were introduced into the LC cassettes in pMBab-Light vector as BssHII/BsiWI and BsrGI/NotI restriction fragments, respectively. The strong human cytomegalovirus early promoter can drive the light and heavy chain genes in both pMBab vectors. Placing the two heavy chains and two light chains in separate vectors eliminated the risk of producing any of the parental antibodies due to monotransfection. Additionally, the heavy chain variable region of an antibody having higher expression levels may be cloned into the constant region cassette comprising the "knob" to minimize production of half antibodies. Further, the CH3 domains of the heavy chains may be engineered as described herein such that only one chain binds protein A.

Example 5

Expression Purification and Analysis of Variants

Figure 4:
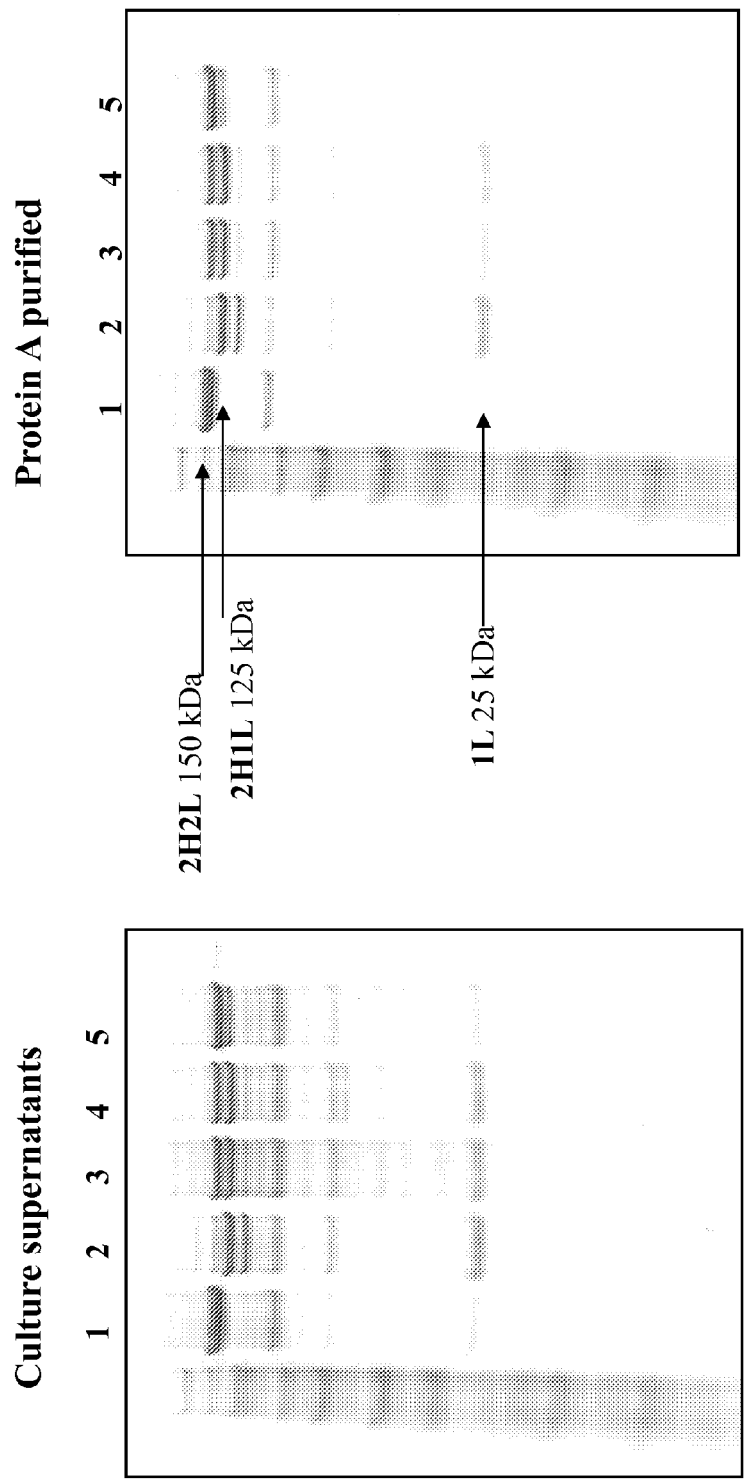
FIG. 4 shows SDS-PAGE analysis under non-reducing conditions of IL6/RAGE bispecific monovalent antibody (MBab) variants 10, 11 and 12 (V10, V11 and V12), each having an alternative (i.e. relocated) interchain disulfide bond in the anti-RAGE portion of the molecule. The left panel shows culture supernatants from HEK293F cells transfected with pMBab vectors, as described in Example 1 and Example 5, for the expression of: anti-IL6 WT+anti-RAGE WT (lane 1); anti-IL6 WT+anti-RAGE (-Cys) (lane 2); heavy anti-IL6 WT+anti-RAGE V10 (lane 3); anti-IL6 WT+anti-RAGE V11 (lane 4); and anti-IL6 WT+anti-RAGE V12 (lane 5). Each heavy chain included CH3 modifications to facilitate HC heterodimerization, and the V10, V11 and V12 modifications also included -Cys modifications. In the right panel, the arrows each indicate: 2H2L (about 150 kDa)—IgG with 2 each heavy and 2 light chains; 2H1L (about 125 kDa)—IgG missing a light chain; and 1L (about 25 kDa)—free light chain. The -Cys variant resulted in the production of an unpaired light chain which was remedied by introduction of disulphide bond variants described herein, with V12 having the most efficient LC/HC pairing.
Figure 6A:
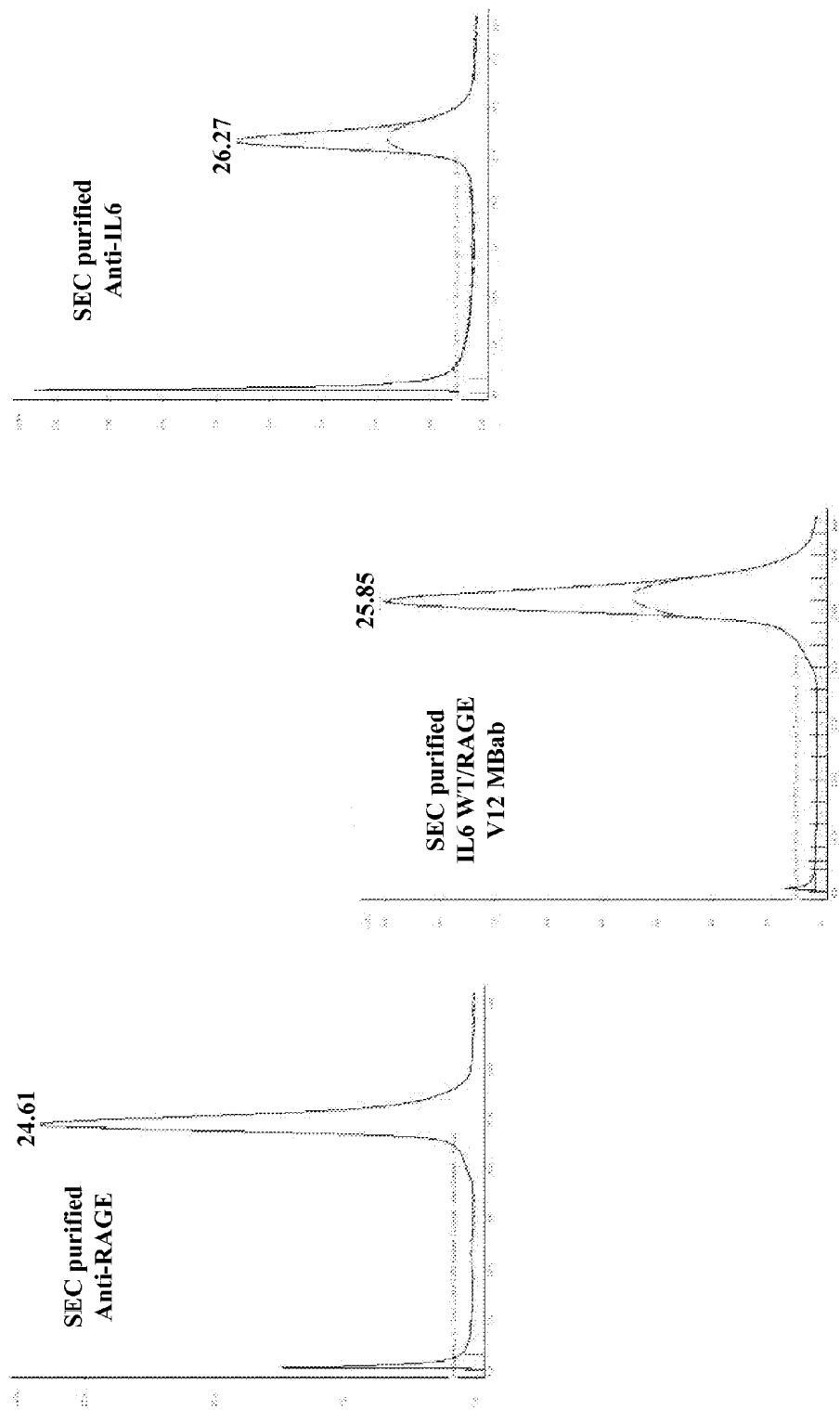

Variants were transiently expressed in HEK293F cells and culture supernatants before and after protein A affinity chromatography were analyzed on SDS-PAGE under reducing and nonreducing conditions. As shown in FIG. 4, removal of the native interchain Cysteines forming the disulfide linkage between the heavy and light of the anti-RAGE portion of the molecule lead to the separation of the light chain on a SDS-PAGE under nonreducing conditions and resulted in a migration profile of 125 kDa and 25 kDa that correspond to 2H1L and a separate light chain. A similar migration profile was seen for the antibodies comprising the V1 and V3 variants with one arm lacking the native interchain cysteine (data not shown). The presence of the free light chain in the protein A purified fractions indicates that the antibodies properly assemble in solution and can be purified as intact antibodies having 2 light chains and two heavy chains. Variants lacking the native interchain Cysteines, yet carrying an alternative interchain disulfide linkage, were tested for their ability to reconstitute the 150 kDa migration profile that indicates the formation of the alternative interchain disulfide linkage and correct assembly of the two pairs of heavy and light chains. While variants 10 and 11 (V10 and V11) demonstrated some reconstitution of the 150 kDa migration profile and reduction in the amount of free light chain, variant 12 (V12) demonstrated full reconstitution of the 150 kDa molecular marker with an overall identical migration profile as the WT IgG molecule with native interchain disulfides in Fab and knob-into-hole in CH3 (knob-into-hole IgG) (FIG. 4). Analysis of the oligomeric state of the protein A purified fraction of variant 12 (V12) on an analytical size-exclusion HPLC (SEC-HPLC and SEC multi-angle light scattering (SEC-MALS)) indicated that the monomeric MBab represented about 85% with about 10% unpaired half IgG and about 5% of aggregates (FIG. 6B). Following preparative SEC, variant 12 (V12) was purified to near homogeneity of greater than 99% monomer and overall similar SEC profile as the parental anti-RAGE and anti-IL6 mAbs.

The crystal structure of a V12 carring Fab was solved. The electron densisty confirmed the formation of a new disulfide bond between the heavy and light chain at the location of the newly introduced cysteine residues (data not shown).

Figure 7B:
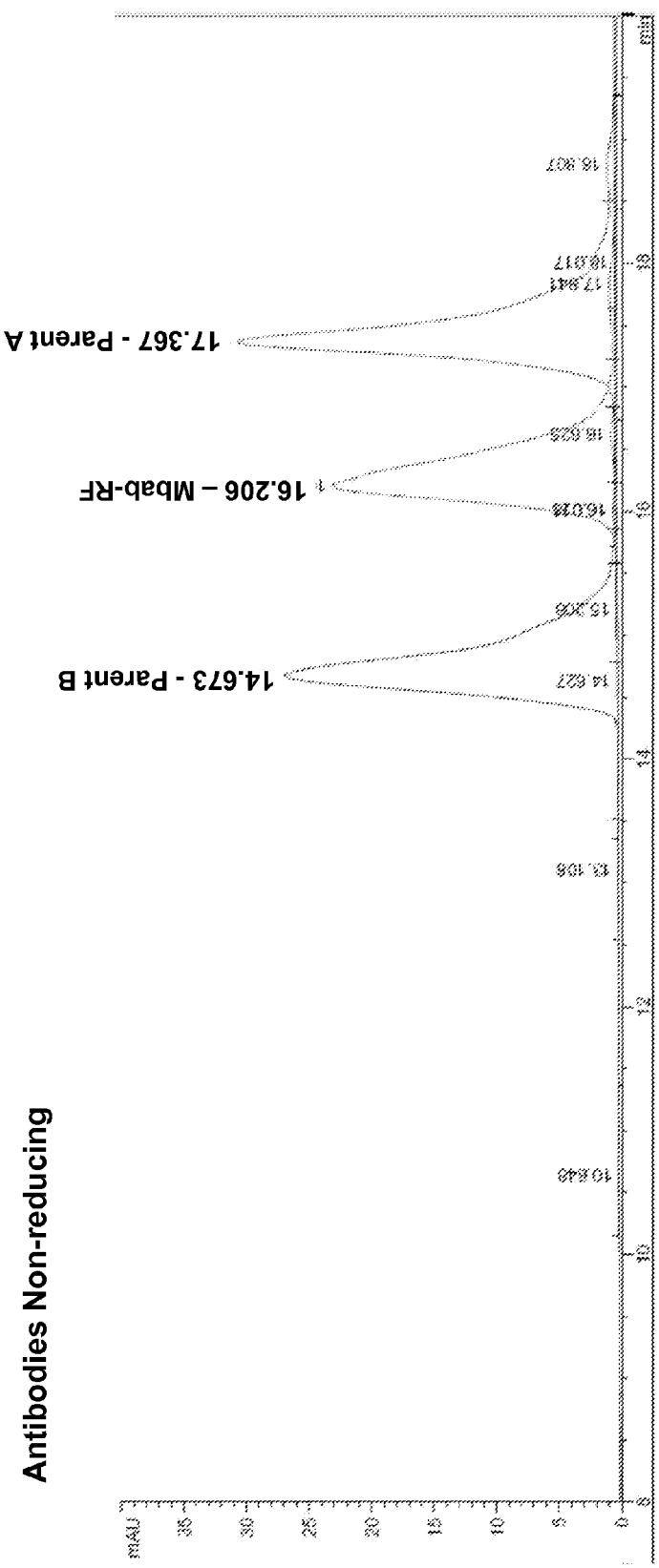
Figure 7C:
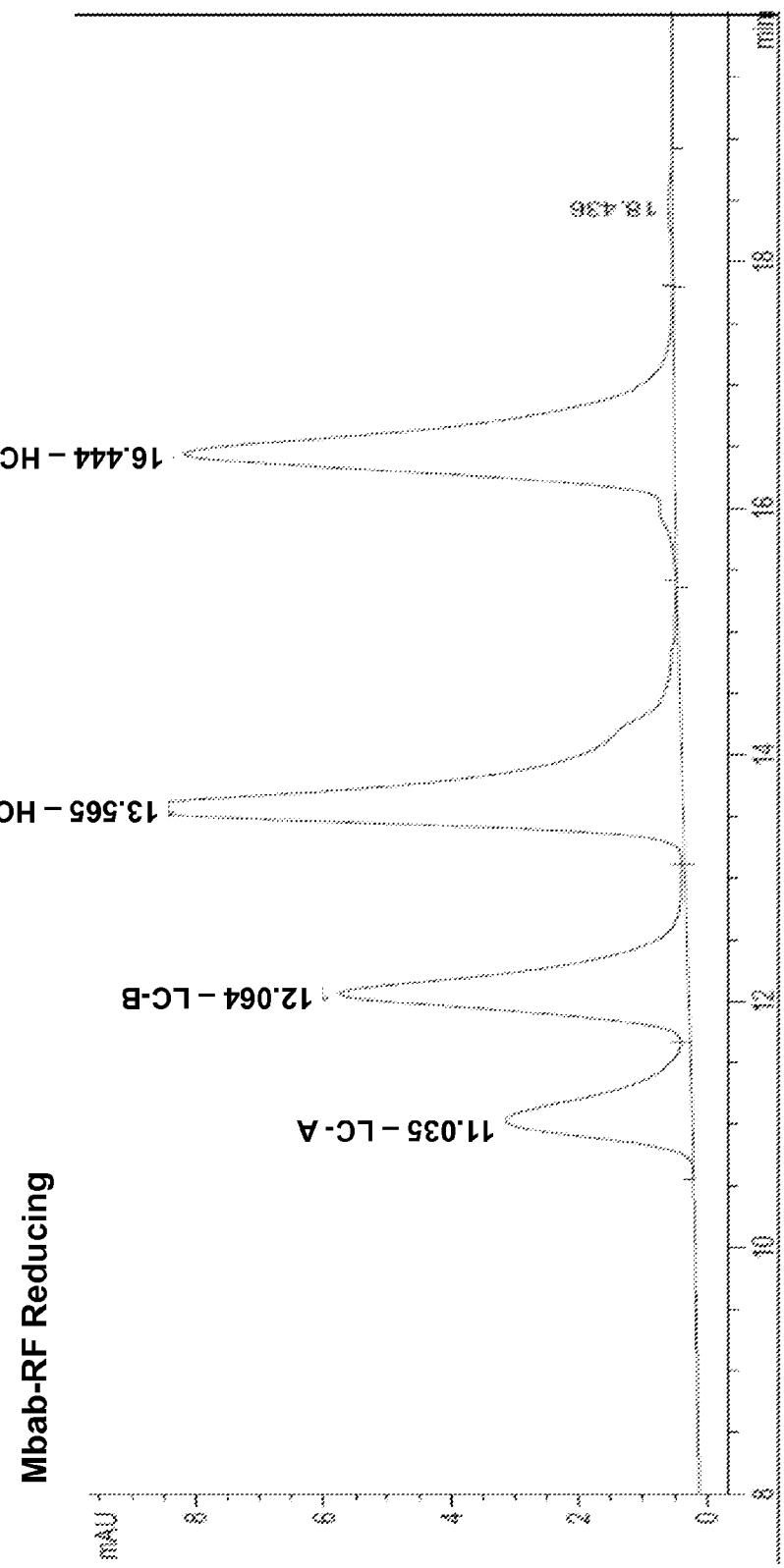

Uneven expression of the 4 chains comprising the MBab molecule may lead to the formation of 3 types of byproducts; Hole-Hole homodimers, Hole-half-IgG and LC-mispaired byproduct due to excess of one of the light chains. The formation of "Hole-Hole" homodimer byproducts was previously reported (Ridgway, et al. 1996, Prot Eng 9:617-21; Merchant et al. (1998) Nat Biotech 16:677-681). It was demonstrated that substitution of H is 435 in IgG1 CH3 domain with the corresponding Arg 435 from IgG3 ablate protein A binding capabilities (Jendeberg et al., 1997, J Immunol Methods 201:25-34). The additional substitution of Tyr436Phe was made to reduce immunogenicity by keeping all human antibody sequence (Jendeberg, et al. ibid). For efficient removal of "Hole" related byproducts, residues H435 and Y436 in CH3 domain of the "Hole" heavy chain were mutated to the corresponding R435 and F436 respectively, as in IgG3. The resulting hIgG1 "Hole" heavy chain carrying mutations H435R and Y436F was named "Hole-RF". A MBab construct comprised of an anti-antigenA (Hole heavy chain; lambda light chain) and anti-antigenB (Knob heavy chain; kappa light chain) carrying the RF mutation in "Hole" heavy chain (designated "MBab-RF") was transiently expressed in HEK293F cells. The expression yields of the MBab-RF (190 mg/l) correlated with the expression profile of the two parental antibodies (200 to 348 mg/l). SDS-PAGE analysis of the protein A purified fractions under non-reducing and reducing conditions shows no excess of "Hole" heavy chain but rather equal distribution of "Hole" and "Knob" heavy chains (FIG. 7A, left panel, lanes 1 and 2, respectively). The SEC profile of the protein A purified MBab-RF indicated ~97.5% monomer and ~2.5% of aggregates with no unpaired half-IgG byproduct (FIG. 7A, right panel). The migration profile of the protein A purified parental IgGs and MBab-RF under non-reducing conditions by RP-HPLC indicated that the MBab-RF with an elution center of ~16.2 min migrated between parental B (14.7 min) and parental A (17.4 min) (FIG. 7B). This data again confirms that the MBab-RF is comprised of equal amounts of "Hole" and "Knob" heavy chains with no excess of the "Hole" heavy chain. Analysis of the oligomeric state of the protein A purified fraction of the MBab-RF by RP-HPLC under reducing conditions indicated excess of the antigenB light-chain over the antigenA light-chain at a ratio of 1.0 to 0.6 leading to ~25% antigenB kappa light-chain mispaired byproduct (FIG. 7C).

Figure 8A:
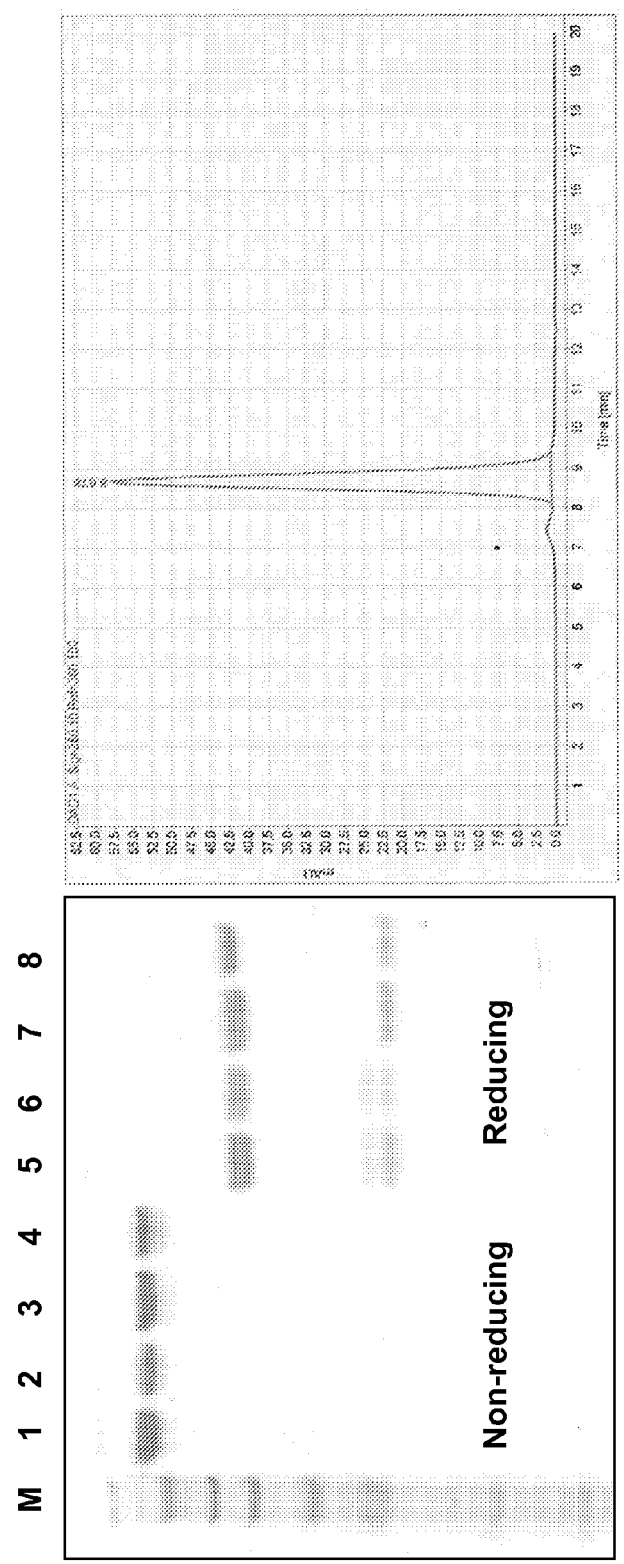
FIG. 8A-C show analysis of LambdaSelect purified MBab-RF construct comprising a lambda light chain for antigenA binding (antigenA heavy chain comprises "Hole" in addition to the "RF" substitution) and a kappa light chain for antigenB binding (antigen heavy chain comprise "Knob").
Figure 8B:
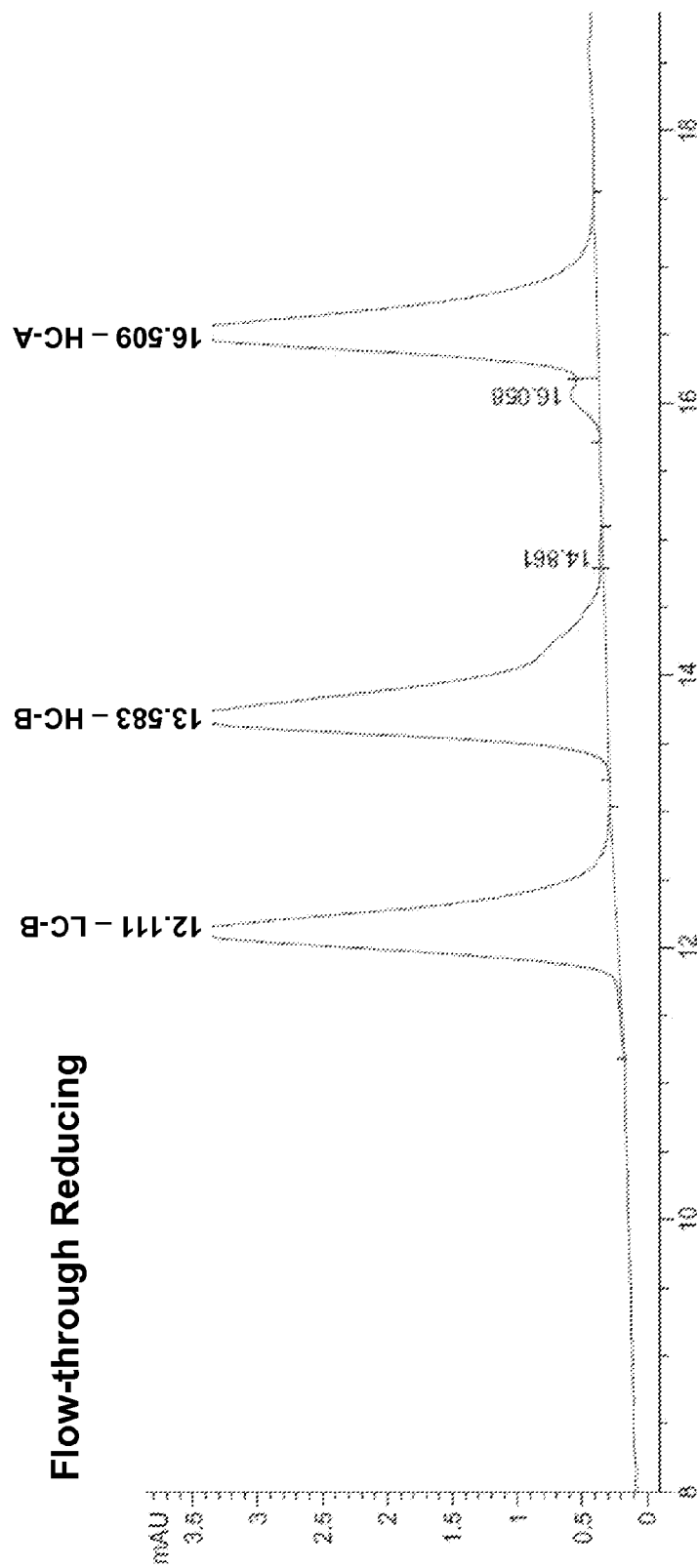
Figure 8C:
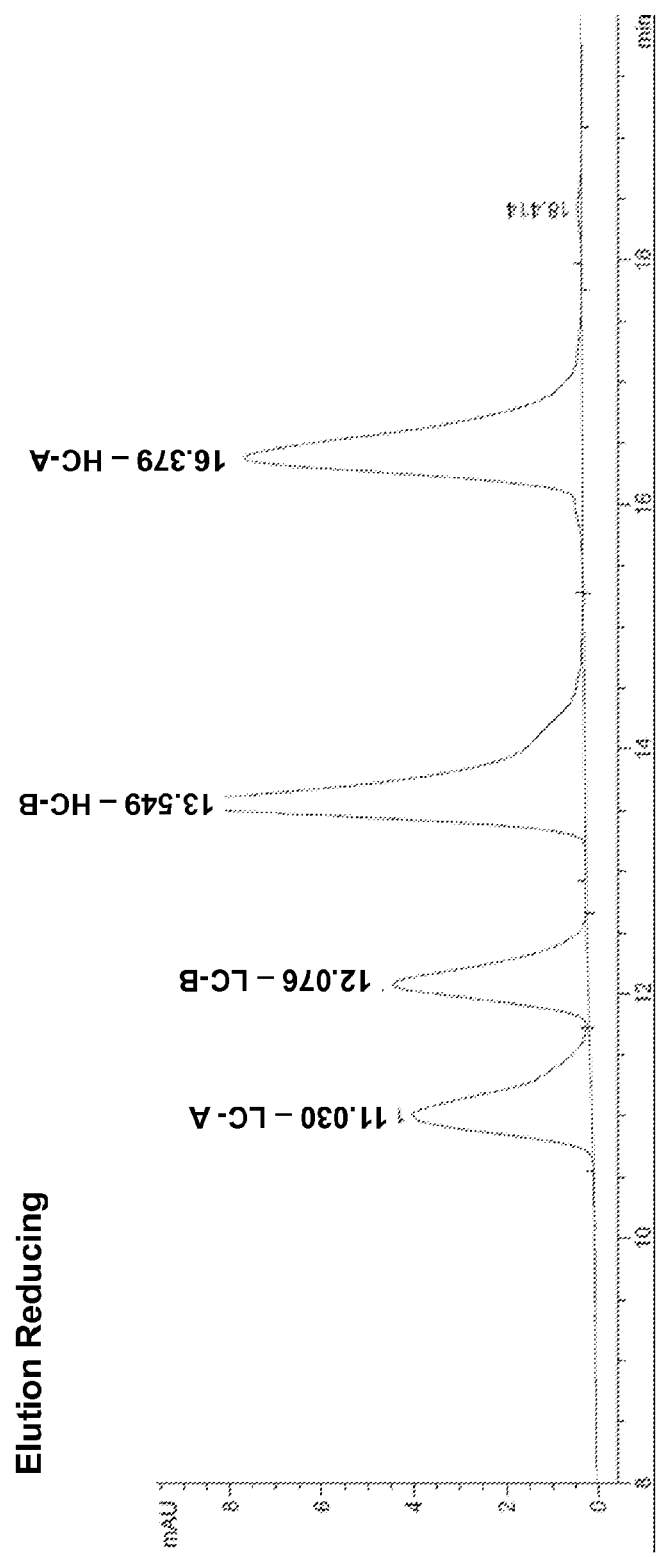

For efficient removal of mispaired light-chain byproducts, selective light-chain affinity chromatography is implemented, as described herein using affinity media selective for the lambda to capture the desired MBab and allowing the mispaired antibodies comprising two kappa chains to be removed. As illustrated in FIG. 8 subsequent separation of the protein A purified fraction of the MBab-RF on LambdaFabSelect affinity column resulted with removal of the antigenB light-chain mispaired byproduct yielding pure and correctly assembled MBab-RF product. SDS-PAGE analysis under reducing and non-reducing conditions shows equal amounts of the two light chains for the LambdaFabSelect purified sample while the protein in the flow-thorough carries only the cMET light-chain (FIG. 8A, left side compare lanes 6 and 7). The SEC profile of the LambdaFabSelect purified MBab-RF indicated 100% monomer with no aggregates (FIG. 8A, right side). Analysis of the oligomeric state of the LambdaFabSelect purified fractions of the MBab-RF by RP-HPLC under reducing conditions indicated that the protein in the flow-through corresponded with the antigenA light-mispaired byproduct (FIG. 8B) while the protein in the eluted fraction corresponded with a pure MBab comprised of equal amounts of the two light chains (FIG. 8C).

Example 6

Determination of Variant Bispecificity by AlphaLISA

Figure 5A:
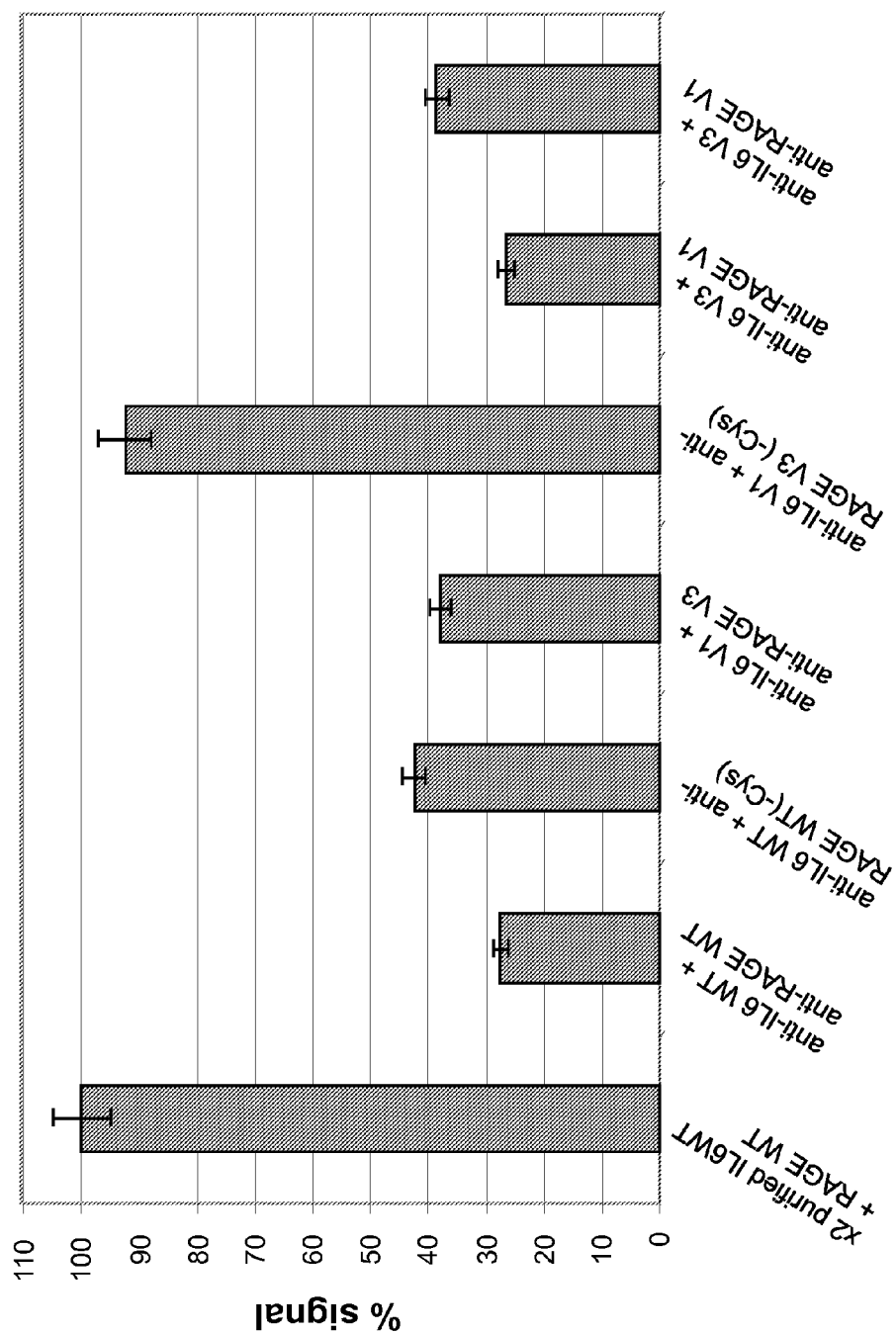
FIG. 5 shows a determination of bispecificity of IL6/RAGE antibodies using an AlphaLISA screen. The -Cys variants had no interchain disulfide bonds in the anti-RAGE Fab. The V10, V11 and V12 variants had alternative interchain disulfide bonds in the anti-RAGE Fab. The V12 variant yielded almost 100% bispecific IgG, while the WT Fabs resulted in less than 30%. The -Cys, V10 and V11 variants each showed a modest improvement (about 42%, about 40%, and about 33%, respectively).

To determine bispecificity and concurrent binding of the two binding sites, an AlphaLISA assay was developed as indicated in Example 1. Briefly, simultaneous binding of the two binding sites to RAGE and IL6 antigens brought the donor and acceptor beads into close proximity that resulted in a recorded signal. To quantitate the level of bispecificity of the variants, a reference monovalent bispecific IgG was generated by co-expression of DNA plasmids of the parental anti-IL6 and anti-RAGE antibodies in a single cell. Spontaneous pairing of the light and heavy chains should result, in theory, with 12.5% of the total protein produced as monovalent bispecific IgG. Sequential affinity chromatography first on an IL6 column and then on a RAGE column resulted in a pure monovalent bispecific IgG with no engineering involved. The AlphaLISA signal obtained with the 2-step purified monovalent bispecific was used to set a reference of 100% bispecificity (FIG. 5). The combination of variants 1 and 3 showed a small increase in the AlphaLISA bispecificity assay over the knob-into-hole IgG, which was further enhanced by the addition of a single (–Cys). The combination of IL6 V1 and RAGE V3 (–Cys) showed the largest increase in the AlphaLISA bispecificity assay over the knob-into-hole IgG (FIG. 5A). In agreement with the SDS-PAGE analysis, while variants 10 and 11 (V10 and V11) demonstrated modest improvement in the AlphaLISA bispecificity assay over the knob-into-hole IgG, variant 12 (V12) demonstrated nearly 100% bispecificity (FIG. 5b).

Example 7

Kinetics and Concurrent Binding by Octet Analysis

Figure 9A:
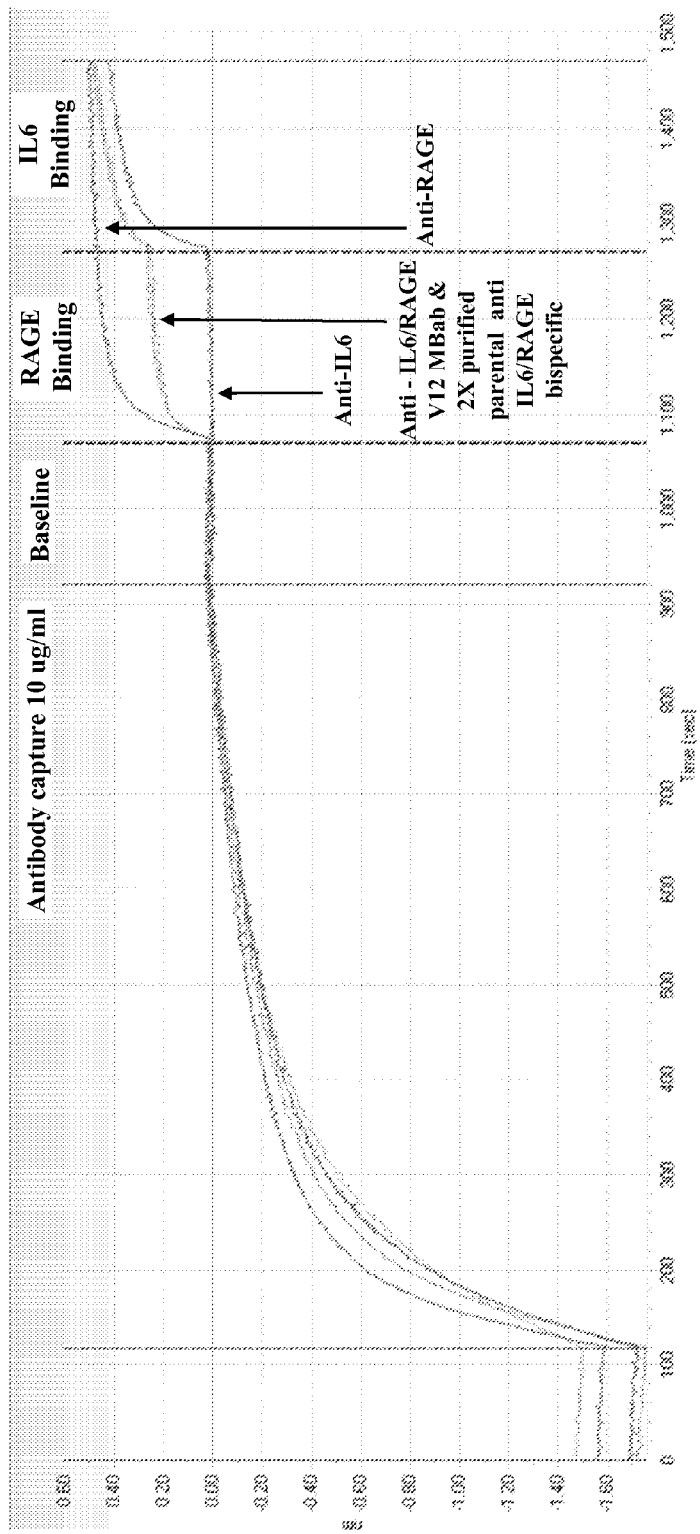
Figure 9B:
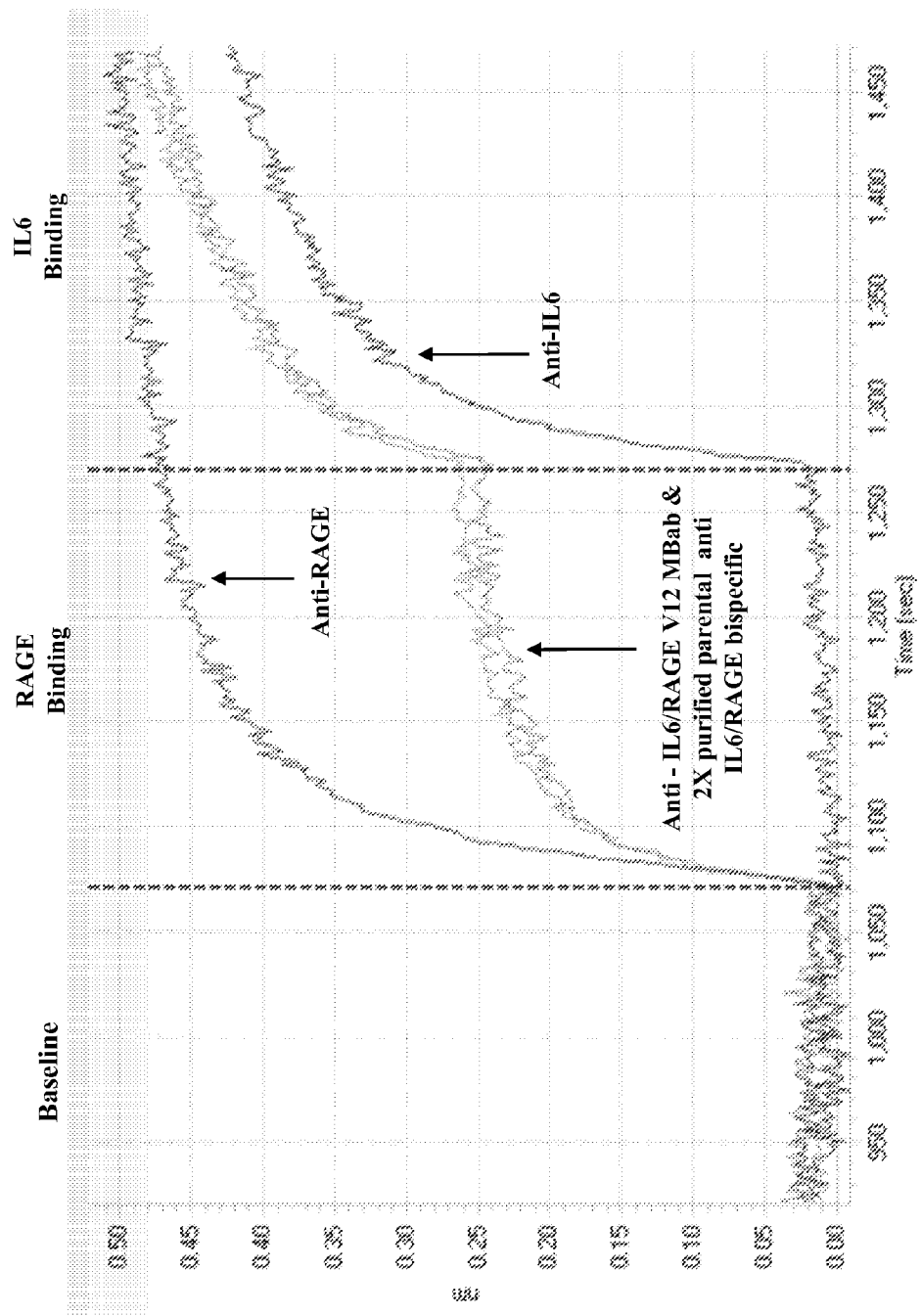
FIG. 9B shows an expansion of the baseline, RAGE and IL6 binding portions of the traces. The two parent antibodies showed a single increase in signal in response to binding their specific antigen, while the anti-IL6 WT/anti-RAGE V12 MBab showed an increase in signal in response to both RAGE and IL6, which demonstrated bispecificity and simultaneous antigen binding. The anti-IL6 WT/anti-RAGE V12 MBab had an identical concurrent binding profile as the 2× purified bispecific generated by co-expression of the two parental antibodies followed by sequential affinity purification on IL-6 and RAGE affinity columns.
Figure 10A:
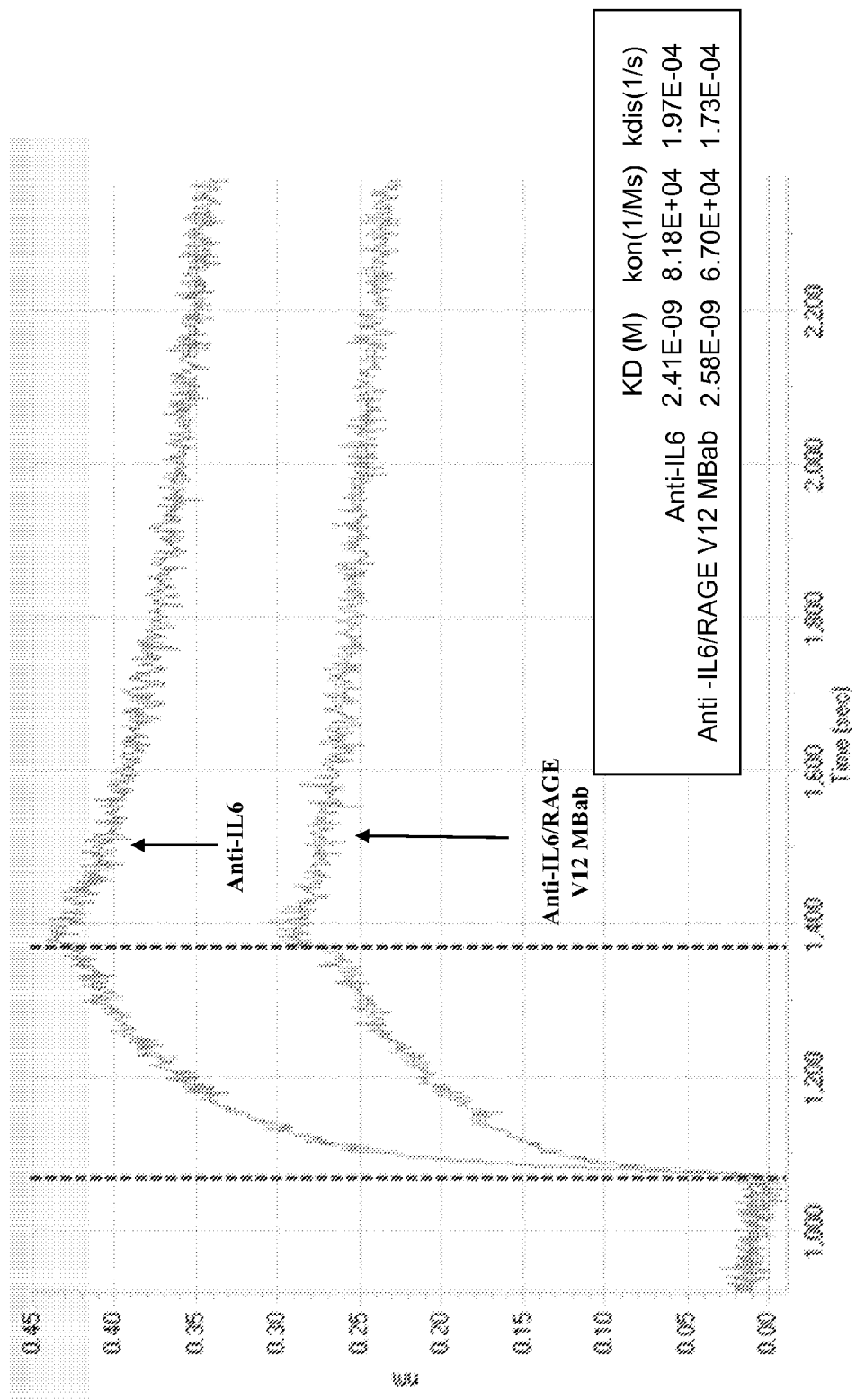
FIG. 10A and FIG. 10B show binding kinetics of the anti-IL6/anti-RAGE V12 MBab and parental antibodies. The binding affinities of the anti-IL6 WT/anti-RAGE V12 MBab for IL6 (FIG. 10A) and RAGE (FIG. 10B) were comparable to the parental antibodies (anti-IL6 and anti-RAGE).
Figure 10B:
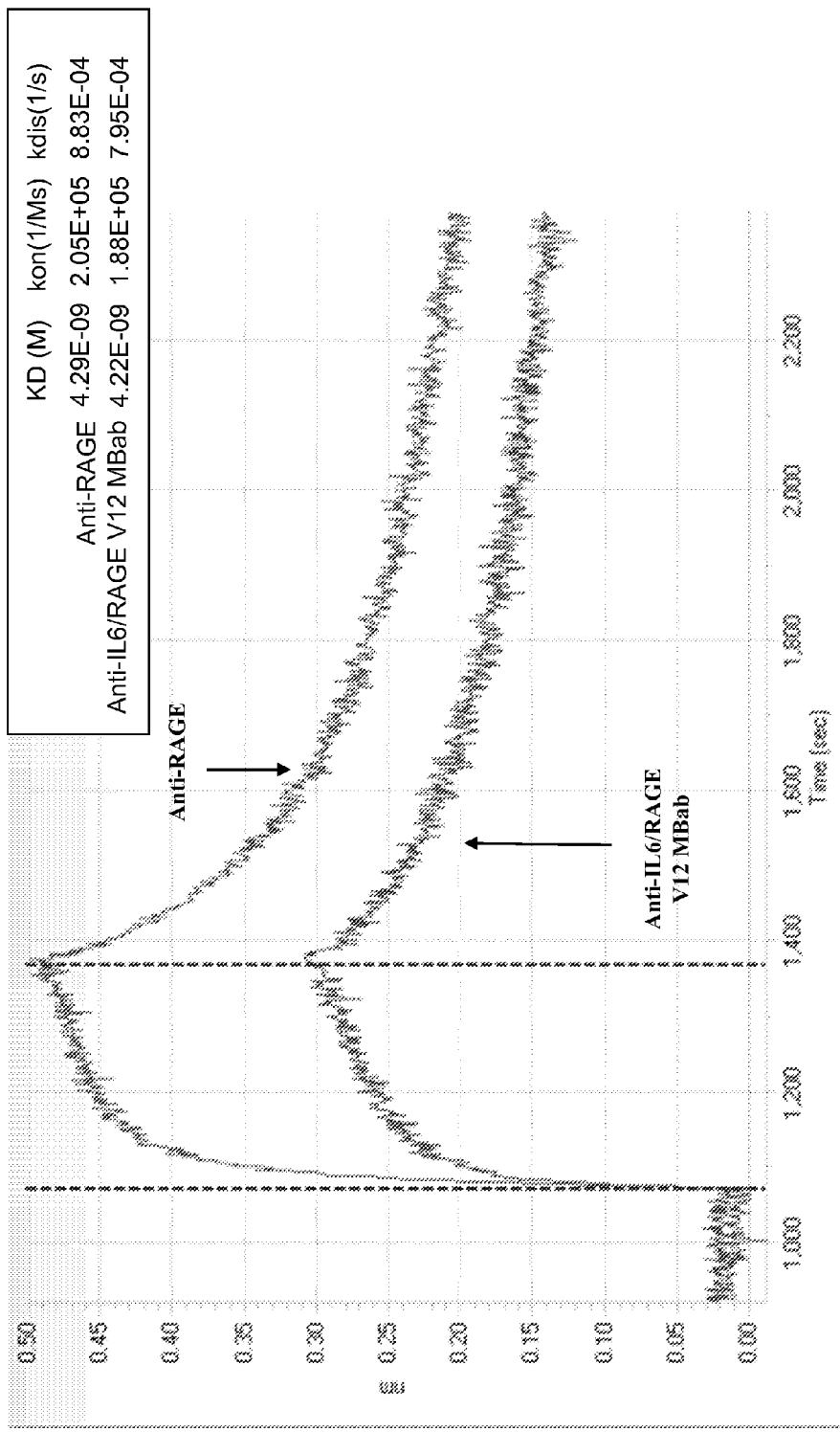

The bispecificity and concurrent binding of variant 12 (V12) MBab to RAGE and IL6 antigens was further characterized by biolayer interferometry on an Octet384 using capture format I described above. The following antibodies: variant 12 MBab, anti-RAGE, anti-IL6 and the 2-step purified monovalent bispecific derivative, were captured on anti-Fc sensors and then tested for specific antigen binding. While the parental anti-IL6 and anti-RAGE demonstrated specific binding only to their respective antigen, variant 12 MBab and the 2-step purified monovalent bispecific displayed identical concurrent binding profile to RAGE and IL6 antigens (FIG. 9). When tested for its binding kinetics to RAGE and IL6 antigens, variant 12 demonstrated the same kinetic affinities (KD) as the parental antibodies to the respective antigens with overall similar kon and koff rates as indicated in FIG. 10.

Example 8

Production and analysis of HER2/EGFR MBab

Figure 11A:
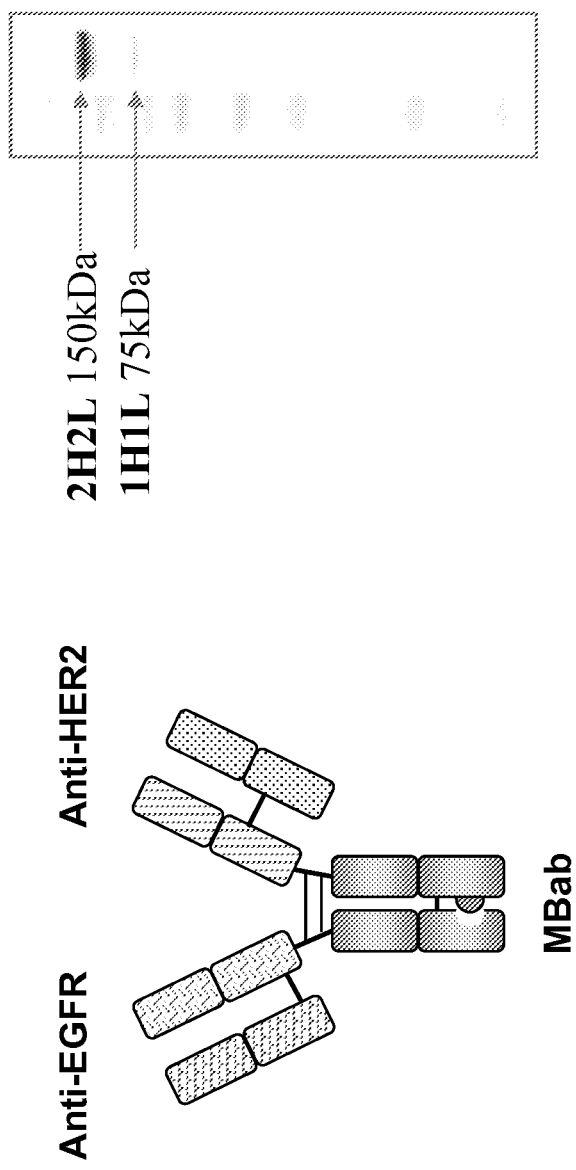
FIGS. 11A to 11D show expression and analysis of anti-EGFR WT/anti-HER2 variant 12 monovalent bispecific antibody (EGFR/HER2V12 MBab).
Figure 11B:
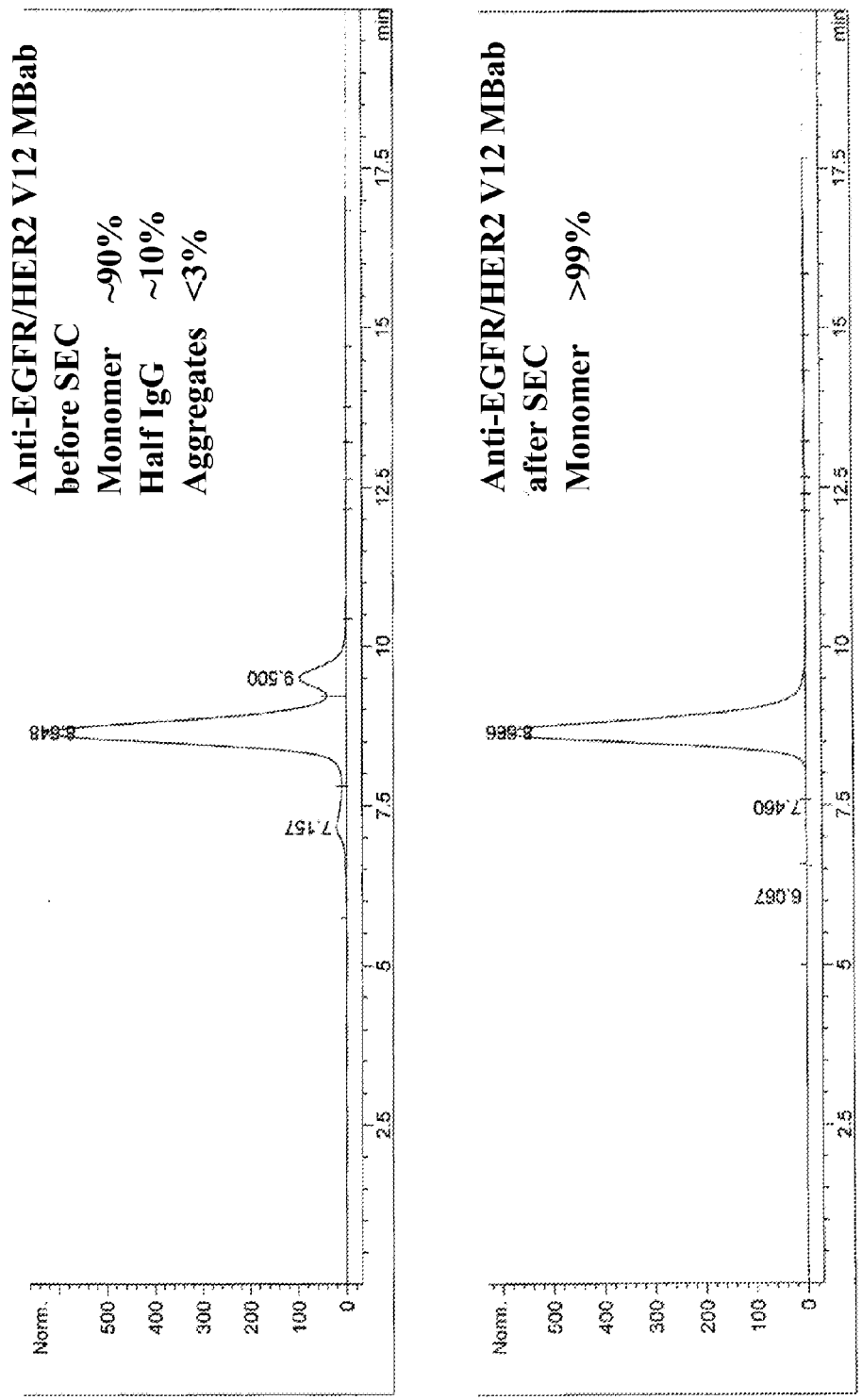
Figure 11C:
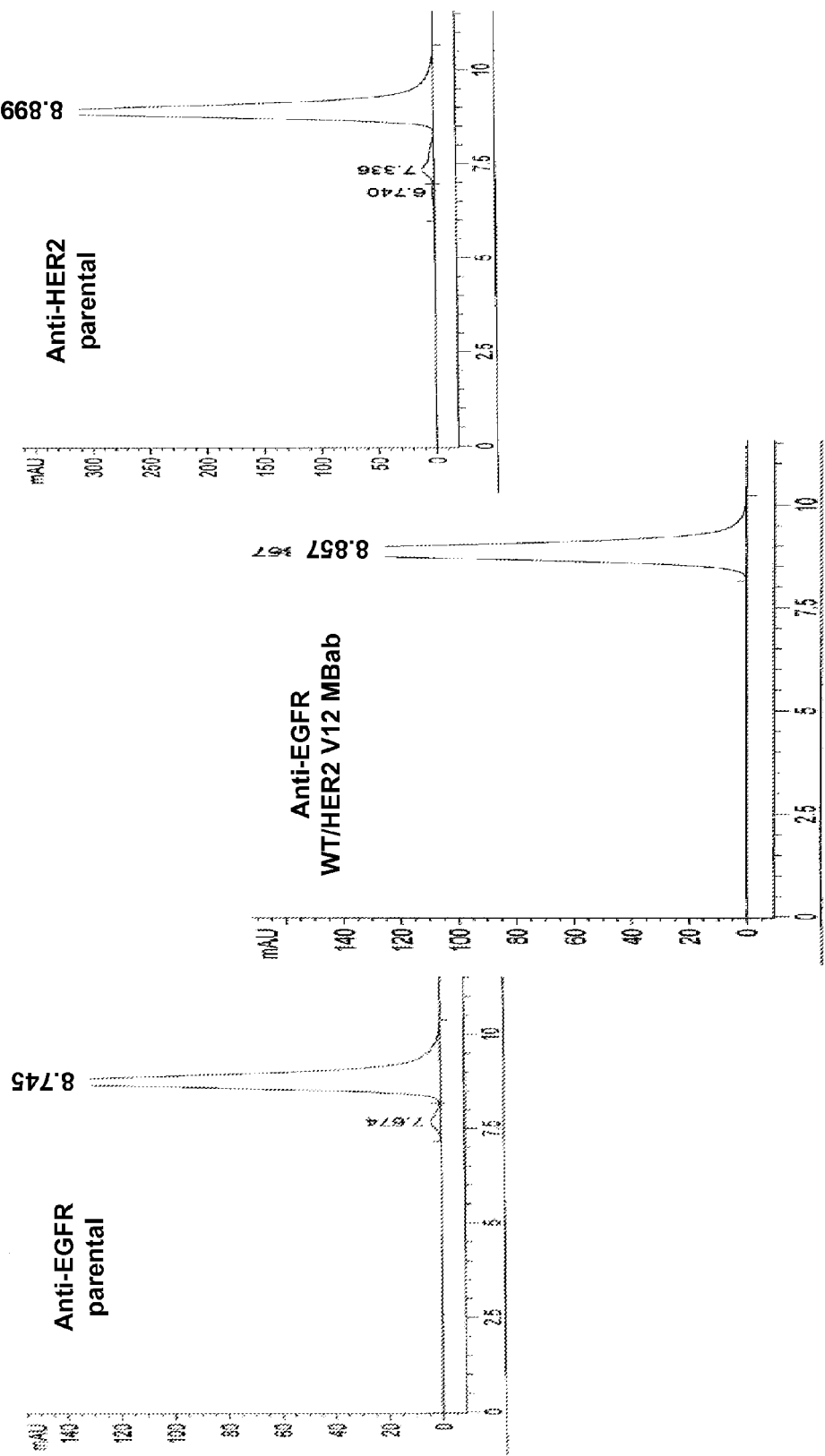
Figure 11D:
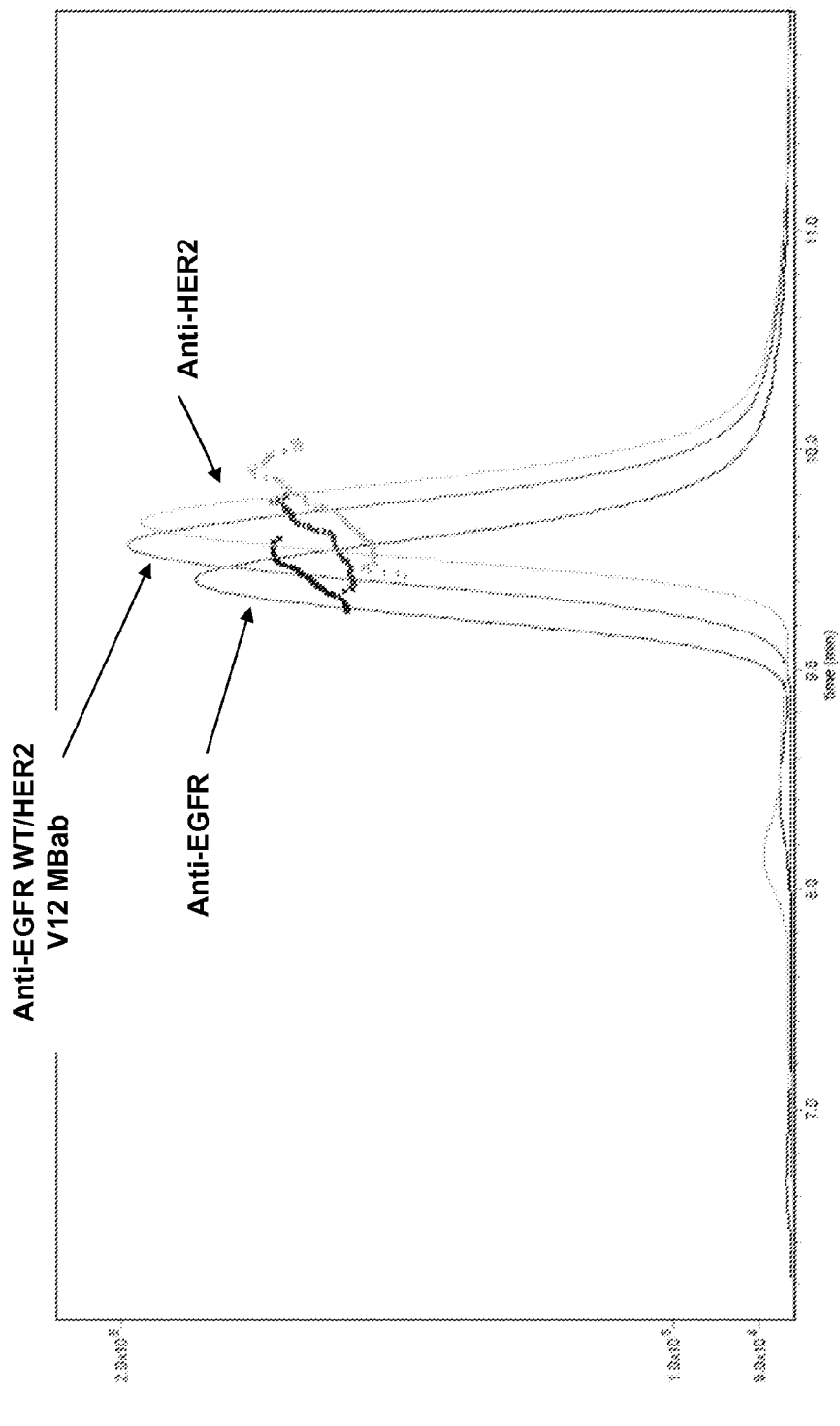

To evaluate the therapeutic significance of the MBab molecule and to further validate the platform, a monovalent bispecific antibody (MBab) with similar binding characteristics as two clinically approved antibodies; Herceptin® and Erbitux® (Cetuximab) was generated (FIG. 11A, left panel). Simultaneous treatment with Herceptin® and Cetuximab can lead to far greater tumor regression in human xenografts, as compared to the effect of each mAb alone (Larbouret et al. (2001) Clin. Cancer Res. 13:3356-3362). Following transient co-transfection of the pMBab-Heavy and pMBab-Light vectors in HEK293F cells, culture supernatants were purified on protein A affinity chromatography. SDS-PAGE analysis under non-reducing conditions showed that the majority of the antibody was produced correctly with 2 heavy chains and 2 light chains (FIG. 11A, right panel). The expression yields of the MBab (150 mg/l) correlated with the expression profile of the two parental antibodies; anti-HER2 (200 mg/l) and anti-EGFR (90 mg/l). The SEC-HPLC profile of the protein A purified MBab indicated about 90% monomer, about 10% unpaired half IgG and less than 3% of aggregates. Following preparative SEC, the HER2/EGFR MBab was purified to near homogeneity of greater than 99% monomer (FIG. 11B) and overall similar SEC profile as the parental mAbs (FIG. 11C). SEC-MALS analysis indicated MW values of 154.8 KD for the MBab and 158.5 KD and 154.0 KD for anti-EGFR and anti-HER2, respectively. The migration profiles of the three antibodies indicated that the MBab with an elution center of about 9.28 min migrated between anti-EGFR (9.20 min) and anti-HER2 (9.33 min) (FIG. 11D).

Example 9

Concurrent Binding Analysis by Octet Analysis

Figure 12A:
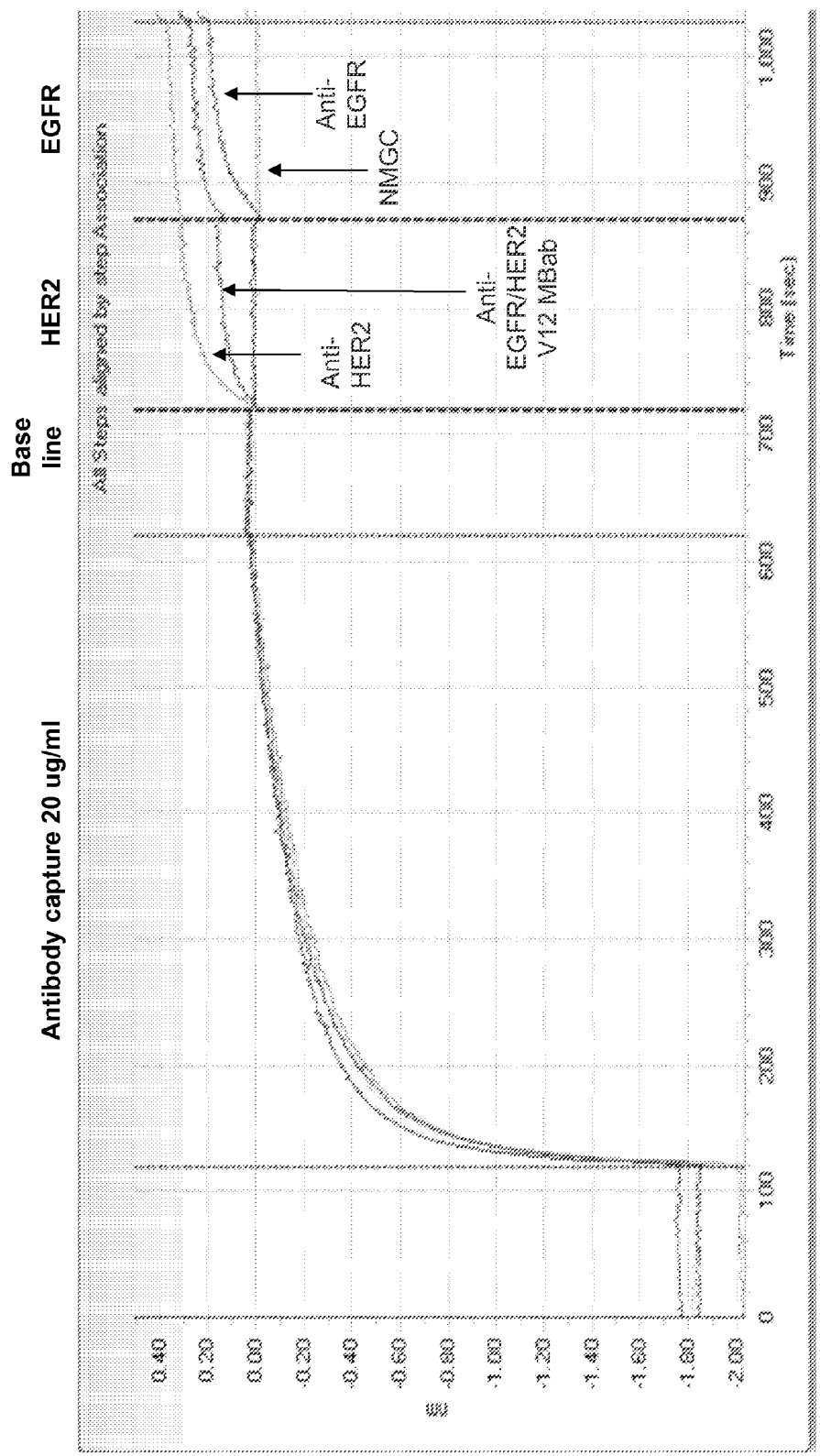
FIG. 12A and FIG. 12B show bispecificity of the anti-EGFR WT/anti-HER2V12 monovalent bispecific antibody (EGFR/HER2V12 MBab), as determined by Octet analysis (capture format I).
Figure 12B:
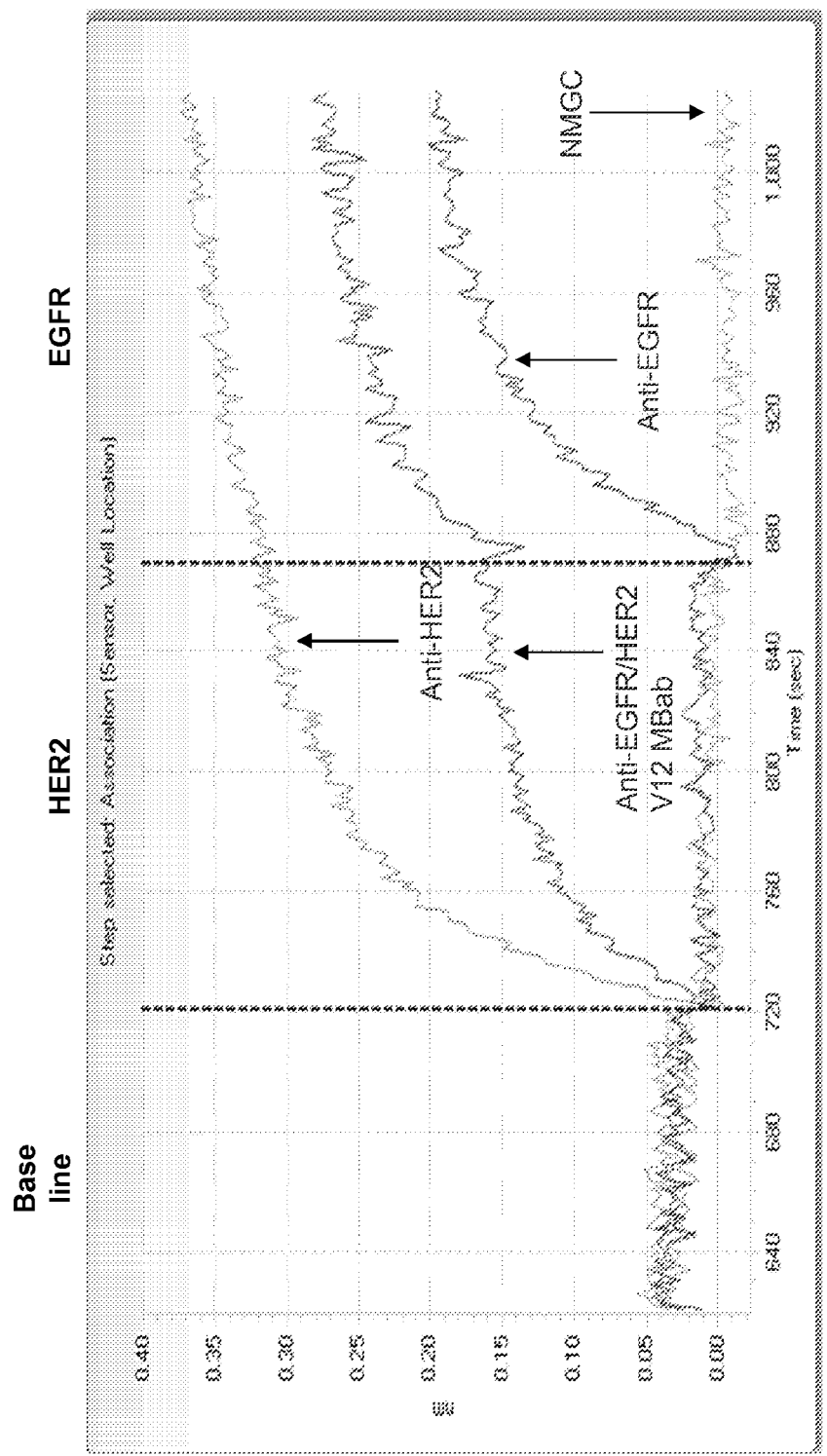

The bispecificity and concurrent binding of the HER2/EGFR MBab to HER2 and EGFR antigens was determined by Octet analysis using format I described above. Following capture on an anti-Fc sensor the MBab demonstrated concurrent binding profiles to HER2 and EGFR antigens while the parental antibodies demonstrated specific binding only to their respective antigens (FIG. 12).

Figure 13A:
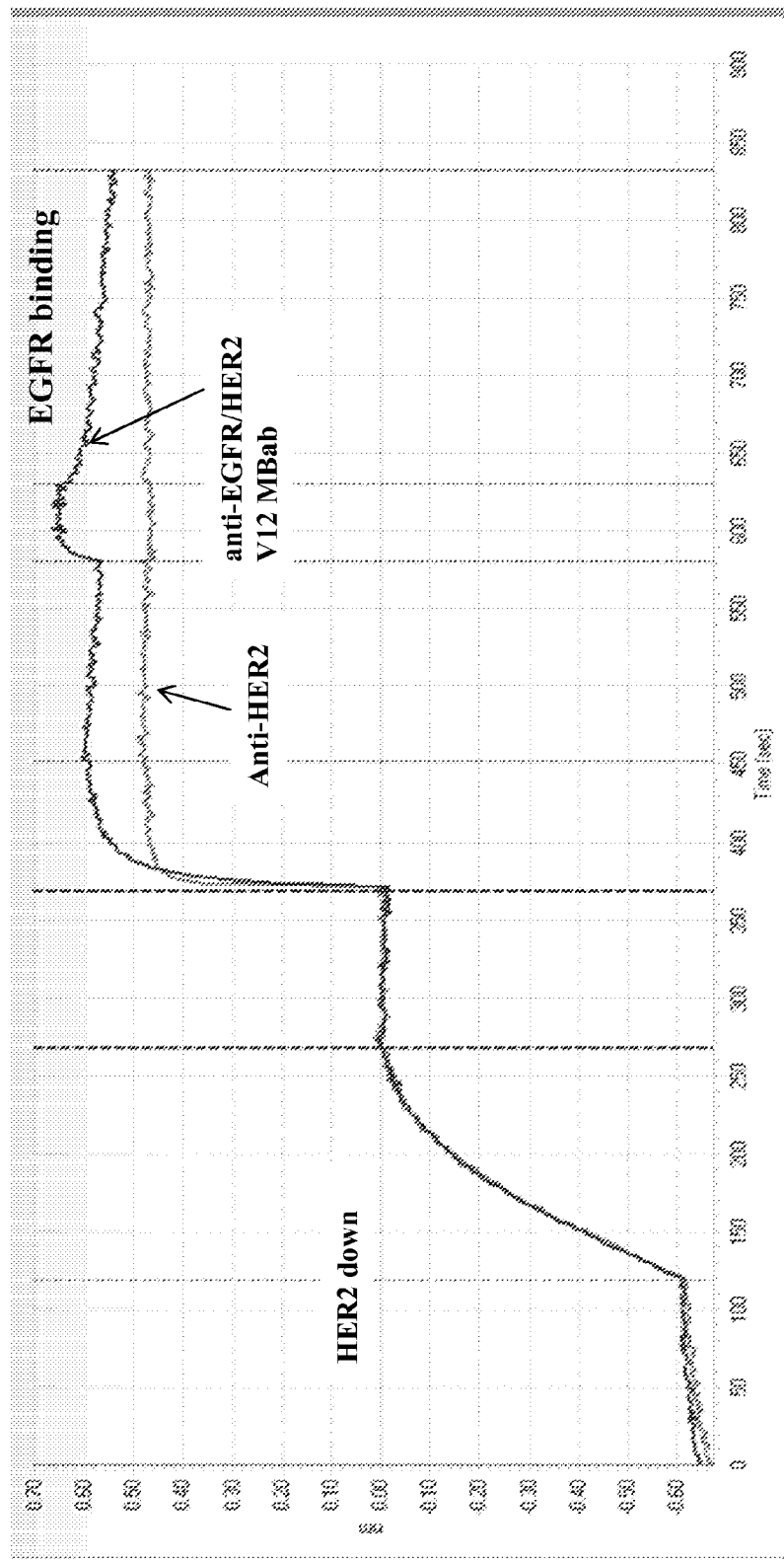
FIG. 13A and FIG. 13B show bispecificity of the anti-EGFR WT/anti-HER2V12 monovalent bispecific antibody (EGFR/HER2V12 MBab), as determined by Octet analysis (capture format II).
Figure 13B:
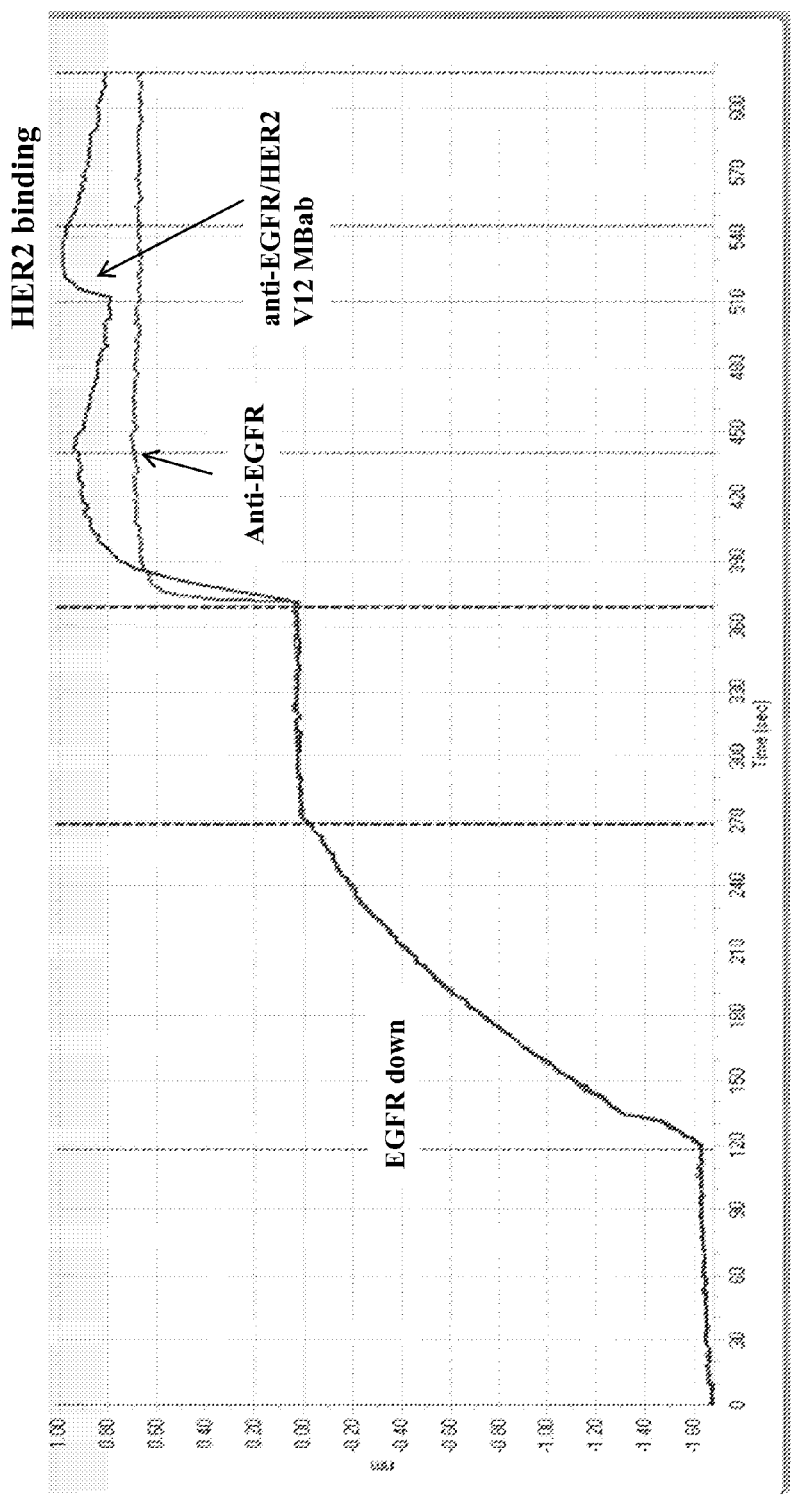

In addition, the bispecificity and concurrent binding of the Her2/EGFR MBab to HER2 and EGFR antigens was determined by Octet analysis using an alternative capture format (format II described above). Following capturing of biotinylated EGFR or biotinylated HER2 on Streptavidin High Binding Capacity sensors the MBab demonstrated concurrent binding profile to the corresponding unlabeled antigen while the parental anti-HER2 and anti-EGRF antibodies demonstrated specific binding only to their respective antigen (FIG. 13)

Example 10

Thermal stability analysis by differential scanning calorimetry

Figure 14A:
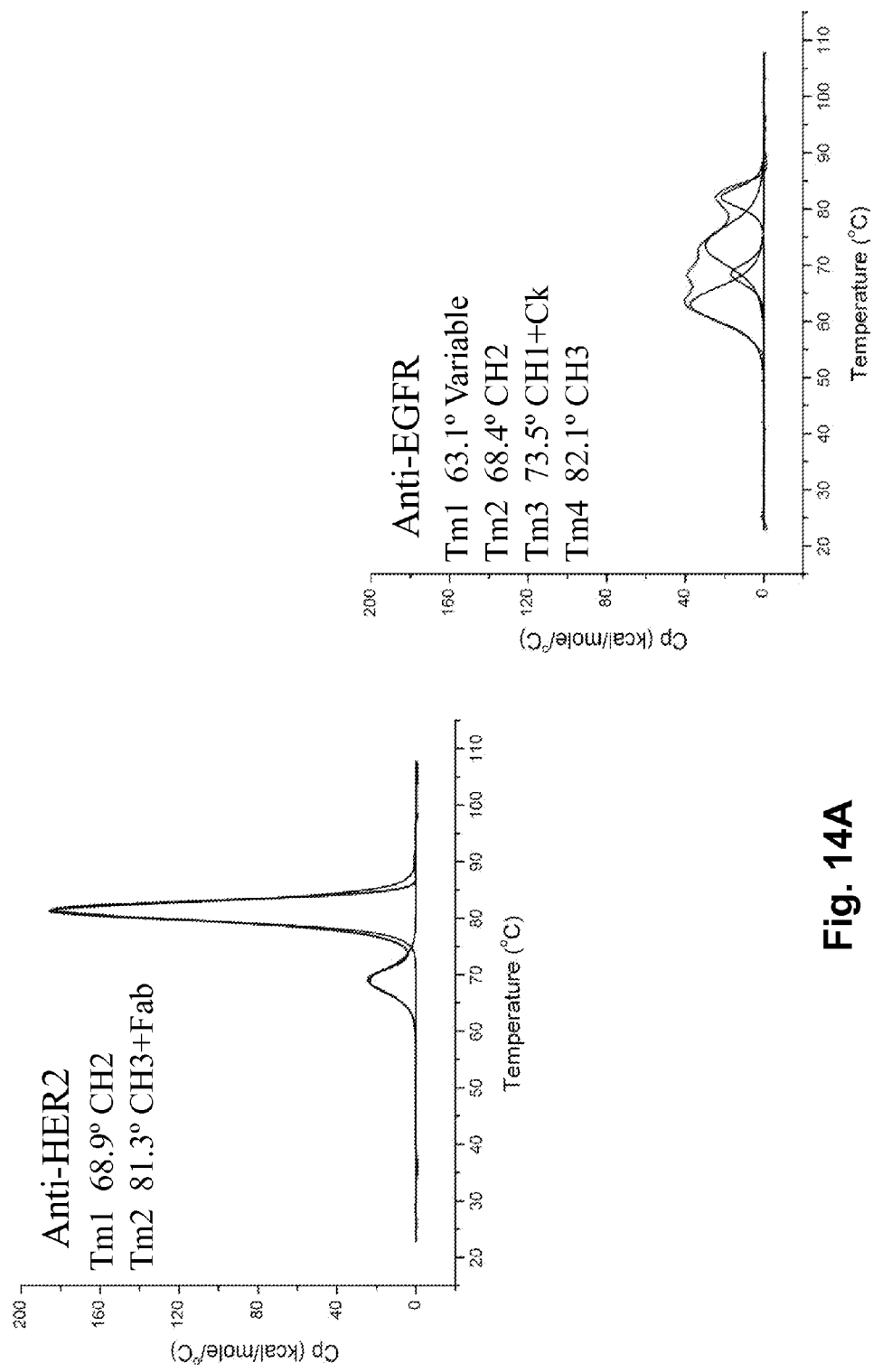
FIG. 14A and FIG. 14B show thermal stability studies using differential scanning calorimetry analysis.
Figure 14B:
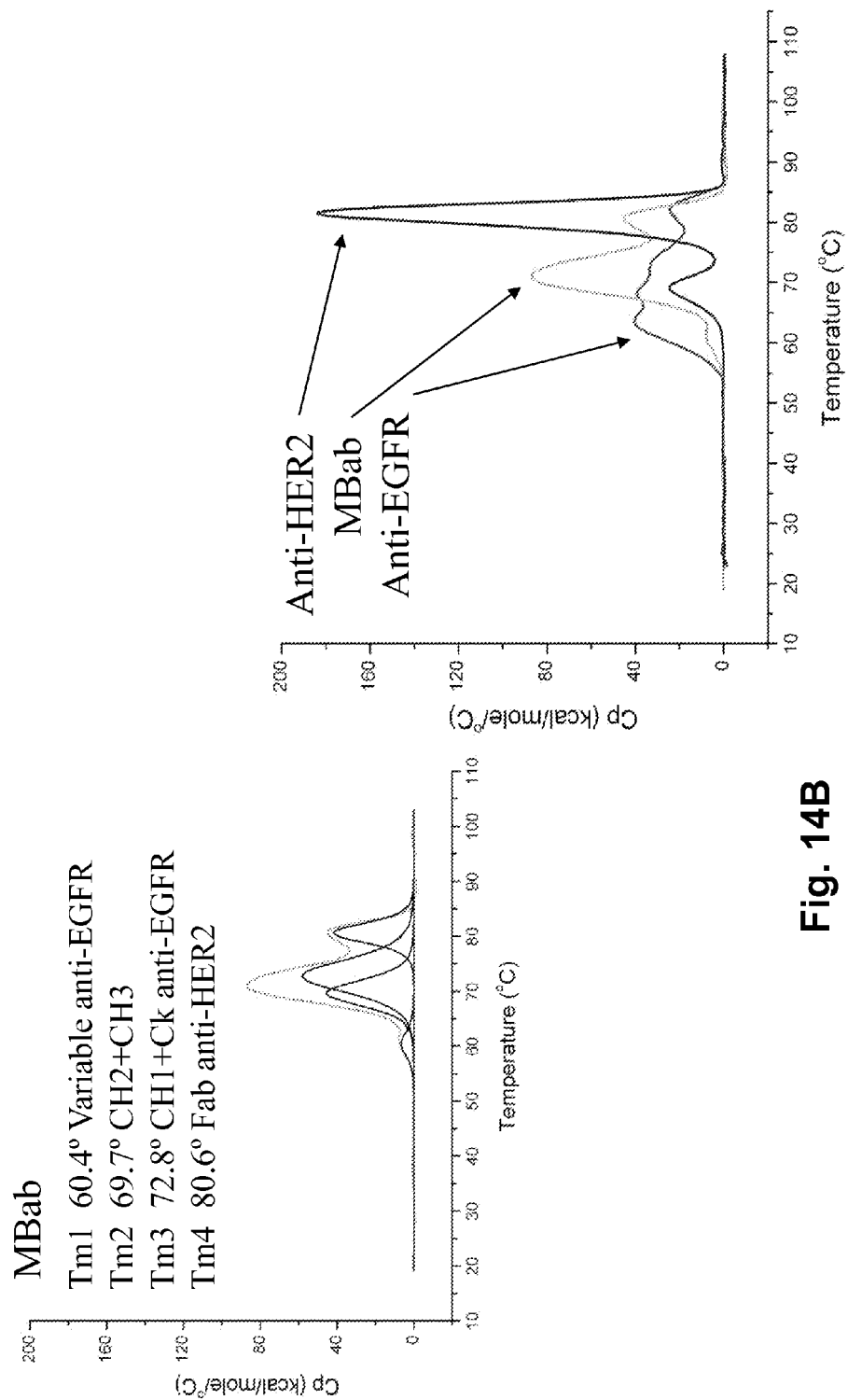
Figure 15A:
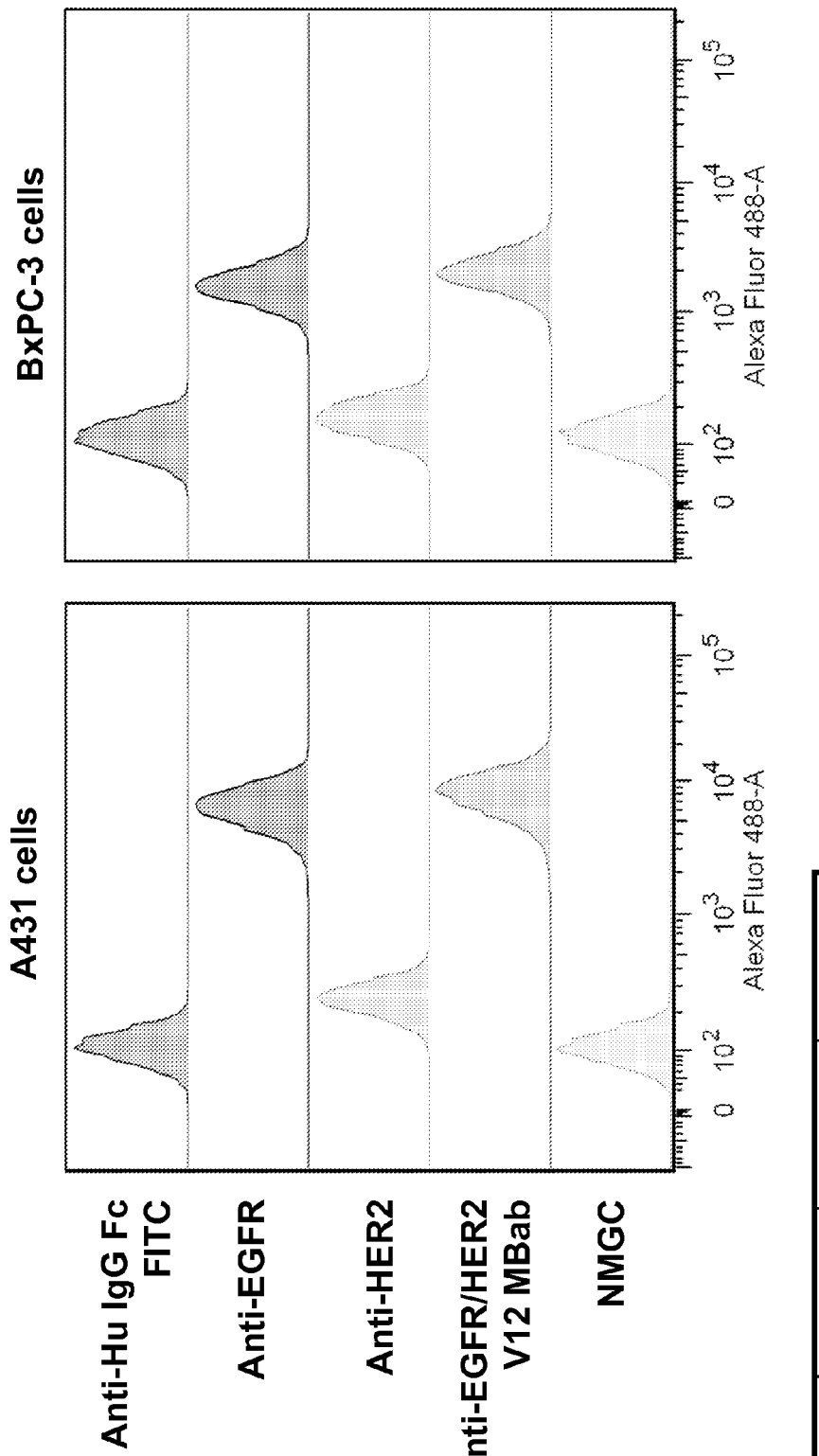
FIGS. 15A and 15B show cell-binding properties of anti-EGFR WT/anti-HER2 variant 12 monovalent bispecific antibody (EGFR/HER2V12 MBab), as determined by Flow Cytometry analysis. Anti-EGFR/HER2V12 MBab bound to cells expressing different levels of EGFR and HER2, similar to the parental antibody whose target was predominant for the particular cell type.
Figure 15B:
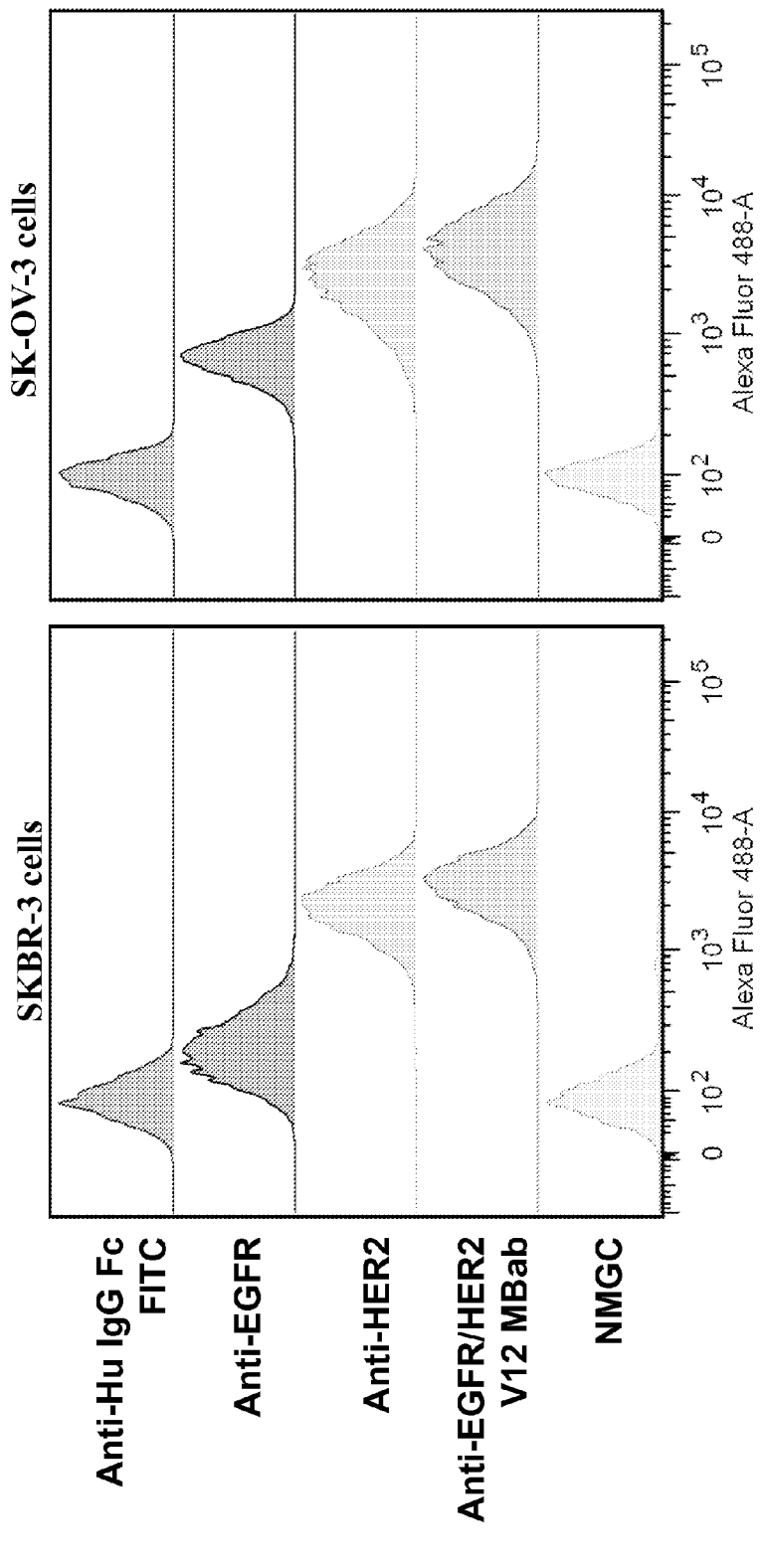

The thermal stability of anti-HER2, anti-EGFR, and HER2/EGFR V12 MBab was assessed using DSC (FIG. 14). The DSC thermogram of anti-HER2 showed two distinct unfolding transitions with denaturation temperatures (Tm) of 68.9° C. and 81.3° C. (FIG. 14A, top left). These transitions corresponded to the denaturation of CH2, and Fab+CH3 domains, respectively. The DSC thermogram of anti-EGFR revealed four transitions (FIG. 14A, bottom right). The chimeric Fab domain of anti-EGFR displayed separate $T_m$ values for CH1, Ck and VH, and Vk domains of 73.5° C. and 63.1° C., respectively. The CH2 and CH3 domains of anti-EGFR demonstrated Tm values of 68.4° C. and 82.1° C., respectively. Deconvolution of the HER2/EGFR V12 MBab DSC thermogram revealed 4 transitions (FIG. 14B, top left). By comparing the unfolding transition temperatures of HER2/EGFR V12 MBab with those of the parental antibodies it was deduced that the peak with a Tm of 60.4° C. corresponded to the denaturation transition of anti-EGFR variable domains. In parallel, the peak with a Tm of 73.5° C. corresponded to the denaturation transition of anti-EGFR CH1 and Ck domains. In some cases, incorporation of the knob-into-hole mutations in CH3 domain can reduce the Tm of the CH3 domain from about 80.0° C. to about 69.0° C. Therefore, the peak with a Tm of 69.7° C. corresponded to the denaturation transition of the CH2 and CH3 domains. Consequently, the peak with a Tm of 80.6° C. corresponded to the denaturation transition of anti-HER2Fab domain. The three DSC thermograms superimposed (FIG. 14B, bottom right) indicated that the denaturation transition of anti-HER2Fab domain overlapped with the HER2/EGFR V12 MBab peak at a Tm of about 80.0° C. This indicated that the alternative interchain disulfide engineered into the anti-HER2Fab portion of the HER2/EGFR V12 MBab did not destabilize the overall folding of the Fab scaffold. Altogether, the thermal stability studies confirmed that the HER2/EGFR V12 MBab displayed similar unfolding transitions as conventional IgG antibodies.

Example 11

Papain Digested QTOF LC-MS Mapping

The papain digested Q-TOF LC-MS results confirmed the expected Fab regions of the HER2/EGFR V12 MBab protein. The Fab (B) region of the HER2/EGFR V12 MBab eluting at 10.7 minutes was identified as LC+anti-HER2 (1-224) and LC+anti-HER2 (1-227). The retention time and cleavage sites were consistent with the parental anti-HER2 IgG, anti-HER2 Fab WT and anti-HER2V12 Fab samples. The Fab (A) region of the HER2/EGFR V12 MBab eluting at 11.9 minutes was identified as LC+anti-EGFR (1-226). This cleavage site and retention time was consistent with the Fab region of the parental anti-EGFR IgG.

Example 12

Cellular Binding by Flow Cytometry

The cell-binding properties of the Her2/EGFR V12 MBab to four tumor cell-lines expressing varying levels of HER2 and EGFR was tested by flow-cytometry and compared to the cellular binding activities of the two parental antibodies. The results presented in FIG. 15 show that the staining intensities of the parental anti-HER2 and anti-EGFR antibodies corresponded with the levels of HER2 and EGFR antigens on the various tumor cells. However, the MBab consistently maxed the staining intensity of the parental antibody that scored the highest FACS signal in cells with different levels of HER2 and EGFR.

Example 13

Cell-viability assays

Figure 16A:
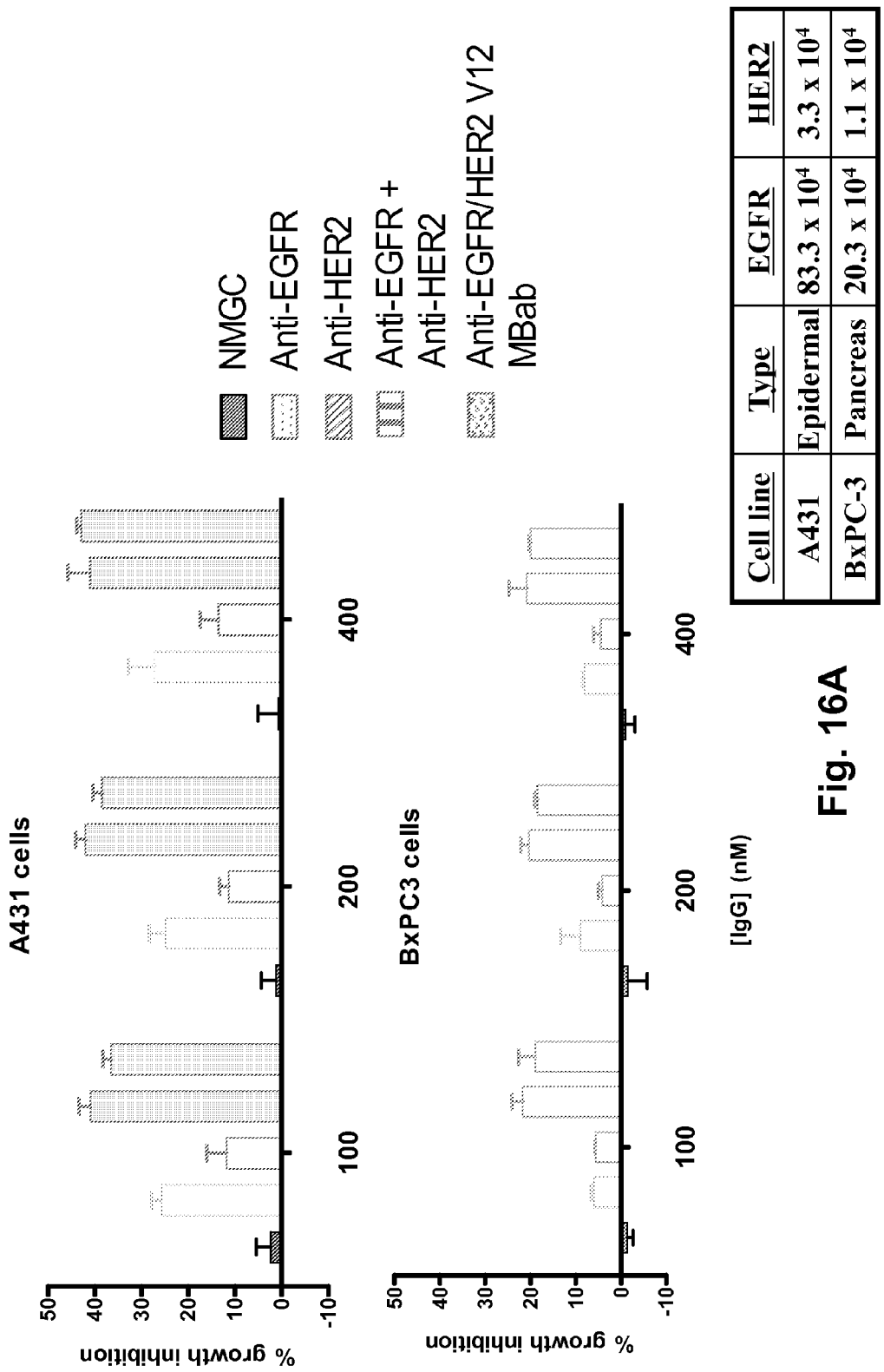
Figure 16B:
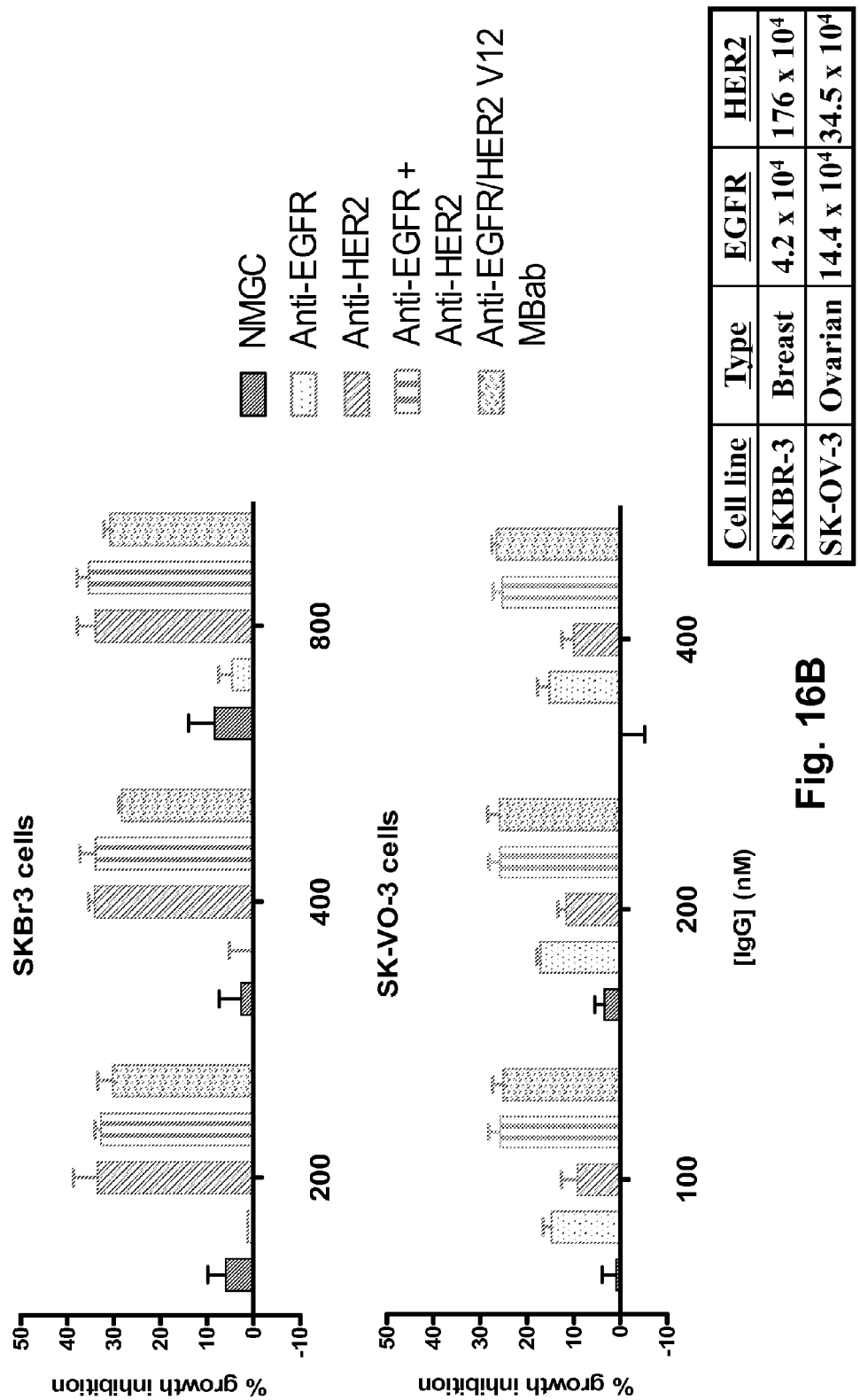

To evaluate the therapeutic application of the Her2/EGFR V12 MBab, the potency of the molecule was tested in in-vitro cell-killing experiments. In some cases, the additive or synergistic therapeutic activity obtained with combination treatment of anti-EGFR and anti-HER2 can occur in tumors with similar or higher levels of EGFR over HER2 (see e.g., Larbouret et al. (2001) Clin. Cancer Res. 13:3356-3362). To demonstrate this, four tumor cell-lines were selected with varying levels of HER2 and EGFR. The cell-killing activity of the MBab was compared with that of the parental antibodies alone and combination treatment with the two parental antibodies. The results presented in FIG. 16 show that with A431 cells that express about 25 fold more EGFR over HER2, the Her2/EGFR V12 MBab demonstrated an additive cell killing activity that was similar to that of the combination of the two parental mAbs and a much more potent activity than that of each mAb alone. The same additive killing profile was seen with BxPc3 cells that express about 20 fold more EGFR and also with SK-OV-3 cells that express relatively similar levels of the two antigens. However, for SKBR3 cells that express greater than 40 fold more HER2 over EGFR, no additive killing effects were obtained with the MBab or the combination treatment with the two parental antibodies. The cell killing titration curve of MBab revealed that at high antibody concentration the Her2/EGFR V12 MBab conferred additive cell killing activity to the same level as the combination treatment and higher than that of each mAb alone, however, at lower antibody concentrations the Her2/EGFR V12 MBab demonstrated reduced activity in comparison with the combination treatment (FIG. 16C). This behavior was most likely attributed to the monovalency of the Her2/EGFR V12 MBab that resulted with lack of avidity effects. This unique property of the MBab might confer less target related toxicity.

Example 14

Binding Kinetics to Fc Receptors

To assess the impact of the knob-into-hole mutations as well as the V12 mutations in CL-CH1 interface on the engagement with various human Fc receptors, a variety of MBab constructs were generated and their binding kinetics to human Fc receptors was measured and compared with that of the corresponding parental IgG1. Dissociation constants (KDs) were determined by steady state equilibrium binding assay on a ProteOn. The parental IgGs used in this study were; the parental anti-EGFR, anti-HER2 and a control hIgG1 (NMGC). The MBab constructs generated for this study included the following combinations: HER2/EGFR, EGFR/EGFR, HER2/HER2, EGFR/NMGC and NMGC/HER2. The KD values summarized in Table 9 revealed no differences in binding kinetics to any of the Fc receptors tested between MBab constructs and their corresponding parental IgGs as well as with reported values for human IgG1 isotype.

TABLE 9

KD values for Fc Receptor and C1q binding

Antibody KD [nM]

| Ligand | Fcγ R Ia | Fcγ R IIa | Fcγ R IIb | Fcγ R IIIa 158F | Fcγ R IIIa 158V | Hu FcRn pH 6 | C1q |
|---|---|---|---|---|---|---|---|
| EGFR/HER2 MBab | 7.86 | 960 | 5390 | 2540 | 315 | 1050 | 174 |
| EGFR/EGFR knob-hole | 7.64 | 916 | 5240 | 2420 | 277 | 1050 | 164 |
| HER2/HER2 knob-hole | 9.42 | 954 | 5310 | 2510 | 294 | 1070 | 151 |
| NMGC IgG1 | 9.94 | 906 | 5650 | 2210 | 246 | 810 | 28.9 |
| EGFR IgG1 | 7.11 | 1000 | 4640 | 2440 | 284 | 1100 | 120 |
| HER2 IgG1 | 8.1 | 903 | 5620 | 2270 | 253 | 998 | 83.3 |
| EGFR/NMGC MBab | 9.82 | 1020 | 4710 | 2620 | 288 | 1210 | 131 |
| NMGC/HER2 MBab | 9.84 | 991 | 4640 | 2450 | 270 | 1010 | 95.5 |
| Reported human IgG1 | 10-200 | 500-3000 | 800-7000 | 500-5000 | 500-5000 | 100-2500 | 100-700 |

Example 15

Antibody-Dependent Cellular Cytotoxicity and Binding to FcγRIIIa and C1q

Figure 17A:
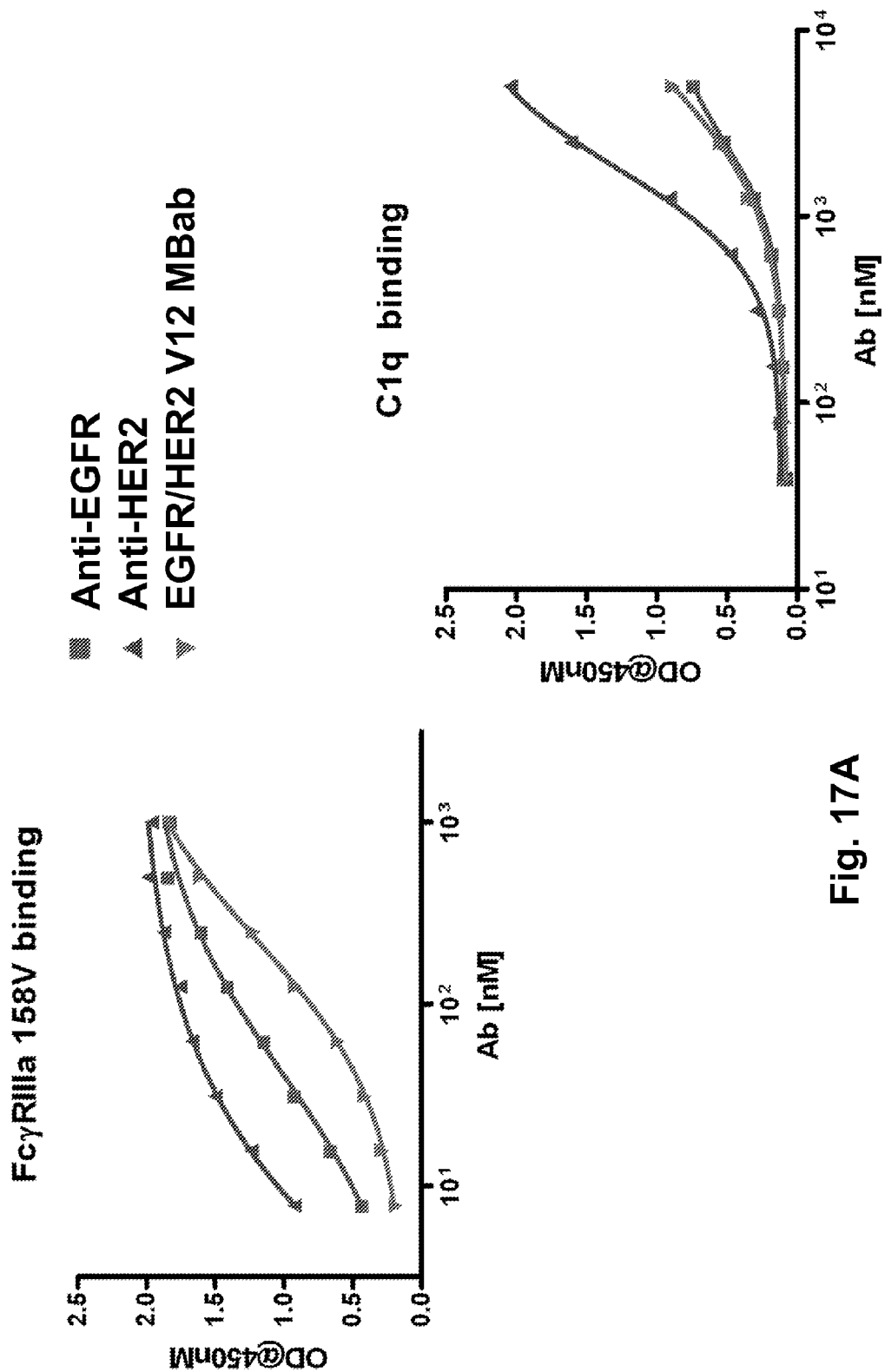
FIG. 17A and FIG. 17B show FcγRIIIa and C1q binding and ADCC activity.
Figure 17B:
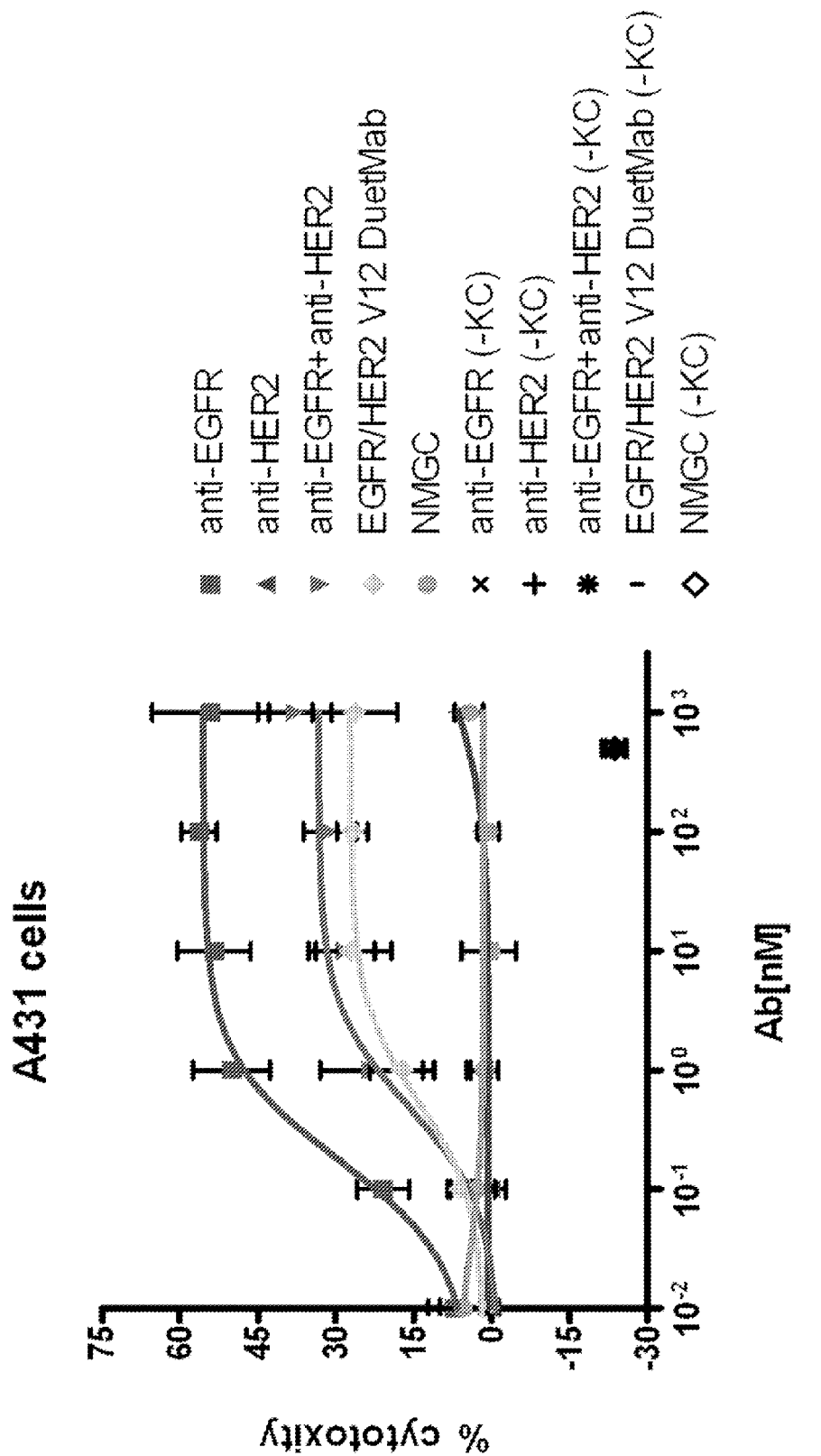

The ability to maintain binding to FcγRIIIa and C1q can be a key indicator for the ability of an antibody to elicit ADCC and CDC. In this example, the MBab was tested for direct binding to FcγRIIIa and C1q by ELISA and also for its ability to elicit ADCC in A431 cells. The results presented in FIG. 17A show that the MBab exhibited binding to FcγRIIIa and C1 q. Furthermore, in ADCC studies, the MBab elicited similar ADCC activities as the combination with the two parental antibodies. The parental anti-HER2 alone showed no ADCC activity while Cetuximabanti-EGFR exhibited stronger ADCC activity (FIG. 17B).

Example 16

Figure 20A:
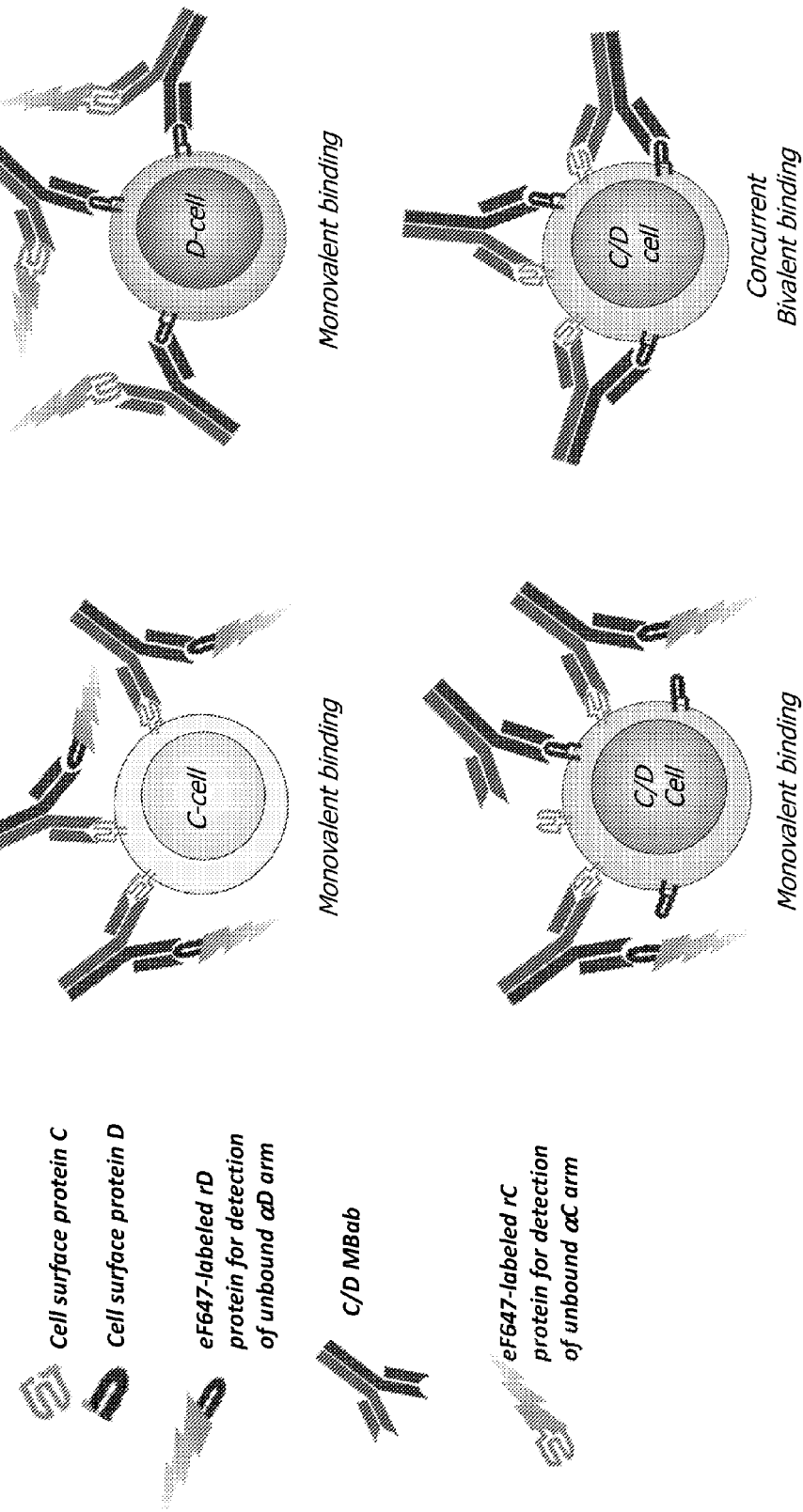
FIG. 20A-C shows preferential binding and improved selectively of MBab.
Figure 20B:
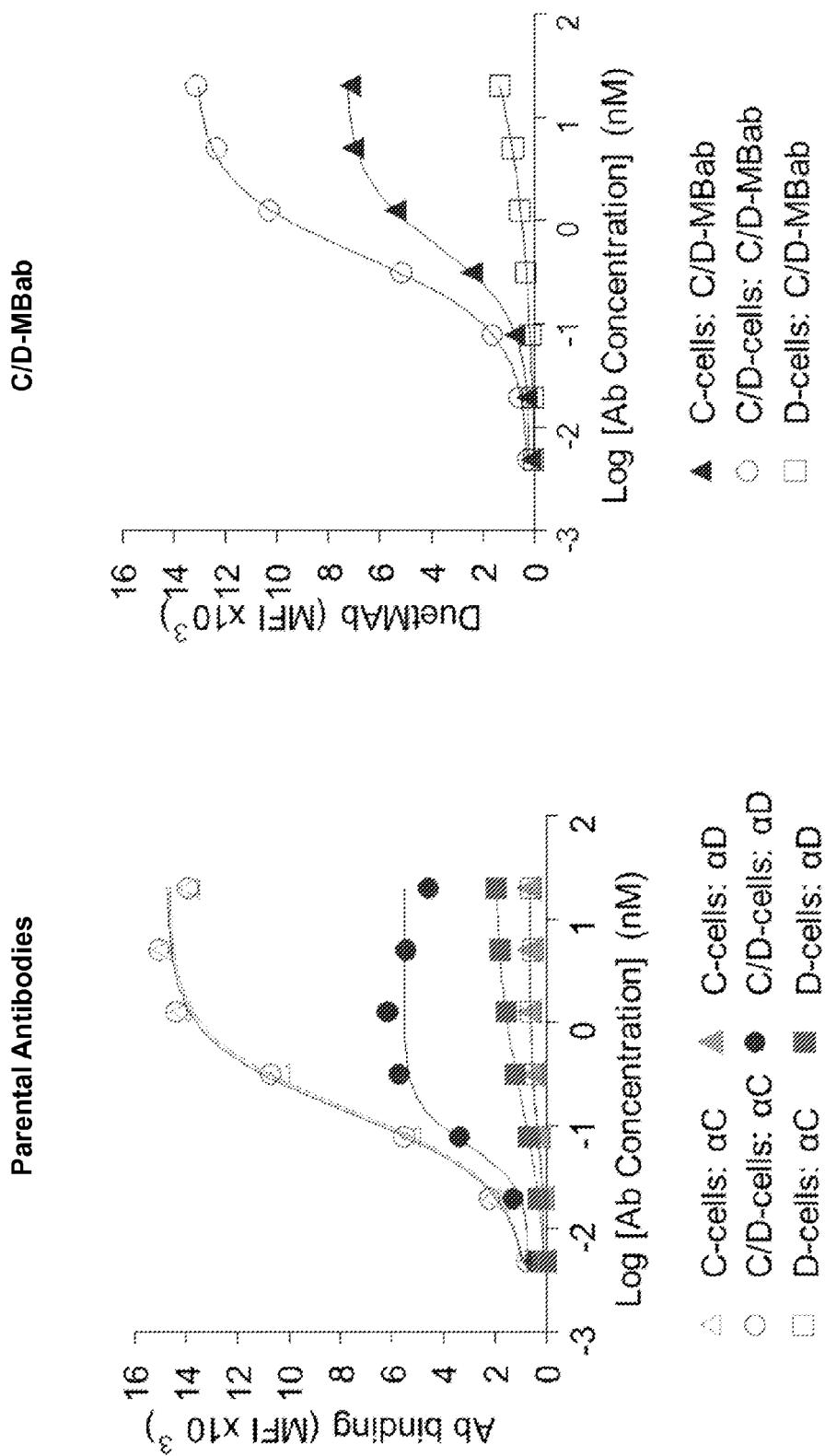
Figure 20C:
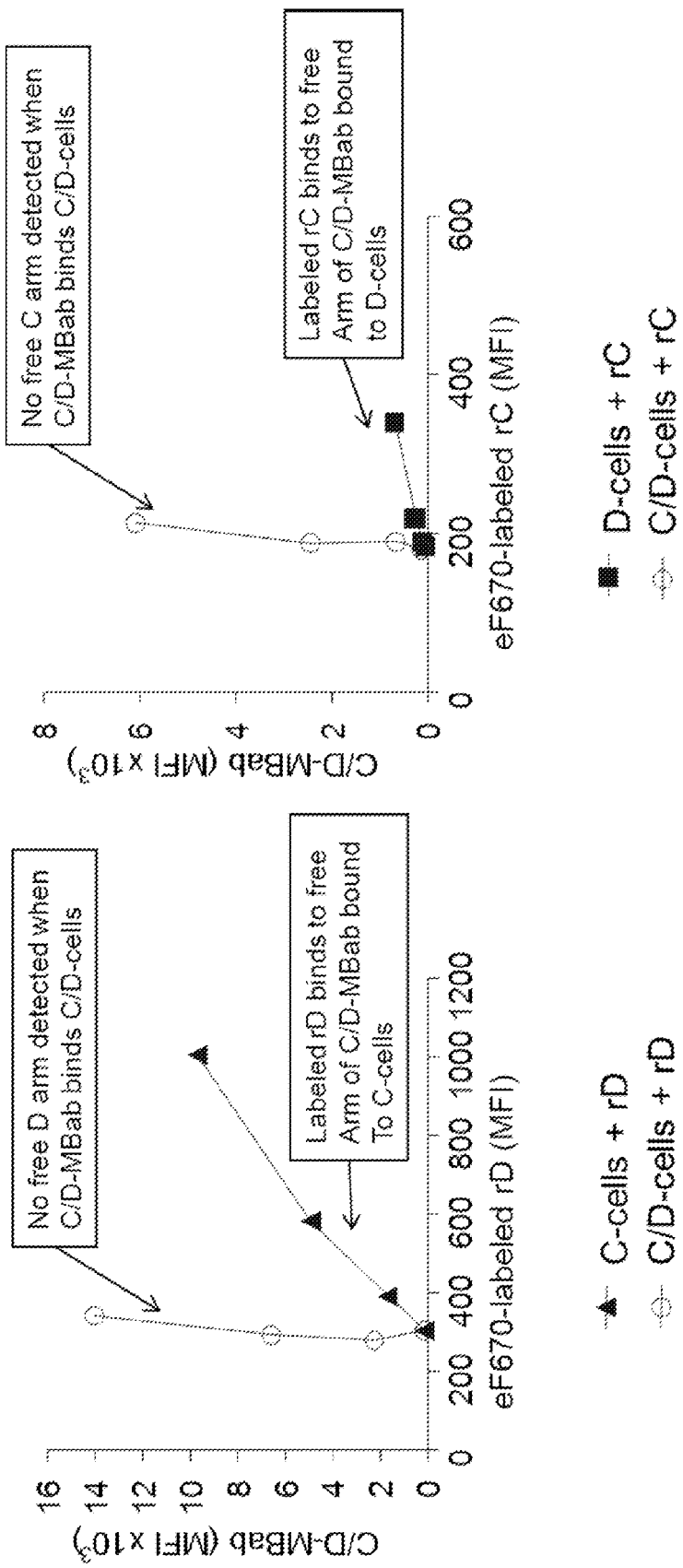

Preferential Binding and Improved Selectivity by Concurrent Binding to Two Antigens on a Single Cell To demonstrate preferential binding and improved selectivity by concurrent binding to two cell surface antigens (referred to here as antigens C and D) on a single cell a MBab comprised of an anti-C and an anti-D was generated (designated C/D-MBab). Preferential binding of the C/D-MBab to cells expressing both target antigens (C and D) was analyzed by means of flow-cytometry by mixing pre-stained populations of cells expressing C only (C cells), cell expressing D only (D cells) and cells expressing both C and D (C/D cells) at 1:1:1 ratio in a single well followed by incubation with the parental IgGs or C/D-MBab. As shown in (FIG. 20B left and right panels, respectively) the C/D-MBab demonstrated preferential binding to C/D cells expressing both cell surface antigens C and D antigens. To confirm that the preferential binding to C/D cells was due to concurrent bivalent engagement with both cell surface antigens C and D, soluble recombinant C and D proteins labeled with fluorescent Alexa Fluor® 647 were used to trace for unbound arms of the C/D-MBab molecule. In essence, if the C/D-MBab is monovalently bound to the cell surface, one arm will remain free to bind to the soluble fluorescent forms of C or D proteins which can be detected by flow cytometric analysis (schematically depicted in FIG. 20A). A key control for the study is the use of cell population known to express only one of the target antigens. In this event, any C/D-MBab that binds to the surface can only do so monovalently, leaving the unbound arm free to be detected by Alexa Fluor 647-labeled recombinant protein. Incubation of the C/D-MBab with C cells which express no D led to a concentration dependent fluorescent signal following incubation with Alexa Fluor 647 labeled recombinant D protein indicating that for every molecule of C/D-MBab bound to antigen C on the cell surface, while the anti-D arm was free to bind Alexa Fluor 647 labeled recombinant D protein (FIG. 20C left panel). In the same manner, incubation of the C/D-MBab with D cells, that express only antigen D and no antigen C resulted with a concentration dependent fluorescent signal following addition of Alexa Fluor 647 labeled recombinant C protein indicating that for every molecule of C/D-MBab bound to antigen D on the cell surface, the anti-C arm was free to bind Alexa Fluor 647 labeled recombinant C protein (FIG. 20C, right panel). However, when the C/D-MBab was incubated with C/D cells no increase in fluorescent signal was seen following addition of Alexa Fluor 647 labeled recombinant D protein or Alexa Fluor 647 labeled recombinant C protein indicating that both C/D-MBab arms are concurrently engaged and neither recombinant protein can bind to the cell-antibody complex, hence, only a PE signal is seen (FIG. 20C, both panels). The relationship between the amount of C/D-MBab on the cell surface and the amount of soluble recombinant protein that is able to bind ultimately provides evidence of concurrent bivalent, or monovalent binding of C/D-MBab to the cell surface. Where it is evident that C/D-MBab is bound to the cell surface, but no free arm is detected, it can be concluded that both arms are concurrently engaged with their target antigen.

Example 16

Examples of Sequences

Provided hereafter are non-limiting examples of certain amino acid sequences.

TABLE 8

Examples of Sequences

| Name | Type | SEQ ID NO | Sequence |
|---|---|---|---|
| Human IgG1 heavy chain constant region | AA | 1 | ASTKGPSVFPLAPSSKSTSGGTAALGCLVKDYFPEPVTVSWNSGALTSGVHTFPA VLQSSGLYSLSSWTVPSSSLGTQTYICNVNHKPSNTKVDKX$_1$*VEPKSCDKTHTC PPCPAPELLGGPSVFLFPPKPKDTLMISRTPEVTCVVVDVSHEDPEVKFNVVYVD GVEVHNAKTKPREEQYNSTYRVVSVLTVLHQDWLNGKEYKCKVSNKALPAPIEKT ISKAKGQPREPQVYTLPPSRX$_2$*EX$_3$*TKNQVSLTCLVKGFYPSDIAVEWESNGQP ENNYKTTPPVLDSDGSFFLYSKLTVDKSRWQQGNVFSCSVMHEX$_4$*LHNHYTQKS LSLSPGK<br>*X$_1$ = Lys or Arg; X$_2$ = Asp or Glu; X$_3$ = Leu or Met; X$_4$ = Ala or Gly |
| Human IgG2 heavy chain constant region | AA | 2 | ASTKGPSVFPLAPCSRSTSESTAALGCLVKDYFPEPVTVSWNSGALTSGVHTFPAV LQSSGLYSLSSVVTVX$_1$*SSX$_2$*X$_3$*GTQTYTCNVDHKPSNTKVDKTVERKCCVECP PCPAPPVAGPSVFLFPPKPKDTLMISRTPEVTCVVVDVSHEDPEVQFNWYVDGX$_4$*E VHNAKTKPREEQFNSTFRVVSVLTVVHQDWLNGKEYKCKVSNKGLPAPIEKTISKT KGQPREPQVYTLPPSREEMTKNQVSLTCLVKGFYPSDIX$_5$*VEWESNGQPENNYKT TPPMLDSDGSFFLYSKLTVDKSRWQQGNVFSCSVMHEALHNHYTQKSLSLSPGK<br>*X$_1$ = Pro or Thr; X$_2$ = Asn or Ser; X$_3$ = Phe or Leu; X$_4$ = Val or Met; X$_5$ = Ala or Ser |
| Human IgG3 heavy chain constant region | AA | 3 | ASTKGPSVFPLAPCSRSTSGGTAALGCLVKDYFPEPVTVSWNSGALTSGVHTFPA VLQX$_1$*SGLYSLSSVVTVPSSX$_2$*X$_3$*GTQTYTCNVNHKPSNTKVDKRVELKTPLG DTTHTCPRCPEPKSCDTPPPCPRCPEPKSCDTPPPCPRCPEPKSCDTPPPCPRCP APELLGGPSVFLFPPKPKDTLMISRTPEVTCVVVDVSHEDPEVQFKWYVDGVEVH NAKTKPREEQYNSTFRVVSVLTVLHQDWLNGKEYKCKVSNKALPAPIEKTISKTK GQPREPQVYTLPPSREEMTKNQVSLTCLVKGFYPSDIAVEWESSGQPENNYNTTP PMLDSDGSFFLYSKLTVDKSRWQQGNIFSCSVMHEALHNRFTQKSLSLSPGK<br>*X$_1$ = Ser or Thr; X$_2$ = Asn or Ser; X$_3$ = Phe or Leu |
| Human IgG4 heavy chain constant region | AA | 4 | ASTKGPSVFPLAPCSRSTSESTAALGCLVKDYFPEPVTVSWNSGALTSGVHTFPA VLQSSGLYSLSSWTVPSSSLGTKTYTCNVDHKPSNTKVDKRVESKYGPPCPSCPA PEFLGGPSVFLFPPKPKDTLMISRTPEVTCVVVDVSQEDPEVQFNVVYVDGVEVH NAKTKPREEQFNSTYRVVSVLTVLHQDWLNGKEYKCKVSNKGLPSSIEKTISKAK GQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGK |
| Human Kappa light chain constant region | AA | 5 | RTVAAPSVFIFPPSDEQLKSGTASVVCLLNNFYPREAKVQWKVDNX$_1$*LQSGNSQ ESVTEQDSKDSTYSLSSTLTLSKADYEKHKX$_2$*YACEVTHQGLSSPVTKSFNRGEC<br>*X$_1$ = Ala or Val; X$_2$ = Val or Leu |
| Human Lambda light chain constant region | AA | 6 | QPKAX$_1$*PX$_2$*VTLFPPSSEELQANKATLVCLISDFYPGAVTVAWKADX$_3$*SPVKAGV ETX$_4$*TPSKQSNNKYAASSYLSLTPEQWKSHX$_5$*SYSCQVTHEGSTVEKTVAPTEC<br>*X$_1$ = Ala or Asn; X$_2$ = Ser or Thr; X$_3$ = Ser or Gly; X$_4$ = Thr or Lys; X$_5$ = Arg or Lys |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. In addition, U.S. Provisional Application No. 61/577,956 filed Dec. 20, 2011; is incorporated by reference in its entirety for all purposes.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. Thus, it should be understood that although the present technology has been specifically disclosed by representative aspects, embodiments and optional features, modification and variation of the concepts herein disclosed may be resorted to by those skilled in the art, and such modifications and variations are considered within the scope of this technology.

What is claimed is:

1. A bispecific antibody comprising:
   (a) an Fc region comprising a modified heavy chain, wherein the CH1 region of the modified heavy chain comprises
      (i) a substitution of a native cysteine to a non-cysteine amino acid, and
      (ii) a substitution of a native non-cysteine amino acid to a cysteine amino acid;
   (b) a modified corresponding light chain, wherein the CL region of the modified light chain comprises
      (i) a substitution of a native cysteine to a non-cysteine amino acid, and
      (ii) a substitution of a native non-cysteine amino acid to a cysteine amino acid;
   (c) a second Fc region comprising a second heavy chain; and
   (d) a second corresponding light chain,
   wherein the modified heavy chain is directly linked to the corresponding modified light chain, and on a separate target binding arm, the second heavy chain is directly linked to the second corresponding light chain, and
   wherein the substituted cysteine of the modified heavy chain, resulting from the substitution of the native non-cysteine amino acid to the cysteine amino acid, and the substituted cysteine of the modified corresponding light chain, resulting from the substitution of the native non-cysteine amino acid to the cysteine amino acid, can form a disulphide bond, wherein the substitutions in the modified heavy chain and modified corresponding light chain are selected from the group consisting of variants V10, V10-2a, V10-2b, V10-3, V10-4, V11, V11-2a, V11-2b, V11-3, V11-4, V12, V12-2a, V12-2b, V12-3 and V12-4 as provided in Table 4.

2. The bispecific antibody of claim 1, wherein
   (a) the second heavy chain and second corresponding light chain do not comprise a substitution of a native non-cysteine amino acid to a cysteine amino acid and do not comprise a substitution of a native cysteine to a non-cysteine amino acid; and/or
   (b) the two light chains each comprise a VL domain and a CL domain, wherein the VL domains have different amino acid sequences and the CL domains have different amino acid sequences; and/or
   (c) the two heavy chains each comprise a VH domain, a CH1 domain and an Fc region, wherein the VH domains have different amino acid sequences, the CH1 domains have different amino acid sequences, and the Fc regions have different amino acid sequences, optionally wherein one light chain is a kappa light chain and one light chain is a lambda light chain.

3. The bispecific antibody of claim 2, wherein the two heavy chains form a heterodimer.

4. The bispecific antibody of claim 1, wherein the antibody specifically binds to two independent antigens or to two independent epitopes on the same antigen.

5. The bispecific antibody of claim 1, wherein the Fc region of either or both heavy chains comprises one or more modifications optionally wherein the modifications facilitate heterodimerization of the heavy chains.

6. The bispecific antibody of claim 5, wherein the modifications in the Fc region are selected from those provided in Tables 5 and 6.

7. The bispecific antibody of claim 5, wherein the Fc region of either or both heavy chains comprises one or more modifications that alter protein A binding and are only present in one heavy chain, wherein:
(a) the antibody is an IgG1, an IgG2 or an IgG4 and the modifications in the Fc region that alter protein A binding is the amino acid substitution H435R/Y436F; or
(b) the antibody is IgG3 and the modifications in the Fc region that alter protein A binding is the amino acid substitution R435H/F436Y, and wherein numbering is according to the EU index.

8. The bispecific antibody of claim 5, wherein:
(a) the modified heavy chain Fc region comprises the amino acid substitution T366W, and the second heavy chain Fc region comprises the amino acid substitution Y407V/T366S/L368A; or
(b) the modified heavy chain Fc region comprises the amino acid substitution Y407V/T366S/L368A, and the second heavy chain Fc region comprises the amino acid substitution T366W, wherein numbering is according to the EU index.

9. The bispecific antibody of claim 8, wherein:
(a) the modified heavy chain Fc region further comprises the amino acid substitution S354C, and the second heavy chain Fc region further comprises the amino acid substitution Y349C; or
(b) the modified heavy chain Fc region further comprising the amino acid substitution Y349C, and the second heavy chain Fc region further comprises the amino acid substitution S354C, wherein numbering is according to the EU index.

10. The bispecific antibody of claim 5, further comprising modifications in the Fc region that alter the half-life of the antibody, wherein the half-life depends on FcRn binding affinity and/or modifications in the Fc region that alter the effector function, wherein the binding affinity for an Fc gamma receptor or C1q complement protein is increased or decreased.

11. A composition comprising the bispecific antibody of claim 1 and an excipient.

* * * * *